United States Patent
Ghosh et al.

(10) Patent No.: US 7,211,672 B2
(45) Date of Patent: May 1, 2007

(54) PGD2 RECEPTOR ANTAGONISTS FOR THE TREATMENT OF INFLAMMATORY DISEASES

(75) Inventors: Shomir Ghosh, Brookline, MA (US); Amy M. Elder, Arlington, MA (US); Kenneth G. Carson, Needham, MA (US); Kevin Sprott, Boston, MA (US); Sean Harrison, Belmont, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 30 days.

(21) Appl. No.: 10/678,872

(22) Filed: Oct. 3, 2003

(65) Prior Publication Data

US 2004/0082609 A1    Apr. 29, 2004

Related U.S. Application Data

(60) Provisional application No. 60/416,501, filed on Oct. 4, 2002.

(51) Int. Cl.
C07D 215/38    (2006.01)
C07D 215/44    (2006.01)

(52) U.S. Cl. ............... 546/157; 546/159; 514/313; 514/314

(58) Field of Classification Search ........ 514/313, 514/314; 546/157, 159
See application file for complete search history.

(56) References Cited

U.S. PATENT DOCUMENTS

| | | | |
|---|---|---|---|
| 5,258,510 A | 11/1993 | Ogawa et al. | |
| 6,048,873 A | 4/2000 | Vasudevan et al. | |
| 6,147,089 A | 11/2000 | DeNinno et al. | |
| 6,197,786 B1 | 3/2001 | DeNinno et al. | |
| 6,291,677 B1 | 9/2001 | Vasudevan et al. | |
| 6,310,075 B1 | 10/2001 | DeNinno et al. | |
| 6,313,107 B1 | 11/2001 | Vasudevan et al. | |
| 6,313,142 B1 | 11/2001 | Damon et al. | |
| 6,362,198 B1 | 3/2002 | Goldstein et al. | |
| 6,362,199 B1 | 3/2002 | DiFabio | |
| 6,395,751 B1 | 5/2002 | DeNinno et al. | |
| 6,489,478 B1 | 12/2002 | DeNinno et al. | |
| 6,586,448 B1 | 7/2003 | DeNinno et al. | |
| 6,600,045 B2 | 7/2003 | Damon et al. | |
| 2002/0022218 A1 | 2/2002 | Li et al. | |

FOREIGN PATENT DOCUMENTS

| | | | |
|---|---|---|---|
| EP | 0987251 A1 | 3/2000 | |
| EP | 0992496 A1 | 4/2000 | |
| EP | 1125929 A1 | 8/2001 | |
| EP | 1221439 A1 | 7/2002 | |
| JP | P200253557 A | 2/2002 | |
| WO | WO 91/05549 | 5/1991 | |
| WO | WO 94/01113 | 1/1994 | |
| WO | WO 0006153 A1 | 2/2000 | |
| WO | WO 0017165 A1 | 3/2000 | |
| WO | WO 0017166 A1 | 3/2000 | |
| WO | WO 0140190 A1 | 6/2001 | |
| WO | WO 0149675 A1 | 7/2001 | |
| WO | WO 0158875 A2 | 8/2001 | |
| WO | WO 0176629 A1 | 10/2001 | |
| WO | WO 0211710 A2 | 2/2002 | |
| WO | WO 0218361 A2 | 3/2002 | |
| WO | WO 0222585 A1 | 3/2002 | |
| WO | WO 02058652 A1 | 8/2002 | |
| WO | WO 02079165 A1 | 10/2002 | |
| WO | WO 02088069 A2 | 11/2002 | |
| WO | WO 03097042 A1 | 11/2003 | |
| WO | WO 03097598 A1 | 11/2003 | |
| WO | WO 03105849 A1 | 12/2003 | |
| WO | WO 2004/035543 A1 | 4/2004 | |
| WO | WO04052863 A1 | 6/2004 | |
| WO | WO05007094 A2 | 12/2006 | |

OTHER PUBLICATIONS

Funabashi, CA 72:31075, 1969.*
Zalukajevs, CA 48:56687, 1951.*
Zalukajevs, CA 62:22149, 1964.*
Zalukajevs, CA 59:54789, 1963.*
Zalukaev, CA 67:53250, 1967.*
Zalukaev, CA 65:81601, 1966.*

* cited by examiner

Primary Examiner—D. Margaret Seaman

(57) ABSTRACT

Disclosed herein are compounds represented by Structural Formula (I):

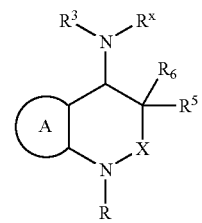

(I), wherein the variables are defined herein.

Also disclosed is the use of such compounds for inhibiting the G-protein coupled receptor referred to as chemoattractant receptor-homologous molecule expressed on Th2 ("CRTH2") for the treatment of inflammatory disorders.

21 Claims, No Drawings

PGD2 RECEPTOR ANTAGONISTS FOR THE TREATMENT OF INFLAMMATORY DISEASES

CROSS-REFERENCE TO RELATED APPLICATION

This application claims the benefit of U.S. Provisional Application 60/416,501, filed Oct. 4, 2002.

BACKGROUND OF THE INVENTION

PGD2 belongs to the class of prostaglandins derived from arachidonic acid. It is the predominant prostanoid produced by activated mast cells and is involved in the pathogenesis of allergic diseases such as asthma, rhinitis and atopic dermatitis (see Lewis et al. J. Immunol. 129:1627 (1982), Hardy et al., N. Eng. J. Med. 311: 209 (1984), Murray et al., N. Eng. J. Med. 315: 800 (1986), Barry et al., Br. J. Pharmacol. 94:773 (1988). PGD2 is a ligand for the DP receptor and was initially thought to elicit all its biological actions through this receptor. The role of the DP receptor in allergic asthma has been demonstrated with DP deficient mice (see Matsuoka et al Science 287: 2013 (2000)). More recently PGD2 was identified as the ligand for another G-protein coupled receptor referred to as "chemoattractant receptor-homologous molecule expressed on Th2" or simply "CRTH2" (see Tanaka et al., J. Immunol. 164:2277 (2000), and U.S. Patent Application Publication No. US2002/0022218). CRTh2 is expressed on basophils, eosinophils and immune helper cells of the Th2 type. Th2 cells have been shown to be involved in the orchestration of allergic response (see Wills-Karp, Annual Review of Immunology, 17: 255 (1999)). It has been shown that PGD2 induces chemotaxis in Th2 cells and eosinophils via the CRTH2 receptor, suggesting that CRTh2 may play a pro-inflammatory role in allergic diseases (see Hirai et al. J. Exp. Med. 193: 255 (2001). It has also been shown that in atopic dermatitis patients there is an increase in circulating T cells expressing CRTh2 which correlates with the severity of the disease. (see Cosmi et al. Eur. J. Immunol. 30: 2972 (2000), Iwazaki et al. J. Investigative Dermatology, 119: 609 (2002). Thus, PGD2 is involved in various aspects of inflammation through its receptors DP and CRTh2. Antagonists of CRTH2 and DP are therefore expected to be useful in the treatment of PGD2 mediated disorders. Unfortunately, there are few if any known CRTH2 inhibitors. As a consequence, clinicians will be unable to exploit these discoveries until new CRTH2 inhibitors are developed.

SUMMARY OF THE INVENTION

It has now been found that certain 1,2,3,4-tetrahydroquinolin-4-yl-amines are potent inhibitors of CRTH2. For example, many compounds effectively inhibited the binding of PGD2 to HEK-293 cells which stably express CRTH2 at a $K_i$ of less than 1.0 μM. Based on this discovery, inhibitors of CRTH2, pharmaceutical compositions comprising these inhibitors and methods of inhibiting CRTH2 activity in a subject in need of such treatment are disclosed herein.

One embodiment of the present inventions is a compound represented by Structural Formula (I):

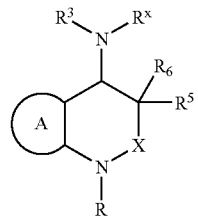

Ring A is an optionally substituted monocyclic aromatic ring;

R is $-X_1-R^1$;

$R^x$ is $-X_2-R^4$, and $R^3$ is an optionally substituted, cycloaliphatic group, aromatic group or non-aromatic heterocyclic group; or $-NR^xR^3$, taken together, is an optionally substituted non-aromatic nitrogen containing heterocyclic group;

X is $-C(O)-$ or $-C(R^2)_2-$;

$X_1$ and $X_2$ are each independently a bond, S(O), S(O)$_2$, C(O) or C(O)NH;

$R^1$ is H or an optionally substituted, cycloaliphatic group, aromatic group or non-aromatic heterocyclic group; provided that when $X_1$ is a bond, SO or SO$_2$, then $R^1$ is not H;

each $R^2$ is independently $-H$, $-X_4-R^8$ or an optionally substituted, aliphatic group, cycloaliphatic group, aromatic group or non-aromatic heterocyclic group;

$R^4$ is $-H$, $-X_6-R^{10}$ or an optionally substituted, aliphatic group, cycloaliphatic group, aromatic group or non-aromatic heterocyclic group; provided that when $X_2$ is a bond, SO or SO$_2$, then $R^4$ is not H;

$X_4$ and $X_6$ are each independently a straight or branched hydrocarbyl group optionally substituted with one or more groups selected from the group consisting of halo, $-OH$, $=O$, $C_1-C_3$ alkoxy, nitro and cyano;

$R^5$ and $R^6$ are each independently H or $C_1-C_3$ alkyl;

$R^7$, $R^8$, $R^9$ and $R^{10}$ are each independently H, $-C(O)OR''$ or an optionally substituted, cycloaliphatic group, aromatic group or non-aromatic heterocyclic group;

R'' is H or $R^{13}$; and $R^{13}$ is $C_1-C_6$ alkyl or $C_3-C_8$ cycloalkyl;

Another embodiment of the present invention method is a method of inhibiting CRTH2 in a subject in need of CRTH2 inhibition. The method comprises the step of administering to the subject an effective amount of a compound represented by Structural Formula (I).

Yet another embodiment of the present invention is a pharmaceutical composition. The pharmaceutical composition comprises a pharmaceutically acceptable carrier or diluent and a compound represented by Structural Formula (I). The pharmaceutical compositions can be used in therapy, for example, to inhibit CRTH2 activity in a subject in need of such treatment.

Yet another embodiment of the present invention is the use of a compound represented by Structural Formula (I) for the manufacture of a medicament for inhibiting CRTH2 activity in a subject in need of such treatment. The medicament comprises an effective amount of the compound.

The disclosed compounds are effective inhibitors of CRTH2 activity and, as such, are expected to be useful in the treatment and prevention of diseases mediated by CRTH2 activity, including, but not limited to, inflammatory diseases such as (allergic) asthma, atopic dermatitis, allergic rhinitis, systemic anaphylaxis or hypersensitivity responses, drug allergies (e.g., to penicillin, cephalosporins), insect sting allergies, chronic obstructive pulmonary disorder (COPD) and inflammatory dermatoses such as dermatitis, eczema, allergic contact dermatitis, and urticaria. atherosclerosis, restenosis, myositis (including polymyositis, dermatomyositis) and other diseases with an inflammatory component such as rheumatoid arthritis, osteoarthritis, and inflammatory bowel disease (IBD).

DETAILED DESCRIPTION OF THE INVENTION

The present invention is directed to inhibitors of the chemoattractant receptor-homologous molecule expressed on Th2 cells, also referred to herein as "CRTH2". The prostaglandin PGD2 is a natural ligand for CRTH2, where it binds and induces at least some of its pro-inflammatory activity. Thus, the disclosed compounds can be used to inhibit CRTH2 activity; to inhibit PGD2 activity and to inhibit or treat (therapeutically or prophylactically) inflammatory disorders and allergic conditions mediated by CRTH2 and/or PGD2. Immune system cells which express CRTH2 include Th2 cells, eosinophils and basophils. Thus, the disclosed compounds can be advantageously used to inhibit inflammatory disorders and allergic conditions mediated by these cells.

In a first preferred embodiment of the present invention, X is —CHR²—, R² is —H, methyl or ethyl; R³ is a substituted or unsubstituted aromatic group; R⁵ and R⁶ are —H; and the remainder of the variables in Structural Formula (I) are as defined above. More preferably, the compound is represented by a structural formula selected from Structural Formulas (VII)–(VIII):

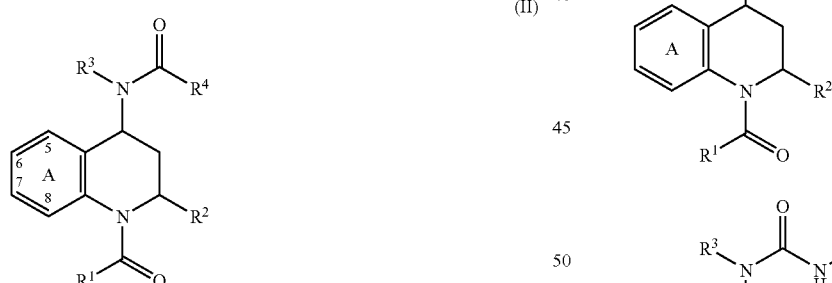

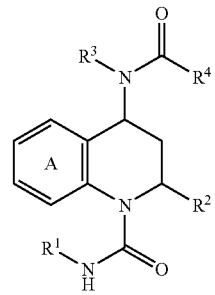

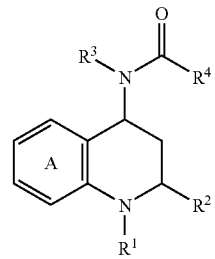

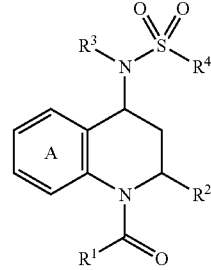

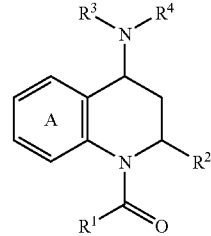

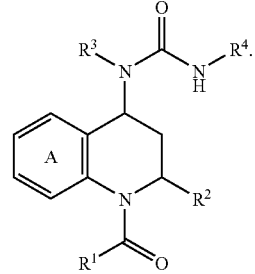

The variables in Structural Formulas (II)–(VIII) are as described above for Structural Formula (I). Preferred values for these variables are provided below.

Phenyl Ring A is a substituted or unsubstituted phenyl group. Suitable substituents for Phenyl Ring A are provided in the section below describing suitable aryl ring substituents.

$R^1$ in Structural Formulas (II)–(IV) and (VI)–(VIII) is —H, optionally substituted, cycloaliphatic group, aromatic group or non-aromatic heterocyclic group, provided that $R^1$ in Structural Formulas (III) is not —H; and $R^1$ in Structural Formula (V) is —$(CH_2)_n$—$R^{13}$.

$R^2$ in Structural Formulas (III)–(VIII) is —H, methyl or ethyl.

$R^3$ in Structural Formulas (II)–(VIII) is an optionally substituted phenyl group.

$R^4$ in Structural Formulas (II)–(VI) and (VIII) is —H, —$CH_2C(O)R^{14}$, —$CH_2R^{15}$, —$CH_2OR^{14}$ or an optionally substituted C1–C3 alkyl group or an optionally substituted cycloalkyl group, aromatic group or non-aromatic heterocyclic group, provided that $R^4$ in Structural Formula (VI) is not —H; and $R^4$ in Structural Formulas (VII) is —$(CH_2)_n$—$R^{13}$.

$R^{13}$—H, —$CH_2C(O)R^{14}$, —$CH_2R^{15}$, —$CH_2OR^{14}$ or an optionally substituted C1–C3 alkyl group or an optionally substituted cycloalkyl group, aromatic group or non-aromatic heterocyclic group.

Each $R^{14}$ is independently an —H or an optionally substituted alkyl group, aromatic group, cycloalkyl group or non-aromatic heterocyclic group.

Each $R^{15}$ is independently an optionally aromatic group, cycloalkyl group or non-aromatic heterocyclic group.

n is 0, 1, 2 or 3.

More preferred values for $R_1$, $R^4$ and $R^{13}$ In Structural Formulas (II)–(VII) are $R^1$ and $R^{13}$ are an optionally substituted, phenyl, pyridyl, furanyl, thiophenyl, isoxazolyl, imidazolyl, pyrazolyl, pyrrolyl, benzofuranyl, tetrazolyl, thiazolyl, benzyl, benzothiazolyl, benzoimidazolyl, benzotriazolyl, benzomorpholinyl, benzopyrazolyl, indolyl, —$CH_2$—(N-pyridyl), —$CH_2$-furanyl, —$CH_2$-thiophienyl, —$CH_2$-isoxazolyl, —$CH_2$-imidazolyl, —$CH_2$-pyrazolyl, —$CH_2$-pyrollyl, —$CH_2$-benzofuranyl, —$CH_2$-tetrazolyl, —$CH_2$-thiazolyl, —$CH_2$-tetrazolyl, —$CH_2$-benzothiazolyl, —$CH_2$-benzimidazolyl, —$CH_2$—O-phenyl, —$CH_2C(O)$-phenyl, naphthalimidyl, tetrahydrofuranyl, cyclohexyl, cyclopentyl or cyclopropyl group; and $R^4$ are $C_1$–$C_4$ alkyl, —$CH_2OH$, —$CH_2OCH_3$, —$CH_2OCH_2CH_3$, —$CH_2CH_2OCH_3$, —$CH_2CH_2OCH_2CH_3$ or an optionally substituted, phenyl, pyridyl, furanyl, thiophenyl, isoxazolyl, imidazolyl, pyrazolyl, pyrrolyl, benzofuranyl, tetrazolyl, benzyl, benzothiazolyl, benzoimidazolyl, benzotriazolyl, benzomorpholinyl, benzopyrazolyl, indolyl, —$CH_2$—(N-pyridyl), —$CH_2$-furanyl, —$CH_2$-thiophienyl, —$CH_2$-isoxazolyl, —$CH_2$-imidazolyl, —$CH_2$-pyrazolyl, —$CH_2$-pyrollyl, —$CH_2$-benzofuranyl, —$CH_2$-tetrazolyl, —$CH_2$-thiazolyl, —$CH_2$-tetrazolyl, —$CH_2$-benzothiazolyl, —$CH_2$-benzimidazolyl, —$CH_2$—O-phenyl, —$CH_2C(O)$-phenyl, naphthalimidyl, tetrahydrofuranyl, cyclohexyl, cyclopentyl or cyclopropyl group, wherein $R^1$, $R^4$ and $R^{13}$ are independently selected; and Ring A is optionally substituted at the five, six, seven and/or the eight position. Even more preferably, the compounds in Structural Formulas (II)–(VIII) have one of the following features and preferably all of the following features: Phenyl Ring A is optionally substituted at the five, six, seven and/or eight position with $R^{11}$; $R^1$ is phenyl, thiophenyl, furanyl, pyridyl, oxazolyl, benzotriazole, pyriridinyl, isoxazolyl or benzomorpholinyl, each group being optionally substituted with $R^{11}$; $R^3$ is [$R^{11}$]-phenyl; and $R^4$ is methyl, ethyl, propyl, iso-propyl, n-butyl, sec-butyl, tert-butyl, —$CH_2OCH_3$ or —$CH_2OCH_2CH_3$. Especially preferred are compounds represented by Structural Formulas (II)–(VIII) wherein Phenyl Ring A is optionally substituted at the six and/or seven position with $R^{11}$; $R^1$ is thiophenyl, [$R^{11}$]-thiophenyl, oxazolyl, [$R^{11}$]-oxazolyl, pyridinyl, [$R^{11}$]-pyridinyl, benzotriazolyl, [$R^{11}$]-benzotriazolyl, benzomorpholinyl, [$R^{11}$]-benzomorpholinyl, phenyl or phenyl substituted with one to four groups selected from the group consisting of halo, —$OR^o$ and —$N(R^{11})_2$, [$R^{11}$]-oxazolyl, oxazolyl and

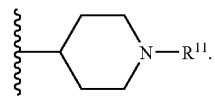

$R^3$ is phenyl substituted with one to four atoms or groups selected from the group consisting of Br, Cl, —$CH_3$, —$N(R^{16})_2$, —NHC(O)OR'', —$S(O)_2CH_3$, —$S(O)_2N(R^{16})_2$ and —$R^{13}C(O)N(R^{16})_2$.

In third preferred embodiment, Ring A in Structural Formulas (I) is a monocyclic heteroaryl group such as thiophene, furan, pyridine, pyrazole, pyrrole, [2,3]pyrimidine, [3,4]pyrimidine, [4,5]pyrimidine, [5,6]pyrimidine, oxazole, isoxazole or 1,2,3-triazole, each group being optionally substituted with $R^{11}$ When Ring A has these values, then the compound preferably has at least one and preferably all of the following features: X is —$CHR^2$—, $R^2$ are —H, methyl or ethyl; $R^5$ and $R^6$ are —H; and $R^3$ is a substituted or unsubstituted phenyl group. When the compound has at least one or all of these features, then preferably $R^1$ and $R^4$ are independently —H, —$CH_2C(O)R^{14}$, —$CH^2R^5$ or —$CH_2OR^{14}$ or an optionally substituted alkyl group, cycloalkyl group, aromatic group or non-aromatic heterocyclic group; and $R^{14}$ and $R^{15}$ are as described above for Structural Formula (II).

When Ring A in Structural Formula (I) is a monocyclic heteroaryl, as described in the preceding paragraph, commonly selected values for $X_1$ and $X_2$ are as follows: $X_1$ and $X_2$ are both C(O); $X_1$ is $S(O)_2$ and $X_2$ is C(O); $X_1$ is C(O)NH and $X_2$ is C(O); $X_1$ is a bond and $X_2$ is C(O); and $X_2$ is C(O); $X_1$ is C(O) and $X_2$ is $S(O)_2$; $X_1$ is C(O) and; $X_1$ is C(O) and $X_2$ is a bond; or $X_1$ is C(O) and $X_2$ is C(O)NH. Alternatively, Phenyl Ring A in Structural Formulas (II)–(VIII) is replaced with one of the monocyclic aromatic groups described in the preceding paragraph and the remainder of the variables are as described above.

In a fourth preferred embodiment, $R_2$ in Structural Formulas (I)–(VIII) is —H, C1–C4 alkyl, halogentated C1–C6 alkyl, C3–C8 cycloalkyl, substituted C3–C8 cycloalkyl, phenyl, substituted phenyl, $C(O)OR^{16}$, benzyl, substituted benzyl or —$(CH_2)_nO(CH_2)_m$; $R^{16}$ is C1–C6 alkyl; n and m are positive integers such n+m=6; and the remainder of the variables are as described above.

Specific examples of compounds of the present invention are shown Tables 1–6.

Also disclosed herein is a compound represented by Structural Formula (II) and methods of use thereof for inhibiting CRTH2 in a subject in need of treatment therefore and pharmaceutical compositions comprising the same, wherein $R^1$ has the value corresponding to any one of the compounds in Table 1–6 and $R^3$ and $R^4$ are as described above for Structural Formula (II).

Also disclosed herein is a compound represented by Structural Formula (II) and methods of use thereof for inhibiting CRTH2 in a subject in need of treatment therefore and pharmaceutical compositions comprising the same, wherein $R^3$ has the value corresponding to any one of the compounds in Table 1–6 and $R^1$ and $R^4$ are as described above for Structural Formula (II).

Also disclosed herein is a compound represented by Structural Formula (II) and methods of use thereof for inhibiting CRTH2 in a subject in need of treatment therefore and pharmaceutical compositions comprising the same, wherein $R^4$ has the value corresponding to any one of the compounds in Table 1–6 and $R^1$ and $R^3$ are as described above for Structural Formula (II).

Also disclosed herein is a compound represented by Structural Formula (III) and methods of use thereof for inhibiting CRTH2 in a subject in need of treatment therefore and pharmaceutical compositions comprising the same, wherein $R^3$ has the value corresponding to any one of the compounds in Table 1–6 and $R^1$ and $R^4$ are as described above for Structural Formula (III).

Also disclosed herein is a compound represented by Structural Formula (III) and methods of use thereof for inhibiting CRTH2 in a subject in need of treatment therefore and pharmaceutical compositions comprising the same, wherein $R^4$ has the value corresponding to any one of the compounds in Table 1–6 and $R^1$ and $R^3$ are as described above for Structural Formula (III).

Also disclosed herein is a compound represented by Structural Formula (III) and methods of use thereof for inhibiting CRTH2 in a subject in need of treatment therefore and pharmaceutical compositions comprising the same, wherein $R^1$ has the value corresponding to any one of the compounds in Table 1–6 and $R^3$ and $R^4$ are as described above for Structural Formula (III).

Also disclosed herein is a compound represented by Structural Formula (IV) and methods of use thereof for inhibiting CRTH2 in a subject in need of treatment therefore and pharmaceutical compositions comprising the same, wherein $R^3$ has the value corresponding to any one of the compounds in Table 1–6 and $R^1$ and $R^4$ are as described above for Structural Formula (IV).

Also disclosed herein is a compound represented by Structural Formula (IV) and methods of use thereof for inhibiting CRTH2, wherein $R^4$ has the value corresponding to any one of the compounds in Table 1–6 and $R^1$ and $R^3$ are as described above for Structural Formula (IV).

Also disclosed herein is a compound represented by Structural Formula (IV) and methods of use thereof for inhibiting CRTH2, wherein $R^1$ has the value corresponding to any one of the compounds in Table 1–6 and $R^3$ and $R^4$ are as described above for Structural Formula (IV).

Also disclosed herein is a compound represented by Structural Formula (V) and methods of use thereof for inhibiting CRTH2 in a subject in need of treatment therefore and pharmaceutical compositions comprising the same, wherein $R^3$ has the value corresponding to any one of the compounds in Table 1–6 and $R^1$ and $R^4$ are as described above for Structural Formula (V).

Also disclosed herein is a compound represented by Structural Formula (V) and methods of use thereof for inhibiting CRTH2 in a subject in need of treatment therefore and pharmaceutical compositions comprising the same, wherein $R^4$ has the value corresponding to any one of the compounds in Table 1–6 and $R^1$ and $R^3$ are as described above for Structural Formula (V).

Also disclosed herein is a compound represented by Structural Formula (V) and methods of use thereof for inhibiting CRTH2 in a subject in need of treatment therefore and pharmaceutical compositions comprising the same, wherein $R^1$ has the value corresponding to any one of the compounds in Table 1–6 and $R^3$ and $R^4$ are as described above for Structural Formula (V).

Also disclosed herein is a compound represented by Structural Formula (VI) and methods of use thereof for inhibiting CRTH2 in a subject in need of treatment therefore and pharmaceutical compositions comprising the same, wherein $R^3$ has the value corresponding to any one of the compounds in Table 1–6 and $R^1$ and $R^4$ are as described above for Structural Formula (VI).

Also disclosed herein is a compound represented by Structural Formula (VI) and methods of use thereof for inhibiting CRTH2 in a subject in need of treatment therefore and pharmaceutical compositions comprising the same, wherein $R^4$ has the value corresponding to any one of the compounds in Table 1–6 and $R^1$ and $R^3$ are as described above for Structural Formula (VI).

Also disclosed herein is a compound represented by Structural Formula (VI) and methods of use thereof for inhibiting CRTH2 in a subject in need of treatment therefore and pharmaceutical compositions comprising the same, wherein $R^1$ has the value corresponding to any one of the compounds in Table 1–6 and $R^3$ and $R^4$ are as described above for Structural Formula (VI).

Also disclosed herein is a compound represented by Structural Formula (VII) and methods of use thereof for inhibiting CRTH2 in a subject in need of treatment therefore and pharmaceutical compositions comprising the same, wherein $R^3$ has the value corresponding to any one of the compounds in Table 1–6 and $R^1$ and $R^4$ are as described above for Structural Formula (VII).

Also disclosed herein is a compound represented by Structural Formula (VII) and methods of use thereof for inhibiting CRTH2 in a subject in need of treatment therefore and pharmaceutical compositions comprising the same, wherein $R^4$ has the value corresponding to any one of the compounds in Table 1–6 and $R^1$ and $R^3$ are as described above for Structural Formula (VII).

Also disclosed herein is a compound represented by Structural Formula (VII) and methods of use thereof for inhibiting CRTH2 in a subject in need of treatment therefore and pharmaceutical compositions comprising the same, wherein $R^1$ has the value corresponding to any one of the compounds in Table 1–6 and $R^3$ and $R^4$ are as described above for Structural Formula (VII).

Also disclosed herein is a compound represented by Structural Formula (VIII) and methods of use thereof for inhibiting CRTH2 in a subject in need of treatment therefore and pharmaceutical compositions comprising the same, wherein $R^3$ has the value corresponding to any one of the compounds in Table 1–6 and $R^1$ and $R^4$ are as described above for Structural Formula (VIII).

Also disclosed herein is a compound represented by Structural Formula (VIII) and methods of use thereof for inhibiting CRTH2 in a subject in need of treatment therefore and pharmaceutical compositions comprising the same, wherein $R^4$ has the value corresponding to any one of the compounds in Table 1–6 and $R^1$ and $R^3$ are as described above for Structural Formula (VIII).

Also disclosed herein is a compound represented by Structural Formula (VIII) and methods of use thereof for inhibiting CRTH2 in a subject in need of treatment therefore and pharmaceutical compositions comprising the same, wherein $R^1$ has the value corresponding to any one of the compounds in Table 1–6 and $R^3$ and $R^4$ are as described above for Structural Formula (VIII).

In certain aspects, the following compounds are excluded from the present invention: 2-Methyl-N-phenyl-N-[1,2,3,4-tetrahydro-2-methyl-1-(2-methyl-1-oxobutyl)-4-quinolinyl]-butamide; N-(1-Acetyl-1,2,3,4-tetrahydro-2-methyl-4- quinolinyl)-N-phenyl-heptamide; N-phenyl-N-[1,2,3,4-tetrahydro-2-methyl-1-(1-oxo-3-phenylpropyl)-4-quinolinyl]-benzenepropanamide; N-phenyl-N-[1,2,3,4-tetrahydro-2-methyl-1-(3-nitrobenzoyl)-4-quinolinyl]-hexanamide; N-[1,1'-biphenyl]-3-yl-N-[1,2,3,4-tetrahydro-1-(4-methoxybenzoyl)-2-methyl-4-quinolinyl]-acetamide; N-(1-benzoyl-1,2,3,4-tetrahydro-2-methyl-4-quinolinyl)-N-(4-nitrophenyl)-heptanamide; N-(1-benzoyl-1,2,3,4-tetrahydro-2-methyl-4-quinolinyl)-N-(4-methoxyphenyl)-2-methyl-propanamide; N-[1-(4-fluorobenzoyl)-1,2,3,4-tetrahydro-2-methyl-4-quinolinyl]-N-phenyl-butanamide; N-phenyl-N-[1,2,3,4-tetrahydro-1-(3-methoxybenzoyl)-2-methyl-4-quinolinyl]-pentanamide; 2-ethyl-N-[1-(2-ethyl-1-oxobutyl)-1,2,3,4-tetrahydro-2,8-dimethyl-4-quinolinyl]-N-(2-methylphenyl)-butanamide; N-[1-[(4-fluorophenyl)acetyl]-1,2,3,4-tetrahydro-2-methyl-4-quinolinyl]-N-phenyl-propanamide; N-phenyl-N-[1,2,3,4-tetrahydro-2-methyl-1-(4-nitrobenzoyl)-4-quinolinyl]-octanamide; N-cyclohexyl-4-[(cyclohexylamino)carbonyl]phenylamino]-3,4-dihydro-2-methyl-1(2H)-quinolinecarboxamide; N-[1-(4-ethylbenzoyl)-1,2,3,4-tetrahydro-2,8-dimethyl-4-quinolinyl]-N-(2-methylphenyl)-3-(4-nitrophenyl)-2-propenamide; 3-(4-methoxyphenyl)-N-phenyl-N-[1,2,3,4-tetrahydro-1-[3-(4-methoxyphenyl)-1-oxo-2-propenyl]-2-methyl-4-quinolinyl]-2-propenamide; 4-[(ethoxyoxoacetyl)phenylamino]-3,4-dihydro-2-methyl-∀-oxo-ethyl ester-1(2H)-quinolineacetic acid; N-[1-(3-cyclohexyl-1-oxopropyl)-1,2,3,4-tetrahydro-2-methyl-4-quinolinyl]-N-phenyl-cyclohexanepropanamide; 4-(acetylphenylamino)-3,4-dihydro-2-methyl-gamma-oxo-1(2H)-quinolinepentanoic acid; N-(1-benzoyl-1,2,3,4-tetrahydro-2-methyl-4-quinolinyl)-2,2-dimethyl-N-phenyl-propanamide; N-(1-benzoyl-6-bromo-1,2,3,4-tetrahydro-2-methyl-4-quinolinyl)-N-phenyl-pentanamide; N-[1-(2-furanylcarbonyl)-1,2,3,4-tetrahydro-2-methyl-4-quinolinyl]-N-phenyl-acetamide; 2-methyl-N-phenyl-N-[1,2,3,4-tetrahydro-1-(3-methoxybenzoyl)-2-methyl-4-quinolinyl]-propanamide; N-[1-[(1,3-dihydro-1,3-dioxo-2H-isoindol-2-yl)acetyl]-1,2,3,4-tetrahydro-2-methyl-4-quinolinyl]-N-phenyl-acetamide; 2,2,2-trifluoro-N-phenyl-N-[1,2,3,4-tetrahydro-1-(3-methoxybenzoyl)-2-methyl-4-quinolinyl]-acetamide; 2-ethyl-N-[1-(2-ethyl-1-oxobutyl)-1,2,3,4-tetrahydro-2-methyl-4-quinolinyl]-N-phenyl-butanamide; N-(1-benzoyl-1,2,3,4-tetrahydro-2-methyl-4-quinolinyl)-N-(3-methoxyphenyl)-acetamide; N-phenyl-N-[1,2,3,4-tetrahydro-2-methyl-1-(1-oxohexyl)-4-quinolinyl]-acetamide; N-(1-acetyl-1,2,3,4-tetrahydro-2-methyl-4-quinolinyl)-N-phenyl-2-thiophenecarboxamide; N-[1-(2-fluorobenzoyl)-1,2,3,4-tetrahydro-2-methyl-4-quinolinyl]-N-phenyl-hexanamide; N-phenyl-N-[1,2,3,4-tetrahydro-1-(4-methoxybenzoyl)-2-methyl-4-quinolinyl]-hexanamide; N-phenyl-N-[1,2,3,4-tetrahydro-1-(4-methoxybenzoyl)-2-methyl-4-quinolinyl]-hexanamide; N-[1-(cyclopropylcarbonyl)-1,2,3,4-tetrahydro-2-methyl-4-quinolinyl]-N-phenyl-cyclopropanecarboxamide; N-(1-benzoyl-1,2,3,4-tetrahydro-2-methyl-4-quinolinyl)-N-(4-methylphenyl)-acetamide; 2-methyl-N-phenyl-N-[1,2,3,4-tetrahydro-2-methyl-1-(2-methyl-1-oxopropyl)-4-quinolinyl]-propanamide; N-phenyl-N-[1,2,3,4-tetrahydro-1-(4-methoxybenzoyl)-2-methyl-4-quinolinyl]-2-thiophenecarboxamide; 1-(3,5-dinitrobenzoyl)-N-formyl-1,2,3,4-tetrahydro-2-methyl-N-phenyl-4-quinolinamine; N-[1-(4-chloro-3-nitrobenzoyl)-1,2,3,4-tetrahydro-2-methyl-4-quinolinyl]-N-phenyl-acetamide; N-phenyl-N-[1,2,3,4-tetrahydro-2-methyl-1-(3-nitrobenzoyl)-4-quinolinyl]-acetamide; N-phenyl-N-[1,2,3,4-tetrahydro-1-(3-methoxybenzoyl)-2-methyl-4-quinolinyl]-hexanamide; N-[1-(2-furanylcarbonyl)-1,2,3,4-tetrahydro-2-methyl-4-quinolinyl]-N-phenyl-2-furancarboxamide; N-phenyl-N-[1,2,3,4-tetrahydro-2-methyl-1-(1-oxopropyl)-4-quinolinyl]-acetamide; N-phenyl-N-[1,2,3,4-tetrahydro-1-[3-(4-methoxyphenyl)-1-oxo-2-propenyl]-2-methyl-4-quinolinyl]-acetamide; 3-(2-furanyl)-N-[1-[3-(2-furanyl)-1-oxo-2-propenyl]-1,2,3,4-tetrahydro-2-methyl-4-quinolinyl]-N-phenyl-2-propenamide; N-[1-[2-(1,3-dihydro-1,3-dioxo-2H-isoindol-2-yl)-1-oxo-3-phenylpropyl]-1,2,3,4-tetrahydro-2-methyl-4-quinolinyl]-N-phenyl-octanamide; N-[1-(3-chlorobenzoyl)-1,2,3,4-tetrahydro-2-methyl-4-quinolinyl]-N-phenyl-acetamide; Relative stereochemistry N-phenyl-N-[(2R,4S)-1,2,3,4-tetrahydro-2-methyl-1-(1-oxopropyl)-4-quinolinyl]-acetamide; Relative stereochemistry N-[(2R,4S)-1-benzoyl-1,2,3,4-tetrahydro-2-methyl-4-quinolinyl]-2-methyl-N-phenyl-propanamide; Relative stereochemistry N-[(2R,4S)-1-acetyl-1,2,3,4-tetrahydro-2-methyl-4-quinolinyl]-N-phenyl-hexanamide; Relative stereochemistry N-[(2R,4S)-1-acetyl-1,2,3,4-tetrahydro-2-methyl-4-quinolinyl]-N-phenyl-propanamide; Relative stereochemistry N-[(2R,4S)-1-acetyl-1,2,3,4-tetrahydro-2-methyl-4-quinolinyl]-N-phenyl-heptanamide; Relative stereochemistry N-[(2R,4S)-1-benzoyl-1,2,3,4-tetrahydro-2-methyl-4-quinolinyl]-2,2-dimethyl-N-phenyl-propanamide; N-[1-(3-fluorobenzoyl)-1,2,3,4-tetrahydro-2-methyl-4-quinolinyl]-N-phenyl-acetamide; N-[1-[4-(1,1-dimethylethyl)benzoyl]-1,2,3,4-tetrahydro-2-methyl-4-quinolinyl]-N-phenyl-acetamide; N-(1-acetyl-1,2,3,4-tetrahydro-2-methyl-4-quinolinyl)-2-methyl-N-phenyl-propanamide; 2,2,2-trifluoro-N-phenyl-N-[1,2,3,4-tetrahydro-2-methyl-1-(trifluoroacetyl)-4-quinolinyl]-acetamide; Relative stereochemistry N-[(2R,4S)-1-acetyl-1,2,3,4-tetrahydro-2-methyl-4-quinolinyl]-2,2-dimethyl-N-phenyl-propanamide; Relative stereochemistry N-[(2R,4S)-1-acetyl-1,2,3,4-tetrahydro-2-methyl-4-quinolinyl]-N-phenyl-butanamide; Relative stereochemistry N-[(2R,4S)-1-benzoyl-1,2,3,4-tetrahydro-2-methyl-4-quinolinyl]-N-phenyl-acetamide; Relative stereochemistry N-phenyl-N-[(2R,4S)-1,2,3,4-tetrahydro-2-methyl-1-(1-oxoheptyl)-4-quinolinyl]-acetamide; Relative stereochemistry N-phenyl-N-[(2R,4S)-1,2,3,4-tetrahydro-2-methyl-1-(1-oxohexyl)-4-quinolinyl]-acetamide; Relative stereochemistry N-[(2R,4S)-1-acetyl-1,2,3,4-tetrahydro-2-methyl-4-quinolinyl]-N-phenyl-pentanamide; N-phenyl-N-[1,2,3,4-tetrahydro-2-methyl-1-(1-oxo-3-phenyl-2-propenyl)-4-quinolinyl]-acetamide; Relative stereochemistry N-[(2R,4S)-1-benzoyl-1,2,3,4-tetrahydro-2-methyl-4-quinolinyl]-N-phenyl-heptanamide; Relative stereochemistry N-[(2R,4S)-1-acetyl-1,2,3,4-tetrahydro-2-methyl-4-quinolinyl]-N-phenyl-acetamide; Relative stereochemistry N-[(2R,4S)-1-benzoyl-1,2,3,4-tetrahydro-2-methyl-4-quinolinyl]-N-phenyl-pentanamide; N-phenyl-N-[1,2,3,4-tetrahydro-2-methyl-1-(tricyclo[3.3.1.13,7]dec-1-ylcarbonyl)-4-quinolinyl]-acetamide; N-phenyl-N-[1,2,3,4-tetrahydro-2-methyl-1-(1-oxopropyl)-4-quinolinyl]-propanamide; N-phenyl-N-[1,2,3,4-tetrahydro-2-methyl-1-(2-thienylcarbonyl)-4-quinolinyl]-acetamide; N-phenyl-N-[1,2,3,4-tetrahydro-1-(4-methoxybenzoyl)-2-methyl-4-quinolinyl]-2-furancarboxamide; N-phenyl-N-[1,2,3,4-tetrahydro-1-(4-methoxybenzoyl)-2-methyl-4-quinolinyl]-acetamide; N-[1-(3,5-dinitrobenzoyl)-1,2,3,4-tetrahydro-2-methyl-4-quinolinyl]-N-phenyl-acetamide; N-phenyl-N-[1,2,3,4-tetrahydro-2-methyl-1-(4-nitrobenzoyl)-4-quinolinyl]-acetamide; N-phenyl-N-[1,2,3,4-tetrahydro-1-(2-iodobenzoyl)-2-methyl-4-quinolinyl]-acetamide; N-phenyl-N-[1,2,3,4-tetrahydro-2-methyl-1-(2-methyl-1-oxopropyl)-4-quinolinyl]-acetamide; N-phenyl-N-[1,2,3,4-tetrahydro-2-methyl-1-[(4-methylphenyl)sulfonyl]-4-quinolinyl]-acetamide; N-phenyl-N-[1,2,3,4-tetrahydro-2-methyl-1-[(4-nitrophenyl)methyl]4-quinolinyl]-acetamide; N-phenyl-N-[1,2,3,4-tetrahydro-1-(3-methoxybenzoyl)-2-methyl-4-quinolinyl]-acetamide; N-(1-acetyl-1,2,3,4-tetrahydro-2-methyl-4-quinolinyl)-N-phenyl-butanamide; N-phenyl-N-[1,2,3,4-tetrahydro-2-methyl-1-(1-oxobutyl)-4-quinolinyl]-acetamide; N-(1-benzoyl-1,2,3,4-tetrahydro-2-methyl-4-quinolinyl)-N-phenyl-hexanamide; N-(1-benzoyl-1,2,3,4-tetrahydro-2-methyl-4-quinolinyl)-N-phenyl-pentanamide; N-(1-benzoyl-1,2,3,4-tetrahydro-2-methyl-4-quinolinyl)-N-phenyl-propanamide; 1-benzoyl-1,2,3,4-tetrahydro-4-(N-phenylacetamido)quinaldine; N-(1-acetyl-6-bromo-1,2,3,4-tetrahydro-2-methyl-4-quinolinyl)-N-phenyl-acetamide; N-(1-acetyl-1,2,3,4-tetrahydro-2-methyl-6-nitro-4-quinolyl)-acetanilide; N-(1-acetyl-6-chloro-1,2,3,4-tetrahydro-2-methyl-4-quinolyl)-acetanilide; N-(1-acetyl-1,2,3,4-tetrahydro-2-methyl-4-quinolinyl)-N-phenyl-acetamide; N-(1-benzoyl-6-bromo-1,2,3,4-tetrahydro-2-methyl-4-quinolinyl)-N-phenyl-acetamide; N-(1-benzoyl-6-chloro-1,2,3,4-tetrahydro-2-methyl-4-quinolinyl)-N-phenyl-acetamide; N-(1-benzoyl-1,2,3,4-tetrahydro-2-methyl-4-quinolinyl)-N-phenyl-butanamide; N-phenyl-N-[1,2,3,4-tetrahydro-1-(3-fluorobenzoyl)-2-methyl-4-quinolinyl]-hexanamide. N-[1-(3-Chloro-benzoyl)-2-methyl-1,2,3,4-tetrahydro-quinolin-4-yl]-N-phenyl-acetamide; N-[1-(4-Fluoro-benzoyl)-2-methyl-6-nitro-1,2,3,4-tetrahydro-quinolin-4-yl]-N-phenyl-acetamide; Pentanoic acid (1-benzoyl-6-bromo-2-methyl-1,2,3,4-tetrahydro-quinolin-4-yl)-phenyl-amide; N-(1-Benzoyl-6-chloro-2-methyl-1,2,3,4-tetrahydro-quinolin-4-yl)-N-phenyl-acetamide; N-[6-Chloro-1-(4-fluoro-benzoyl)-2-methyl-1,2,3,4-tetrahydro-quinolin-4-yl]-N-phenyl-acetamide; N-[6-Bromo-1-(4-fluoro-benzoyl)-2-methyl-1,2,3,4-tetrahydro-quinolin-4-yl]-N-phenyl-acetamide; N-(1-Benzoyl-6-nitro-2-methyl-1,2,3,4-tetrahydro-quinolin-4-yl)-N-phenyl-acetamide; N-(1-Benzoyl-2-methyl-1,2,3,4-tetrahydro-quinolin-4-yl)-N-phenyl-butyramide; N-[1-(3-Methoxy-benzoyl)-2-methyl-1,2,3,4-tetrahydro-quinolin-4-yl]-2,2-dimethyl-N-phenyl-propionamide Many of the disclosed CRTH2 inhibitors contain one or more chiral centers. The presence of chiral centers in a molecule gives rise to stereoisomers. For example, a pair of optical isomers, referred to as "enantiomers", exist for every chiral center in a molecule; and a pair of diastereomers exist for every chiral center in a compound having two or more chiral centers. Even though Structural Formulas (I)–(VIII) do not explicitly depict stereochemistry, it is to be understood that these formulas encompass enantiomers free from the corresponding optical isomer, racemic mixtures, mixtures enriched in one enantiomer relative to its corresponding optical isomer, a diastereomer free of other diastereomers, a pair of diastereomers free from other diastereomeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s).

A preferred diastereomeric pair is when $R_2$ and $NR^xR^3$ in Structural Formulas (I)–(VIII) are cis relative to one another. By way of example, the cis diastereomeric pair for the compound represented by Structural Formula (II) is shown below in Structural Formulas (IX) and (X):

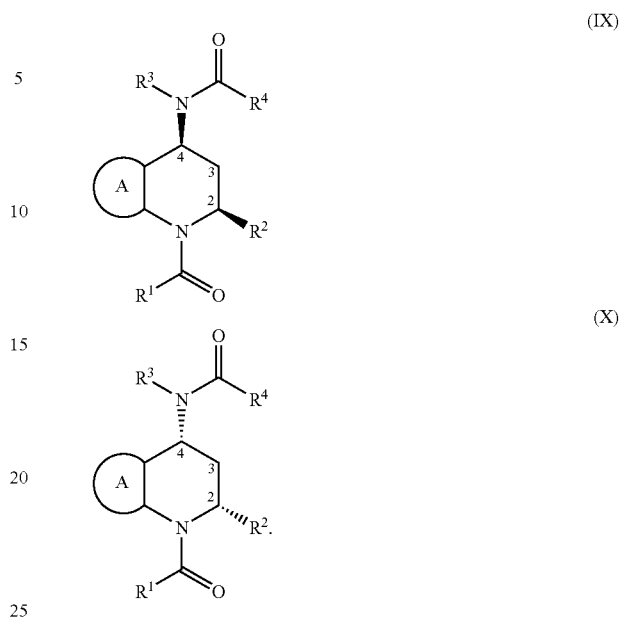

The preferred configuration for $R^2$ and $NR^xR^3$ (depicted by $N(R^3)(COR^4)$ in Structural Formulas (IX) and (X) is (2R, 4S), as shown in Structural Formula (IX). Thus, Structural Formula (IX) represents a preferred optical isomer for the compound represented by Structural Formula (II). Similarly, the corresponding (2R,4S) optical isomer for the compounds represented by Structural Formulas (I) and (III)–(VIII) and Tables 1–6 are also specifically disclosed. The more preferred configuration for $R^2$ and $NR^xR^3$ (depicted by $N(R^3)(COR^4)$) in Structural Formulas (IX) and (X) is (2S, 4R), as shown in Structural Formula (X). Thus, Structural Formula (X) represents a more preferred optical isomer for the compound represented by Structural Formulas (I) and (III)–(VIII) and in Tables 1–6. As used herein, a structure depicting one optical isomer or a reference to one optical isomer is meant to include enantiomeric mixtures which are enriched with the depicted or referenced enantiomer relative to its optical isomer, for example, an enantiomeric excess of at least 50%, 75%, 90%, 95% 99%, or 99.5%. As used herein, a structure depicting a diastereomeric pair or a reference to one diasteromeric pair is meant to include mixtures which are enriched with the depicted or referenced diastereomeric pair relative to other diastereomers or diastereomeric pair(s) for the compound, for example, a molar excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided in Scheme 1 and 2.

In certain instances compounds of the present invention may be associated in isolated form with solvent or water, as in a "solvate" or "hydrate". References to the disclosed compounds or structural formulas depicting the disclosed compounds are meant to include such solvates and hydrates.

The term "aliphatic" as used herein means straight-chain or branched hydrocarbons which are completely saturated or which contain one or more units of unsaturation, but which are not aromatic. An aliphatic group is typically $C_{1-8}$, more typically $C_{1-6}$. For example, suitable aliphatic groups include substituted or unsubstituted linear or branched alkyl, alkenyl, alkynyl groups and hybrids thereof. The terms "alkyl", "alkoxy", "hydroxyalkyl", "alkoxyalkylene", and "alkoxycarbonyl", used alone or as part of a larger moiety includes both straight and branched saturated chains containing one to eight carbon atoms. The terms "alkenyl" and alkynyl" used alone or as part of a larger moiety shall include both straight and branched chains containing two to eight carbon atoms and one or more double and/or triple bonds, respectively.

The term "cycloaliphatic" used alone or as part of a larger moiety shall include cyclic $C_3$–$C_{10}$ hydrocarbons which are completely saturated or which contain one or more units of unsaturation, but which are not aromatic. Cycloaliphatic groups are typically $C_{3-10}$, more typically $C_{3-7}$. A "cycloalkyl" is an cyclic aliphatic group that is completely saturated.

"Alkoxy" means (alkyl)-O—; "alkoxyalkylene" means (alkyl)-O-(alkylene) such as methoxymethylene ($CH_3OCH_2$); "hydroxyalkyl" means hydroxy substituted alkyl group; "alkoxy carbonyl means a carbonyl substituted with a carbonyl as in (alkyl)-O—C(O)—; and "aralkyl" mean alkyl substituted with an aromatic group. A "C1–C4 aralkyl group", for example, has a C1–C4 alkyl group substituted with an aromatic group.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aromatic group" used alone or as part of a larger moiety as in "aralkyl", "aralkoxy", or "aryloxyalkyl", includes to carbocyclic aromatic ring groups and heteroaryl rings groups. The term "aromatic group" may be used interchangeably with the terms "aryl", "aryl ring" or "aromatic ring".

Carbocyclic aromatic ring groups have only carbon ring atoms and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (aliphatic or heterocyclic), such as in an indanyl, phthalimidyl, naphthimidyl, phenantriidinyl, or tetrahydronaphthyl, where the radical or point of attachment is on the aromatic ring.

The term "heteroaryl" or "heteroaromatic", used alone or as part of a larger moiety as in "heteroaralkyl" or "heteroarylalkoxy", refers to heteroaromatic ring groups having five to fourteen members, including monocyclic heteroaromatic rings and polycyclic aromatic rings in which a monocyclic aromatic ring is fused to one or more other carbocyclic or heteroaromatic aromatic rings. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisazolyl. Also included within the scope of the term "heteroaryl", as it is used herein, is a group in which a heteroaryl ring is fused to one or more cycloaliphatic or non-aromatic heterocyclic groups where the radical or point of attachment is on the heteroaromatic ring. Examples include tetrahydroquinolinyl, tetrahydroisoquinolinyl, and pyrido [3,4-d]pyrimidinyl. The term "heteroaryl" may be interchangeably with the term "heteroaryl ring" or the term "heteroaromatic".

The term "non-aromatic heterocyclic ring", used alone or as part of a larger moiety as in "hetercyclylalkyl", refers to non-aromatic ring systems typically having five to fourteen members, preferably five to ten, in which one or more ring carbons, preferably one to four, are each replaced by a heteroatom such as N, O, or S. Examples of non-aromatic heterocyclic rings include 3-1H-benzimidazol-2-one, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrorolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, and benzothianyl.

A "hydrocarbyl group" is a polymethylene group, i.e., —$(CH_2)_n$—, wherein n is a positive integer. Preferably, n is an integer from 1 to 6, more preferably from 2 to 4 and more preferably from 2 to 3. A "substituted hydrocarbyl" is a hydrocarbyl group in which one or more methylene hydrogen atoms are replaced with a substituent. Suitable substituents are as described below for a substituted aliphatic group. Preferred substituents for the hydrocarbyl groups represented by $X_3$–$X_6$ are halo, —OH, =O, C1–C3 alkyl, C1–C3 alkoxy, nitro and cyano.

A hydrocarbyl group can be optionally interrupted by one or more functional groups. A hydrocarbyl is interrupted by a functional group when one of the internal methylenes is replaced with the functional group. Examples of suitable "interrupting functional groups" include —O—, —S—, —N($R^a$)—, —S(O)—, —$SO_2$—, —C(O)—, —OC(O)—, —N(R$^a$)C(O)—, —C(O)N(R$^a$)—, —SO$_2$N(R$^a$)—, and —N(R$^a$)SO$_2$—. R$^a$ is —H or a C1–C3 alkyl group.

An aromatic group (including Ring A, carbocyclic aromatic, heteroaryl, aralkyl, aralkoxy, aryloxyalkyl and heteroaralkyl and the like) group may contain one or more substituents. Examples of suitable substituents on an unsaturated carbon atom of an aromatic group include a halogen —R$^o$, —OR$^o$, —SR$^o$, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R')$_2$, —NR'CO$_2$R$^o$, —NR'C(O)R$^o$, —NR'NR'C(O)R$^o$, —N(R')C(O)N(R')$_2$, —NR'NR'C(O)N(R')$_2$, —NR'NR'CO$_2$R$^o$, —C(O)C(O)R$^o$, —C(O)CH$_2$C(O)R$^o$, —CO$_2$R$^o$, —C(O)R$^o$, —C(O)N(R$^o$)$_2$, —OC(O)N(R)$_2$, —S(O)$_2$R$^o$, —SO$_2$N(R')$_2$, —S(O)R$^o$, —NR'SO$_2$N(R')$_2$, —NR'SO$_2$R$^o$, —C(=S)N(R')$_2$, —(CH$_2$)$_y$N(R$^o$)$_2$, —C(=NH)—N(R')$_2$, —(CH$_2$)$_y$NHC(O)R$^o$, —(CH$_2$)$_y$NHC(O)CH(V—R$^o$)(R$^o$). R' is R$^o$, —CO$_2$R$^o$, —SO$_2$R$^o$ or —C(O)R$^o$ and preferably hydrogen, C$_{1-6}$ aliphatic, CO$_2$R$^o$, SO$_2$R$^o$ or C(O)R$^o$. R$^o$ is hydrogen or substituted or unsubstituted aliphatic, cycloaliphatic, aromatic, aralkyl or non-aromatic heterocyclic group, and preferably hydrogen, C$_{1-6}$ alkyl, phenyl (Ph), —CH$_2$ (Ph), aralkyl, non-aromatic heterocyclic group or heteroaryl; y is 0–6; and V is C1–C6 alkylene group. Examples of substituents on the aliphatic group or the phenyl ring of R$^o$ include amino, alkylamino, dialkylamino, aminocarbonyl, halogen, alkyl, aminoalkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An alphatic group or a non-aromatic heterocycle may contain one or more substituents. Examples of suitable substituents on the saturated carbon of an aliphatic group of a non-aromatic heterocycle include those listed above for the unsaturated carbon of an aromatic group and the following: =O, =S, =NNHR*, =NN(R*)$_2$, =NNHC(O)R*, =NNHCO$_2$(alkyl), =NNHSO$_2$ (alkyl), or =NR*. Each R* is independently selected from hydrogen, an unsubstituted aliphatic group or a substituted aliphatic group. Examples of substituents on the aliphatic group represented by R* include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the substitutable nitrogen of a heteroaryl or non-aromatic heterocyclic group include —R$^+$, —N(R$^+$)$_2$, —C(O)R$^+$, —CO$_2$R$^+$, —C(O)C(O)R$^+$, —C(O)CH$_2$C(O)R$^+$, —S$_2$R$^+$, —SO$_2$N(R$^+$)$_2$, —C(=S)N(R$^+$)$_2$, —C(=NH)—N(R$^+$)$_2$, and —NR$^+$SO$_2$R$^+$; wherein R$^+$ is hydrogen, an aliphatic group, a substituted aliphatic group, phenyl (Ph), substituted Ph, —O(Ph), substituted —O(Ph), CH$_2$(Ph), or an unsubstituted heteroaryl or non-aromatic heterocyclic ring. Examples of substituents on the aliphatic group or the phenyl ring represented by R$^+$ include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

Additionally, pharmaceutically acceptable salts of the compounds disclosed herein are also included in the present invention and can be used in the compositions and methods disclosed herein. For example, an acid salt of a compound containing an amine or other basic group can be obtained, by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

Salts of compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

The disclosed compounds, pharmaceutical compositions and methods can be used to inhibit CRTH2 activity; to inhibit PGD2 activity including DP activity and to inhibit or treat (therapeutically or prophylactically) disorders with an inflammatory component and allergic conditions mediated by CRTH2 and/or PGD2 and/or DP. They can also be used to inhibit inflammatory disorders and allergic conditions mediated by Th2 cells, eosinophils and basophils.

Examples of allergic conditions for which the disclosed compounds, pharmaceutical compositions and methods are believed to be particularly effective include allergic asthma, atopic dermatitis, allergic rhinitis and chronic obstructive pulmonary disease (COPD). Other allergic conditions include systemic anaphylaxis or hypersensitivity responses, drug allergies (e.g., to penicillin, cephalosporins), insect sting allergies and dermatoses such as dermatitis, eczema, atopic dermatitis, allergic contact dermatitis and urticaria.

Examples of diseases with an inflammatory component for which the disclosed compounds, pharmaceutical composition and methods are believed to be particularly effective include rheumatoid arthritis, osteoarthritis, inflammatory bowel disease [e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis] and disorders of the skin [e.g., psoriasis, erythema, pruritis, and acne].

Many autoimmune diseases also have an inflammatory component. Examples include multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease). The inflammatory component of these disorders is believed to be mediated, at least in part, by CRTH2.

Diseases characterized by repurfusion have an inflammatory component that is believed to be mediated, at least in part by, by CRTH2. Examples include stroke, cardiac ischemia, and the like. The disclosed compounds and compositions also can be used to treat these disorders.

Other diseases and conditions with an inflammatory component believed to be mediated by CRTH2 include mastitis (mammary gland), vaginitis, cholecystitis, cholangitis or pericholangitis (bile duct and surrounding tissue of the liver), chronic bronchitis, chronic sinusitis, chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases and sarcoidosis. Yet other diseases or conditions with inflammatory components which are amendable to treatment according to methods disclosed herein include vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

A subject with one of the aforementioned diseases or conditions is said "to be in need of CRTH2 inhibition". The subject with a disease or condition of this type is "treated" when at least one of the symptoms associated with the disease or condition is alleviated (therapeutic treatment) or inhibited or prevented (prophylactic treatment), in whole or in part.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like). As noted above, a "subject in need of CRTH2 inhibition" is a subject in whom a beneficial therapeutic or prophylactic effect can be achieved by inhibiting CRTH2 function or activity.

An "effective amount" of the disclosed CRTH2 inhibitors is the quantity which inhibits CRTH2 activity in a subject in need of such inhibition, or which, when administered to a subject which has a condition or disease which can be prophylactically or therapeutically treated by inhibiting CRTH2 activity, ameliorates the symptoms of the disease, delays the onset of the symptoms and/or increases longevity. The precise amount of CRTH2 inhibitor administered to the subject will depend on the type and severity of the disease or condition and on the characteristics of the subject, such as general health, age, sex, body weight and tolerance to drugs. The dosage may also vary according to the route of administration, which includes oral, aerosol, rectal, transdermal, subcutaneous, intravenous, intramuscular, intraperitoneal and intranasal. The skilled artisan will be able to determine appropriate dosages depending on these and other factors. An "effective amount" typically ranges between about 0.01 mg/kg/day to about 100 mg/kg/day, preferably beween about 0.5 mg/kg/day to about 50 mg/kg/day.

The CRTH2 inhibitors described herein, and the pharmaceutically acceptable salts thereof can be used in pharmaceutical preparations in combination with a pharmaceutically acceptable carrier or diluent. Suitable pharmaceutically acceptable carriers include inert solid fillers or diluents and sterile aqueous or organic solutions. The CRTH2 inhibitor will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19th edition, Mack Publishing Co., Easton, Pa. (1995).

For oral administration, the CRTH2 inhibitor or salts thereof can be combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

For parental administration, the disclosed CRTH2 inhibitor, or salts thereof can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

The invention is illustrated by the following examples which are not intended to be limiting in any way.

Experimental Section:

General. All reactions involving air-sensitive reagents were performed under a nitrogen atmosphere. Reagents were used as received from commercial suppliers unless otherwise noted. $^1$H NMR data were recorded using the Bruker UltraShield 300 MHz/54 mm instrument equipped with Bruker B-ACS60 Auto Sampler or the Varian 300 MHz instrument. Intermediates and final compounds were purified by flash chromatography using one of the following instruments: 1. Biotage 4-channel Quad UV Flash Collector equipped with a Quad 1 Pump Module and the Quad 12/25 Cartridge module. 2. Biotage 12-channel Quad UV Flash Collector equipped with a Quad 3 Pump Module and a Quad 3 Cartridge module. 3. ISCO combi-flash chromatography instrument. LC/MS spectra were obtained using a Micro-Mass Platform LC (Phenomenex C18 column, 5 micron, 50×4.6 mm) equipped with a Gilson 215 Liquid Handler. Standard LC/MS conditions is as follows:

| Formic acid-Standard conditions: | |
|---|---|
| % C (Water) | 95.0 |
| % D (Acetonitrile) | 5.0 |
| % Formic Acid | 0.1 |

-continued

Formic acid-Standard conditions:

| Flow (ml/min) | 3.500 |
| Stop Time (mins) | 4.4 |
| Min Pressure (bar) | 0 |
| Max Pressure (bar) | 400 |
| Oven Temperature Left (° C.) | 25.0 |
| Oven Temperature Right (° C.) | 25.0 |

HP1100 LC Pump Gradient Timetable
The gradient Timetable contains 5 entries which are:

| Time | A % | B % | C % | D % | Flow | Pressure |
|---|---|---|---|---|---|---|
| 0.00 | 0.0 | 0.0 | 95.0 | 5.0 | 3.500 | 400 |
| 3.50 | 0.0 | 0.0 | 0.0 | 100.0 | 3.500 | 400 |
| 4.30 | 0.0 | 0.0 | 0.0 | 100.0 | 3.500 | 400 |
| 4.40 | 0.0 | 0.0 | 95.0 | 5.0 | 4.000 | 400 |
| 5.00 | 0.0 | 0.0 | 95.0 | 5.0 | 4.000 | 400 |

LC-MS data were acquired using the "Formic acid-Standard" method unless otherwise noted.

Scheme 1

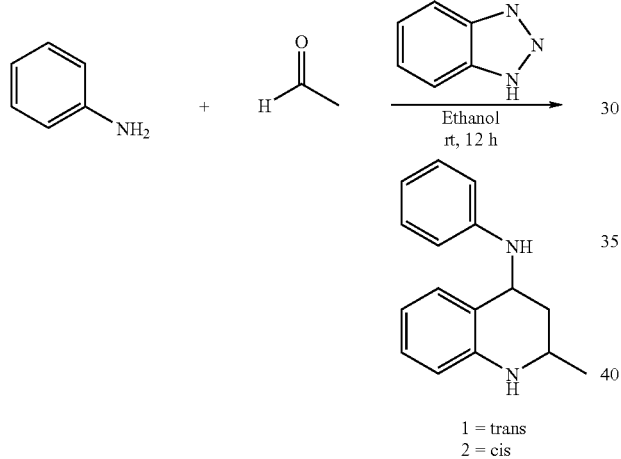

1 = trans
2 = cis (±)-Cis- and (±)-trans-(2-ethyl-1,2,3,4-tetrahydro-quinolin-4-yl)-phenyl-amine (1) & (2)

A 250 mL flask under nitrogen atmosphere was charged with aniline (1.0 g, 10.7 mmol, 1.0 equiv), acetaldehyde (0.599 mL, 10.7 mmol), benzotriazole (0.255 g, 2.1 mmol, 0.2 equiv) and dry toluene (100 mL) (Caution: an exotherm was observed). The precipitated benzotriazole/aldehyde adduct was observed immediately. The solution was allowed to stir at room temperature for 12 h. The precipitate that forms after stirring over night was filtered and washed with minimal diethyl ether, to afford the cis-isomer exclusively. The trans-isomer could be obtained by concentration of the filtrate. The residue was purified by Biotage flash system (95% hexane/5% diethyl ether) to yield the cis and trans isomers as a mixture. The resulting oily residue was then triturated with hexane to separate the cis isomer as a white solid and the filtrate was concentrated to give the trans isomer.

(±)-Cis-isomer—$^1$H-NMR (CDCl$_3$) δ: 1.24 (d, 3H), 1.52 (q, 1H), 2.38 (dddd, 1H), 3.63 (m, 1H), 3.75 (bs, 2H, —NH), 4.83 (dd, 1H), 6.51 (d, 1H), 6.68 (m, 4H), 7.05 (m, 1H), 7.19–7.26 (m, 2H), 7.39 (d, 1H).

(±)-Trans-isomer—$^1$H-NMR (CDCl$_3$) δ: 1.22 (d, 3H), 1.56 (m, 1H), 2.20 (dt, 1H), 3.4 (m, 1H), 3.89 (bs, 2H, —NH), 4.55 (dt, 1H), 6.56 (dd, 1H), 6.66–6.75 (m, 4H), 7.08 (m, 1H), 7.19–7.26 (m, 3H).

Scheme 2

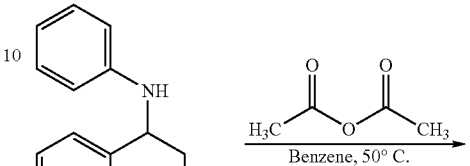

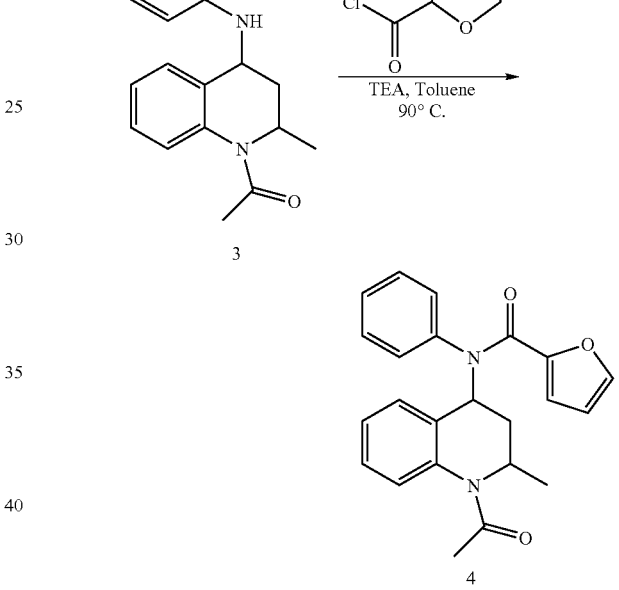

Cis-(±)-1-(2-methyl-4-phenylamino-3,4-dihydro-2H-quinolin-1-yl)-ethanone (3)

A 30 mL flask under nitrogen atmosphere was charged with (±)-cis-(2-methyl-1,2,3,4-tetrahydro-quinolin-4-yl)-phenyl-amine (0.520 g, 2.2 mmol, 1.0 equiv), and acetic anhydride (0.209 mL, 2.2 mmol, 1.0 equiv) and dry toluene (31 mL). The solution was heated to 50° C. for 15 h. The reaction mixture was evaporated in vacuo. The residue was purified by Biotage flash system (70% hexane/30% ethyl acetate) to yield the 2-acetyl cis isomers 67% yield.

$^1$H-NMR (CDCl$_3$) δ: 1.17 (d, 3H), 1.25 (q, 1H), 2.19 (s, 3H), 2.22 (bs, 1H), 2.65 (m, 1H), 4.21 (dd, 1H), 4.96 (m, 1H), 6.65 (d, 2H), 6.75 (t, 1H), 7.12–7.33 (m, 6H).

Cis-(±)-furan-2-carboxylic acid (1-acetyl-2-methyl-1,2,3,4-tetrahydro-quinolin-4-yl)-phenyl-amide (4)

A round bottom flask under nitrogen atmosphere was charged with cis-1-(2-methyl-4-phenylamino-3,4-dihydro-2H-quinolin-1-yl)-ethanone (0.163 g, 0.58 mmol, 1.0 equiv) and 2-furoyl chloride (0.285 mL, 2.9 mmol, 5.0 equ), pyridine (1.0 equiv.) and dry toluene (3 mL). The solution was heated to 90° C. for 15 h. The reaction mixture was evaporated in vacuo. The residue was purified by Biotage flash system (50% hexane/50% ethyl acetate) to yield the cis isomer 40% yield.

¹H-NMR (CDCl₃) δ: 1.08 (d, 3H), 1.63 (m, 1H), 2.14 (s, 3H), 2.2 (bs, 1H), 4.77 (m, 1H), 5.75 (bs, 1H), 6.23 (dd, 1H), 7.12–7.45 (m, 10H).

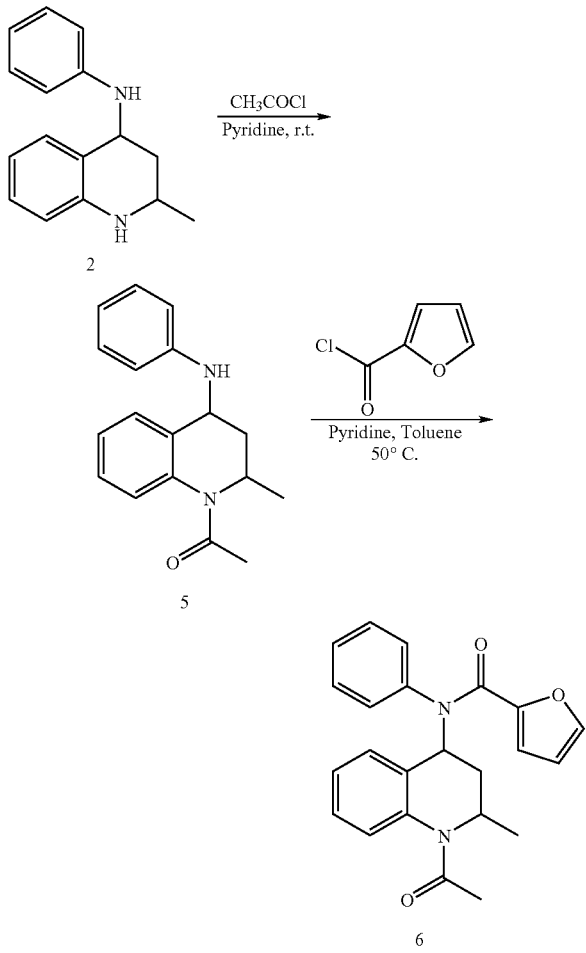

Scheme 3

(±)-Trans-1-(2-Methyl-4-phenylamino-3,4-dihydro-2H-quinolin-1-yl)-ethanone (5)

A 30 mL flask under nitrogen atmosphere was charged with (±)-trans-(2-methyl-1,2,3,4-tetrahydro-quinolin-4-yl)-phenyl-amine (0.260 g, 1.1 mmol, 1.0 equiv) and acetyl chloride (0.075 mL, 1.0 mmol, 0.95 equ) in pyridine (5 mL). The solution was allowed to stir at room temperature for 6 h. The reaction mixture was evaporated in vacuo. The residue was purified by Biotage flash system (70% hexane/30% ethyl acetate to 60% hexane/40% ethyl acetate to 50% hexane/50% ethyl acetate) to yield the 2-acetyl trans isomers 35% yield.

¹H-NMR (CDCl₃) δ: 1.19 (d, 3H), 1.76 (m, 1H), 2.17 (s, 3H), 2.52 (dd, 1H), 4.60 (t, 1H), 4.93 (m, 1H), 6.67 (d, 2H), 6.71 (t, 1H), 7.13–7.36 (m, 6H), 7.41 (d, 1H).

(±)-Trans-furan-2-carboxylic acid (1-acetyl-2-methyl-1,2,3,4-tetrahydro-quinolin-4-yl)-phenyl-amide (6)

A round bottom flask under nitrogen atmosphere was charged with (±)-trans-1-(2-methyl-4-phenylamino-3,4-dihydro-2H-quinolin-1-yl)-ethanone (0.110 g, 0.39 mmol, 1.0 equiv) and 2-furoyl chloride (0.193 mL, 1.9 mmol, 5.0 equ), pyridine (1.0 equ.) and dry toluene (5 mL). The solution was heated to 50° C. for 5 h. The reaction mixture was evaporated in vacuo. The residue was purified by Biotage flash system (30% hexane/70% ethyl acetate to 50% hexane/50% ethyl acetate) to yield the trans isomer 34% yield.

¹H-NMR (CDCl₃) δ: 1.11 (d, 3H), 1.76 (s, 3H), 2.07 (dd, 1H), 2.37 (m, 1H), 5.00 (m, 1H), 5.48 (d, 1H), 6.14 (dd, 1H), 6.29 (t, 1H), 6.90 (m, 1H), 6.99 (m, 1H), 7.22–7.32 (m, 6H), 7.34 (d, 1H), 7.54 (dd, 1H).

(±)-Cis-N-(1-Acetyl-2-methyl-1,2,3,4-tetrahydro-quinolin-4-yl)-4-fluoro-N-phenyl-benzamide (7)

A 30 mL flask under nitrogen atmosphere was charged with (±)-cis-(2-methyl-1,2,3,4-tetrahydro-quinolin-4-yl)-phenyl-amine (0.520 g, 2.2 mmol, 1.0 equiv) and acetic anhydride (0.209 mL, 2.2 mmol, 1.0 eq.) and dry toluene (31 mL). The solution was heated to 50° C. for 15 h. The reaction mixture was evaporated in vacuo. The residue was purified by Biotage flash system (70% hexane/30% ethyl acetate) to yield the 2-acetyl cis isomers 67% yield.

¹H-NMR (CDCl₃) δ: 1.17 (d, 3H), 1.25 (q, 1H), 2.19 (s, 3H), 2.22 (bs, 1H), 2.65 (m, 1H), 4.21 (dd, 1H), 4.96 (m, 1H), 6.65 (d, 2H), 6.75 (t, 1H), 7.12–7.33 (m, 6H).

A round bottom flask under nitrogen atmosphere was charged with (±)-cis-1-(2-methyl-4-phenylamino-3,4-dihydro-2H-quinolin-1-yl)-ethanone (1.0 equiv) and 2-fluorobenzoyl chloride (5.0 equ), pyridine (1.0 equ.) and dry toluene (3 mL). The solution was heated to 90° C. for 15 h. The reaction mixture was evaporated in vacuo. The residue was purified by Biotage flash system (50% hexane/50% ethyl acetate) to yield the cis isomer 40% yield.

¹H-NMR (CDCl₃) δ: 1.1 (3H, d), 1.2 (1H, m), 2.1 (3H, s), 2.1 (1H, m), 4.8 (1H, m), 5.4 (1H, m), 6.8 (2H, m), 6.9–7.4 (9H, m), 7.5 (1H, m).

MS m/z: 403 (M+1).

(±)-Trans-N-(1-Acetyl-2-methyl-1,2,3,4-tetrahydro-quinolin-4-yl)-4-fluoro-N-phenyl-benzamide (8)

A 30 mL flask under nitrogen atmosphere was charged with (±)-trans-(2-methyl-1,2,3,4-tetrahydro-quinolin-4-yl)-phenyl-amine (0.260 g, 1.1 mmol, 1.0 equiv) and acetyl chloride (0.075 mL, 1.0 mmol, 0.95 equ) in pyridine (5 mL). The solution was allowed to stir at room temperature for 6 h. The reaction mixture was evaporated in vacuo. The residue was purified by Biotage flash system (70% hexane/30% ethyl acetate to 60% hexane/40% ethyl acetate to 50% hexane/50% ethyl acetate) to yield the 2-acetyl trans isomers 35% yield.

¹H-NMR (CDCl₃) δ: 1.19 (d, 3H), 1.76 (m, 1H), 2.17 (s, 3H), 2.52 (dd, 1H), 4.60 (t, 1H), 4.93 (m, 1H), 6.67 (d, 2H), 6.71 (t, 1H), 7.13–7.36 (m, 6H), 7.41 (d, 1H).

A round bottom flask under nitrogen atmosphere was charged with (±)-trans-1-(2-methyl-4-phenylamino-3,4-dihydro-2H-quinolin-1-yl)-ethanone (1.0 equiv) and 4-fluorobenzoyl chloride (5.0 equ), pyridine (1.0 equ.) and dry toluene (5 mL). The solution was heated to 50° C. for 5 h. The reaction mixture was evaporated in vacuo. The residue was purified by Biotage flash system (30% hexane/70% ethyl acetate to 50% hexane/50% ethyl acetate) to yield the trans isomer 34% yield.

¹H-NMR (CDCl₃) δ: 1.2 (3H, d), 1.9 (3H, s), 2.0 (1H, m), 2.3 (1H, m), 5.0 (1H, m), 6.2 (1H, m), 6.6–6.8 (4H, m), 7.1 (3H, m), 7.3 (4H, m), 7.6 (1H, m).

MS m/z: 403 (M+1).

General Procedure A

Scheme 4

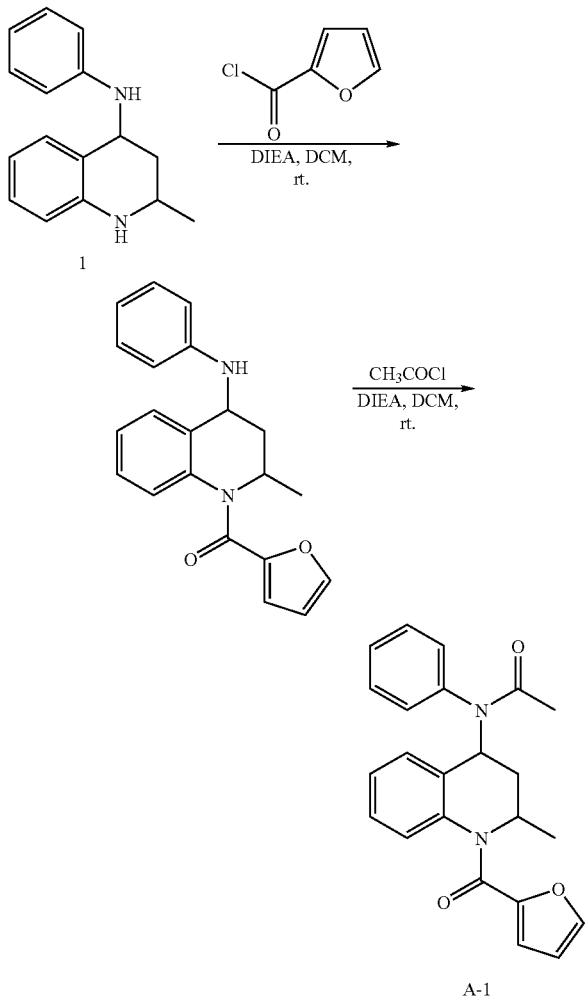

(±)-Cis-N-[1-(furan-2-carbonyl)-2-methyl-1,2,3,4-tetrahydro-quinolin-4-yl]-N-phenyl-acetamide (A-1)

To a solution of (±)-cis-(2-Methyl-1,2,3,4-tetrahydro-quinolin-4-yl)-phenyl-amine (430 mg, 1.83 mmol) in dichloromethane (18 mL) at room temperature was added diisopropylethylamine (318 uL, 1.83 mmol) followed by 2-furoyl chloride. It was allowed to let stir at room temperature for 12 h. The mixture was poured into water and extracted with dichloromethane. The extracts were washed with 1 M(aq) NaOH and brine, dried over magnesium sulfate, filtered and concentrated. The crude residue was purified by silica gel chromatography (80% hexanes/20% ethyl acetate) to afford the amide (500 mg, 83%).

To a solution of (±)-cis-furan-2-yl-(2-methyl-4-phenylamino-3,4-dihydro-2H-quinolin-1-yl)-methanone (360 mg, 1.0 mmol) in methylene chloride (5 mL) was added diisopropylethylamine (1.9 mL, 10 mmol) followed by acetyl chloride (388 uL, 5 mmol). The mixture was stirred at room temperature over night. The mixture was poured into water and extracted with dichloromethane. The extracts were washed with 1 M (aq) NaOH and brine, dried over magnesium sulfate, filtered and concentrated. The crude residue was purified by silica gel chromatography (50% hexanes/ 50% ethyl acetate) to afford the amide (230 mg, 57%).

$^1$H-NMR (CDCl$_3$) δ: 1.12 (d, 3H), 1.25 (t, 1H), 2.01 (s, 3H), 2.32 (m, 1H), 4.12 (sextet, 1H), 5.49 (bs, 1H), 6.22 (m, 2H), 6.84 (d, 1H), 7.10 (t, 1H), 7.28–7.31 (m, 4H), 7.38 (m, 4H).

MS m/z: 375 (M+1).

(±)-Cis-2-methoxy-N-[1-(3-methoxy-benzoyl)-2-methyl-1,2,3,4-tetrahydro-quinolin-4-yl]-N-phenyl-acetamide (A-2)

(±)-Cis-2-methoxy-N-[1-(3-methoxy-benzoyl)-2-methyl-1,2,3,4-tetrahydro-quinolin-4-yl]-N-phenyl-acetamide was made following general procedure A, substituting 3-methoxybenzoyl chloride for 2-furoyl chloride and methoxyacetyl chloride for acetyl chloride.

$^1$H-NMR (CDCl$_3$) δ: 1.14 (d, 3H), 1.25 (t, 1H), 2.33 (m, 1H), 3.39 (s, 3H), 3.60 (s, 3H), 3.85 (d, 1H), 3.98 (d, 1H), 4.79 (sextet, 1H), 5.62 (bs, 1H), 6.53 (d, 1H), 6.72 (s, 1H), 6.81 (d, 1H), 6.92 (t, 1H), 7.08 (t, 1H), 7.16 (t, 1H), 7.29 (m, 2H), 7.35–7.42 (m, 3H).

MS m/z: 445 (M+1).

(±)-Cis-4-chloro-N-[1-(3-methoxy-benzoyl)-2-methyl-1,2,3,4-tetrahydro-quinolin-4-yl]-N-phenyl-benzamide (A-3)

(±)-Cis-4-Chloro-N-[1-(3-methoxy-benzoyl)-2-methyl-1,2,3,4-tetrahydro-quinolin-4-yl]-N-phenyl-benzamide was made following general procedure A, substituting 3-methoxybenzoyl chloride for 2-furoyl chloride and 4-chlorobenzoyl chloride for acetyl chloride.

$^1$H-NMR (CDCl$_3$) δ: 1.24 (d, 3H), 1.26 (m, 1H), 2.29 (m, 1H), 3.60 (s, 3H), 4.84 (sextet, 1H), 5.92 (bs, 1H), 6.58 (d, 1H), 6.78 (d, 2H), 6.82 (s, 1H), 6.95 (t, 1H), 7.08 (t, 2H), 7.16–7.25 (m, 7H), 7.34 (d, 2H), 7.53 (d, 1H).

MS m/z: 511.0 (M+1).

(±)-Cis-N-[1-(3-Methoxy-benzoyl)-2-methyl-1,2,3,4-tetrahydro-quinolin-4-yl]-N-phenyl-isobutyramide (A-4)

(±)-Cis-N-[1-(3-methoxy-benzoyl)-2-methyl-1,2,3,4-tetrahydro-quinolin-4-yl]-N-phenyl-isobutyramide was made following general procedure A, substituting 3-methoxybenzoyl chloride for 2-furoyl chloride and isobutyryl chloride for acetyl chloride.

$^1$H-NMR (CDCl$_3$) δ: 1.14 (d, 9H), 1.23 (t, 1H), 2.28 (m, 1H), 2.65 (sextet, 1H), 3.65 (s, 3H), 4.77 (sextet, 1H), 5.63 (bs, 1H), 6.51 (d, 1H), 6.67 (d, 1H), 6.78 (d, 1H), 6.86 (m, 2H), 7.01 (t, 1H), 7.14 (t, 1H), 7.24–7.37 (m, 6H).

MS m/z: 443.0 (M+1).

(±)-Cis-N-[2-Methyl-1-(thiophene-2-carbonyl)-1,2,3,4-tetrahydro-quinolin-4-yl]-N-phenyl-acetamide (A-5)

(±)-Cis-N-[2-methyl-1-(thiophene-2-carbonyl)-1,2,3,4-tetrahydro-quinolin-4-yl]-N-phenyl-acetamide was made following general procedure A, substituting 2-thiophene carbonyl chloride for 2-furoyl chloride.

(±)-Cis-N-[2-methyl-1-(thiophene-2-carbonyl)-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)— and (2S,4R)—N-[2-methyl-1-(thiophene-2-carbonyl)-1,2,3,4-tetrahydro-quinolin-4-yl]-N-phenyl-acetamide (A-11 & A-10, respectively).

$^1$H-NMR (CDCl$_3$) δ: 1.15 (d, 3H), 1.25 (m, 1H), 2.02 (s, 3H), 2.31 (m, 1H), 4.73 (sextet, 1H), 5.53 (bs, 1H), 6.68 (dd, 1H), 6.77 (t, 1H), 6.88 (d, 1H), 7.06 (t, 1H), 7.25–7.32 (m, 4H), 7.39 (m, 4H).

MS m/z: 391.0 (M+1).

(±)-Cis-N-[1-(4-tert-butyl-benzoyl)-2-methyl-1,2,3,4-tetrahydro-quinolin-4-yl]-N-phenyl-acetamide (A-6)

(±)-Cis-N-[1-(4-tert-butyl-benzoyl)-2-methyl-1,2,3,4-tetrahydro-quinolin-4-yl]-N-phenyl-acetamide was made following general procedure A, substituting 4-tert-butylbenzoyl chloride for 2-furoyl chloride.

(±)-Cis-N-[1-(4-tert-butyl-benzoyl)-2-methyl-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[1-(4-tert-butyl-benzoyl)-2-methyl-1,2,3,4-tetrahydro-quinolin-4-yl]-N-phenyl-acetamide (A-8 & A-9, respectively).

$^1$H-NMR (CDCl$_3$) δ: 1.14 (d, 3H), 1.16 (m, 1H), 1.23 (s, 9H), 2.04 (s, 3H), 2.33 (m, 1H), 4.78 (sextet, 1H), 5.62 (bs, 1H), 6.53 (d, 1H), 6.91 (t, 1H), 7.15–7.40 (m, 11H).

MS m/z: 441 (M+1).

(±)-Cis-N-[1-(4-fluoro-benzoyl)-2-methyl-1,2,3,4-tetrahydro-quinolin-4-yl]-N-phenyl-acetamide (A-7)

(±)-Cis-N-[1-(4-fluoro-benzoyl)-2-methyl-1,2,3,4-tetrahydro-quinolin-4-yl]-N-phenyl-acetamide was made following general procedure A, substituting 4-fluorobenzoyl chloride for 2-furoyl chloride.

(±)-Cis-N-[1-(4-fluoro-benzoyl)-2-methyl-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[1-(4-fluoro-benzoyl)-2-methyl-1,2,3,4-tetrahydro-quinolin-4-yl]-N-phenyl-acetamide (A-52 & A-44, respectively).

$^1$H-NMR (CDCl$_3$) δ: 1.13 (d, 3H), 1.25 (m, 1H), 2.03 (s, 3H), 2.32 (m, 1H), 4.78 (sextet, 1H), 5.62 (bs, 1H), 6.47 (d, 1H), 6.83–6.95 (m, 3H), 7.16–7.40 (m, 9H).

MS m/z: 403 (M+1).

(±)-Cis-N-[2-methyl-1-(5-methyl-thiophene-2-carbonyl)-1,2,3,4-tetrahydro-quinolin-4-yl]-N-phenyl-acetamide (A-12)

(±)-Cis-N-[2-methyl-1-(5-methyl-thiophene-2-carbonyl)-1,2,3,4-tetrahydro-quinolin-4-yl]-N-phenyl-acetamide was made following general procedure A, substituting 5-methyl-2-thiophenecarbonyl chloride for 2-furoyl chloride.

(±)-Cis-N-[2-methyl-1-(5-methyl-thiophene-2-carbonyl)-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[2-methyl-1-(5-methyl-thiophene-2-carbonyl)-1,2,3,4-tetrahydro-quinolin-4-yl]-N-phenyl-acetamide (A-59 & A-60, respectively).

$^1$H-NMR (CDCl$_3$) δ: 1.07 (m, 1H), 1.12 (d, 3H), 2.01 (s, 3H), 2.31 (m, 1H), 2.39 (s, 3H), 4.69 (sextet, 1H), 5.50 (bs, 1H), 6.44 (s, 1H), 6.51 (d, 1H), 6.94 (d, 1H), 7.09 (t, 1H), 7.21–7.30 (m, 3H), 7.39–7.41 (m, 4H).

MS m/z: 405 (M+1)

(±)-Cis-N-[2-methyl-1-(4-methyl-2-pyrazin-2-yl-thiazole-5-carbonyl)-1,2,3,4-tetrahydro-quinolin-4-yl]-N-phenyl-acetamide (A-13)

(±)-Cis-N-[2-ethyl-1-(4-methyl-2-pyrazin-2-yl-thiazole-5-carbonyl)-1,2,3,4-tetrahydro-quinolin-4-yl]-N-phenyl-acetamide was made following general procedure A, substituting 4-methyl-2-(2-pyrazinyl)-1,3-thiazole-5-carbonyl chloride for 2-furoyl chloride.

$^1$H-NMR (CDCl$_3$) δ: 1.18 (d, 3H), 1.77 (bs, 1H), 2.03 (s, 3H), 2.10 (s, 3H), 2.32 (m, 1H), 4.79 (sextet, 1H), 5.50 (bs, 1H), 6.74 (d, 1H), 7.03 (t, 1H), 7.26–7.41 (m, 7H), 8.55 (d, 1H), 9.32 (s, 1H).

MS m/z: 484 (M+1).

(±)-Cis-N-[2-methyl-1-(3-methyl-thiophene-2-carbonyl)-1,2,3,4-tetrahydro-quinolin-4-yl]-N-phenyl-acetamide (A-14)

(±)-Cis-N-[2-methyl-1-(3-methyl-thiophene-2-carbonyl)-1,2,3,4-tetrahydro-quinolin-4-yl]-N-phenyl-acetamide was made following general procedure A, substituting 3-methyl-2-thiophenecarbonyl chloride for 2-furoyl chloride.

$^1$H-NMR (CDCl$_3$) δ: 1.13 (d, 3H), 1.16 (m, 1H), 1.80 (s, 3H), 2.00 (s, 3H), 2.29 (m, 1H), 4.73 (sextet, 1H), 5.49 (bs, 1H), 6.56 (d, 1H), 6.66 (d, 1H), 6.97 (t, 1H), 7.16 (d, 2H), 7.25 (d, 2H), 7.32 (d, 1H), 7.38 (bs, 3H).

MS m/z: 405 (M+1).

(±)-Cis-N-[2-methyl-1-(5-phenyl-thiophene-2-carbonyl)-1,2,3,4-tetrahydro-quinolin-4-yl]-N-phenyl-acetamide (A-15)

(±)-Cis-N-[2-methyl-1-(5-phenyl-thiophene-2-carbonyl)-1,2,3,4-tetrahydro-quinolin-4-yl]-N-phenyl-acetamide was made following general procedure A, substituting 5-phenyl-2-thiophenecarbonyl chloride for 2-furoyl chloride.

$^1$H-NMR (CDCl$_3$) δ: 1.15 (d, 3H), 1.17 (m, 1H), 2.03 (s, 3H), 2.31 (m, 1H), 4.73 (sextet, 1H), 5.55 (bs, 1H), 6.59 (s, 1H), 6.95 (d, 2H), 6.99 (s, 1H), 7.10 (t, 1H), 7.26–7.44 (m, 9H), 7.53 (d, 2H).

MS m/z: 467 (M+1).

(±)-Cis-N-[2-methyl-1-(4-methyl-2-phenyl-thiazole-5-carbonyl)-1,2,3,4-tetrahydro-quinolin-4-yl]-N-phenyl-acetamide (A-16)

(±)-Cis-N-[2-methyl-1-(4-methyl-2-phenyl-thiazole-5-carbonyl)-1,2,3,4-tetrahydro-quinolin-4-yl]-N-phenyl-acetamide was made following general procedure A, substituting 4-methyl-2-phenyl-1,3-thiazole-5-carbonyl chloride for 2-furoyl chloride.

$^1$H-NMR (CDCl$_3$) δ: 1.16 (d, 3H), 1.18 (m, 1H), 2.03 (s, 3H), 2.14 (s, 3H), 2.32 (m, 1H), 4.74 (sextet, 1H), 5.53 (bs, 1H), 6.77 (d, 2H), 7.04 (t, 1H), 7.24–7.28 (m, 3H), 7.38–7.40 (m, 7H), 7.83 (d, 2H).

MS m/z: 482 (M+1).

(±)-Cis-N-[2-methyl-1-(4-methyl-[1,2,3]thiadiazole-5-carbonyl)-1,2,3,4-tetrahydro-quinolin-4-yl]-N-phenyl-acetamide (A-17)

(±)-Cis-N-[2-methyl-1-(4-methyl-[1,2,3]thiadiazole-5-carbonyl)-1,2,3,4-tetrahydro-quinolin-4-yl]-N-phenyl-acetamide was made following general procedure A, substituting 4-methyl-[1,2,3]thiadiazole-5-carbonyl chloride for 2-furoyl chloride.

$^1$H-NMR (CDCl$_3$) δ: 1.17 (d, 3H), 1.21 (m, 1H), 2.01 (s, 3H), 2.36 (s, 3H), 2.24 (m, 1H), 4.81 (sextet, 1H), 5.48 (bs, 1H), 6.52 (d, 1H), 6.98 (t, 1H), 7.22–7.26 (m, 3H), 7.37–7.42 (m, 4H).

MS m/z: 407 (M+1).

(±)-Cis-N-[1-(5-isopropyl-thiophene-2-carbonyl)-2-methyl-1,2,3,4-tetrahydro-quinolin-4-yl]-N-phenyl-acetamide (A-19)

(±)-Cis-N-[1-(5-isopropyl-thiophene-2-carbonyl)-2-methyl-1,2,3,4-tetrahydro-quinolin-4-yl]-N-phenyl-acetamide was made following general procedure A, substituting 5-isopropylthiophene carbonyl chloride for 2-furoyl chloride.

$^1$H-NMR (CDCl$_3$) δ: 1.11 (d, 3H), 1.15 (m, 1H), 1.19–1.25 (m, 6H), 2.01 (s, 3H), 2.30 (m, 1H), 2.70 (m, 1H), 4.69 (sextet, 1H), 5.51 (bs, 1H), 6.45 (s, 1H), 6.55 (s, 1H), 6.87–6.95 (m, 1H), 7.04–7.08 (m, 1H), 7.27 (s, 3H), 7.38 (s, 4H).

MS m/z: 433 (M+1).

(±)-Cis-N-[2-methyl-1-(3,4,5-trifluoro-benzoyl)-1,2,3,4-tetrahydro-quinolin-4-yl]-N-phenyl-acetamide (A-20)

(±)-Cis-N-[2-methyl-1-(3,4,5-trifluoro-benzoyl)-1,2,3,4-tetrahydro-quinolin-4-yl]-N-phenyl-acetamide was made following general procedure A, substituting 3,4,5-trifluorobenzoyl chloride for 2-furoyl chloride.

$^1$H-NMR (CDCl$_3$) δ: 1.12 (d, 3H), 1.21 (m, 1H), 2.03 (s, 3H), 2.31 (m, 1H), 4.71 (sextet, 1H), 5.55 (bs, 1H), 6.50 (d, 1H), 6.82 (t, 1H), 6.99 (t, 1H), 7.06 (t, 1H), 7.24–7.27 (m, 3H), 7.39 (m, 3H), 7.46 (d, 1H).

MS m/z: 439 (M+1).

(±)-Cis-N-[1-(4-fluoro-3-methyl-benzoyl)-2-methyl-1,2,3,4-tetrahydro-quinolin-4-yl]-N-phenyl-acetamide (A-21)

(±)-Cis-N-[1-(4-fluoro-3-methyl-benzoyl)-2-methyl-1,2,3,4-tetrahydro-quinolin-4-yl]-N-phenyl-acetamide was made following general procedure A, substituting 4-fluoro-3-methyl benzoyl chloride for 2-furoyl chloride.

$^1$H-NMR (CDCl$_3$) δ: 1.12 (d, 3H), 1.22 (m, 1H), 2.04 (s, 3H), 2.15 (s, 3H), 2.29 (m, 1H), 4.75 (sextet, 1H), 5.60 (bs, 1H), 6.50 (d, 1H), 6.73 (t, 1H), 6.86 (s, 1H), 6.93 (t, 1H), 7.15–7.39 (m, 8H).

MS m/z: 417 (M+1).

(±)-Cis-N-[1-(4-fluoro-3-trifluoromethyl-benzoyl)-2-methyl-1,2,3,4-tetrahydro-quinolin-4-yl]-N-phenyl-acetamide (A-22)

(±)-Cis-N-[1-(4-fluoro-3-trifluoromethyl-benzoyl)-2-methyl-1,2,3,4-tetrahydro-quinolin-4-yl]-N-phenyl-acetamide was made following general procedure A, substituting 4-fluoro-3-(trifluoromethyl)-benzoyl chloride for 2-furoyl chloride.

$^1$H-NMR (CDCl$_3$) δ: 1.15 (d, 3H), 1.24 (m, 1H), 2.04 (s, 3H), 2.33 (m, 1H), 4.75 (sextet, 1H), 5.58 (bs, 1H), 6.46 (d, 1H), 6.87–6.96 (m, 3H), 7.10–7.41 (m, 6H), 7.49 (d, 1H), 7.74 (d, 1H).

MS m/z: 471 (M+1).

(±)-Cis-N-[1-(3-chloro-4-fluoro-benzoyl)-2-methyl-1,2,3,4-tetrahydro-quinolin-4-yl]-N-phenyl-acetamide (A-23)

(±)-Cis-N-[1-(3-chloro-4-fluoro-benzoyl)-2-methyl-1,2,3,4-tetrahydro-quinolin-4-yl]-N-phenyl-acetamide was made following general procedure A, substituting 3-chloro-4-fluorobenzoyl chloride for 2-furoyl chloride.

$^1$H-NMR (CDCl$_3$) δ: 1.13 (d, 3H), 1.24 (m, 1H), 2.04 (s, 3H), 2.31 (m, 1H), 4.76 (sextet, 1H), 5.59 (bs, 1H), 6.50 (d, 1H), 6.85 (d, 2H), 6.96 (t, 1H), 7.21 (t, 1H), 7.27 (m, 2H), 7.39 (m, 4H), 7.50 (d, 1H).

MS m/z: 437 (M+1).

(±)-Cis-N-[2-methyl-1-(2,4,6-trifluoro-benzoyl)-1,2,3,4-tetrahydro-quinolin-4-yl]-N-phenyl-acetamide (A-24)

(±)-Cis-N-[2-methyl-1-(2,4,6-trifluoro-benzoyl)-1,2,3,4-tetrahydro-quinolin-4-yl]-N-phenyl-acetamide was made following general procedure A, substituting 2,4,6-trifluorobenzoyl chloride for 2-furoyl chloride.

$^1$H-NMR (CDCl$_3$) δ: 1.13 (d, 3H), 1.21 (m, 1H), 2.05 (s, 3H), 2.29 (m, 1H), 4.86 (sextet, 1H), 5.45 (bs, 1H), 6.35 (t, 1H), 6.70 (d, 2H), 6.95 (t, 1H), 7.2–7.5 (m, 7H).

MS m/z: 439 (M+1).

(±)-Cis-N-[1-(4-chloro-benzoyl)-2-methyl-1,2,3,4-tetrahydro-quinolin-4-yl]-N-phenyl-propionamide (A-25)

(±)-Cis-N-[1-(4-chloro-benzoyl)-2-methyl-1,2,3,4-tetrahydro-quinolin-4-yl]-N-phenyl-propionamide was made following general procedure A, substituting 4-chlorobenzoyl chloride for 2-furoyl chloride and propionyl chloride for acetyl chloride.

$^1$H-NMR (CDCl$_3$) δ: 1.09 (t, 3H), 1.12 (d, 3H), 1.22 (m, 1H), 2.23 (m, 3H), 4.73 (sextet, 1H), 5.58 (bs, 1H), 6.46 (d, 1H), 6.78 (d, 1H), 6.88 (t, 1H), 6.98 (t, 1H), 7.15 (t, 1H), 7.18–7.44 (m, 8H).

MS m/z: 433 (M+1).

(±)-Cis-N-[2-methyl-1-(4-trifluoromethoxy-benzoyl)-1,2,3,4-tetrahydro-quinolin-4-yl]-N-phenyl-acetamide (A-26)

(±)-Cis-N-[2-methyl-1-(4-trifluoromethoxy-benzoyl)-1,2,3,4-tetrahydro-quinolin-4-yl]-N-phenyl-acetamide was made following general procedure A, substituting 4-(trifluoromethoxy)benzoyl chloride for 2-furoyl chloride.

$^1$H-NMR (CDCl$_3$) δ: 1.16 (d, 3H), 1.24 (m, 1H), 2.28 (m, 3H), 4.78 (sextet, 1H), 5.61 (bs, 1H), 6.46 (d, 1H), 6.91 (t, 1H), 6.92 (t, 1H), 7.02 (d, 2H), 7.18 (t, 1H), 7.23–7.27 (m, 4H), 7.33 (d, 1H), 7.39 (s, 3H).

MS m/z: 469 (M+1).

(±)-Cis-N-[2-methyl-1-(3-trifluoromethoxy-benzoyl)-1,2,3,4-tetrahydro-quinolin-4-yl]-N-phenyl-acetamide (A-27)

(±)-Cis-N-[2-methyl-1-(3-trifluoromethoxy-benzoyl)-1,2,3,4-tetrahydro-quinolin-4-yl]-N-phenyl-acetamide was made following general procedure A, substituting 3-(trifluoromethoxy)benzoyl chloride for 2-furoyl chloride.

$^1$H-NMR (CDCl$_3$) δ: 1.14 (t, 3H), 1.15 (d, 3H), 1.25 (m, 1H), 2.25 (m, 3H), 4.78 (sextet, 1H), 5.59 (bs, 1H), 6.46 (d, 1H), 6.91 (t, 1H), 6.95 (d, 1H), 7.12–7.27 (m, 6H), 7.34 (d, 1H), 7.39 (s, 3H).

MS m/z: 469 (M+1).

(±)-Cis-N-[2-methyl-1-(3-phenyl-isoxazole-5-carbonyl)-1,2,3,4-tetrahydro-quinolin-4-yl]-N-phenyl-propionamide (A-28)

(±)-Cis-N-[2-methyl-1-(3-phenyl-isoxazole-5-carbonyl)-1,2,3,4-tetrahydro-quinolin-4-yl]-N-phenyl-propionamide was made following general procedure A, substituting 3-phenyl-5-isoxazole carbonyl chloride for 2-furoyl chloride and propionyl chloride for acetyl chloride.

$^1$H-NMR (CDCl$_3$) δ: 1.14 (t, 3H), 1.19 (d, 3H), 1.61 (m, 1H), 2.24 (m, 3H), 4.78 (sextet, 1H), 5.49 (bs, 1H), 6.34 (bs, 1H), 6.85 (d, 1H), 7.10 (t, 1H), 7.26 (s, 3H), 7.32 (t, 1H), 7.40 (m, 6H), 7.67 (s, 2H).

MS m/z: 466 (M+1).

(±)-Cis-N-{2-methyl-1-[4-(5-methyl-tetrazol-1-yl)-benzoyl]-1,2,3,4-tetrahydro-quinolin-4-yl}-N-phenyl-propionamide (A-29)

(±)-Cis-N-{2-methyl-1-[4-(5-methyl-tetrazol-1-yl)-benzoyl]-1,2,3,4-tetrahydro-quinolin-4-yl}-N-phenyl-propionamide was made following general procedure A, substituting 4-(5-methyl-1H-tetrazole-1-yl)-benzoyl chloride for 2-furoyl chloride and propionyl chloride for acetyl chloride.

$^1$H-NMR (CDCl$_3$) δ: 1.16 (t, 3H), 1.17 (d, 3H), 1.24 (m, 1H), 2.26 (m, 3H), 2.55 (s, 3H), 4.82 (sextet, 1H), 5.64 (bs, 1H), 6.50 (d, 1H), 6.94 (t, 1H), 7.21–7.41 (m, 11H).

MS m/z: 481 (M+1).

(±)-Cis-N-{1-[3-(4-chloro-phenyl)-isoxazole-5-carbonyl]-2-methyl-1,2,3,4-tetrahydro-quinolin-4-yl}-N-phenyl-propionamide (A-30)

(±)-Cis-N-{1-[3-(4-chloro-phenyl)-isoxazole-5-carbonyl]-2-methyl-1,2,3,4-tetrahydro-quinolin-4-yl}-N-phenyl-propionamide was made following general procedure A substituting 3-(4-chlorophenyl)-5-isoxazole carbonyl chloride for 2-furoyl chloride and propionyl chloride for acetyl chloride.

$^1$H-NMR (CDCl$_3$) δ: 1.21 (m, 6H), 1.24 (m, 1H), 2.23 (m, 3H), 4.76 (sextet, 1H), 5.48 (bs, 1H), 6.28 (s, 1H), 6.84 (d, 1H), 7.07 (m, 2H), 7.26–7.67 (m, 7H), 7.78 (d, 1H), 8.03 (t, 2H).

MS m/z: 500 (M+1).

(±)-Cis-N-[1-(4-fluoro-benzoyl)-2-methyl-1,2,3,4-tetrahydro-quinolin-4-yl]-2-hydroxy-N-phenyl-acetamide (A-31)

(±)-N-[1-(4-fluoro-benzoyl)-2-methyl-1,2,3,4-tetrahydro-quinolin-4-yl]-2-hydroxy-N-phenyl-acetamide was made following general procedure A substituting 4-fluorobenzoyl chloride for 2-furoyl chloride and acetoxyacetyl chloride for acetyl chloride.

$^1$H-NMR (CDCl$_3$) δ: 1.13 (d, 3H), 1.22 (m, 1H), 2.39 (m, 1H), 3.42 (s, 1H), 3.85 (d, 1H), 4.04 (d, 1H), 4.77 (sextet, 1H), 5.54 (bs, 1H), 6.49 (d, 1H), 6.85 (t, 2H), 6.94 (t, 1H), 7.18–7.27 (m, 5H), 7.33 (d, 1H), 7.43 (s, 3H).

MS m/z: 419 (M+1).

(±)-Cis-N-[1-(1H-indole-2-carbonyl)-2-methyl-1,2,3,4-tetrahydro-quinolin-4-yl]-N-phenyl-propionamide (A-32)

(±)-Cis-N-[1-(1H-indole-2-carbonyl)-2-methyl-1,2,3,4-tetrahydro-quinolin-4-yl]-N-phenyl-propionamide was made following general procedure A substituting indole-2-carbonyl chloride for 2-furoyl chloride and propionyl chloride for acetyl chloride.

$^1$H-NMR (CDCl$_3$) δ: 1.25 (t, 3H), 1.26 (d, 3H), 1.27 (m, 1H), 2.36 (m, 3H), 4.86 (sextet, 1H), 5.62 (bs, 1H), 5.95 (s, 1H), 7.11 (t, 1H), 7.18 (t, 2H), 7.29 (t, 1H), 7.37 (m, 4H), 7.44–7.55 (m, 5H).

MS m/z: 438 (M+1).

(±)-Cis-N-[2-methyl-1-(4-pyrazol-1-yl-benzoyl)-1,2,3,4-tetrahydro-quinolin-4-yl]-N-phenyl-propionamide (A-33)

(±)-Cis-N-[2-methyl-1-(4-pyrazol-1-yl-benzoyl)-1,2,3,4-tetrahydro-quinolin-4-yl]-N-phenyl-propionamide was made following general procedure A substituting 4-(1H-pyrazol-1-yl)-benzoyl chloride for 2-furoyl chloride and propionyl chloride for acetyl chloride.

$^1$H-NMR (CDCl$_3$) δ: 1.03 (t, 3H), 1.11 (d, 3H), 1.20 (m, 1H), 2.19 (m, 3H), 4.73 (sextet, 1H), 5.62 (bs, 1H), 6.39 (s, 1H), 6.48 (d, 1H), 6.86 (t, 1H), 7.10–7.34 (m, 9H), 7.48 (d, 2H), 7.65 (s, 1H), 7.81 (s, 1H).

MS m/z: 465 (M+1).

(±)-Cis-N-[1-(benzofuran-2-carbonyl)-2-methyl-1,2,3,4-tetrahydro-quinolin-4-yl]-N-phenyl-propionamide (A-34)

(±)-Cis-N-[1-(benzofuran-2-carbonyl)-2-methyl-1,2,3,4-tetrahydro-quinolin-4-yl]-N-phenyl-propionamide was made following general procedure A substituting 2-benzofuran carbonyl chloride for 2-furoyl chloride and propionyl chloride for acetyl chloride.

$^1$H-NMR (CDCl$_3$) δ: 1.04 (t, 3H), 1.07 (d, 3H), 1.18 (m, 1H), 2.19 (m, 3H), 4.69 (sextet, 1H), 5.54 (bs, 1H), 6.41 (d, 1H), 6.70–7.39 (m, 12H), 7.43 (d, 1H).

MS m/z: 439 (M+1).

(±)-Cis-N-[1-(3-chloro-benzoyl)-2-methyl-1,2,3,4-tetrahydro-quinolin-4-yl]-N-phenyl-propionamide (A-35)

(±)-Cis-N-[1-(3-chloro-benzoyl)-2-methyl-1,2,3,4-tetrahydro-quinolin-4-yl]-N-phenyl-propionamide was following general procedure A made substituting 3-chlorobenzoyl chloride for 2-furoyl chloride and propionyl chloride for acetyl chloride.

$^1$H-NMR (CDCl$_3$) δ: 1.09 (t, 3H), 1.12 (d, 3H), 1.22 (m, 1H), 2.23 (m, 3H), 4.73 (sextet, 1H), 5.58 (bs, 1H), 6.46 (d, 1H), 6.78 (d, 1H), 6.88 (t, 1H), 6.98 (t, 1H), 7.15 (t, 1H), 7.18–7.44 (m, 8H).

MS m/z: 433 (M+1).

(±)-Cis-{4-[2-methyl-4-(phenyl-propionyl-amino)-3,4-dihydro-2H-quinoline-1-carbonyl]-phenoxy}-acetic Acid Ethyl Ester (A-36)

(±)-Cis-{4-[2-methyl-4-(phenyl-propionyl-amino)-3,4-dihydro-2H-quinoline-1-carbonyl]-phenoxy}-acetic acid ethyl ester was made from (±)-N-[1-(4-Hydroxy-benzoyl)-2-methyl-1,2,3,4-tetrahydro-quinolin-4-yl]-N-phenyl-propionamide. (±)-N-[1-(4-Methoxy-benzoyl)-2-methyl-1,2,3,4-tetrahydro-quinolin-4-yl]-N-phenyl propionamide (0.147 g) was dissolved in DMF (5 mL) at room temperature. Sodium hydride (60% in oil, 0.021 g) was added and the mixture allowed to stir 30 min. Ethyl 4-bromoacetate (0.065 g) was added and the reaction was allowed to stir over night. Ethanol was added and the reaction was concentrated in vacuo. The crude residue was purified by silica gel chromatography (80/20 hexanes/ethyl acetate—50/50 hexanes ethyl acetate gradient) to afford the product (130 mg, 73%).

$^1$H-NMR (CDCl$_3$) δ: 1.08–1.16 (m, 9H), 1.21 (t, 1H), 2.24 (m, 3H), 4.09 (q, 2H), 4.53 (s, 2H), 4.74 (sextet, 1H), 5.59 (bs, 1H), 6.48 (d, 1H), 6.67 (d, 2H), 6.89 (t, 1H), 7.11–7.37 (m, 9H).

MS m/z: 500 (M+1).

(±)-Cis-N-[1-(4-hydroxy-benzoyl)-2-methyl-1,2,3,4-tetrahydro-quinolin-4-yl]-N-phenyl-propionamide (A-37)

(±)-Cis-N-[1-(4-hydroxy-benzoyl)-2-methyl-1,2,3,4-tetrahydro-quinolin-4-yl]-N-phenyl-propionamide was made from (±)-cis-N-[1-(4-methoxy-benzoyl)-2-methyl-1,2,3,4-tetrahydro-quinolin-4-yl]-N-phenyl-propionamide substituting 3-chlorobenzoyl chloride. (±)-Cis-N-[1-(4-methoxy-benzoyl)-2-methyl-1,2,3,4-tetrahydro-quinolin-4-yl]-N-phenyl-propionamide was (0.548 g, 0.001 mol) was dissolved in dichloromethane and a solution of BBr$_3$ (1.0 M in dichloromethane, 10 mL) was added; the reaction was allowed to stir at room temperature for 4 h or until no starting material remained. The reaction was carefully washed with sat NaHCO$_3$ and brine. The organics were dried over MgSO$_4$, filtered and concentrated under reduced pressure. The phenol was concentrated and the residue was purified by Biotage flash chromatography using 100% EtOAc to give a white solid, 68% yield.

$^1$H-NMR (CDCl$_3$) δ: 1.09 (d, 3H), 1.11 (t, 3H), 1.19 (m, 1H), 2.26 (m, 3H), 4.74 (sextet, 1H), 5.54 (bs, 1H), 6.46 (d, 1H), 6.53 (d, 1H), 6.96 (t, 1H), 7.14–7.40 (m, 9H).

MS m/z: 415 (M+1)

(±)-Cis-N-[1-(4-methoxy-benzoyl)-2-methyl-1,2,3,4-tetrahydro-quinolin-4-yl]-N-phenyl-propionamide (A-38)

(±)-Cis-N-[1-(4-methoxy-benzoyl)-2-methyl-1,2,3,4-tetrahydro-quinolin-4-yl]-N-phenyl-propionamide was made following general procedure A substituting 4-methoxybenzoyl chloride for 2-furoyl chloride and propionyl chloride for acetyl chloride.

$^1$H-NMR (CDCl$_3$) δ: 1.12 (d, 3H), 1.15 (t, 3H), 1.17 (m, 1H), 2.23 (m, 3H), 3.74 (s, 3H), 4.74 (sextet, 1H), 5.61 (bs, 1H), 6.52 (d, 1H), 6.67 (d, 2H), 6.92 (d, 1H), 7.17 (d, 2H), 7.25–7.34 (m, 4H), 7.39 (bs, 3H).

MS m/z: 429 (M+1).

(±)-Cis—{4-[2-Methyl-4-(phenyl-propionyl-amino)-3,4-dihydro-2H-quinoline-1-carbonyl]-phenoxy}-acetic Acid (A-39)

(±)-Cis-{4-[2-methyl-4-(phenyl-propionyl-amino)-3,4-dihydro-2H-quinoline-1-carbonyl]-phenoxy}-acetic acid was made from (±)-cis-{4-[2-methyl-4-(phenyl-propionyl-amino)-3,4-dihydro-2H-quinoline-1-carbonyl]-phenoxy}-acetic acid ethyl ester. (±)-Cis-{4-[2-methyl-4-(phenyl-propionyl-amino)-3,4-dihydro-2H-quinoline-1-carbonyl]- phenoxy)}-acetic acid ethyl ester was dissolved in ethanol (5 mL) and 0.5 mL of 1N NaOH was added at room temperature. The reaction was allowed to stir for 4 h. The ethanol was removed in vacuo and the aqueous solution was acidified with 1N HCl to give a white precipitate which was filtered to give the desired product in 88% yield.

$^1$H-NMR (CDCl$_3$) δ: 1.12 (d, 3H), 1.16 (t, 3H), 1.15 (m, 1H), 2.28 (m, 3H), 4.52 (s, 2H), 4.74 (sextet, 1H), 5.63 (bs, 1H), 6.50 (d, 1H), 6.68 (d, 2H), 6.91 (t, 1H), 7.16 (t, 1H), 7.18 (d, 2H), 7.26–7.32 (m, 4H), 7.40 (bs, 2H).

MS m/z: 473.0 (M+1).

(±)-Cis-N-{2-methyl-1-[4-(2-morpholin-4-yl-ethoxy)-benzoyl]-1,2,3,4-tetrahydro-quinolin-4-yl}-N-phenyl-propionamide (A-40)

(±)-Cis-N-{2-methyl-1-[4-(2-morpholin-4-yl-ethoxy)-benzoyl]-1,2,3,4-tetrahydro-quinolin-4-yl}-N-phenyl-propionamide was made from (±)-cis-N-[1-(4-hydroxy-benzoyl)-2-methyl-1,2,3,4-tetrahydro-quinolin-4-yl]-N-phenyl-propionamide. (±)-Cis-N-[1-(4-methoxy-benzoyl)-2-methyl-1,2,3,4-tetrahydro-quinolin-4-yl]-N-phenyl-propionamide was dissolved in DMF (5 mL) at room temperature. Sodium hydride (60% in oil, 0.061 g) was added and the mixture allowed to stir 30 min. 4-(2-chloroethyl)morpholine hydrochloride (0.143 g) was added and the reaction was allowed to stir over night. Ethanol was added and the reaction was concentrated in vacuo. The residue was partition between ethyl acetate and water, then extracted 3× with ethyl acetate, dried over MgSO$_4$, filtered and concentrated. The crude residue was purified by silica gel chromatography (2/98 methanol/dichloromethane—5/95 methanol/dichloromethane gradient) to afford the product (200 mg).

$^1$H-NMR (CDCl$_3$) δ: 1.09 (d, 3H), 1.12 (m, 4H), 1.22 (s, 4H), 2.23 (m, 3H), 2.50 (s, 4H), 2.70 (m, 2H), 4.01 (t, 2H), 4.70 (sextet, 1H), 5.59 (bs, 1H), 6.49 (d, 1H), 6.64 (d, 2H), 6.89 (t, 1H), 7.13 (d, 2H), 7.23–7.36 (m, 7H).

MS m/z: 528.1 (M+1).

(±)-Cis-N-[1-(4-carbamoylmethoxy-benzoyl)-2-methyl-1,2,3,4-tetrahydro-quinolin-4-yl]-N-phenyl-propionamide (A-41)

(±)-Cis-N-[1-(4-carbamoylmethoxy-benzoyl)-2-methyl-1,2,3,4-tetrahydro-quinolin-4-yl]-N-phenyl-propionamide was made from (±)-cis-N-[1-(4-hydroxy-benzoyl)-2-methyl-1,2,3,4-tetrahydro-quinolin-4-yl]-N-phenyl-propionamide. (±)-Cis-N-[1-(4-hydroxy-benzoyl)-2-methyl-1,2,3,4-tetrahydro-quinolin-4-yl]-N-phenyl-propionamide (0.120 g) was dissolved in DMF (5 mL) at room temperature. Sodium hydride (60% in oil, 0.70 g) was added and the mixture allowed to stir 30 min. 2-Bromoacetamide (0.320 g) was added and the reaction was allowed to stir over night. Ethanol was added and the reaction was concentrated in vacuo. The residue was partitioned between ethyl acetate and water, then extracted 3× with ethyl acetate, dried over MgSO$_4$, filtered and concentrated down. The crude residue was purified by silica gel chromatography (2/98 methanol/dichloromethane—10/90 methanol/dichloromethane gradient) to afford the product (20 mg, 15%).

$^1$H-NMR (CDCl$_3$) δ: 1.12 (d, 3H), 1.14 (t, 3H), 1.24 (t, 1H), 2.25 (m, 3H), 4.42 (s, 2H), 4.73 (sextet, 1H), 5.61 (bs, 1H), 5.79 (s, 1H), 6.49 (d, 2H), 6.70 (d, 2H), 6.92 (t, 1H), 7.14–7.39 (m, 8H).

MS m/z: 472.0 (M+1).

(±)-Cis-N-{1-[4-(2-hydroxy-2-methyl-propoxy)-benzoyl]-2-methyl-1,2,3,4-tetrahydro-quinolin-4-yl}-N-phenyl-propionamide (A-42)

(±)-Cis-N-{1-[4-(2-hydroxy-2-methyl-propoxy)-benzoyl]-2-methyl-1,2,3,4-tetrahydro-quinolin-4-yl}-N-phenyl-propionamide was made from (±)-Cis-{4-[2-methyl-4-(phenyl-propionyl-amino)-3,4-dihydro-2H-quinoline-1-carbonyl]-phenoxy}-acetic acid ethyl ester. (±)-Cis-{4-[2-methyl-4-(phenyl-propionyl-amino)-3,4-dihydro-2H-quinoline-1-carbonyl]-phenoxy}-acetic acid ethyl ester (0.170 g) was dissolved in THF and cooled to 0° C. Methylmagnesium bromide (3.0M sol in diethyl ether, 0.5 mL) was added and the reaction was allowed to stir at 0° C. for 30 min. The reaction was quenched with a saturated solution of ammonium chloride and diluted with ethyl acetate. The organics were seperated and washed with brine, dried over MgSO$_4$, filtered and concentrated down. The crude residue was purified by silica gel chromatography (50/50 hexanes/ethyl acetate—75/25 hexanes ethyl acetate gradient) to afford the product (132 mg, 80%).

$^1$H-NMR (CDCl$_3$) δ: 1.10 (d, 3H), 1.14 (t, 3H), 1.23 (t, 1H), 1.29 (s, 6H), 2.24 (m, 3H), 3.70 (s, 2H), 4.74 (sextet, 1H), 5.61 (bs, 1H), 6.50 (d, 1H), 6.66 (d, 2H), 6.91 (t, 1H), 7.13 (t, 1H), 7.14 (d, 2H), 7.25 (d, 1H), 7.32 (d, 1H), 7.37 (bs, 4H).

MS m/z: 487.1 (M+1).

(±)-Cis-N-[1-(4-dimethylcarbamoylmethoxy-benzoyl)-2-methyl-1,2,3,4-tetrahydro-quinolin-4-yl]-N-phenyl-propionamide (A-43)

(±)-Cis-N-[1-(4-dimethylcarbamoylmethoxy-benzoyl)-2-methyl-1,2,3,4-tetrahydro-quinolin-4-yl]-N-phenyl-propionamide was made from (±)-cis-{4-[2-methyl-4-(phenyl-propionyl-amino)-3,4-dihydro-2H-quinoline-1-carbonyl]-phenoxy}-acetic acid. (±)-Cis-{-4-[2-Methyl-4-(phenyl-propionyl-amino)-3,4-dihydro-2H-quinoline-1-carbonyl]-phenoxy}-acetic acid (0.146 g) was dissolved in THF (2 mL) at room temperature. HOBt (0.063 g), EDCI (0.071 g), and dimethylamine (2.0M solution in THF, 0.162 mL) was added along with 2 drops of DMF and stirred at room temperature for 11 h. The reaction was diluted with ethyl acetate, washed with 1N NaOH, 1N HCl and brine. The organics were dried over MgSO$_4$, filtered and concentrated down. The crude residue was purified by silica gel chromatography (100% ethyl acetate) to afford the product (84 mg, 54%).

$^1$H-NMR (CDCl$_3$) δ: 1.10 (d, 3H), 1.13 (t, 3H), 1.22 (t, 1H), 2.23 (m, 3H), 2.94 (s, 3H), 3.00 (s, 3H), 4.60 (s, 2H), 4.71 (sextet, 1H), 5.58 (bs, 1H), 6.49 (d, 1H), 6.70 (d, 2H), 6.89 (t, 1H), 7.13 (d, 1H), 7.24 (d, 2H), 7.30 (d, 1H), 7.37 (bs, 7H).

MS m/z: 500.1 (M+1).

(±)-Cis-N-[1-(3-dimethylamino-benzoyl)-2-methyl-1,2,3,4-tetrahydro-quinolin-4-yl]-N-phenyl-propionamide (A-45)

(±)-Cis-N-[1-(3-dimethylamino-benzoyl)-2-methyl-1,2,3,4-tetrahydro-quinolin-4-yl]-N-phenyl-propionamide was made following general procedure A, substituting 3-dimethylaminobenzoyl chloride for 2-furoyl chloride and propionyl chloride for acetyl chloride.

$^1$H-NMR (300 MHz, CDCl$_3$) δ: 1.11–1.24 (m, 7H), 2.12–2.40 (m, 3H), 2.83 (s, 6H), 4.80 (ddd, 1H), 5.59 (br s, 1H), 6.49 (d, 1H), 6.55–6.69 (m, 3H), 6.92 (dd, 1H), 7.00 (ddd, 1H), 7.15 (ddd, 1H), 7.23–7.34 (m, 3H), 7.35–7.44 (m, 3H).

MS m/z: 442 (M+1).

(±)-Cis-N-[1-(4-dimethylamino-benzoyl)-2-methyl-1,2,3,4-tetrahydro-quinolin-4-yl]-N-phenyl-propionamide (A-46)

(±)-Cis-N-[1-(4-dimethylamino-benzoyl)-2-methyl-1,2,3,4-tetrahydro-quinolin-4-yl]-N-phenyl-propionamide was made following general procedure A substituting 4-dimethylaminobenzoyl chloride for 2-furoyl chloride and propionyl chloride for acetyl chloride.

$^1$H-NMR (300 MHz, CDCl$_3$) δ: 1.09–1.28 (m, 7H), 2.12–2.39 (m, 3H), 2.93 (s, 6H), 4.73 (ddd, 1H), 5.61 (br s, 1H), 6.47 (d, 2H), 6.62 (d, 1H), 6.96 (dd, 1H), 7.12–7.20 (m, 3H), 7.26–7.36 (m, 3H), 7.38–7.46 (m, 3H).

MS m/z: 442 (M+1).

(±)-Cis-N-[2-methyl-1-(pyridine-3-carbonyl)-1,2,3,4-tetrahydro-quinolin-4-yl]-N-phenyl-propionamide (A-47)

(±)-Cis-[2-ethyl-1-(pyridine-3-carbonyl)-1,2,3,4-tetrahydro-quinolin-4-yl]-N-phenyl-propionamide was made following general procedure A substituting 3-pyridinyl chloride for 2-furoyl chloride and propionyl chloride for acetyl chloride.

$^1$H-NMR (300 MHz, CDCl$_3$) δ: 1.08–1.32 (m, 7H), 2.16–2.44 (m, 3H), 4.84 (ddd, 1H), 5.62 (br s, 1H), 6.53 (d, 1H), 6.97 (dd, 1H), 7.11 (dd, 1H), 7.20–7.51 (m, 8H), 8.55 (dd, 1H), 8.68 (br s, 1H).

MS m/z: 400 (M+1).

(±)-Cis-N-[1-(4-fluoro-benzoyl)-2-methyl-1,2,3,4-tetrahydro-quinolin-4-yl]-4-methoxy-N-phenyl-butyramide (A-48)

(±)-Cis-N-[1-(4-fluoro-benzoyl)-2-methyl-1,2,3,4-tetrahydro-quinolin-4-yl]-4-methoxy-N-phenyl-butyramide was made following general procedure A substituting 4-fluorobenzoyl chloride for 2-furoyl chloride and 4-methoxy-butyryl chloride for acetyl chloride.

$^1$H-NMR (300 MHz, CDCl$_3$) δ: 1.08–1.20 (m, 4H), 1.86–2.02 (m, 2H), 2.21–2.41 (m, 3H), 3.26 (m, 3H), 3.28–3.44 (m, 2H), 4.76 (ddd, 1H), 5.64 (br s, 1H), 6.43 (d, 1H), 6.83–6.96 (m, 3H), 7.17–7.34 (m, 5H), 7.36–7.51 (m, 4H).

MS m/z: 461 (M+1).

(±)-Cis-2-(acetyl-methyl-amino)-N-[1-(4-fluoro-benzoyl)-2-methyl-1,2,3,4-tetrahydro-quinolin-4-yl]-N-phenyl-acetamide (A-49)

(±)-Cis-2-(acetyl-methyl-amino)-N-[1-(4-fluoro-benzoyl)-2-methyl-1,2,3,4-tetrahydro-quinolin-4-yl]-N-phenyl-acetamide was made following general procedure A substituting 4-fluorobenzoyl chloride for 2-furoyl chloride and (acetyl-methyl-amino)-acetyl chloride for acetyl chloride.

$^1$H-NMR (300 MHz, CDCl$_3$) δ: 1.10–1.18 (m, 4H), 2.13 (s, 3H), 2.27–2.43 (m, 1H), 3.14 (m, 3H), 3.77 (d, 1H), 4.03 (d, 1H), 4.76 (ddd, 1H), 5.55 (br s, 1H), 6.45 (d, 1H), 6.81–6.95 (m, 3H), 7.15–7.26 (m, 3H), 7.31–7.49 (m, 5H), 7.54 (d, 1H).

MS m/z=474 (M+1).

(±)-Cis-cyclohexanecarboxylic acid [1-(3-methoxy-benzoyl)-2-methyl-1,2,3,4-tetrahydro-quinolin-4-yl]-phenylamide (A-54)

(±)-Cis-cyclohexanecarboxylic acid [1-(3-methoxy-benzoyl)-2-methyl-1,2,3,4-tetrahydro-quinolin-4-yl]-phenylamide was made following general procedure A substituting 3-methoxybenzoyl chloride for 2-furoyl chloride and cyclohexane carbonyl chloride for acetyl chloride.

$^1$H-NMR (CDCl$_3$) δ: 0.8 (8H, m), 1.5–1.8 (5H, m), 2.0–2.4 (3H, m), 3.7 (3H, d), 4.8 (1H, m), 5.6 (1H, d), 6.2–6.6 (2H, m), 6.6–7.5 (11H, m).

MS m/z: 483 (M+1).

(±)-Cis-isoxazole-5-carboxylic acid [1-(3-methoxy-benzoyl)-2-methyl-1,2,3,4-tetrahydro-quinolin-4-yl]-phenylamid (A-55)

(±)-Cis-isoxazole-5-carboxylic acid [1-(3-methoxy-benzoyl)-2-methyl-1,2,3,4-tetrahydro-quinolin-4-yl]-phenylamide was made following general procedure A substituting 3-methoxybenzoyl chloride for 2-furoyl chloride and isoxazole-5-carbonyl chloride for acetyl chloride.

$^1$H-NMR (CDCl$_3$) δ: 1.2 (3H, d), 1.2 (1H, m), 2.4 (1H, m), 3.6 (3H, s), 4.9 (1H, m), 5.8 (1H, m), 6.4 (1H, d), 6.7–7.7 (12H, m), 8.2 (1H, s), 8.4 (1H, m).

MS m/z: 468 (M+1).

(±)-Cis-N-[1-(furan-3-carbonyl)-2-methyl-1,2,3,4-tetrahydro-quinolin-4-yl]-N-phenyl-acetamide (A-56)

(±)-Cis-N-[1-(furan-3-carbonyl)-2-methyl-1,2,3,4-tetrahydro-quinolin-4-yl]-N-phenyl-acetamide was made following general procedure A substituting 3-furoyl chloride for 2-furoyl chloride.

$^1$H-NMR (CDCl$_3$) δ: 1.1 (3H, d), 1.2 (1H, m), 2.0 (3H, s), 2.2 (1H, m), 4.7 (1H, m), 5.5 (1H, m), 5.9 (1H, s), 6.9 (1H, d), 7.1 (2H, m) 7.2–7.4 (7H, m).

MS m/z: 375 (M+1).

(±)-Cis-N-[1-(3-fluoro-benzoyl)-2-methyl-1,2,3,4-tetrahydro-quinolin-4-yl]-N-phenyl-acetamide (A-61)

(±)-Cis-N-[1-(3-fluoro-benzoyl)-2-methyl-1,2,3,4-tetrahydro-quinolin-4-yl]-N-phenyl-acetamide was made following general procedure A substituting 3-fluorobenzoyl chloride for 2-furoyl chloride.

$^1$H-NMR (CDCl$_3$) δ: 1.1 (3H, d), 1.1 (1H, m), 2.0 (3H, s), 2.3 (1H, m), 4.7 (1H, m), 5.6 (1H, m), 6.4 (1H, d), 6.8 (1H, d), 6.9–7.4 (11H, m).

MS m/z: 403 (M+1).

(±)-Cis-N-[1-(3,4-difluoro-benzoyl)-2-methyl-1,2,3,4-tetrahydro-quinolin-4-yl]-N-phenyl-acetamide (A-62)

(±)-Cis-N-[1-(3,4-difluoro-benzoyl)-2-methyl-1,2,3,4-tetrahydro-quinolin-4-yl]-N-phenyl-acetamide was made following general procedure A substituting 3,4-difluorobenzoyl chloride for 2-furoyl chloride.

$^1$H-NMR (CDCl$_3$) δ: 1.1 (3H, d), 1.1 (1H, m), 2.0 (3H, s), 2.3 (1H, m), 4.7 (1H, m), 5.6 (1H, m), 6.5 (1H, d), 6.8–7.0 (4H, d), 7.3–7.5 (7H, m).

MS m/z: 421 (M+1).

(±)-Cis-N-[1-(benzo[b]thiophene-3-carbonyl)-2-methyl-1,2,3,4-tetrahydro-quinolin-4-yl]-N-phenyl-acetamide (A-63)

(±)-Cis-N-[1-(benzo[b]thiophene-3-carbonyl)-2-methyl-1,2,3,4-tetrahydro-quinolin-4-yl]-N-phenyl-acetamide was made following general procedure A substituting benzo[b]thiophene-3-carbonyl chloride for 2-furoyl chloride.

$^1$H-NMR (CDCl$_3$) δ: 1.2 (3H, d), 1.3 (1H, m), 2.0 (3H, s), 2.3 (1H, m), 4.9 (1H, m), 5.7 (1H, m), 6.5 (1H, d), 6.8 (1H, m), 7.1–7.5 (10H, m), 7.8 (1H, d), 8.0 (1H, d).

MS m/z: 442 (M+2).

(±)-Cis-N-[1-(3,5-dimethyl-thiophene-2-carbonyl)-2-methyl-1,2,3,4-tetrahydro-quinolin-4-yl]-N-phenyl-acetamide (A-64)

(±)-Cis-N-[1-(3,5-dimethyl-thiophene-2-carbonyl)-2-methyl-1,2,3,4-tetrahydro-quinolin-4-yl]-N-phenyl-acetamide was made following general procedure A substituting 3,5-dimethyl-thiophene-2-carbonyl chloride for 2-furoyl chloride.

$^1$H-NMR (CDCl$_3$) δ: 1.1 (3H, d), 1.1 (1H, m), 1.7 (3H, s), 2.0 (3H, d), 2.0 (1H, m), 2.3 (3H, s), 4.7 (1H, m), 5.5 (1H, m), 6.2 (1H, s), 6.7 (1H, d), 7.0 (1H, t), 7.1–7.4 (7H, m).

MS m/z: 419 (M+1).

(±)-Cis-N-[1-(3-fluoro-benzoyl)-2-methyl-1,2,3,4-tetrahydro-quinolin-4-yl]-N-phenyl-isobutyramide (A-65)

(±)-Cis-N-[1-(3-fluoro-benzoyl)-2-methyl-1,2,3,4-tetrahydro-quinolin-4-yl]-N-phenyl-isobutyramide was made following general procedure A substituting 3-fluorobenzoyl chloride for 2-furoyl chloride and isopropyl chloride for acetyl chloride.

$^1$H-NMR (CDCl$_3$): 1.0–1.2 (10H, m), 2.3 (1H, m), 2.7 (1H, m), 4.8 (1H, m), 5.6 (1H, m), 6.5 (1H, m), 6.8–7.6 (12H, m).

MS m/z: 431 (M+1).

(±)-Cis-N-[1-(4-fluoro-benzoyl)-2-methyl-1,2,3,4-tetrahydro-quinolin-4-yl]-N-phenyl-isobutyramide (A-66)

(±)-Cis-N-[1-(4-fluoro-benzoyl)-2-methyl-1,2,3,4-tetrahydro-quinolin-4-yl]-N-phenyl-isobutyramide was made following general procedure A substituting 4-fluorobenzoyl chloride for 2-furoyl chloride and isopropyl chloride for acetyl chloride.

$^1$H-NMR (CDCl$_3$) δ: 1.0–1.2 (10H, m), 2.3 (1H, m), 2.6 (1H, m), 4.8 (1H, m), 5.6 (1H, m), 6.5 (1H, d), 6.8–7.0 (3H, m), 7.1–7.4 (9H, m).

MS m/z: 431 (M+1).

(±)-Cis-N-[1-(2,4-dimethyl-thiazole-5-carbonyl)-2-methyl-1,2,3,4-tetrahydro-quinolin-4-yl]-N-phenyl-acetamide (A-67)

(±)-Cis-N-[1-(2,4-dimethyl-thiazole-5-carbonyl)-2-methyl-1,2,3,4-tetrahydro-quinolin-4-yl]-N-phenyl-acetamide was made following general procedure A substituting 2,4-dimethyl-thiazole-5-carbonyl chloride for 2-furoyl chloride.

$^1$H-NMR (CDCl$_3$) δ: 1.2 (3H, d), 1.2 (1H, m), 2.0 (3H, s), 2.2 (3H, s), 2.3 (1H, m), 2.6 (3H, s), 4.7 (1H, m), 5.4 (1H, m), 6.8 (1H, d), 7.1 (2H, m), 7.2–7.5 (6H, m).

MS m/z: 420 (M+1).

(±)-Cis-N-[1-(furan-2-carbonyl)-2-methyl-1,2,3,4-tetrahydro-quinolin-4-yl]-N-phenyl-propionamide (A-68)

(±)-Cis-N-[1-(furan-2-carbonyl)-2-methyl-1,2,3,4-tetrahydro-quinolin-4-yl]-N-phenyl-propionamide was made following general procedure A substituting propionyl chloride for acetyl chloride.

$^1$H-NMR (CDCl$_3$) δ: 1.0–1.2 (7H, m), 2.2–2.4 (3H, m), 4.7 (1H, m), 5.4 (1H, m), 6.2 (2H, m), 6.8 (1H, d), 7.0–7.4 (9H, m).

MS m/z: 389 (M+1).

(±)-Cis-N-[1-(4-fluoro-benzoyl)-2-methyl-1,2,3,4-tetrahydro-quinolin-4-yl]-N-phenyl-butyramide (A-69)

(±)-Cis-N-[1-(4-fluoro-benzoyl)-2-methyl-1,2,3,4-tetrahydro-quinolin-4-yl]-N-phenyl-butyramide was made following general procedure A substituting 4-fluorobenzoyl chloride for 2-furoyl chloride and butyryl chloride for acetyl chloride.

$^1$H-NMR (CDCl$_3$) δ: 0.8 (3H, t), 1.2 (3H, d), 1.2 (1H, m), 1.5 (2H, m), 2.0 (3H, m), 4.7 (1H, m), 5.4 (1H, m), 6.5 (1H, d), 6.6–6.8 (4H, m), 6.9–7.3 (8H, m).

MS m/z: 432 (M+2).

(±)-Cis-N-[1-(4-fluoro-benzoyl)-2-methyl-1,2,3,4-tetrahydro-quinolin-4-yl]-2-phenoxy-N-phenyl-acetamide (A-72)

(±)-Cis-N-[1-(4-fluoro-benzoyl)-2-methyl-1,2,3,4-tetrahydro-quinolin-4-yl]-2-phenoxy-N-phenyl-acetamide was made following general procedure A substituting 4-fluorobenzoyl chloride for 2-furoyl chloride and 1-chloro-3-phenoxy-propan-2-one for acetyl chloride.

$^1$H-NMR (CDCl$_3$) δ: 1.1 (3H, d), 1.1 (1H, m), 2.3 (1H, m), 4.5 (2H, s), 4.7 (1H, m), 5.7 (1H, m), 6.4 (1H, d), 6.7–6.9 (7H, m), 7.1–7.4 (9H, m), 10.0 (1H, m).

MS m/z: 496 (M+2).

(±)-Cis-N-[1-(4-fluoro-benzoyl)-2-methyl-1,2,3,4-tetrahydro-quinolin-4-yl]-3-N-diphenyl-propionamide (A-73)

(±)-Cis-N-[1-(4-Fluoro-benzoyl)-2-methyl-1,2,3,4-tetrahydro-quinolin-4-yl]-3-N-diphenyl-propionamide was made following general procedure A substituting 4-fluorobenzoyl chloride for 2-furoyl chloride and 3-phenylpropionyl chloride for acetyl chloride.

$^1$H-NMR (CDCl$_3$) δ: 1.2 (3H, d), 1.2 (1H, m), 2.2 (1H, m), 2.7 (2H, t), 3.1 (2H, t), 4.7 (1H, m), 5.7 (1H, m), 6.6 (1H, d), 6.8–7.6 (17H, m).

MS m/z: 494 (M+2).

(±)-Cis-N-[1-(benzo[b]thiophene-2-carbonyl)-2-methyl-1,2,3,4-tetrahydro-quinolin-4-yl]-N-phenyl-propionamide (A-75)

(±)-Cis-N-[1-(benzo[b]thiophene-2-carbonyl)-2-methyl-1,2,3,4-tetrahydro-quinolin-4-yl]-N-phenyl-propionamide was made following general procedure A substituting benzo[b]thiophene-2-carbonyl chloride for 2-furoyl chloride and propionyl chloride for acetyl chloride.

$^1$H-NMR (CDCl$_3$) δ: 1.1–1.2 (7H, m), 2.1–2.3 (3H, m), 4.8 (1H, m), 5.6 (1H, m), 6.9 (1H, d), 7.0 (2H, m), 7.2–7.5 (9H, m), 7.6 (1H, d), 7.8 (1H, d).

MS m/z: 456 (M+2).

(±)-Cis-N-[1-(4-cyano-benzoyl)-2-methyl-1,2,3,4-tetrahydro-quinolin-4-yl]-N-phenyl-propionamide (A-76)

(±)-Cis-N-[11-(4-cyano-benzoyl)-2-methyl-1,2,3,4-tetrahydro-quinolin-4-yl]-N-phenyl-propionamide was made following general procedure A substituting 4-cyanobenzoyl chloride for 2-furoyl chloride and propionyl chloride for acetyl chloride.

$^1$H-NMR (CDCl$_3$) δ: 1.1–1.3 (7H, m), 2.2–2.4 (3H, m), 4.8 (1H, m), 5.6 (1H, m), 6.4 (1H, d), 6.9 (1H, t), 7.2–7.6 (11H, m).

MS m/z: 424 (M+1).

(±)-Cis-N-[1-(3-fluoro-4-methoxy-benzoyl)-2-methyl-1,2,3,4-tetrahydro-quinolin-4-yl]-N-phenyl-propionamide (A-77)

(±)-Cis-N-[1-(3-fluoro-4-methoxy-benzoyl)-2-methyl-1,2,3,4-tetrahydro-quinolin-4-yl]-N-phenyl-propionamide was made following general procedure A substituting 3-fluoro-4-methoxybenzoyl chloride for 2-furoyl chloride and propionyl chloride for acetyl chloride.

$^1$H-NMR (CDCl$_3$) δ: 1.1–1.2 (7H, m), 2.1–2.3 (3H, m), 3.8 (3H, s), 4.8 (1H, m), 5.6 (1H, m), 6.5 (1H, d), 6.7 (1H, t), 6.8 (1H, d), 6.9 (1H, t), 7.2–7.5 (8H, m).

MS m/z: 447 (M+1).

(±)-Cis-N-[1-(4-methoxy-3-methyl-benzoyl)-2-methyl-1,2,3,4-tetrahydro-quinolin-4-yl]-N-phenyl-propionamide (A-78)

(±)-Cis-N-[1-(4-methoxy-3-methyl-benzoyl)-2-methyl-1,2,3,4-tetrahydro-quinolin-4-yl]-N-phenyl-propionamide was made following general procedure A substituting 3-methyl-4-methoxybenzoyl chloride for 2-furoyl chloride and propionyl chloride for acetyl chloride.

$^1$H-NMR (CDCl$_3$) δ: 0.9–1.1 (7H, m), 1.8–2.2 (6H, m), 3.8 (3H, s), 4.8 (1H, m), 5.6 (1H, m), 6.5 (2H, m), 6.7–7.8 (10H, m).

MS m/z: 443 (M+1).

(±)-Cis-N-[1-(4-ethoxy-benzoyl)-2-methyl-1,2,3,4-tetrahydro-quinolin-4-yl]-N-phenyl-propionamide (A-79)

(±)-Cis-N-[1-(4-ethoxy-benzoyl)-2-methyl-1,2,3,4-tetrahydro-quinolin-4-yl]-N-phenyl-propionamide was made following general procedure A substituting 4-ethoxybenzoyl chloride for 2-furoyl chloride and propionyl chloride for acetyl chloride.

$^1$H-NMR (CDCl$_3$) δ: 1.1–1.3 (7H, m), 1.4 (3H, t), 2.2–2.4 (3H, m), 4.0 (2H, q), 4.8 (1H, m), 5.6 (1H, m), 6.5 (1H, d), 6.9 (2H, d), 6.9 (1H, t), 7.2–7.6 (9H, m).

MS m/z: 443 (M+1).

(±)-Cis-N-[2-methyl-1-(4-trifluoromethyl-benzoyl)-1,2,3,4-tetrahydro-quinolin-4-yl]-N-phenyl-propionamide (A-80)

(±)-Cis-N-[2-methyl-1-(4-trifluoromethyl-benzoyl)-1,2,3,4-tetrahydro-quinolin-4-yl]-N-phenyl-propionamide was made following general procedure A substituting 4-trifluoromethylbenzoyl chloride for 2-furoyl chloride and propionyl chloride for acetyl chloride.

$^1$H-NMR (CDCl$_3$) δ: 1.1–1.3 (7H, m), 2.2–2.4 (3H, m), 4.8 (1H, m), 5.6 (1H, m), 6.4 (1H, d), 6.9 (1H, t), 7.2–7.6 (11H, m).

MS m/z: 319 (M−147).

(±)-Cis-N-[1-(4-benzyl-morpholine-2-carbonyl)-2-methyl-1,2,3,4-tetrahydro-quinolin-4-yl]-N-phenyl-propionamide (A-81)

(±)-Cis-N-[1-(4-benzyl-morpholine-2-carbonyl)-2-methyl-1,2,3,4-tetrahydro-quinolin-4-yl]-N-phenyl-propionamide was made following general procedure A substituting 4-benzyl-morpholine-2-carbonyl chloride for 2-furoyl chloride and propionyl chloride for acetyl chloride.

$^1$H-NMR (CDCl$_3$) δ: 1.1–1.2 (7H, m), 2.1–2.3 (4H, m), 2.6 (3H, m), 3.5 (2H, m), 3.9 (1H, m), 4.2 (1H, m), 4.7 (1H, m), 5.2 (1H, m), 7.1–7.5 (14H, m).

MS m/z: 498 (M+1).

(±)-Cis-N-[1-(4-ethyl-morpholine-2-carbonyl)-2-methyl-1,2,3,4-tetrahydro-quinolin-4-yl]-N-phenyl-propionamide (A-82)

(±)-Cis-N-[1-(4-Ethyl-morpholine-2-carbonyl)-2-methyl-1,2,3,4-tetrahydro-quinolin-4-yl]-N-phenyl-propionamide was made following general procedure A substituting 4-ethyl-morpholine-2-carbonyl chloride for 2-furoyl chloride and propionyl chloride for acetyl chloride.

$^1$H-NMR (CDCl$_3$) δ: 1.1–1.2 (10H, m), 2.1–2.4 (6H, m), 2.6 (2H, m), 3.6 (1H, t), 3.9 (1H, m), 4.2 (1H, m), 4.7 (1H, m), 5.2 (1H, m), 7.2–7.5 (14H, m).

MS m/z: 436 (M+1).

(±)-Cis-N-[2-methyl-1-(4-phenoxy-benzoyl)-1,2,3,4-tetrahydro-quinolin-4-yl]-N-phenyl-propionamide (A-83)

(±)-Cis-N-[2-methyl-1-(4-phenoxy-benzoyl)-1,2,3,4-tetrahydro-quinolin-4-yl]-N-phenyl-propionamide was made following general procedure A substituting 4-phenoxy benzoyl chloride for 2-furoyl chloride and propionyl chloride for acetyl chloride.

$^1$H-NMR (CDCl$_3$) δ: 1.0–1.2 (7H, m), 2.2–2.4 (3H, m), 4.7 (1H, m), 5.6 (1H, m), 6.5 (1H, d), 6.5 (1H, d), 6.8 (2H, d), 7.0–7.4 (15H, m).

MS m/z: 491 (M+1).

(±)-Cis-N-[1-(4-fluoro-3-methoxy-benzoyl)-2-methyl-1,2,3,4-tetrahydro-quinolin-4-yl]-N-phenyl-propionamide (A-84)

(±)-Cis-N-[1-(4-fluoro-3-methoxy-benzoyl)-2-methyl-1,2,3,4-tetrahydro-quinolin-4-yl]-N-phenyl-propionamide was made following general procedure A substituting 4-fluoro-3-methoxy benzoyl chloride for 2-furoyl chloride and propionyl chloride for acetyl chloride.

$^1$H-NMR (CDCl$_3$) δ: 1.0–1.2 (7H, m), 2.2–2.4 (3H, m), 3.6 (3H, s), 4.7 (1H, m), 5.6 (1H, m), 6.4 (1H, d), 6.7–6.9 (4H, m), 7.1–7.4 (7H, m).

MS m/z: 447 (M+1).

(±)-Cis-N-[1-(4-methoxy-3-trifluoromethyl-benzoyl)-2-methyl-1,2,3,4-tetrahydro-quinolin-4-yl]-N-phenyl-propionamide (A-85)

(±)-Cis-N-[1-(4-methoxy-3-trifluoromethyl-benzoyl)-2-methyl-1,2,3,4-tetrahydro-quinolin-4-yl]-N-phenyl-propionamide was made following general procedure A substituting 4-methoxy-3-trifluoromethyl benzoyl chloride for 2-furoyl chloride and propionyl chloride for acetyl chloride.

$^1$H-NMR (CDCl$_3$): 1.0–1.2 (7H, m), 2.2–2.4 (3H, m), 3.8 (3H, s), 4.7 (1H, m), 5.6 (1H, m), 6.5 (1H, d), 6.7 (1H, d), 7.0 (2H, m), 7.2–7.4 (7H, m), 7.8 (1H, s).

MS m/z: 497 (M+1).

(±)-Cis-N-[1-(2,3-dihydro-benzofuran-5-carbonyl)-2-methyl-1,2,3,4-tetrahydro-quinolin-4-yl]-N-phenyl-propionamide (A-86)

(±)-Cis-N-[1-(2,3-dihydro-benzofuran-5-carbonyl)-2-methyl-1,2,3,4-tetrahydro-quinolin-4-yl]-N-phenyl-propionamide was made following general procedure A substituting 2,3-dihydro-benzofuran-5-carbonyl chloride for 2-furoyl chloride and propionyl chloride for acetyl chloride.

$^1$H-NMR (CDCl$_3$): 1.1–1.2 (7H, m), 2.1–2.3 (3H, m), 4.5 (2H, t), 4.8 (1H, m), 5.6 (1H, m), 6.5 (2H, m), 6.9 (2H, m), 7.1–7.4 (7H, m).

MS m/z: 441 (M+1).

(±)-Cis-N-{2-methyl-1-[4-(3-methyl-ureido)-benzoyl]-1,2,3,4-tetrahydro-quinolin-4-yl}-N-phenyl-acetamide (A-87)

(±)-Cis-N-{2-methyl-1-[4-(3-methyl-ureido)-benzoyl]-1,2,3,4-tetrahydro-quinolin-4-yl}-N-phenyl-acetamide was made from (±)-cis-N-[1-(4-amino-benzoyl)-2-methyl-1,2,3,4-tetrahydro-quinolin-4-yl]-N-phenyl-acetamide. (±)-Cis-N-[1-(4-amino-benzoyl)-2-methyl-1,2,3,4-tetrahydro-quinolin-4-yl]-N-phenyl-propionamide was made following general procedure A, substituting 4-nitrobenzoyl chloride for 2-furoyl chloride and propionyl chloride for acetyl chloride. The resulting nitro analog was reduced with Pd/C (10%) in ethanol in a Parr shaker at 35 psi. (±)-Cis-N-[1-(4-amino-benzoyl)-2-methyl-1,2,3,4-tetrahydro-quinolin-4-yl]-N-phenyl-acetamide (150 mg, 0.376 mmol) was dissolved in 10 ml toluene and 64 mg methylisocyanate (1.13 mmol) was added. The resulting reaction mixture was stirred at room temperature for 2 hours, then was heated to 50° C. overnight. The mixture was concentrated under vacuum. The residue was purified by silica gel chromatography, eluting with methanol-dichloromethane (1:19) to give the title compound (87 mg, 51%).

$^1$H-NMR (CDCl$_3$) δ: 1.1 (3H, d), 1.1 (1H, m), 2.0 (3H, s), 2.3 (1H, m), 2.7 (3H, s), 4.7 (1H, m), 5.1 (2H, m), 5.6 (1H, m), 6.5 (1H, d), 6.9–7.0 (6H, m), 7.2 (1H, t), 7.2–7.4 (5H, m).

MS m/z: 457 (M+1).

(±)-Cis-N-[1-(4-diethylamino-benzoyl)-2-methyl-1,2,3,4-tetrahydro-quinolin-4-yl]-N-phenyl-acetamide (A-88)

(±)-Cis-N-[1-(4-diethylamino-benzoyl)-2-methyl-1,2,3,4-tetrahydro-quinolin-4-yl]-N-phenyl-acetamide was made from (±)-cis-N-[1-(4-amino-benzoyl)-2-methyl-1,2,3,4-tetrahydro-quinolin-4-yl]-N-phenyl-acetamide. (±)-Cis-N-[1-(4-amino-benzoyl)-2-methyl-1,2,3,4-tetrahydro-quinolin-4-yl]-N-phenyl-acetamide was dissolved in methylene chloride and ethyl iodide (1.5 equiv.) was added followed by K$_2$CO$_3$. The reaction was allowed to stir at room temperature for 12 h. The reaction mixture was filtered and concentrated under vacuum. The residue was purified by silica gel chromatography, eluting with methanol-dichloromethane (1:19) to give the title compound.

$^1$H-NMR (CDCl$_3$) δ: 1.0–1.2 (10H, m), 2.0 (3H, s), 2.4 (1H, m), 3.3 (4H, q), 4.7 (1H, m), 5.6 (1H, m), 6.4 (2H, d), 6.6 (1H, d), 6.9 (1H, t), 7.0–7.4 (9H, m).

MS m/z: 456 (M+1).

(±)-Cis-{4-[4-(acetyl-phenyl-amino)-2-methyl-3,4-dihydro-2H-quinoline-1-carbonyl]-phenylamino}-acetic Acid (A-89)

(±)-Cis-{4-[4-(acetyl-phenyl-amino)-2-methyl-3,4-dihydro-2H-quinoline-1-carbonyl]-phenylamino}-acetic acid was made from (±)-cis-N-[1-(4-amino-benzoyl)-2-methyl-1,2,3,4-tetrahydro-quinolin-4-yl]-N-phenyl-acetamide. (±)-Cis-N-[1-(4-amino-benzoyl)-2-methyl-1,2,3,4-tetrahydro-quinolin-4-yl]-N-phenyl-acetamide was dissolved in dimethylformamide and bromoacetic acid ethyl ester was added followed by K$_2$CO$_3$. The reaction was allowed to heat to 90° C. for 12 h. The reaction mixture was filtered and concentrated under vacuum. The residue was purified by silica gel chromatography, eluting with methanol-dichloromethane (2:18) to give the ester. The ester was hydrolyzed using NaOH (aqueous) in methanol and water to give the title compound.

$^1$H-NMR (CDCl$_3$) δ: 1.1 (3H, d), 1.1 (1H, m), 2.0 (3H, s), 2.3 (1H, m), 3.6 (1H, s), 4.7 (3H, b), 5.6 (1H, m), 6.3 (1H, m), 6.6 (1H, d), 6.8–7.4 (11H, m).

MS m/z: 458 (M+1).

(±)-Cis-[N-[1-(4-methanesulfonylamino-benzoyl)-2-methyl-1,2,3,4-tetrahydro-quinolin-4-yl]-N-phenyl-propionamide (A-90)

(±)-Cis-{N-[1-(4-methanesulfonylamino-benzoyl)-2-methyl-1,2,3,4-tetrahydro-quinolin-4-yl]-N-phenyl-propionamide was made from (±)-cis-N-[1-(4-amino-benzoyl)-2-methyl-1,2,3,4-tetrahydro-quinolin-4-yl]-N-phenyl-acetamide. (±)-cis-N-[1-(4-amino-benzoyl)-2-methyl-1,2,3,4-tetrahydro-quinolin-4-yl]-N-phenyl-acetamide (50 mg, 0.12 mmol) was dissolved in 5 ml DMF and methanesulfonic anhydride (21 mg, 0.12 mmol) was added. The resulting reaction mixture was heated to 45° C. and stirred for 1 hour. The mixture was concentrated under vacuum. The residue was purified by silica gel chromatography, eluting with methanol-dichloromethane (1:9) to give the title compound (15 mg, 25%).

$^1$H-NMR (CDCl$_3$) δ: 1.1–1.2 (7H, m), 2.1–2.3 (3H, m), 3.0 (3H, s), 4.7 (1H, m), 5.6 (1H, m), 6.5 (1H, d), 6.7 (2H, d), 6.9 (1H, t), 7.1 (2H, m), 7.2–7.4 (7H, m).

MS m/z: 491 (M).

(±)-Cis-N-[6-Fluoro-1-(4-fluoro-benzoyl)-2-methyl-1,2,3,4-tetrahydro-quinolin-4-yl]-N-(4-fluoro-phenyl)-propionamide (A-91)

(±)-Cis-N-[6-fluoro-1-(4-fluoro-benzoyl)-2-methyl-1,2,3,4-tetrahydro-quinolin-4-yl]-N-(4-fluoro-phenyl)-propionamide was made following general procedure A, substituting 4-fluorobenzoyl chloride for 2-furoyl chloride, (±)-cis-(6-fluoro-2-methyl-1,2,3,4-tetrahydro-quinolin-4-yl)-(4-fluoro-phenyl)-amine for (±)-cis-(2-methyl-1,2,3,4-tetrahydro-quinolin-4-yl)-phenyl-amine and propionyl chloride for acetyl chloride. (±)-Cis-(6-fluoro-2-methyl-1,2,3,4-tetrahydro-quinolin-4-yl)-(4-fluoro-phenyl)-amine was synthesized following the reactions detailed in scheme 1, substituting 4-fluoroaniline for aniline.

$^1$H-NMR (CDCl$_3$) δ: 1.1–1.2 (6H, m), 2.2–2.4 (4H, m), 4.8 (1H, dd), 5.4–5.6 (1H, br), 6.4 (1H, dd), 6.6 (1H, td), 6.8–7.0 (2H, m), 7.0–7.4 (6H, m).

MS m/z: 453 (M+1).

(±)-Cis-N-[6-bromo-1-(4-fluoro-benzoyl)-2-methyl-12,4-tetrahydro-quinolin-4-yl]-N-(4-bromo-phenyl)-propionamide (A-92)

(±)-Cis-N-[6-bromo-1-(4-fluoro-benzoyl)-2-methyl-1,2,3,4-tetrahydro-quinolin-4-yl]-N-(4-bromo-phenyl)-propionamide was made following general procedure A, substituting 4-fluorobenzoyl chloride for 2-furoyl chloride, (±)-cis-(6-bromo-2-methyl-1,2,3,4-tetrahydro-quinolin-4-yl)-(4-bromo-phenyl)-amine for (±)-cis-(2-methyl-1,2,3,4-tetrahydro-quinolin-4-yl)-phenyl-amine and propionyl chloride for acetyl chloride. (±)-cis-(6-bromo-2-methyl-1,2,3,4-tetrahydro-quinolin-4-yl)-(4-bromo-phenyl)-amine was synthesized following the reactions detailed in scheme 1, substituting 4-bromoaniline for aniline.

$^1$H-NMR (CDCl$_3$) δ: 1.1–1.2 (6H, m), 1.6 (1H, m), 2.2–2.4 (3H, m), 4.8 (1H, m), 5.4–5.6 (1H, br), 6.4 (1H, d), 6.8 (2H, m), 7.0–7.4 (6H, M), 7.8–7.9 (2H, m).

MS m/z: 573 (M+1).

(±)-Cis-N-[1-(3-ethoxy-benzoyl)-2-methyl-1,2,3,4-tetrahydro-quinolin-4-yl]-N-phenyl-acetamide (A-93)

(±)-Cis-N-[1-(3-ethoxy-benzoyl)-2-methyl-1,2,3,4-tetrahydro-quinolin-4-yl]-N-phenyl-acetamide was made following general procedure A, substituting 3-ethoxybenzoyl chloride for 2-furoyl chloride.

$^1$H-NMR (CDCl$_3$) δ: 1.2 (3H, m), 1.4 (4H, m), 2.1 (3H, s), 2.4 (1H, m), 4.0 (2H, m), 4.9 (1H, m), 5.6 (1H, br), 6.6 (1H, d), 6.9 (2H, m), 7.0 (1H, m), 7.2 (1H, m), 7.3 (1H, m), 7.4–7.5 (7H, m).

MS m/z: 429 (M+1).

(±)-Cis-N-[1-(4-isopropoxy-benzoyl)-2-methyl-1,2,3,4-tetrahydro-quinolin-4-yl]-N-phenyl-propionamide (A-94)

(±)-Cis-N-[1-(4-isopropoxy-benzoyl)-2-methyl-1,2,3,4-tetrahydro-quinolin-4-yl]-N-phenyl-propionamide was made following general procedure A, substituting 4-isopropoxybenzoyl chloride for 2-furoyl chloride and propionyl chloride for acetyl chloride.

$^1$H-NMR (CDCl$_3$) δ: 0.9–1.2 (12H, m), 1.4 (1H, m), 2.0 (3H, m), 4.3 (1H, m), 4.5 (1H, m), 5.4 (1H, br), 6.3 (1H, d), 6.4 (2H, d), 6.7 (1H, m), 6.9–7.2 (9H, m).

MS m/z: 457 (M+1).

(±)-Cis-N-[1-(1-isopropyl-1H-benzotriazole-5-carbonyl)-2-methyl-1,2,3,4-tetrahydro-quinolin-4-yl]-N-phenyl-propionamide (A-95)

(±)-Cis-N-[1-(1-Isopropyl-1H-benzotriazole-5-carbonyl)-2-methyl-1,2,3,4-tetrahydro-quinolin-4-yl]-N-phenyl-propionamide was made following general procedure A, substituting 1-isopropyl-1H-benzotriazole-5-carbonyl chloride for 2-furoyl chloride and propionyl chloride for acetyl chloride.

$^1$H-NMR (CDCl$_3$) δ: 1.3 (7H, m), 1.8 (6H, m), 2.4 (3H, m), 5.0 (1H, m), 5.1 (1H, m), 5.7 (1H, br), 6.6 (1H, d), 7.0 (1H, m), 7.2–7.5 (9H, m), 8.3 (1H, s).

MS m/z: 482 (M+1).

(±)-Cis-N-[1-(3-Ethoxy-benzoyl)-2-methyl-1,2,3,4-tetrahydro-quinolin-4-yl]-N-phenyl-propionamide (A-96)

(±)-Cis-N-[1-(3-ethoxy-benzoyl)-2-methyl-1,2,3,4-tetrahydro-quinolin-4-yl]-N-phenyl-propionamide was made following general procedure A, substituting 3-ethoxybenzoyl chloride for 2-furoyl chloride and propionyl chloride for acetyl chloride.

¹H-NMR (CDCl₃) δ: 1.2 (6H, m), 1.5 (4H, m), 2.4 (3H, m), 4.0 (2H, m), 4.9 (1H, m), 5.7 (1H, br), 6.6 (1H, d), 6.8 (1H, d), 6.9 (1H, m), 7.1 (2H, m), 7.2 (1H, m), 7.3–7.6 (7H, m).

MS m/z: 443 (M+1).

(±)-Cis-4-{4-[2-methyl-4-(phenyl-propionyl-amino)-3,4-dihydro-2H-quinoline-1-carbonyl]-phenyl}-piperidine-1-carboxylic Acid Ethyl Ester (A-97)

(±)-Cis-4-{4-[2-methyl-4-(phenyl-propionyl-amino)-3,4-dihydro-2H-quinoline-1-carbonyl]-phenyl}-piperidine-1-carboxylic acid ethyl ester was made following general procedure A, substituting 4-(4-chlorocarbonyl-phenyl)-piperidine-1-carboxylic acid ethyl ester for 2-furoyl chloride and propionyl chloride for acetyl chloride.

¹H-NMR (CDCl₃) δ: 1.1–1.3 (10H, m), 1.5 (2H, m), 1.7 (2H, m), 2.3 (3H, m), 2.6 (1H, m), 2.8 (2H, t), 4.1 (2H, m), 4.2 (2H, m), 4.8 (1H, m), 5.6 (1H, br), 6.5 (1H, d), 6.9 (1H, m), 7.2 (2H, m), 7.3–7.4 (9H, m).

MS m/z: 554 (M+1).

(±)-Cis-N-[2-methyl-1-(4-piperidin-4-yl-benzoyl)-1,2,3,4-tetrahydro-quinolin-4-yl]-N-phenyl-propionamide (A-98)

(±)-Cis-N-[2-methyl-1-(4-piperidin-4-yl-benzoyl)-1,2,3,4-tetrahydro-quinolin-4-yl]-N-phenyl-propionamide was prepared from (±)-cis-4-{4-[2-methyl-4-(phenyl-propionyl-amino)-3,4-dihydro-2H-quinoline-1-carbonyl]-phenyl}-piperidine-1-carboxylic acid ethyl ester. (±)-Cis-4-{4-[2-methyl-4-(phenyl-propionyl-amino)-3,4-dihydro-2H-quinoline-1-carbonyl]-phenyl}-piperidine-1-carboxylic acid ethyl ester (96 mg, 0.17 mmol) was dissolved in acetonitrile (2 mL). Iodotrimetylsilane (74 uL, 0.51 mmol) was added and the reaction was allowed to stir at room temperature over night. Excess reagent was quenched by the addition of methanol (1 mL) and the mixture was concentrated under reduced pressure. The crude residue was partitioned between ethyl acetate and saturated aqueous sodium bicarbonate. The extracts were washed with 1 M sodium hydroxide, saturated aqueous sodium thiosulfate and brine, dried over sodium sulfate, filtered, concentrated and purified by silica gel chromatography (3:1 methylene chloride/methanol) (77 mg, 94%).

¹H-NMR (CDCl₃) δ: 1.1 (6H, m), 1.3 (1H, t), 1.6 (2H, m), 1.7 (2H, d), 2.3 (3H, m), 2.6 (1H, m), 2.7 (2H, t), 3.2 (2H, d), 4.8 (1H, m), 5.6 (1H, br), 6.5 (1H, d), 6.9 (1H, m), 7.0 (2H, d), 7.2 (3H, m), 7.3–7.4 (6H, m).

MS m/z: 482 (M+1).

(±)-Cis-N-[1-(4-Bromo-benzoyl)-2-methyl-1,2,3,4-tetrahydro-quinolin-4-yl]-N-phenyl-propionamide (A-99)

(±)-Cis-N-[1-(4-bromo-benzoyl)-2-methyl-1,2,3,4-tetrahydro-quinolin-4-yl]-N-phenyl-propionamide was made following general procedure A, substituting 4-bromobenzoyl chloride for 2-furoyl chloride and propionyl chloride for acetyl chloride.

¹H-NMR (CDCl₃) δ: 1.2 (6H, m), 1.25 (1H, m), 2.3 (3H, m), 4.8 (1H, m), 5.6 (1H, br), 6.4 (1H, d), 6.9 (1H, m), 7.1 (2H, d), 7.2 (1H, m), 7.3–7.4 (8H, m).

MS m/z: 477 (M+1).

(±)-Cis-N-{1-[4-(1-acetyl-piperidin-4-yl)-benzoyl]-2-methyl-1,2,3,4-tetrahydro-quinolin-4-yl}-N-phenyl-propionamide (A-100)

To a solution of (±)-cis-(2-methyl-1,2,3,4-tetrahydro-quinolin-4-yl)-phenyl-amine (636 mg, 2.70 mmol) in dichloromethane (10 mL) at room temperature was added diisopropylethylamine (1.04 g, 1.44 mL, 2.98 mmol) followed by freshly prepared 4-(4-chlorocarbonyl-phenyl)-piperidine-1-carboxylic acid tert-butyl ester (2.98 mmol). The mixture was stirred at room temperature over night, poured into water and extracted with dichloromethane. The extracts were washed with 1 M(aq) NaOH and brine, dried over magnesium sulfate, filtered dried and concentrated. The crude residue was purified by silica gel chromatography (100% hexanes to 70/30 hexanes ethyl acetate gradient) to afford the pure amide (827 mg, 58%).

The (±)-cis-4-[4-(2-methyl-4-phenylamino-3,4-dihydro-2H-quinoline-1-carbonyl)-phenyl]-piperidine-1-carboxylic acid tert-butyl ester (827 mg, 1.57 mmol) thus formed was dissolved in methylene chloride (50 mL). Trifluoroacetic acid (3 mL) was added and the mixture was stirred at rt 70 min. Solvent and excess acid were removed under reduced pressure. The crude residue was dissolved in ethyl acetate and neutralized with 1 M sodium hydroxide (to pH=10.5). The aqueous phase was extracted twice with additional ethyl acetate. The extracts were combined and washed with brine, dried over sodium sulfate, filtered and concentrated to afford the crude diamine (676 mg, 100%) as an oil.

To a solution of the piperidine amine obtained above (676 mg, 1.59 mmol) in methylene chloride (25 mL) was added diisopropylethylamine (616 mg, 849 uL, 4.77 mmol), followed by acetyl chloride (162 mg, 156 uL, 2.06 mmol). The mixture was stirred at room temperature over night. The reaction mixture was poured into saturated aqueous sodium bicarbonate and extracted with additional methylene chloride. The extracts were combined, washed with brine, dried over sodium sulfate, filtered, dried and concentrated to afford the piperidine acetamide (844 mg, >100%).

The crude piperidine acetamide obtained above (844 mg) was dissolved in methylene chloride (25 mL) to which was then added diisopropylethylamine (205 mg, 283 uL, 1.59 mmol) followed by propionyl chloride (4.42 g, 4.2 mL, 47.7 mmol). The resulting reaction mixture was stirred at room temperature 96 h and concentrated. The resulting residue was partitioned between ethyl acetate and saturated aqueous sodium bicarbonate. The extracts were washed with brine and dried over sodium sulfate, filtered, dried and concentrated. The crude residue was purified by silica gel chromatography (50/50 ethyl acetate/hexanes to 100% ethyl acetate gradient) to afford the product (437 mg, 52%).

(±)-Cis-N-{1-[4-(1-acetyl-piperidin-4-yl)-benzoyl]-2-methyl-1,2,3,4-tetrahydro-quinolin-4-yl}-N-phenyl-propionamide was separated by chiral HPLC using a chiral cel OD column and eluting with 90% hexane/10% ethanol isocratic system to give (2R,4S)- and (2S,4R)-cis-N-{1-[4-(1-acetyl-piperidin-4-yl)-benzoyl]-2-methyl-1,2,3,4-tetrahydro-quinolin-4-yl}-N-phenyl-propionamide (A-51 & A-50, respectively).

¹H-NMR (CDCl₃) δ: 1.2 (7H, m), 1.6 (2H, m), 1.8 (2H, d), 2.1 (3H, s), 2.3 (3H, m), 2.6 (2H, m), 3.1 (1H, t), 3.9 (1H, m), 4.8 (2H, m), 5.6 (1H, br), 6.5 (1H, d), 6.9 (1H, m), 7.0 (2H, d), 7.1 (2H, d), 7.2–7.4 (7H, m).

MS m/z: 524 (M+1)

(±)-Cis-N-{1-[4-(1-ethyl-piperidin-4-yl)-benzoyl]-2-methyl-1,2,3,4-tetrahydro-quinolin-4-yl}-N-phenyl-propionamide (A-101)

(±)-Cis-N-{1-[4-(1-ethyl-piperidin-4-yl)-benzoyl]-2-methyl-1,2,3,4-tetrahydro-quinolin-4-yl}-N-phenyl-propionamide was made from (±)-cis-N-[2-methyl-1-(4-piperidin-4-yl-benzoyl)-1,2,3,4-tetrahydro-quinolin-4-yl]-N-phenyl-propionamide. (±)-Cis-N-[2-methyl-1-(4-piperidin-4-yl-benzoyl)-1,2,3,4-tetrahydro-quinolin-4-yl]-N-phenyl propionamide was dissolved in dichloromethane (3 mL). Acetaldehyde (18 uL, 0.33 mmol) was added in a single portion. The mixture was stirred at room temperature 30 minutes and then a solution sodium triacetoxyborohydride (35 mg, 0.165 mmol) in dichloromethane (1 mL) was slowly added, followed by 1 drop acetic acid. The mixture was allowed to stir at room temperature over night and was quenched by aqueous sodium bicarbonate. The biphasic mixture was extracted three times with methylene chloride (20 mL); the combined extracts were washed with brine, dried over magnesium sulfate, filtered, concentrated and purified by HPLC to afford the product (35 mg, 62%).

$^1$H-NMR (CDCl$_3$) δ: 1.0–1.2 (9H, m), 1.3 (1H, m), 1.8 (4H, br), 2.0 (2H, m), 2.3 (3H, m), 2.5 (2H, m), 3.1 (3H, m), 4.8 (1H, m), 5.6 (1H, br), 6.5 (1H, d), 6.9 (1H, m), 7.0 (2H, d), 7.1–7.4 (9H, m).

MS m/z: 511 (M+2).

(±)-Cis-N-[2-Methyl-1-(4-nitro-benzoyl)-1,2,3,4-tetrahydro-quinolin-4-yl]-N-phenyl-propionamide (A-102)

(±)-Cis-N-[2-methyl-1-(4-nitro-benzoyl)-1,2,3,4-tetrahydro-quinolin-4-yl]-N-phenyl-propionamide was made following general procedure A, substituting 4-nitrobenzoyl chloride for 2-furoyl chloride and propionyl chloride for acetyl chloride.

$^1$H-NMR (CDCl$_3$) δ: 1.2 (7H, m), 2.3 (3H, m), 4.8 (1H, m), 5.6 (1H, br), 6.4 (1H, d), 6.9 (1H, m), 7.2–7.4 (9H, m), 8.0 (2H, d).

MS m/z: 444 (M+1).

(±)-Cis-N-[1-(4-amino-benzoyl)-2-methyl-1,2,3,4-tetrahydro-quinolin-4-yl]-N-phenyl-propionamide (A-103)

(±)-Cis-N-[1-(4-amino-benzoyl)-2-methyl-1,2,3,4-tetrahydro-quinolin-4-yl]-N-phenyl-propionamide was prepared from (±)-cis-N-[2-methylmethyl-1-(4-nitro-benzoyl)-1,2,3,4-tetrahydro-quinolin-4-yl]-N-phenyl-propionamide. (±)-Cis-N-[2-methyl-1-(4-nitro-benzoyl)-1,2,3,4-tetrahydro-quinolin-4-yl]-N-phenyl-propionamide (200 mg, 0.45 mmol) was dissolved in ethanol (20 mL). Palladium on carbon (10%) was carefully added and the resulting suspension was shaken under hydrogen gas (40 psi) over night. The suspension was filtered through Celite® to remove solids, and the filter cake washed three times with ethanol. Concentration of the solution afforded pure product (160 mg, 86%).

$^1$H-NMR (CDCl$_3$) δ: 1.2 (7H, m), 2.3 (3H, m), 3.9 (2H, br), 4.7 (1H, m), 5.6 (1H, br), 6.4 (2H, d), 6.6 (1H, d), 6.9 (1H, m), 7.0 (2H, d), 7.1 (1H, m), 7.2–7.4 (6H, m).

MS m/z: 414 (M+1).

(±)-Cis-N-[2-methyl-1-(4-pyrrol-1-yl-benzoyl)-1,2,3,4-tetrahydro-quinolin-4-yl]-N-phenyl-propionamide (A-104)

(±)-Cis-N-[2-methyl-1-(4-pyrrol-1-yl-benzoyl)-1,2,3,4-tetrahydro-quinolin-4-yl]-N-phenyl-propionamide was made following general procedure A, substituting 4-pyrrol-1-yl-benzoyl chloride for 2-furoyl chloride and propionyl chloride for acetyl chloride.

$^1$H-NMR (CDCl$_3$) δ: 1.2 (6H, m), 1.3 (1H, m), 2.3 (3H, m), 4.8 (1H, m), 5.6 (1H, br), 6.3 (2H, s), 6.6 (1H, d), 6.9 (1H, m), 7.1 (2H, s), 7.2–7.4 (11H, m).

MS m/z: 464 (M+1).

(±)-Cis-N-[1-(4-acetylamino-benzoyl)-2-methyl-1,2,3,4-tetrahydro-quinolin-4-yl]-N-phenyl-propionamide (A-105)

(±)-Cis-N-[1-(4-acetylamino-benzoyl)-2-methyl-1,2,3,4-tetrahydro-quinolin-4-yl]-N-phenyl-propionamide was prepared from (±)-cis-N-[1-(4-amino-benzoyl)-2-methyl-1,2,3,4-tetrahydro-quinolin-4-yl]-N-phenyl-propionamide. To a solution of (±)-cis-N-[1-(4-amino-benzoyl)-2-methyl-1,2,3,4-tetrahydro-quinolin-4-yl]-N-phenyl-propionamide. (100 mg, 0.24 mmol) in 2.5 ml tetrahydrofuran was added acetyl chloride (44 mL, 0.63 mmol) followed by triethylamine (88 μL, 0.63 mmol). The reaction was stirred at room temperature overnight. The mixture was concentrated under reduced pressure. The residue was purified by silica gel chromatography, eluting with hexane-ethyl acetate (3:1) to give the title compound (51 mg, 46%).

$^1$H-NMR (CDCl$_3$): 1.1 (7H, m), 2.2 (3H, s), 2.3 (3H, m), 4.8 (1H, m), 5.6 (1H, br), 6.5 (1H, d), 6.9 (1H, m), 7.1 (2H, d), 7.2 (1H, d), 7.3–7.4 (8H, m), 8.4 (1H, br).

MS m/z: 456 (M+1)

(±)-Cis-{4-[2-methyl-4-(phenyl-propionyl-amino)-3,4-dihydro-2H-quinoline-1-carbonyl]-phenyl}-carbamic acid ethyl ester (A-106)

(±)-Cis-{4-[2-methyl-4-(phenyl-propionyl-amino)-3,4-dihydro-2H-quinoline-1-carbonyl]-phenyl}-carbamic acid ethyl ester was made from (±)-cis-N-[1-(4-aminoamino-benzoyl)-2-methyl-1,2,3,4-tetrahydro-quinolin-4-yl]-N-phenyl-propionamide, following the method described above in the synthesis of (±)-cis-N-[1-(4-acetylamino-benzoyl)-2-methyl-1,2,3,4-tetrahydro-quinolin-4-yl]-N-phenyl-propionamide, substituting ethyl chloroformate for acetyl chloride.

$^1$H-NMR (CDCl$_3$) δ: 1.1 (6H, m), 1.3 (4H, m), 2.3 (3H, m), 4.2 (2H, m), 4.8 (1H, m), 5.6 (1H, br), 6.5 (1H, d), 6.7 (1H, br), 6.9 (1H, m), 7.1–7.4 (10H, m).

MS m/z: 486 (M+1).

(±)-Cis-N-{2-methyl-1-[4-(4-methyl-piperazin-1-yl)-benzoyl]-1,2,3,4-tetrahydro-quinolin-4-yl}-N-phenyl-propionamide (A-107)

(±)-Cis-N-{2-methyl-1-[4-(4-methyl-piperazin-1-yl)-benzoyl]-1,2,3,4-tetrahydro-quinolin-4-yl}-N-phenyl-propionamide was made from (±)-cis-N-[1-(4-bromo-benzoyl)-2-methyl-1,2,3,4-tetrahydro-quinolin-4-yl]-N-phenyl-propionamide. (±)-Cis-N-[1-(4-bromo-benzoyl)-2-methyl-1,2,3,4-tetrahydro-quinolin-4-yl]-N-phenyl-propionamide (100 mg, 0.22 mmol) was combined with cesium carbonate (355 mg, 1.09 mmol), racemic BINAP (25 mg, 0.04 mmol), Pd$_2$dba$_3$ (36 mmol, 0.04 mmol) and 1-methyl piperazine and dissolved in toluene (10 mL). The reaction mixture was heated at 100° C. under argon overnight. The reaction was cooled to room temperature, filtered and the solids washed with ether. The filtrate was washed with water and brine, dried over magnesium sulfate, filtered and concentrated. The crude product was purified by HPLC.

$^1$H-NMR (CDCl$_3$) δ: 1.2 (6H, m), 1.3 (1H, m), 2.2 (3H, m), 2.3 (3H, s), 2.5 (4H, m), 3.2 (4H, m), 4.7 (1H, m), 5.6 (1H, bs), 6.6 (1H, d), 6.7 (2H, d), 7.0 (1H, m), 7.2–7.4 (9H, m).

MS m/z: 498 (M+2)

(±)-Cis-N-[2-methyl-1-(4-pyrimidin-2-yl-benzoyl)-1,2,3,4-tetrahydro-quinolin-4-yl]-N-phenyl-propionamide (A-108)

(±)-Cis-N-[2-methyl-1-(4-pyrimidin-2-yl-benzoyl)-1,2,3,4-tetrahydro-quinolin-4-yl]-N-phenyl-propionamide was made following general procedure A, substituting 4-pyrimidin-2-yl-benzoyl chloride for 2-furoyl chloride and propionyl chloride for acetyl chloride.

$^1$H-NMR (CDCl$_3$) δ: 1.2 (7H, m), 2.3 (3H, m), 4.8 (1H, m), 5.6 (1H, br), 6.5 (1H, d), 6.9 (1H, m), 7.2–7.4 (10H, m), 8.3 (2H, d), 8.8 (2H, d).

MS m/z: 478 (M+2).

(±)-Cis-N-[2-methyl-1-(4-methyl-3,4-dihydro-2H-benzo[1,4]oxazine-7-carbonyl)-1,2,3,4-tetrahydro-quinolin-4-yl]-N-phenyl-propionamide (A-109)

(±)-Cis-N-[2-methyl-1-(4-methyl-3,4-dihydro-2H-benzo[1,4]oxazine-7-carbonyl)-1,2,3,4-tetrahydro-quinolin-4-yl]-N-phenyl-propionamide was made following general procedure A, substituting 4-methyl-3,4-dihydro-2H-benzo[1,4]oxazine-7-carbonyl chloride for 2-furoyl chloride and propionyl chloride for acetyl chloride.

$^1$H-NMR (CDCl$_3$) δ: 1.1 (6H, m), 1.3 (1H, t), 2.3 (3H, m), 2.8 (3H, s), 3.3 (2H, t), 4.2 (2H, t), 4.7 (1H, m), 5.6 (1H, br), 6.3 (1H, d), 6.5 (1H, d), 6.6 (1H, d), 6.9 (1H, s), 7.0 (1H, m), 7.1 (1H, m), 7.3–7.4 (7H, m).

MS m/z: 471 (M+2).

(±)-Cis-N-[2-Methyl-1-(4-morpholin-4-yl-benzoyl)-1,2,3,4-tetrahydro-quinolin-4-yl]-N-phenyl-propionamide (A-110)

(±)-Cis-N-[2-methyl-1-(4-morpholin-4-yl-benzoyl)-1,2,3,4-tetrahydro-quinolin-4-yl]-N-phenyl-propionamide was made from (±)-cis-N-[1-(4-bromo-benzoyl)-2-methyl-1,2,3,4-tetrahydro-quinolin-4-yl]-N-phenyl-propionamide, following the procedure used to make (±)-cis-N-{2-methyl-1-[4-(4-methyl-piperazin-1-yl)-benzoyl]-1,2,3,4-tetrahydro-quinolin-4-yl}-N-phenyl-propionamide substituting morpholine for 1-methyl piperazine.

(±)-Cis-N-[2-methyl-1-(4-morpholin-4-yl-benzoyl)-1,2,3,4-tetrahydro-quinolin-4-yl]-N-phenyl-propionamide was separated by chiral HPLC using a chiral cel OD column and eluting with 90% hexane/10% ethanol isocratic system to give (2R,4S)- and (2S,4R)-cis-N-[2-methyl-1-(4-morpholin-4-yl-benzoyl)-1,2,3,4-tetrahydro-quinolin-4-yl]-N-phenyl-propionamide (A-120 & A-119, respectively).

$^1$H-NMR (CDCl$_3$) δ: 1.1 (7H, m), 2.3 (3H, m), 3.1 (4H, t), 3.8 (4H, t), 4.7 (1H, m), 5.6 (1H, br), 6.6 (1H, d), 6.7 (2H, d), 6.9 (1H, m), 7.2–7.4 (9H, m).

MS m/z: 485 (M+2).

(±)-Cis-N-{1-[4-(2,5-dimethyl-pyrrol-1-yl)-benzoyl]-2-methyl-1,2,3,4-tetrahydro-quinolin-4-yl}-N-phenyl-propionamide (A-111)

(±)-Cis-N-{1-[4-(2,5-dimethyl-pyrrol-1-yl)-benzoyl]-2-methyl-1,2,3,4-tetrahydro-quinolin-4-yl}-N-phenyl-propionamide was prepared from (±)-cis-N-[1-(4-amino-benzoyl)-2-methyl-1,2,3,4-tetrahydro-quinolin-4-yl]-N-phenyl-propionamide. A solution of (±)-cis-N-[1-(4-amino-benzoyl)-2-methyl-1,2,3,4-tetrahydro-quinolin-4-yl]-N-phenyl-propionamide (150 mg, 0.36 mmol), and propionic acid (0.5 ml) in dry benzene (20 ml) was heated at reflux under argon in a flask equipped with a Dean-Stark trap while stirring with the exclusion of light. The resulting solution was cooled to room temperature, and concentrated under vacuum. Recovered oil was purified by silica gel chromatography, eluting with hexane-ethyl acetate (3:1) to give the title compound (140 mg, 80%).

$^1$H-NMR (CDCl$_3$) δ: 1.2 (7H, m), 2.0 (6H, s), 2.3 (3H, m), 4.8 (1H, m), 5.6 (1H, br), 5.9 (2H, s), 6.5 (1H, d), 6.9 (1H, m), 7.0 (1H, d), 7.2 (2H, m), 7.3–7.4 (8H, m).

MS m/z: 493 (M+2).

(±)-Cis-N-{1-[4-(2-ethyl-butylamino)-benzoyl]-2-methyl-1,2,3,4-tetrahydro-quinolin-4-yl}-N-phenyl-propionamide (A-112)

(±)-Cis-N-{1-[4-(2-ethyl-butylamino)-benzoyl]-2-methyl-1,2,3,4-tetrahydro-quinolin-4-yl}-N-phenyl-propionamide was prepared from (±)-cis-N-[1-(4-amino-benzoyl)-2-methyl-1,2,3,4-tetrahydro-quinolin-4-yl]-N-phenyl-propionamide. To a solution of (±)-cis-N-[1-(4-Amino-benzoyl)-2-methyl-1,2,3,4-tetrahydro-quinolin-4-yl]-N-phenyl-propionamide (75 mg, 0.145 mmol) in dichloromethane (3 mL) was added 2-ethylbutyraldehyde (26 uL, 0.2 mmol) in one portion. The mixture was stirred at room temperature for a 0.5 h before a solution of sodium triacetoxyborohydride (74 mg, 0.348 mmol) 1 ml DCM was added slowly. A single drop of acetic acid was added and the reaction was allowed to stir at room temperature over night. Excess reagent was quenched by the addition of saturated aqueous sodium bicarbonate. The resulting mixture was extracted three times with 20 mL dichloromethane. The combined extracts were washed with brine, dried over magnesium sulfate, filtered and concentrated. Crude product was purified by HPLC to afford the title compound (60 mg, 83%).

$^1$H-NMR (CDCl$_3$) δ: 0.9 (6H, m), 1.2 (7H, m), 1.4 (5H, m), 2.3 (3H, m), 3.0 (2H, d), 4.7 (1H, m), 5.6 (1H, br), 6.3 (2H, d), 6.6 (1H, d), 7.0 (1H, m), 7.1 (2H, d), 7.2 (1H, m), 7.3–7.4 (6H, m).

MS m/z: 499 (M+2).

(±)-Cis-N-[2-Methyl-1-(4-propylamino-benzoyl)-1,2,3,4-tetrahydro-quinolin-4-yl]-N-phenyl-propionamide (A-113)

(±)-Cis-N-[2-methyl-1-(4-propylamino-benzoyl)-1,2,3,4-tetrahydro-quinolin-4-yl]-N-phenyl-propionamide was prepared from (±)-cis-N-[1-(4-amino-benzoyl)-2-methyl-1,2,3,4-tetrahydro-quinolin-4-yl]-N-phenyl-propionamide utilizing the reductive amination conditions described for the synthesis of (±)-cis-N-{1-[4-(2-ethyl-butylamino)-benzoyl]-2-methyl-1,2,3,4-tetrahydro-quinolin-4-yl}-N-phenyl-propionamide. Propionaldehyde was substituted for 2-ethylbutyraldehyde. The reaction was poorly selective and afforded approximately equivalent amounts of mono- and di-alkylated products (i.e., (±)-cis-N-[1-(4-dipropylamino-benzoyl)-2-methyl-1,2,3,4-tetrahydro-quinolin-4-yl]-N-phenyl propionamidel see below).

$^1$H-NMR (CDCl$_3$) δ: 1.0 (3H, m), 1.1 (7H, m), 1.6 (2H, m), 2.3 (3H, m), 3.0 (2H, d), 4.0 (1H, br), 4.7 (1H, m), 5.6 (1H, br), 6.3 (2H, d), 6.6 (1H, d), 6.9 (1H, m), 7.06 (2H, d), 7.14 (1H, m), 7.3–7.4 (6H, m).

MS m/z: 457 (M+2).

(±)-Cis-N-[1-(4-dipropylamino-benzoyl)-2-methyl-1,2,3,4-tetrahydro-quinolin-4-yl]-N-phenyl-propionamide (A-114)

(±)-Cis-N-[1-(4-Dipropylamino-benzoyl)-2-methyl-1,2,3,4-tetrahydro-quinolin-4-yl]-N-phenyl-propionamide was prepared as a by-product in the synthesis of (±)-cis-N-[2-methyl-1-(4-propylamino-benzoyl)-1,2,3,4-tetrahydro-quinolin-4-yl]-N-phenyl-propionamide described above.

$^1$H-NMR (CDCl$_3$) δ: 1.0 (6H, t), 1.1 (6H, m), 1.4 (1H, m), 1.5 (4H, m), 2.3 (3H, m), 3.2 (4H, t), 4.7 (1H, m), 5.6 (1H, br), 6.4 (2H, d), 6.7 (1H, d), 7.0 (1H, m), 7.1–7.2 (3H, m), 7.3–7.4 (6H, m).

MS m/z: 499 (M+2).

(±)-Cis-N-[2-methyl-1-(4-pyrrolidin-1-yl-benzoyl)-1,2,3,4-tetrahydro-quinolin-4-yl]-N-phenyl-propionamide (A-115)

(±)-Cis-N-[2-methyl-1-(4-pyrrolidin-1-yl-benzoyl)-1,2,3,4-tetrahydro-quinolin-4-yl]-N-phenyl-propionamide was made from (±)-cis-N-[1-(4-bromo-benzoyl)-2-methyl-1,2,3,4-tetrahydro-quinolin-4-yl]-N-phenyl-propionamide following the procedure used to make (±)-cis-N-{2-methyl-1-[4-(4-methyl-piperazin-1-yl)-benzoyl]-1,2,3,4-tetrahydro-quinolin-4-yl}-N-phenyl-propionamide substituting pyrollidine for 1-methylpiperazine.

$^1$H-NMR (CDCl$_3$) δ: 1.1 (7H, m), 2.0 (4H, m), 2.3 (3H, m), 3.2 (4H, m), 4.7 (1H, m), 5.6 (1H, br), 6.3 (2H, d), 6.6 (1H, d), 6.9 (1H, m), 7.1–7.4 (9H, m).

MS m/z: 468 (M+1).

(±)-Cis-N-[2-methyl-1-(4-ureido-benzoyl)-1,2,3,4-tetrahydro-quinolin-4-yl]-N-phenyl-propionamide (A-116)

(±)-Cis-N-[2-methyl-1-(4-ureido-benzoyl)-1,2,3,4-tetrahydro-quinolin-4-yl]-N-phenyl-propionamide was made from (±)-cis-N-[1-(4-amino-benzoyl)-2-methyl-1,2,3,4-tetrahydro-quinolin-4-yl]-N-phenyl-propionamide. A mixture of (±)-cis-N-[1-(4-Amino-benzoyl)-2-methyl-1,2,3,4-tetrahydro-quinolin-4-yl]-N-phenyl-propionamide (100 mg, 0.24 mmol) and trimethylsilyl isocyanate (120 µL, 30.72 mmol) in dry DMF (0.5 mL) was stirred at room temperature for 3 days and then concentrated under reduced pressure at 30° C. to dryness. The residual syrup was stirred with ethyl acetate to which was added an additional 10 mL of ethyl acetate with 10 mL water. The pH was adjusted to 3.0 with 3 N HCl, and the separated aqueous layer was extracted with ethyl acetate. The combined ethyl acetate extracts were washed with water and brine, dried over magnesium sulfate and concentrated in vacuo, yielding the product (10 mg, 9% yield).

$^1$H-NMR (CDCl$_3$) δ: 1.2 (7H, m), 2.3 (3H, m), 4.7 (1H, m), 5.1 (2H, br), 5.6 (1H, br), 6.5 (1H, d), 6.9 (5H, m), 7.2 (7H, m), 7.9 (1H, br).

MS m/z: 457 (M+1).

(±)-Cis-2-{4-[4-(acetyl-phenyl-amino)-2-methyl-3,4-dihydro-2H-quinoline-1-carbonyl]-phenylamino}-propionic acid methyl ester (A-117)

(±)-Cis-2-{4-[4-(acetyl-phenyl-amino)-2-methyl-3,4-dihydro-2H-quinoline-1-carbonyl]-phenylamino}-propionic acid methyl ester was prepared from (±)-cis-N-[1-(4-amino-benzoyl)-2-methyl-1,2,3,4-tetrahydro-quinolin-4-yl]-N-phenyl-propionamide. A mixture of (±)-cis-N-[1-(4-amino-benzoyl)-2-methyl-1,2,3,4-tetrahydro-quinolin-4-yl]-N-phenyl-propionamide (210 mg, 0.53 mmol), potassium carbonate (123 mg, 0.89 mmol), and methyl 2-bromopropionate (70 uL, 0.63 mmol) in dry dimethylformamide (2 mL) was heated at 100° C. for 6 h, then cooled to room temperature and stirred with 20 ml water until all of the salts dissolved. The aqueous layer was separated and was extracted with ethyl acetate. The combined extracts were washed with water and brine, dried over magnesium sulfate, filtered and concentrated under reduced pressure. The resulting oil was purified by silica gel chromatography, eluting with (97:3 methylene chloride/methanol) to afford the title compound (220 mg, 87%).

$^1$H-NMR (CDCl$_3$) δ: 1.2 (4H, m), 1.4 (3H, d), 2.0 (3H, s), 2.3 (1H, br), 3.7 (3H, s), 4.1 (1H, m), 4.7 (1H, m), 5.6 (1H, br), 6.3 (2H, d), 6.6 (1H, d), 6.9 (1H, m), 7.0 (2H, d), 7.3–7.4 (7H, m).

MS m/z: 487 (M+2).

(±)-Cis-2-{4-[4-(acetyl-phenyl-amino)-2-methyl-3,4-dihydro-2H-quinoline-1-carbonyl]-phenylamino}-propionamide (A-118)

(±)-Cis-2-{4-[4-(acetyl-phenyl-amino)-2-methyl-3,4-dihydro-2H-quinoline-1-carbonyl]-phenylamino}-propionamide was prepared from (±)-cis-2-{4-[4-(acetyl-phenyl-amino)-2-methyl-3,4-dihydro-2H-quinoline-1-carbonyl]-phenylamino}-propionic acid methyl ester.

To concentrated ammonium hydroxide (2 mL, 2.0 M) were added crude (±)-cis-2-{4-[4-(acetyl-phenyl-amino)-2-methyl-3,4-dihydro-2H-quinoline-1-carbonyl]-phenylamino}-propionic acid methyl ester (180 mg, 0.37 mmol) and trace amount ammonium chloride; the mixture was heated at 100° C. for 6 h in a pressure reactor with good mixing. After cooling to 0° C., the resulting precipitate was filtered and washed with ice-water and extracted with ether. The combined extracts were washed with water and brine, dried over magnesium sulfate and concentrated under reduced pressure. The crude product was purified by HPLC to give the title compound (10 mg, 6%).

$^1$H-NMR (CDCl$_3$) δ: 1.2 (4H, m), 1.5 (3H, d), 2.1 (3H, s), 2.3 (1H, br), 3.8 (1H, s), 4.4 (2H, br), 4.7 (1H, m), 5.6 (2H, m), 6.3 (2H, m), 6.6 (2H, d), 7.0 (1H, m), 7.1 (2H, d), 7.2 (1H, m), 7.3–7.4 (5H, m).

MS m/z: 471 (M+1)

(±)-Cis-N-[1-(3-methoxy-benzoyl)-2-methyl-1,2,3,4-tetrahydro-quinolin-4-yl]-N-phenyl-acetamide (A-123)

(±)-Cis-N-[1-(3-methoxy-benzoyl)-2-methyl-1,2,3,4-tetrahydro-quinolin-4-yl]-N-phenyl-acetamide was made following general procedure A, substituting 3-methoxybenzoyl chloride for 2-furoyl chloride.

(±)-Cis-N-[1-(3-methoxy-benzoyl)-2-methyl-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[1-(3-methoxy-benzoyl)-2-methyl-1,2,3,4-tetrahydro-quinolin-4-yl]-N-phenyl-acetamide (A-126 & A-127, respectively).

$^1$H-NMR (CDCl$_3$) δ: 1.15 (3H, d; overlapping 1H, t), 2.05 (3H, s), 2.33 (1H, m), 3.60 (3H, s), 4.80 (1H, m), 5.65 (1H, m), 6.55 (1H, d), 6.75–6.85 (3H, complex), 6.95 (1H, t), 7.15 (1H, t), 7.25 (1H, t), 7.25–7.55 (6H, m).

MS m/z: 415 (M+1).

(±)-Trans-N-[1-(3-methoxy-benzoyl)-2-methyl-1,2,3,4-tetrahydro-quinolin-4-yl]-N-phenyl-acetamide (A-124)

(±)-Trans-N-[1-(3-methoxy-benzoyl)-2-methyl-1,2,3,4-tetrahydro-quinolin-4-yl]-N-phenyl-acetamide was made following general procedure A, substituting 3-methoxybenzoyl chloride for 2-furoyl chloride, and trans-(2-ethyl-1,2,3,4-tetrahydro-quinolin-4-yl)-phenyl-amine for cis-(2-ethyl-1,2,3,4-tetrahydro-quinolin-4-yl)-phenyl-amine.

(±)-Cis-N-[1-(3-methoxy-benzoyl)-2-methyl-1,2,3,4-tetrahydro-quinolin-4-yl]-N-phenyl-propionamide (A-128)

(±)-Cis-N-[1-(3-methoxy-benzoyl)-2-methyl-1,2,3,4-tetrahydro-quinolin-4-yl]-N-phenyl-propionamide was made following general procedure A, substituting 3-methoxybenzoyl chloride for 2-furoyl chloride, and propionyl chloride for acetyl chloride.

$^1$H-NMR (CDCl$_3$) δ: 1.15 (3H, d; overlapping 3H, t, 1H, t), 2.20 (2H, q), 2.33 (1H, m), 3.65 (3H, s), 4.80 (1H, m), 5.60 (1H, m), 6.55 (1H, d), 6.75–6.85 (3H, complex), 6.95 (1H, t), 7.15 (1H, t), 7.20 (1H, t), 7.25–7.55 (6H, m).

MS m/z: 429 (M+1).

(±)-Cis-N-[6-chloro-1-(3-methoxy-benzoyl)-2-methyl-1,2,3,4-tetrahydro-quinolin-4-yl]-N-(4-chloro-phenyl)-acetamide (A-129)

(±)-Cis-N-[6-chloro-1-(3-methoxy-benzoyl)-2-methyl-1,2,3,4-tetrahydro-quinolin-4-yl]-N-(4-chloro-phenyl)-acetamide was made following general procedure A, substituting 3-methoxybenzoyl chloride for 2-furoyl chloride, and (±)-cis-(6-chloro-2-methyl-1,2,3,4-tetrahydro-quinolin-4-yl)-(4-chloro-phenyl)-amine for (±)-cis-(2-methyl-1,2,3,4-tetrahydro-quinolin-4-yl)-phenyl-amine. (±)-Cis-(6-chloro-2-methyl-1,2,3,4-tetrahydro-quinolin-4-yl)-(4-chloro-phenyl)-amine was synthesized following the reactions detailed in scheme 1, substituting 4-chloroaniline for aniline.

$^1$H-NMR (CDCl$_3$) δ: 1.15 (3H, d; overlapping 1H, t), 2.02 (3H, s), 2.35 (1H, m), 3.65(3H, s), 4.80 (1H, m), 5.60 (1H, m), 6.42 (1H, d), 6.65–6.95 (overlapping 1H, d; 1H, dd; 1H dd), 7.15 (1H, t), 7.20–7.30 (6H, m), 7.40 (1H, d).

MS m/z: 484 (M+1).

(±)-Cis-N-[2-methyl-1-(1-methyl-1H-pyrrole-2-carbonyl)-1,2,3,4-tetrahydro-quinolin-4-yl]-N-phenyl-acetamide (A-130)

(±)-Cis-N-[2-methyl-1-(1-methyl-1H-pyrrole-2-carbonyl)-1,2,3,4-tetrahydro-quinolin-4-yl]-N-phenyl-acetamide was made following general procedure A, substituting 1-methyl-1H-pyrrole-2-carbonyl chloride for 2-furoyl chloride.

$^1$H-NMR (CDCl$_3$) δ: 1.12 (3H, d; overlapping 1H, t), 2.00 (3H, s), 2.35 (1H, m), 3.80 (3H, s), 4.70 (1H, m), 5.50 (1H, m), 5.80 (1H, d), 6.55 (1H, d), 6.80 (1H, d), 7.00 (1H, t), 7.20–7.50 (6H, m).

MS m/z: 388 (M+1).

(±)-Cis-N-[2-methyl-1-(2-methyl-pyridine-4-carbonyl)-1,2,3,4-tetrahydro-quinolin-4-yl]-N-phenyl-propionamide (A-131)

(±)-Cis-N-[2-methyl-1-(2-methyl-pyridine-4-carbonyl)-1,2,3,4-tetrahydro-quinolin-4-yl]-N-phenyl-propionamide was made following general procedure A, substituting 2-methyl-isonicotinoyl chloride for 2-furoyl chloride and propionyl chloride for acetyl chloride.

$^1$H-NMR (CDCl$_3$) δ: 1.11–1.16 (3H, d; overlapping 3H, t, and 1H, t), 2.20–2.35 (overlapping 2H, q; and 1H, m), 2.47 (3H, s), 4.80 (1H, m), 5.60 (1H, m), 6.48 (1H, d), 6.65 (1H, d), 6.85 (1H, t), 7.10–7.40 (8H, m), 8.30 (1H, d).

MS m/z: 414 (M+1).

(±)-Cis-N-[1-(4-fluoro-benzoyl)-2-methyl-1,2,3,4-tetrahydro-quinolin-4-yl]-3-methyl-N-phenyl-butyramide (A-132)

(±)-Cis-N-[1-(4-fluoro-benzoyl)-2-methyl-1,2,3,4-tetrahydro-quinolin-4-yl]-3-methyl-N-phenyl-butyramide was made following general procedure A, substituting 4-fluorobenzoyl chloride for 2-furoyl chloride and 3-methyl-butyryl chloride for acetyl chloride.

$^1$H-NMR (CDCl$_3$) δ: 0.90 (2×3H, d), 1.15 (3H, d; overlapping 1H, t), 2.15 (1H, m), 2.20–2.35 (overlapping 2H, m; 1H, m), 4.80 (1H, m), 5.65 (1H, m), 6.50 (1H, d), 6.90 (4H, complex), 7.20–7.60 (8H, m).

MS m/z: 445 (M+1).

(±)-Cis-N-[2-methyl-1-(6-methyl-pyridine-3-carbonyl)-1,2,3,4-tetrahydro-quinolin-4-yl]-N-phenyl-propionamide (A-133)

(±)-Cis-N-[2-methyl-1-(6-methyl-pyridine-3-carbonyl)-1,2,3,4-tetrahydro-quinolin-4-yl]-N-phenyl-propionamide was made following general procedure A, substituting 6-methyl-nicotinoyl chloride for 2-furoyl chloride and propionyl chloride for acetyl chloride.

$^1$H-NMR (CDCl$_3$) δ: 1.11–1.16 (3H, d; overlapping 3H, t, and 1H, t), 2.20–2.40 (overlapping 2H, q; and 1H, m), 2.49 (3H, s), 4.80 (1H, m), 5.60 (1H, m), 6.48 (1H, d), 6.80–7.00 (1H, d; 1H, t), 7.10–7.50 (9H, m), 8.60 (1H, d).

MS m/z: 414 (M+1).

(±)-Cis-N-[1-(4-fluoro-benzoyl)-2-methyl-1,2,3,4-tetrahydro-quinolin-4-yl]-2-morpholin-4-yl-N-phenyl-acetamide (A-134)

(±)-Cis-N-[1-(4-fluoro-benzoyl)-2-methyl-1,2,3,4-tetrahydro-quinolin-4-yl]-2-morpholin-4-yl-N-phenyl-acetamide was made following general procedure A, substituting 4-fluorobenzoyl chloride for 2-furoyl chloride and morpholinoacetyl chloride for acetyl chloride.

(±)-Cis-N-[1-(2,3-dihydro-benzo[1,4]dioxine-6-carbonyl)-2-methyl-1,2,3,4-tetrahydro-quinolin-4-yl]-N-phenyl-propionamide (A-135)

(±)-Cis-N-[1-(2,3-dihydro-benzo[1,4]dioxine-6-carbonyl)-2-methyl-1,2,3,4-tetrahydro-quinolin-4-yl]-N-phenyl-propionamide was made following general procedure A, substituting (±)-cis-2,3-dihydro-benzo[1,4]dioxine-6-carbonyl chloride for 2-furoyl chloride and propionyl chloride for acetyl chloride.

$^1$H-NMR (CDCl$_3$) δ: 1.10 (3H, d; overlapping 3H, t; 1H, t), 2.10 (2H, q, 1H, m), 4.10 (2×2H, m), 4.70 (1H, m), 5.65 (1H, m), 6.50–6.60 (2×1H, d), 7.20–7.40 (7H, m).

MS m/z: 457 (M+1).

(±)-Cis-N-[2-methyl-1-(5-trifluoromethyl-thiophene-2-carbonyl)-1,2,3,4-tetrahydro-quinolin-4-yl]-N-phenyl-propionamide (A-136)

(±)-Cis-N-[2-methyl-1-(5-trifluoromethyl-thiophene-2-carbonyl)-1,2,3,4-tetrahydro-quinolin-4-yl]-N-phenyl-propionamide was made following general procedure A, substituting 5-trifluoromethyl-thiophene-2-carbonyl chloride for 2-furoyl chloride and propionyl chloride for acetyl chloride.

$^1$H-NMR (CDCl$_3$) δ: 1.10–1.15 (3H, d; overlapping 3H, t; 1H, t), 2.15–2.35 (2H, q, 1H, m), 4.70 (1H, m), 5.55 (1H, m), 6.45 (1H, d), 6.85 (1H, d), 7.00–7.20 (overlapping 1H, d; 1H, t), 7.20–7.60 (7H, m).

MS m/z: 473 (M+1).

(±)-Cis-N-[2-methyl-1-(6-trifluoromethyl-pyridine-3-carbonyl)-1,2,3,4-tetrahydro-quinolin-4-yl]-N-phenyl-propionamide (A-137)

(±)-Cis-N-[2-methyl-1-(6-trifluoromethyl-pyridine-3-carbonyl)-1,2,3,4-tetrahydro-quinolin-4-yl]-N-phenyl-propionamide was made following general procedure A, substituting 6-trifluoromethyl-nicotinoyl chloride for 2-furoyl chloride and propionyl chloride for acetyl chloride.

$^1$H-NMR (CDCl$_3$) δ: 1.10 (3H, d; overlapping 3H, t; 1H, t), 2.00–2.40 (2H, q, 1H, m), 4.80 (1H, m), 5.65 (1H, m), 6.40 (1H, d), 7.00 (1H, d), 7.20–7.50 (9H, m), 8.70 (1H).

MS m/z: 468 (M+1).

(±)-Cis-N-[2-methyl-1-(3-methyl-isoxazole-5-carbonyl)-1,2,3,4-tetrahydro-quinolin-4-yl]-N-phenyl-propionamide (A-138)

(±)-Cis-N-[2-methyl-1-(3-methyl-isoxazole-5-carbonyl)-1,2,3,4-tetrahydro-quinolin-4-yl]-N-phenyl-propionamide was made following general procedure A, substituting 3-methyl-isoxazole-5-carbonyl chloride for 2-furoyl chloride and propionyl chloride for acetyl chloride.

$^1$H-NMR (CDCl$_3$) δ: 1.10 (overlapping 3H, d; 3H, t; 1H, t), 2.10–2.40 (overlapping 3H, s; 2H, q; 1H, m), 4.80 (1H, m), 5.50 (1H, m), 6.80 (1H, d), 7.10 (1H, t), 7.20–7.50 (9H, m).

MS m/z: 404 (M+1).

(±)-Cis-N-[2-methyl-1-(4-oxazol-5-yl-benzoyl)-1,2,3,4-tetrahydro-quinolin-4-yl]-N-phenyl-propionamide (A-139)

(±)-Cis-N-[2-Methyl-1-(4-oxazol-5-yl-benzoyl)-1,2,3,4-tetrahydro-quinolin-4-yl]-N-phenyl-propionamide was made following general procedure A, substituting 4-oxazol-5-yl-benzoyl chloride for 2-furoyl chloride and propionyl chloride for acetyl chloride.

$^1$H-NMR (CDCl$_3$) δ: 1.00–1.20 (overlapping 3H, t; 3H, d; 1H, t), 2.20–2.40 (2H, q; 1H, m), 4.80 (1H, m), 5.65 (1H, m), 6.55 (1H, d), 6.90 (1H, t), 7.20–7.60 (12H, m), 7.90 (1H, s).

MS m/z: 466 (M+1).

(±)-Cis-N-[1-(benzo[c]isoxazole-3-carbonyl)-2-methyl-1,2,3,4-tetrahydro-quinolin-4-yl]-N-phenyl-propionamide (A-140)

(±)-Cis-N-[1-(benzo[c]isoxazole-3-carbonyl)-2-methyl-1,2,3,4-tetrahydro-quinolin-4-yl]-N-phenyl-propionamide was made following general procedure A, substituting benzo

[c]isoxazole-3-carbonyl chloride for 2-furoyl chloride and propionyl chloride for acetyl chloride.

¹H-NMR (CDCl₃) δ: 1.14 (3H, t); 1.23 (3H, d), 2.20 (2H, q), 2.40 (1H, m), 4.80 (1H, m), 5.60 (1H, m), 6.60 (1H, d), 7.00 (3H, complex), 7.00–7.40 (8H, m), 7.55 (1H, d).

MS m/z: 440 (M+1).

(±)-Cis-N-[1-(4-fluoro-benzoyl)-2-methyl-1,2,3,4-tetrahydro-quinolin-4-yl]-N-phenyl-succinamic acid methyl ester (A-141)

(±)-Cis-N-[1-(4-fluoro-benzoyl)-2-methyl-1,2,3,4-tetrahydro-quinolin-4-yl]-N-phenyl-succinamic acid methyl ester was made following general procedure A, substituting 4-fluorobenzoyl chloride for 2-furoyl chloride and 3-chlorocarbonyl-propionic acid methyl ester for acetyl chloride.

(±)-Cis-N-{1-[5-(4-chloro-phenyl)-furan-2-carbonyl]-2-methyl-1,2,3,4-tetrahydro-quinolin-4-yl}-N-phenyl-propionamide (A-142)

(±)-Cis-N-{1-[5-(4-chloro-phenyl)-furan-2-carbonyl]-2-methyl-1,2,3,4-tetrahydro-quinolin-4-yl}-N-phenyl-propionamide was made following general procedure A, substituting 5-(4-chloro-phenyl)-furan-2-carbonyl chloride for 2-furoyl chloride and propionyl chloride for acetyl chloride.

¹H-NMR (CDCl₃) δ: 1.08–1.36 (7H, m), 2.15–2.35 (3H, m), 4.72 (1H, q), 5.40–5.60 (1H, br), 6.53 (2H, d), 6.89 (1H, d), 7.04–7.09 (1H, m), 7.17–7.40 (10H, m).

MS m/z: 499 (M+1).

(±)-Cis-N-{1-[5-(2-chloro-4-trifluoromethyl-phenyl)-furan-2-carbonyl]-2-methyl-1,2,3,4-tetrahydro-quinolin-4-yl}-N-phenyl-propionamide (A-143)

(±)-Cis-N-{1-[5-(2-chloro-4-trifluoromethyl-phenyl)-furan-2-carbonyl]-2-methyl-1,2,3,4-tetrahydro-quinolin-4-yl}-N-phenyl-propionamide was made following general procedure A, substituting 5-(2-chloro-4-trifluoromethyl-phenyl)-furan-2-carbonyl chloride for 2-furoyl chloride and propionyl chloride for acetyl chloride.

¹H-NMR (CDCl₃) δ: 1.08–1.36 (7H, m), 2.15–2.35 (3H, m), 4.72 (1H, q), 5.40–5.60 (1H, br), 6.78–6.87 (2H, m), 7.05–7.49 (11H, m).

MS m/z: 567 (M+1).

(±)-Cis-N-{2-methyl-1-[5-(4-nitro-phenyl)-furan-2-carbonyl]-1,2,3,4-tetrahydro-quinolin-4-yl}-N-phenyl-propionamide (A-144)

(±)-Cis-N-{2-methyl-1-[5-(4-nitro-phenyl)-furan-2-carbonyl]-1,2,3,4-tetrahydro-quinolin-4-yl}-N-phenyl-propionamide propionamide was made following general procedure A, substituting 5-(4-nitro-phenyl)-furan-2-carbonyl chloride for 2-furoyl chloride and propionyl chloride for acetyl chloride.

¹H-NMR (CDCl₃) δ: 1.13–1.22 (7H, m), 2.20–2.36 (3H, m), 4.70 (1H, q), 5.40–5.60 (1H, br), 6.70 (2H, d), 6.87 (1H, d), 7.03 (1H, t), 7.25–7.47 (8H, m), 8.15 (2H, d).

MS m/z: 510 (M+1).

(±)-Cis-N-[2-methyl-1-(5-methyl-isoxazole-3-carbonyl)-1,2,3,4-tetrahydro-quinolin-4-yl]-N-phenyl-propionamide (A-145)

(±)-Cis-N-[2-methyl-1-(5-methyl-isoxazole-3-carbonyl)-1,2,3,4-tetrahydro-quinolin-4-yl]-N-phenyl-propionamide was made following general procedure A, substituting 5-methyl-isoxazole-3-carbonyl chloride for 2-furoyl chloride and propionyl chloride for acetyl chloride.

¹H-NMR (CDCl₃) δ: 1.10–1.27 (7H, m), 2.13–2.35 (6H, m), 4.78 (1H, q), 5.40–5.60 (1H, br), 6.84–6.86 (1H, d), 7.05 (1H, t), 7.22–7.38 (7H, m).

MS m/z: 404 (M+1).

(±)-Cis-N-[2-methyl-1-(2-methyl-thiophene-3-carbonyl)-1,2,3,4-tetrahydro-quinolin-4-yl]-N-phenyl-propionamide (A-146)

(±)-Cis-N-[2-methyl-1-(2-methyl-thiophene-3-carbonyl)-1,2,3,4-tetrahydro-quinolin-4-yl]-N-phenyl-propionamide was made following general procedure A, substituting 2-methyl-thiophene-3-carbonyl chloride for 2-furoyl chloride and propionyl chloride for acetyl chloride.

¹H-NMR (CDCl₃) δ: 1.01–1.27 (7H, m), 2.13–2.39 (6H, m), 4.62–4.78 (1H, m), 5.40–5.60 (1H, br), 6.31–6.45 (2H, m), 6.60–6.83 (2H, m), 7.02–7.38 (6H, m).

MS m/z: 420 (M+1).

(±)-Cis-but-3-enoic acid [1-(4-fluoro-benzoyl)-2-methyl-1,2,3,4-tetrahydro-quinolin-4-yl]-phenyl-amide (A-147)

(±)-Cis-but-3-enoic acid [1-(4-fluoro-benzoyl)-2-methyl-1,2,3,4-tetrahydro-quinolin-4-yl]-phenyl-amide was made following general procedure A, substituting 4-fluorobenzoyl chloride for 2-furoyl chloride and but-3-enoyl chloride for acetyl chloride.

¹H-NMR (CDCl₃) δ: 0.98–1.17 (4H, m), 2.13–2.29 (1H, m), 2.98–3.15 (2H, m), 4.60–4.78 (1H, m), 4.98–5.20 (2H, m), 5.40–5.60 (1H, m), 5.70–5.91 (1H, m), 6.40 (1H, d), 6.75–7.46 (11H, m).

MS m/z: 429 (M+1).

(±)-Cis-N-{1-[3-(4-fluoro-phenyl)-[1,2,4]oxadiazole-5-carbonyl]-2-methyl-1,2,3,4-tetrahydro-quinolin-4-yl}-N-phenyl-propionamide (A-148)

(±)-Cis-N-{1-[3-(4-fluoro-phenyl)-[1,2,4]oxadiazole-5-carbonyl]-2-methyl-1,2,3,4-tetrahydro-quinolin-4-yl}-N-phenyl-propionamide was made following general procedure A, substituting 3-(4-fluoro-phenyl)-[1,2,4]oxadiazole-5-carbonyl chloride for 2-furoyl chloride and propionyl chloride for acetyl chloride.

¹H-NMR (CDCl₃) δ: 1.14 (3H, t), 1.23–1.25 (4H, m), 2.17–2.39 (3H, m), 4.78–4.80 (1H, m), 5.40–5.60 (1H, br), 7.03–7.09 (3H, m), 7.10–7.22 (4H, m), 7.24–7.40 (4H, m), 7.97–8.02 (2H, m).

MS m/z: 485 (M+1).

(±)-Cis-N-(1-benzoyl-2-methyl-1,2,3,4-tetrahydro-quinolin-4-yl)-N-phenyl-acetamide (A-150)

(±)-Cis-N-(1-benzoyl-2-methyl-1,2,3,4-tetrahydro-quinolin-4-yl)-N-phenyl-acetamide was made following general procedure A, substituting benzoyl chloride for 2-furoyl chloride.

¹H-NMR (CDCl₃) δ: 1.14 (3H, d), 1.58–1.69 (1H, m), 2.03 (3H, s), 2.22–2.37 (1H, m), 4.72–4.86 (1H, m), 5.62 (1H, br s), 6.49 (1H, d), 6.88 (1H, t), 7.13–7.46 (12H, m).

MS m/z: 385 (M+1).

(±)-Cis-N-[1-(4-chloro-benzoyl)-2-methyl-1,2,3,4-tetrahydro-quinolin-4-yl]-N-phenyl-acetamide (A-151)

(±)-Cis-N-[1-(4-chloro-benzoyl)-2-methyl-1,2,3,4-tetrahydro-quinolin-4-yl]-N-phenyl-acetamide was made following general procedure A, substituting 4-chlorobenzoyl chloride for 2-furoyl chloride.

¹H-NMR (CDCl₃) δ: 1.14 (3H, d), 1.61 (1H, br s), 2.03 (3H, s), 2.24–2.36 (1H, m), 4.71–4.83 (1H, m), 5.51–5.69 (1H, m), 6.48 (1H, d), 6.93 (1H, t), 7.12–7.28 (7H, m), 7.35–7.40 (4H, m).

MS m/z: 419 (M)

(±)-Cis-N-[1-(4-methoxy-benzoyl)-2-methyl-1,2,3,4-tetrahydro-quinolin-4-yl]-N-phenyl-acetamide (A-152)

(±)-Cis-N-[1-(4-methoxy-benzoyl)-2-methyl-1,2,3,4-tetrahydro-quinolin-4-yl]-N-phenyl-acetamide was made following general procedure A, substituting 4-methoxybenzoyl chloride for 2-furoyl chloride.

$^1$H-NMR (CDCl$_3$) δ: 1.12 (3H, d), 1.65 (1H, br s), 2.03 (3H, s), 2.24–2.37 (1H, m), 3.74 (3H, s), 4.66–4.84 (1H, m), 5.53–5.70 (1H, m), 6.50–6.54 (1H, d), 6.68 (2H, d), 6.89–6.96 (1H, m), 7.05–7.55 (9H, m).

MS m/z: 415 (M+1).

(±)-Cis-N-[2-methyl-1-(2-methyl-benzoyl)-1,2,3,4-tetrahydro-quinolin-4-yl]-N-phenyl-acetamide (A-153)

(±)-Cis-N-[2-methyl-1-(2-methyl-benzoyl)-1,2,3,4-tetrahydro-quinolin-4-yl]-N-phenyl-acetamide was made following general procedure A, substituting 2-toluoyl chloride for 2-furoyl chloride.

$^1$H-NMR (CDCl$_3$) δ: 1.11 (3H, d), 1.60–1.64 (1H, m), 1.97 (3H, s), 2.03–2.3 (4H, m), 4.77–4.89 (1H, m), 5.41–5.58 (1H, m), 6.38–6.44 (1H, m), 6.79 (1H, t), 6.91–7.14 (4H, m), 7.16–7.28 (4H, m), 7.28–7.41 (3H, m).

MS m/z: 399 (M+1).

(±)-Cis-N-[1-(3,5-dimethyl-isoxazole-4-carbonyl)-2-methyl-1,2,3,4-tetrahydro-quinolin-4-yl]-N-phenyl-acetamide (A-154)

(±)-Cis-N-[1-(3,5-dimethyl-isoxazole-4-carbonyl)-2-methyl-1,2,3,4-tetrahydro-quinolin-4-yl]-N-phenyl-acetamide was made following general procedure A, substituting 3,5-dimethyl-isoxazole-4-carbonyl chloride for 2-furoyl chloride.

$^1$H-NMR (CDCl$_3$) δ: 1.13 (3H, d), 1.57–181 (3H, m), 1.96–2.03 (5H, m), 2.15–2.63 (3H, m), 4.66–4.81 (1H, m), 5.41–5.50 (1H, m), 6.12 (1H, d), 7.03–7.15 (1H, m), 7.24–7.48 (7H, m).

MS m/z: 404 (M+1).

(±)-Cis-N-[1-(isoxazole-5-carbonyl)-2-methyl-1,2,3,4-tetrahydro-quinolin-4-yl]-N-phenyl-acetamide (A-155)

(±)-Cis-N-[1-(isoxazole-5-carbonyl)-2-methyl-1,2,3,4-tetrahydro-quinolin-4-yl]-N-phenyl-acetamide was made following general procedure A, substituting isoxazole-5-carbonyl chloride for 2-furoyl chloride.

(±)-Cis-N-[1-(isoxazole-5-carbonyl)-2-methyl-1,2,3,4-tetrahydro-quinolin-4-yl]-N-phenyl-acetamide was separated by chiral HPLC using a chiral cel OD column and eluting with 90% hexane/10% ethanol isocratic system to give (2R,4S)- and (2S,4R)-cis-N-[1-(isoxazole-5-carbonyl)-2-methyl-1,2,3,4-tetrahydro-quinolin-4-yl]-N-phenyl-acetamide (A-70 & A-71, respectively).

$^1$H-NMR (CDCl$_3$) δ: 1.12 (3H, d), 1.64 (1H, s), 1.96 (3H, s), 2.21–2.31 (1H, m), 4.63–4.75 (1H, m), 5.34–5.44 (1H, s), 5.98 (1H, s), 6.70 (1H, d), 7.04 (1H, t), 7.21–7.35 (7H, m), 8.04–8.08 (1H, m).

MS m/z: 376 (M+1).

(±)-Cis-N-(1-cyclohexanecarbonyl-2-methyl-1,2,3,4-tetrahydro-quinolin-4-yl)-N-phenyl-acetamide (A-157)

(±)-Cis-N-(1-cyclohexanecarbonyl-2-methyl-1,2,3,4-tetrahydro-quinolin-4-yl)-N-phenyl-acetamide was made following general procedure A, substituting cyclohexanecarbonyl chloride for 2-furoyl chloride.

$^1$H-NMR (CDCl$_3$) δ: 0.97 (3H, d), 1.13–1.27 (3H, m), 1.31–1.47 (2H, m), 1.58–1.89 (7H, m), 1.99 (3H, s), 2.14–2.24 (1H, m), 2.62–2.71 (1H, m), 4.70–4.78 (1H, m), 5.24–5.29 (1H, m), 7.07–7.10 (1H, m), 7.21–7.24 (2H, m), 7.28–7.33 (2H, m), 7.34–7.42 (4H, m).

MS m/z: 391 (M+1).

(±)-Cis-N-[2-methyl-1-(pyridine-4-carbonyl)-1,2,3,4-tetrahydro-quinolin-4-yl]-N-phenyl-acetamide (A-158)

(±)-Cis-N-[2-methyl-1-(pyridine-4-carbonyl)-1,2,3,4-tetrahydro-quinolin-4-yl]-N-phenyl-acetamide was made following general procedure A, substituting isonicotinoyl chloride for 2-furoyl chloride.

$^1$H-NMR (CDCl$_3$) δ: 1.16 (3H, d), 2.04 (3H, s), 2.25–2.35 (1H, m), 4.75–4.83 (1H, m), 5.56–5.67 (1H, m), 6.45–6.48 (1H, m), 6.92 (1H, t), 7.08 (2H, d), 7.19–7.27 (3H, m), 7.34–7.42 (4H, m), 8.49 (2H, d).

MS m/z: 386 (M+1).

(±)-Cis-N-[1-(2,5-dimethyl-2H-pyrazole-3-carbonyl)-2-methyl-1,2,3,4-tetrahydro-quinolin-4-yl]-N-phenyl-acetamide (A-159)

(±)-Cis-N-[1-(2,5-dimethyl-2H-pyrazole-3-carbonyl)-2-methyl-1,2,3,4-tetrahydro-quinolin-4-yl]-N-phenyl-acetamide was made following general procedure A, substituting 2,5-dimethyl-2H-pyrazole-3-carbonyl chloride for 2-furoyl chloride.

$^1$H-NMR (CDCl$_3$) δ: 1.14 (3H, d), 2.02 (3H, m), 2.07 (3H, m), 2.23–2.32 (2H, m), 4.68–4.76 (1H, m), 5.50 (1H, s), 6.66 (1H, d), 7.04 (1H, t), 7.21–7.28 (4H, m), 7.34–7.48 (4H, m).

MS m/z: 404 (M+1).

(±)-Cis-N-[2-methyl-1-(pyridine-2-carbonyl)-1,2,3,4-tetrahydro-quinolin-4-yl]-N-phenyl-acetamide (A-160)

(±)-Cis-N-[2-methyl-1-(pyridine-2-carbonyl)-1,2,3,4-tetrahydro-quinolin-4-yl]-N-phenyl-acetamide was made following general procedure A, substituting pyridine-2-carbonyl chloride for 2-furoyl chloride.

$^1$H-NMR (CDCl$_3$) δ: 1.17 (3H, d), 1.93–2.03 (1H, m), 2.02 (3H, s), 2.32 (1H, br s), 4.78–4.86 (1H, m), 5.60–5.61 (1H, m), 6.51 (1H, d), 6.86 (1H, t), 6.99 (1H, d), 7.14–7.50 (9H, m), 8.53 (1H, d).

MS m/z: 385 (M+1).

(±)-Cis-N-[1-(isoxazole-5-carbonyl)-2-methyl-1,2,3,4-tetrahydro-quinolin-4-yl]-N-phenyl-propionamide (A-161)

(±)-Cis-N-[1-(isoxazole-5-carbonyl)-2-methyl-1,2,3,4-tetrahydro-quinolin-4-yl]-N-phenyl-propionamide following general procedure A, substituting isoxazole-5-carbonyl chloride for 2-furoyl chloride.

$^1$H-NMR (CDCl$_3$) δ: 0.95–1.20 (5H, m), 2.10–2.30 (4H, m), 4.69–4.74 (1H, m), 5.30–5.43 (1H, m), 5.96 (1H, s), 6.75 (1H, d), 7.75 (1H, t), 7.25–7.38 (8H, m), 8.06 (1H, s).

MS m/z: 390 (M+1).

Scheme 5

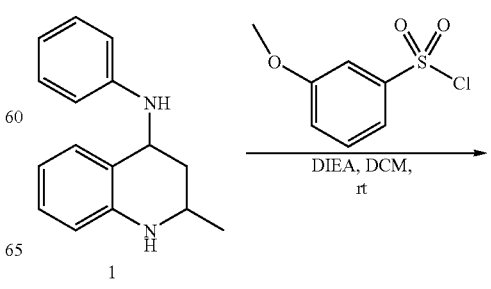

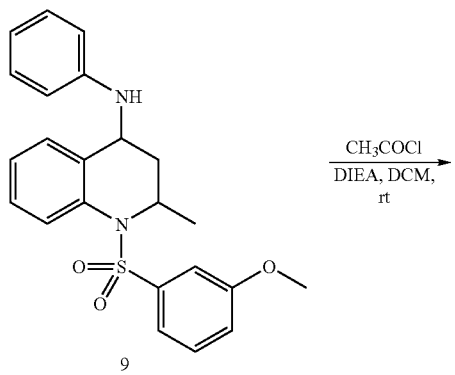
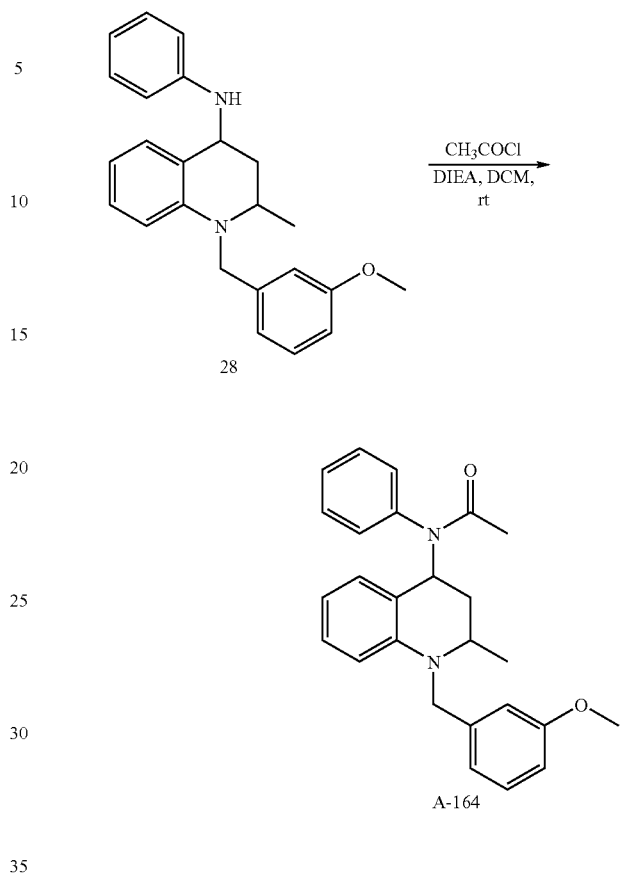

(±)-Cis-N-[1-(3-Methoxy-benzenesulfonyl)-2-methyl-1,2,3,4-tetrahydro-quinolin-4-yl]-N-phenyl-acetamide (A-162)

(±)-Cis-N-[1-(3-methoxy-benzenesulfonyl)-2-methyl-1,2,3,4-tetrahydro-quinolin-4-yl]-N-phenyl-acetamide was synthesized using general procedure A, substituting 3-methoxy-benzenesulfonyl chloride for 2-furoyl chloride.

$^1$H-NMR (CDCl$_3$) δ: 1.4 (3H, d), 1.4 (1H, m), 1.9 (3H, s), 2.0 (1H, m), 3.6 (3H, s), 4.1 (1H, m), 6.4 (1H, m), 6.9–7.4 (12H, m), 7.7 (1H, d).

MS m/z: 451 (M+1).

(±)-Cis-N-[1-(3-Methoxy-benzyl)-2-methyl-1,2,3,4-tetrahydro-quinolin-4-yl]-N-phenyl-acetamide (A-164)

(±)-Cis-N-[1-(3-methoxy-benzyl)-2-methyl-1,2,3,4-tetrahydro-quinolin-4-yl]-N-phenyl-acetamide was synthesized by dissolving (±)-cis-(2-methyl-1,2,3,4-tetrahydro-quinol-4-yl) aniline in dimethylformamide and adding potassium carbonate (1.0–10.0 equiv.), and the 1-bromomethyl-3-methoxy-benzene (1.1–3.0 equiv), catalytic potassium iodide and was stirred at room temperature for 18 hours. The reaction mixture was filtered for removal of inorganic salts and concentrated. The crude mixture was purified by flash chromatography on silica gel using gradient elution hexane-ethyl acetate (5–20%). The corresponding aniline was then acylated as previously described in general procedure A to give (±)-cis-N-[1-(3-methoxy-benzyl)-2-methyl-1,2,3,4-tetrahydro-quinolin-4-yl]-N-phenyl-acetamide.

$^1$H-NMR (CDCl$_3$) δ: 1.15 (3H, d; overlapping 1H, t), 1.90 (1H, m; 2H, m), 2.00 (3H, s), 3.33 (1H, m), 3.60 (3H, s), 4.30 (1H, m), 6.30 (1H, complex), 6.90 (1H, t), 6.90–7.40 (10H, m).

MS m/z: 443 (M+1).

(±)-Cis-N-(1-Benzyl-2-methyl-1,2,3,4-tetrahydro-quinolin-4-yl)-N-phenyl-acetamide (A-165)

(±)-Cis-N-(1-benzyl-2-methyl-1,2,3,4-tetrahydro-quinolin-4-yl)-N-phenyl-acetamide was made following the procedure describing the synthesis of A-164, substituting benzyl bromide for 1-bromomethyl-3-methoxy-benzene.

Scheme 6

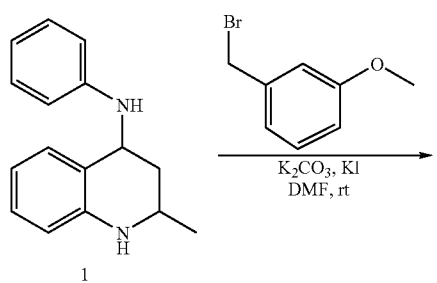

¹H-NMR (CDCl₃) δ: 1.15 (3H, d; overlapping 1H, t), 1.90 (1H, m; 2H, m), 2.00 (3H, s), 3.33 (1H, m), 4.30 (1H, m), 6.30 (1H, m), 6.70 (1H, t), 6.90–7.40 (11H, m).

MS m/z: 413 (M+1).

(±)-Cis-N-(1-Ethyl-2-methyl-1,2,3,4-tetrahydro-quinolin-4-yl)-N-phenyl-acetamide (A-166)

(±)-Cis-N-(1-Ethyl-2-methyl-1,2,3,4-tetrahydro-quinolin-4-yl)-N-phenyl-acetamide was made following the procedure describing the synthesis of A-164, substituting ethyl bromide for 1-bromomethyl-3-methoxy-benzene.

¹H-NMR (CDCl₃) δ: 1.01 (3H, t), 1.15 (3H, d; overlapping 1H, t), 1.40 (1H, m), 1.90–2.00 (overlapping 3H, s; 1H, m), 3.20 (1H, m), 3.40 (1H, q), 3.60 (1H, m), 4.60 (1H, s), 6.20 (1H, br, m), 6.60–6.80 (2H, m), 7.00–7.50 (7H, m).

MS m/z: 309 (M+1).

(±)-Cis-[4-(acetyl-phenyl-amino)-2-methyl-3,4-dihydro-2H-quinolin-1-yl]-aceticacid methyl ester (A-167)

(±)-Cis-[4-(acetyl-phenyl-amino)-2-methyl-3,4-dihydro-2H-quinolin-1-yl]-aceticacid methyl ester was made following the procedure describing the synthesis of A-164, substituting bromo-acetic acid methyl ester for 1-bromomethyl-3-methoxy-benzene.

¹H-NMR (CDCl₃) δ: 1.20 (3H, d; overlapping 1H, t), 1.80 (1H, m, 2.00 (3H, s), 3.40 (1H, m), 3.70 (3H, s), 3.90 (2H, s), 4.50 (1H, m), 6.10 (1H, t), 6.20 (1H, d), 6.75 (1H, m), 6.90–7.10 (3H, complex), 7.20–7.50 (3H, m).

MS m/z: 353 (M+1).

(±)-Cis-[4-(acetyl-phenyl-amino)-2-methyl-3,4-dihydro-2H-quinolin-1-yl]-acetic acid (A-168)

(±)-Cis-[4-(acetyl-phenyl-amino)-2-methyl-3,4-dihydro-2H-quinolin-1-yl]-acetic acid was made from (±)-cis-[4-(acetyl-phenyl-amino)-2-methyl-3,4-dihydro-2H-quinolin-1-yl]-aceticacid methyl ester. To a solution of (±)-cis-[4-(acetyl-phenyl-amino)-2-methyl-3,4-dihydro-2H-quinolin-1-yl]-acetic acid methyl ester was added 1.0 N aqueous sodium hydroxide and heated to 80° C. for 1 hr. The reaction mixture was concentrated and aqueous mixture was acidified to pH 6.0 using hydrochloric acid (1N) followed by extraction with ethyl acetate twice. Organics were dried over sodium sulfate, filtered and concentrated to yield the desired product.

¹H-NMR (CDCl₃) δ: 1.20 (3H, d; overlapping 1H, t), 1.80 (1H, m, 2.00 (3H, s), 3.40 (1H, m), 3.90 (2H, s), 4.50 (1H, m), 6.10 (1H, t), 6.20 (1H, d), 6.75 (1H, m), 6.90–7.10 (3H, m), 7.20–7.50 (3H, m).

MS m/z: 339 (M+1).

Scheme 7

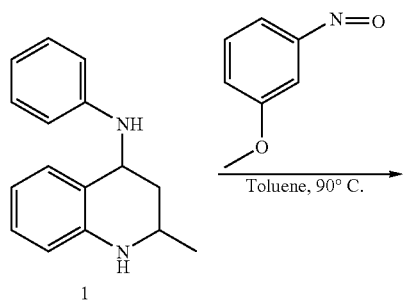

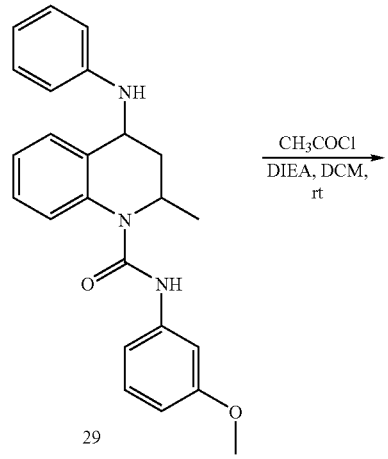

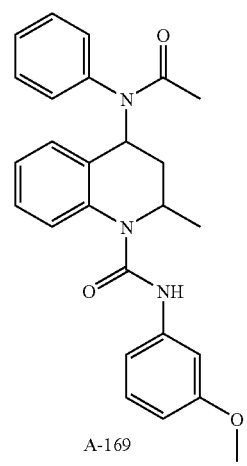

A-169

(±)-Cis-(acetyl-phenyl-amino)-2-methyl-3,4-dihydro-2H-quinoline-1-carboxylicacid (3-methoxy-phenyl)-amide (A-169)

(±)-Cis-(acetyl-phenyl-amino)-2-methyl-3,4-dihydro-2H-quinoline-1-carboxylicacid (3-methoxy-phenyl)-amide was synthesized using general procedure A, substituting 3-methoxyphenylisocyanate for 2-furoyl chloride using the following procedure. To a solution of (±)-cis-(3-methoxyphenyl)-(2-methyl-4-anilino-3,4-dihydro-2H-quinolin-1-yl)-methanone (0.1 g, 0.42 mmol) in toluene was added 3-methoxyphenylisocyanate (0.056 mL, 0.4255 mmol) and the reaction mixture was heated to 90° C. for 18 hours. Reaction was cooled to room temperature and concentrated. The crude mixture was purified by flash chromatography on silica gel using gradient elution hexane-ethyl acetate (80%/20%) to give 38% of the desired product.

¹H-NMR (CDCl₃) δ: 1.1 (3H, d), 1.2 (1H, m), 2.0 (3H, s), 2.3 (1H, m), 3.8 (3H, s), 4.5 (1H, m), 5.4 (1H, m), 6.6 (1H, d), 6.8 (2H, m) 7.1–7.5 (11H, m).

MS m/z: 430 (M+1).

Scheme 8

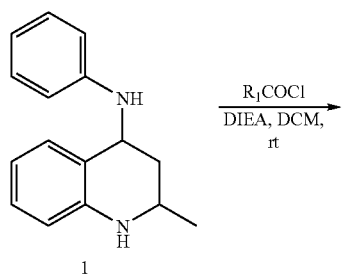

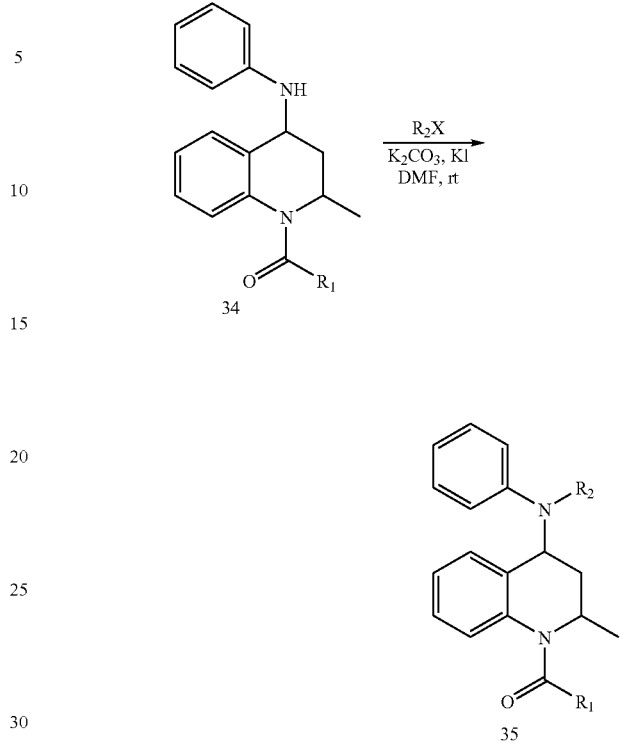

(±)-Cis-N-(1-alkyl/aroyl-2-methyl-1,2,3,4-tetrahydro-quinolin-4-yl)-N-phenyl-alkyl/aryl sulfonamide (±)-Cis-1-(2-Methyl-4-phenylamino-3,4-dihydro-2H-quinolin-1-yl)-alkanone or (±)-cis-(2-Methyl-4-phenylamino-3,4-dihydro-2H-quinolin-1-yl)-aryl-methanone can be prepared from compound 1 using general procedure A, substituting the corresponding sulfonyl chloride for acetyl chloride.

(±)-Cis-1-[4-(alkyl-phenyl-amino)-2-methyl-3,4-dihydro-2H-quinolin-1-yl]-alkanone or (±)-Cis-1-[4-(alkyl-phenyl-amino)-2-methyl-3,4-dihydro-2H-quinolin-1-yl]-aryl methanone (±)-Cis-1-[4-(alkyl-phenyl-amino)-2-methyl-3,4-dihydro-2H-quinolin-1-yl]-alkanone or (±)-cis-1-[4-(alkyl-phenyl-amino)-2-methyl-3,4-dihydro-2H-quinolin-1-yl]-aryl methanone may be prepared from compound 1 using general procedure A, substituting the corresponding alkyl chloride for acetyl chloride and using the alkylation procedure in the synthesis of A-164. Representative examples of compound 35 are shown in the table below.

Scheme 9

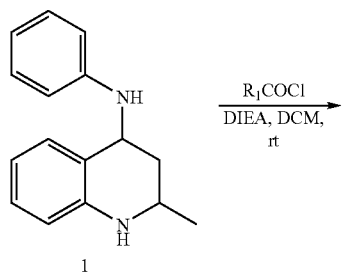

Scheme 10

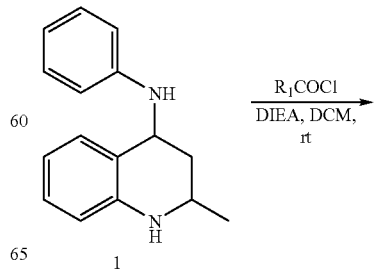

-continued

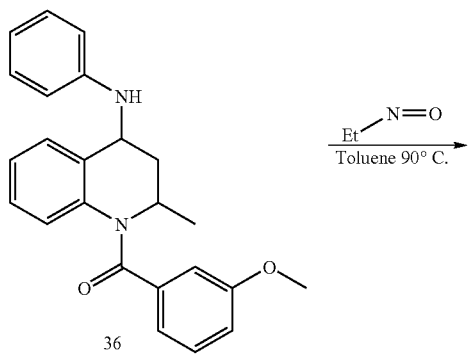

36

(±)-Cis-3-ethyl-1-[1-(3-methoxy-benzoyl)-2-methyl-1,2,3,4-tetrahydro-quinolin-4-yl]-1-phenyl-urea (A-170)

(±)-Cis-3-ethyl-1-[1-(3-methoxy-benzoyl)-2-methyl-1,2,3,4-tetrahydro-quinolin-4-yl]-1-phenyl-urea was synthesized using general procedure A, substituting ethyl isocyanate for acetyl chloride using the following procedure. To a solution of (±)-cis-(3-methoxy-phenyl)-(2-methyl-4-anilino-3,4-dihydro-2H-quinolin-1-yl)-methanone in DMF was added ethyl isocyanate and reaction mixture was heated to 90° C. for 18 hours. The reaction was cooled to room temperature and concentrated. Crude mixture was purified by flash chromatography on silica gel using gradient elution hexane-ethyl acetate (5–20%).

$^1$H-NMR (CDCl$_3$) δ: 1.05–1.20 (3H, t; overlapping 3H, d; and 1H, t), 2.35 (1H, m), 3.30 (2H, q), 3.67 (3H, s), 4.36 (1H, t), 4.80 (1H, m), 5.65 (1H, m), 6.50 (1H, d), 6.65 (1H, d), 6.80 (1H, d), 6.85 (2H, complex), 7.00 (1H, t), 7.18 (1H, t), 7.35–7.50 (6H, m).

MS m/z: 444 (M+1).

Compounds A-163, A-171–A-232 can be prepared by the schemes set forth in Schemes 1–10 and by the general procedures A and others described herein. Those skilled in the art will be able to recognize, or be able to ascertain, using no more than routine experimentation, many equivalents to the specific embodiments of the invention described herein.

TABLE 1

Compounds Derived from General Procedure A

| No. | Structure |
|---|---|
| A-1 | 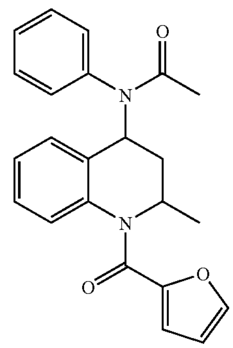 |
| A-2 | 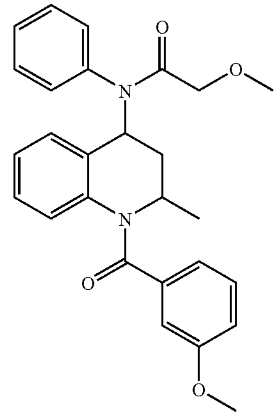 |
| A-3 | 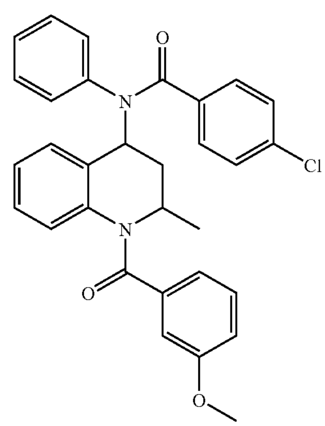 |

TABLE 1-continued
Compounds Derived from General Procedure A
| No. | Structure |
|---|---|
| A-4 | 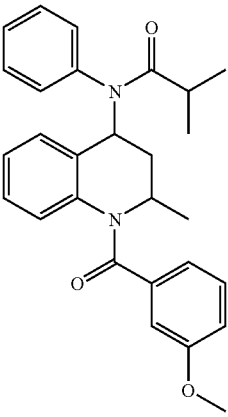 |
| A-5 | 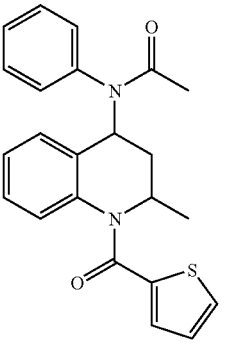 |
| A-6 | 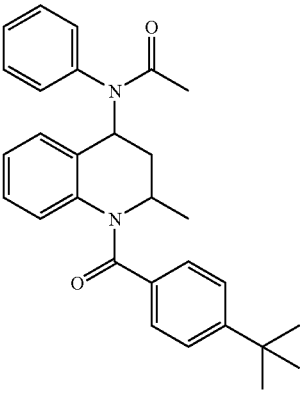 |
| A-7 | 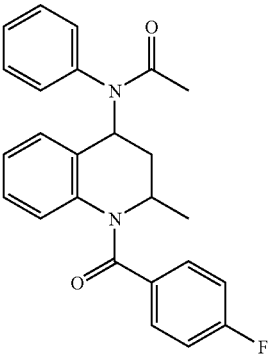 |
| A-8 | 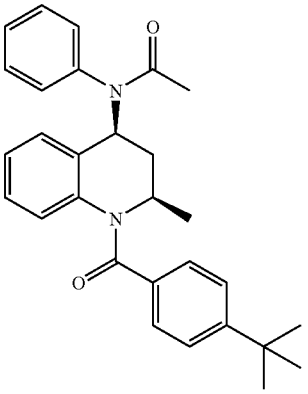 |
| A-9 | 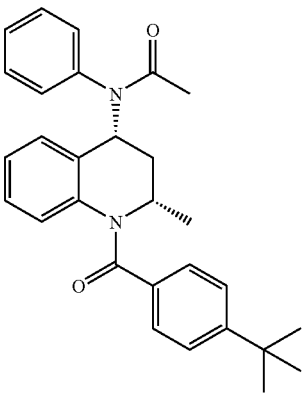 |
| A-10 | 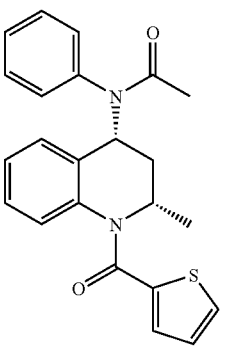 |
| A-11 | 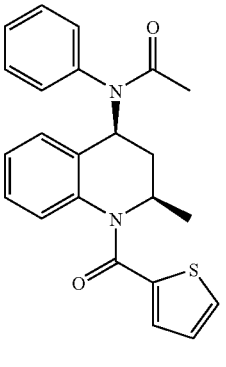 |

TABLE 1-continued

Compounds Derived from General Procedure A

| No. | Structure |
|---|---|
| A-12 | 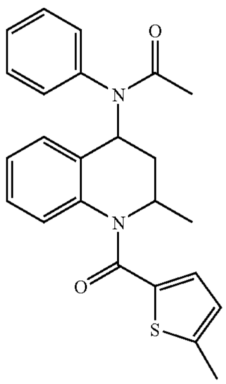 |
| A-13 | 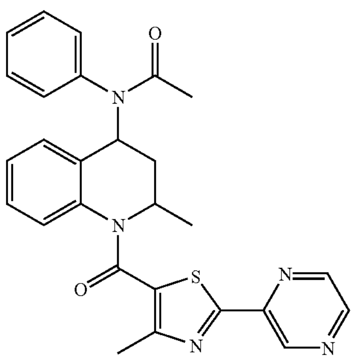 |
| A-14 | 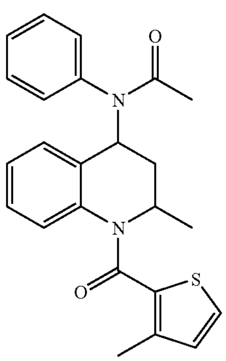 |
| A-15 | 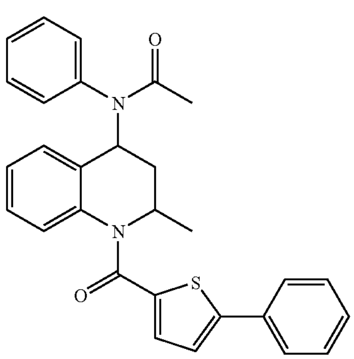 |
| A-16 | 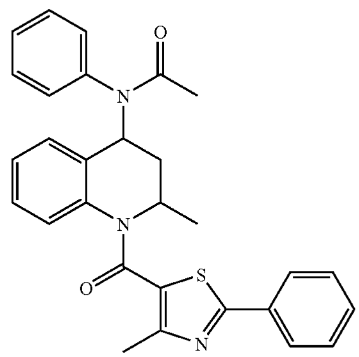 |
| A-17 | 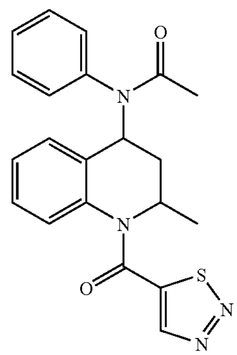 |
| A-18 | 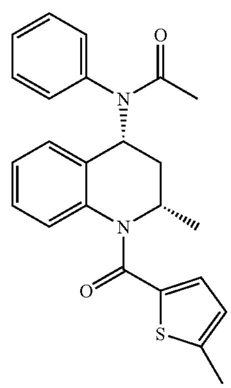 |
| A-19 | 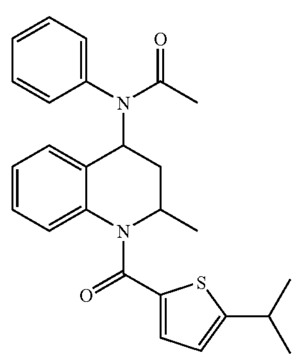 |

TABLE 1-continued

Compounds Derived from General Procedure A

| No. | Structure |
|---|---|
| A-20 | (tetrahydroquinoline core with N-phenyl-N-acetyl at C4, 2-methyl, N1-acyl with 3,4,5-trifluorobenzoyl) |
| A-21 | (tetrahydroquinoline core with N-phenyl-N-acetyl at C4, 2-methyl, N1-acyl with 4-fluoro-3-methylbenzoyl) |
| A-22 | (tetrahydroquinoline core with N-phenyl-N-acetyl at C4, 2-methyl, N1-acyl with 4-fluoro-3-trifluoromethylbenzoyl) |
| A-23 | (tetrahydroquinoline core with N-phenyl-N-acetyl at C4, 2-methyl, N1-acyl with 3-chloro-4-fluorobenzoyl) |
| A-24 | (tetrahydroquinoline core with N-phenyl-N-acetyl at C4, 2-methyl, N1-acyl with 2,4,6-trifluorobenzoyl) |
| A-25 | (tetrahydroquinoline core with N-phenyl-N-propionyl at C4, 2-methyl, N1-acyl with 4-chlorobenzoyl) |
| A-26 | (tetrahydroquinoline core with N-phenyl-N-acetyl at C4, 2-methyl, N1-acyl with 4-trifluoromethoxybenzoyl) |
| A-27 | (tetrahydroquinoline core with N-phenyl-N-acetyl at C4, 2-methyl, N1-acyl with 3-trifluoromethoxybenzoyl) |

TABLE 1-continued
Compounds Derived from General Procedure A
| No. | Structure |
|---|---|
| A-28 | 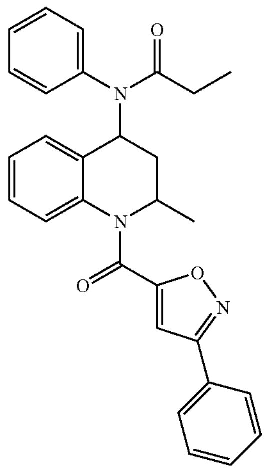 |
| A-29 | 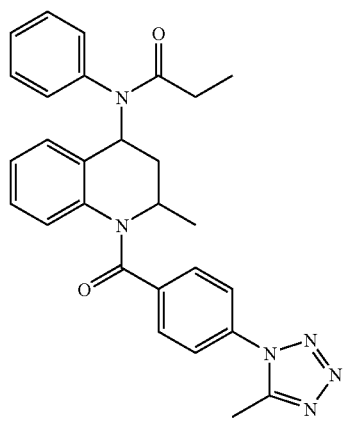 |
| A-30 | 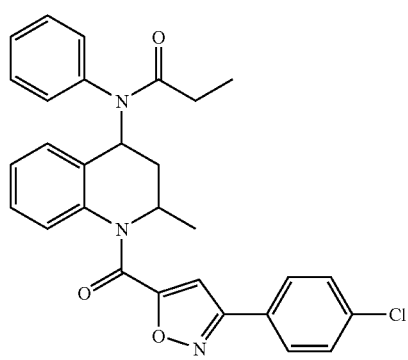 |
TABLE 1-continued
Compounds Derived from General Procedure A
| No. | Structure |
|---|---|
| A-31 | 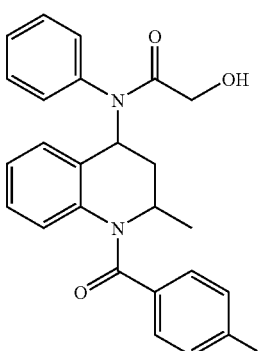 |
| A-32 | 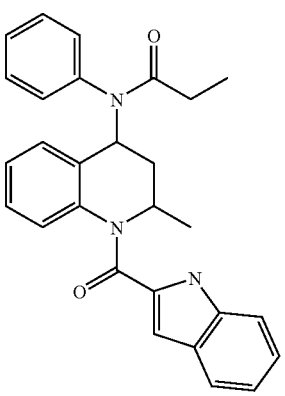 |
| A-33 | 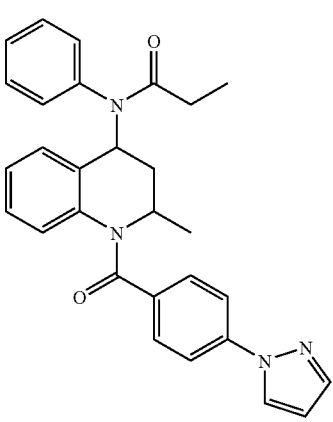 |

TABLE 1-continued

Compounds Derived from General Procedure A

| No. | Structure |
|-----|-----------|
| A-34 | 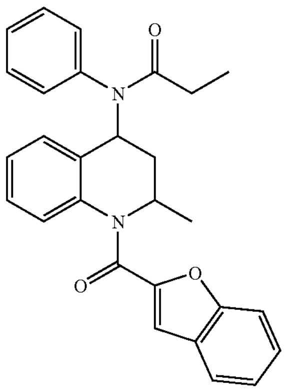 |
| A-35 | 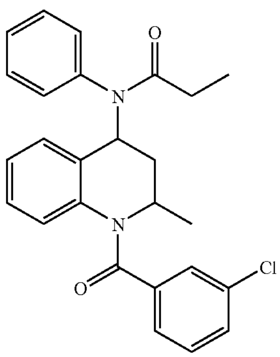 |
| A-36 | 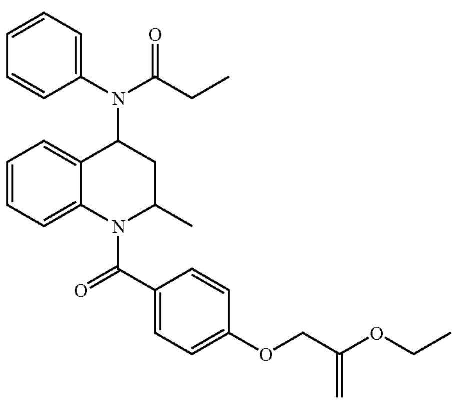 |
| A-37 | 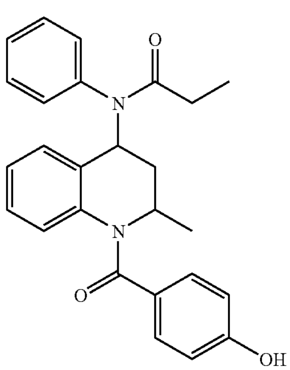 |
| A-38 | |
| A-39 | |
| A-40 | |
| A-41 | |

TABLE 1-continued

Compounds Derived from General Procedure A

| No. | Structure |
|-----|-----------|
| A-42 | |
| A-43 | |
| A-44 | |
| A-45 | 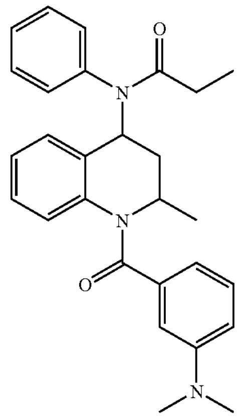 |
| A-46 | 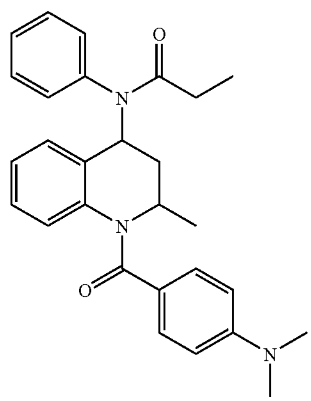 |
| A-47 | 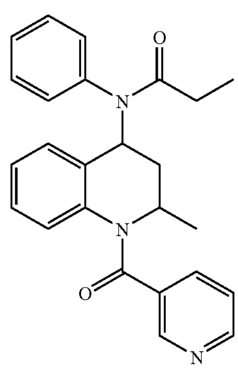 |
| A-48 | 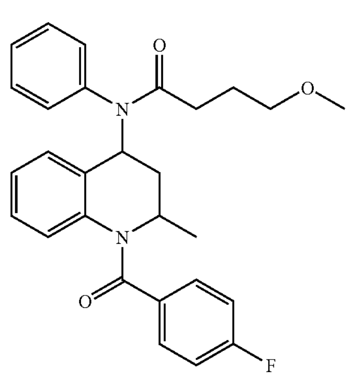 |

TABLE 1-continued
Compounds Derived from General Procedure A
| No. | Structure |
|-----|-----------|
| A-49 | 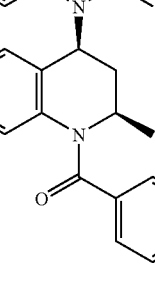 |
| A-50 | 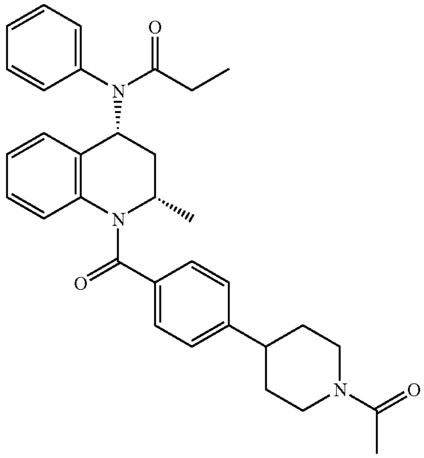 |
| A-51 | 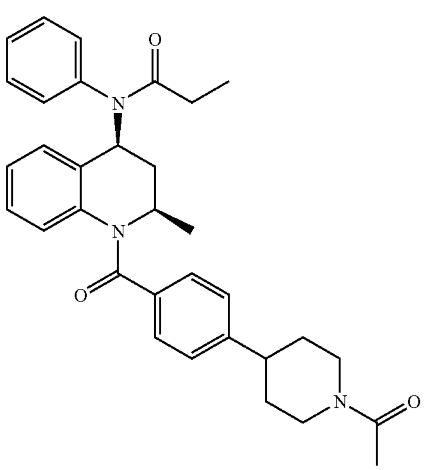 |
TABLE 1-continued
Compounds Derived from General Procedure A
| No. | Structure |
|-----|-----------|
| A-52 | 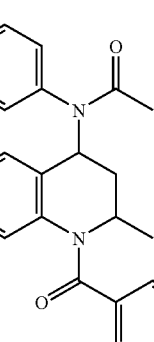 |
| A-53 | 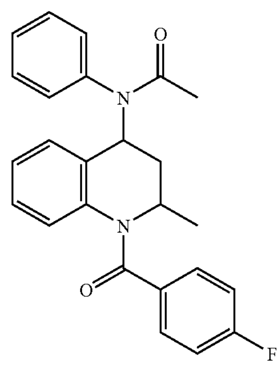 |
| A-54 | 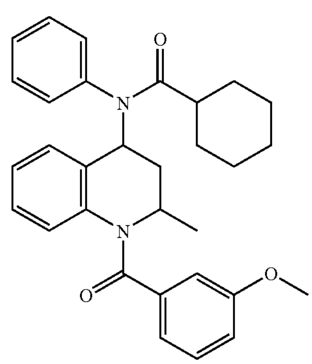 |
| A-55 | 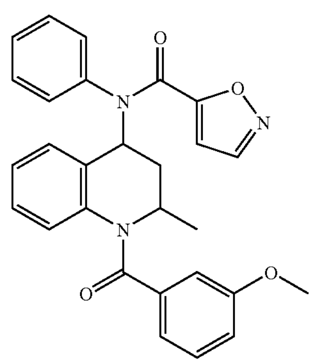 |

TABLE 1-continued

Compounds Derived from General Procedure A

| No. | Structure |
|---|---|
| A-56 | 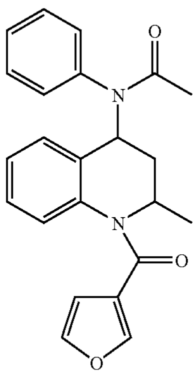 |
| A-57 | 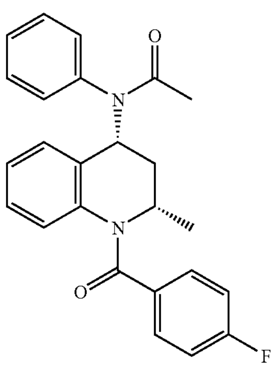 |
| A-58 | 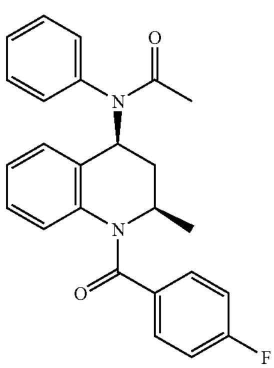 |
| A-59 | 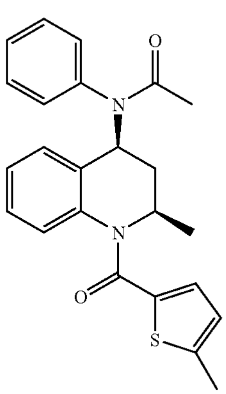 |
| A-60 | |
| A-61 | |
| A-62 | |
| A-63 | |

TABLE 1-continued
Compounds Derived from General Procedure A
| No. | Structure |
|-----|-----------|
| A-64 | 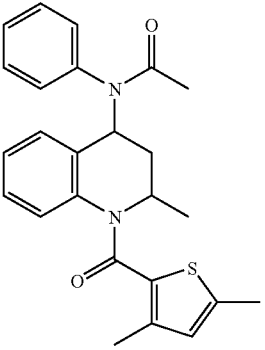 |
| A-65 | 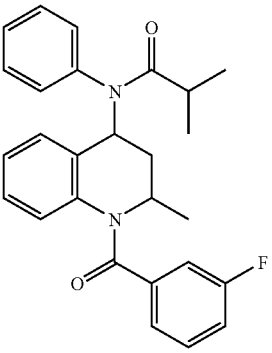 |
| A-66 | 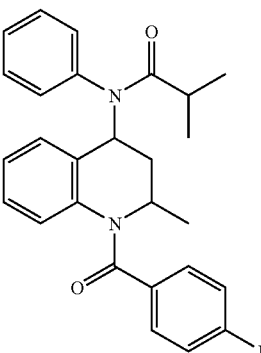 |
| A-67 | 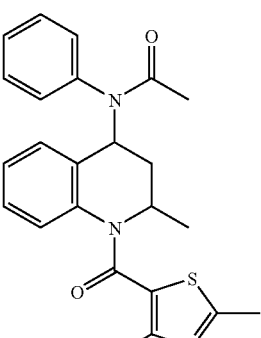 |
| A-68 | 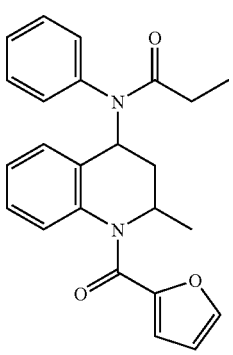 |
| A-69 | 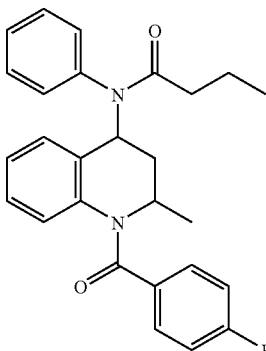 |
| A-70 | 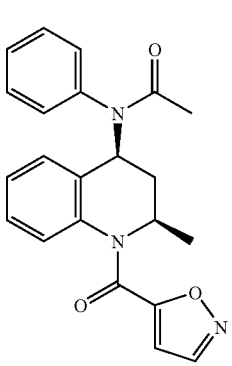 |
| A-71 | 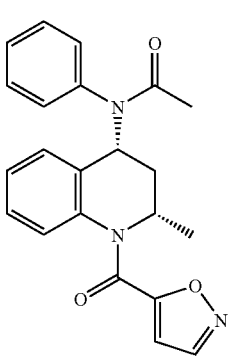 |

TABLE 1-continued

Compounds Derived from General Procedure A

| No. | Structure |
|---|---|
| A-72 | 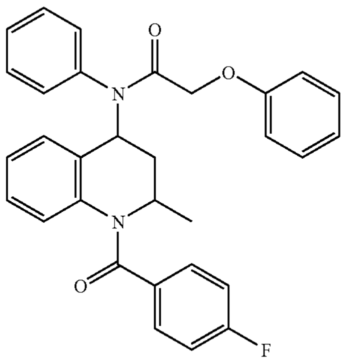 |
| A-73 | 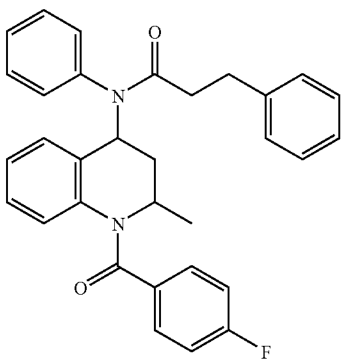 |
| A-74 | 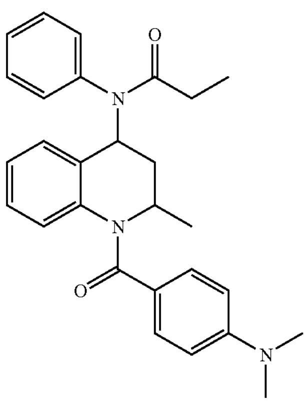 |
| A-75 | 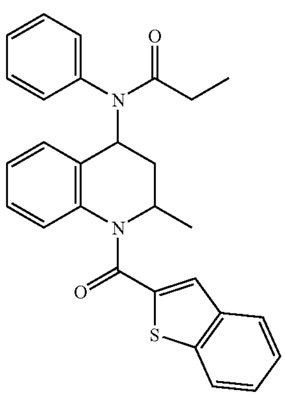 |
| A-76 | |
| A-77 | |
| A-78 | |
| A-79 | |

TABLE 1-continued
Compounds Derived from General Procedure A
| No. | Structure |
|---|---|
| A-80 | 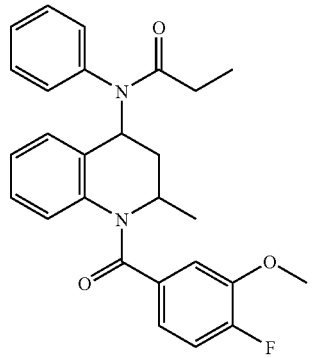 |
| A-81 | 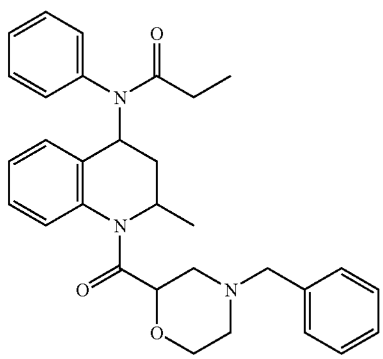 |
| A-82 | 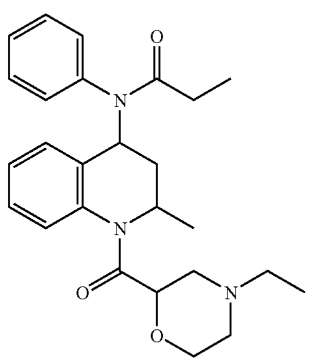 |
| A-83 | 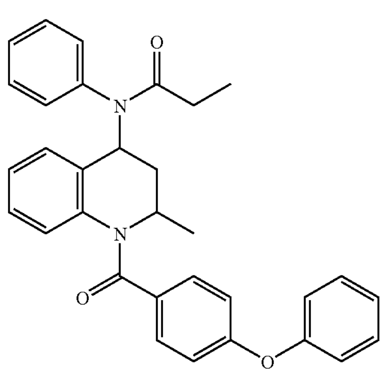 |
| A-84 | 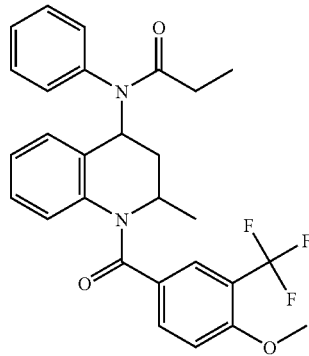 |
| A-85 | |
| A-86 | |
| A-87 | |

TABLE 1-continued
Compounds Derived from General Procedure A
| No. | Structure |
|---|---|
| A-88 | 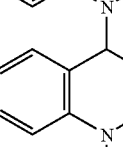 |
| A-89 | 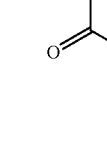 |
| A-90 | 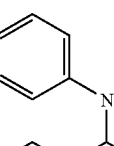 |
| A-91 | 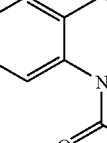 |
| A-92 | 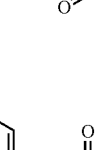 |
| A-93 | 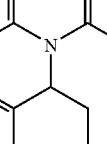 |
| A-94 | 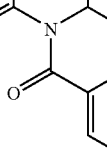 |

TABLE 1-continued
Compounds Derived from General Procedure A
| No. | Structure |
|---|---|
| A-95 | 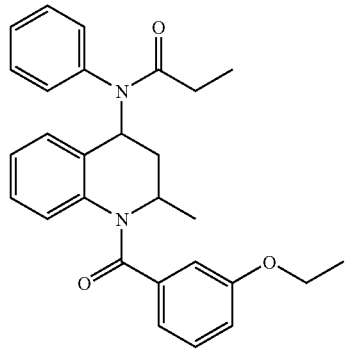 |
| A-96 | 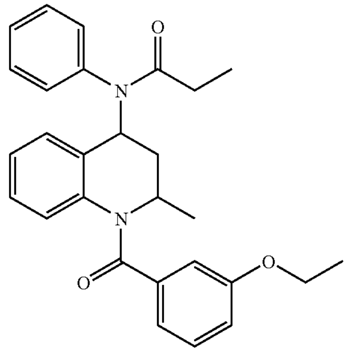 |
| A-97 | 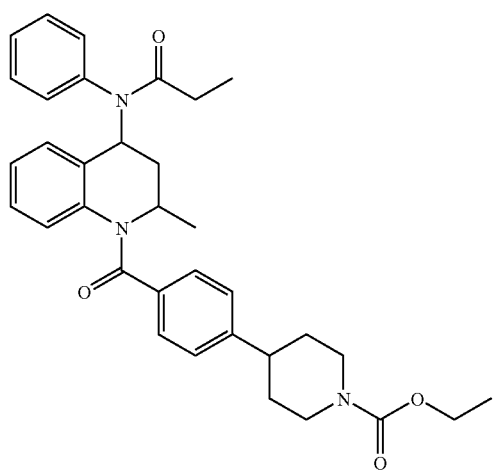 |
TABLE 1-continued
Compounds Derived from General Procedure A
| No. | Structure |
|---|---|
| A-98 | 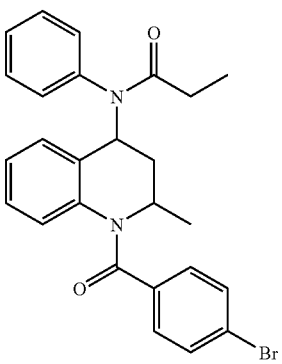 |
| A-99 | 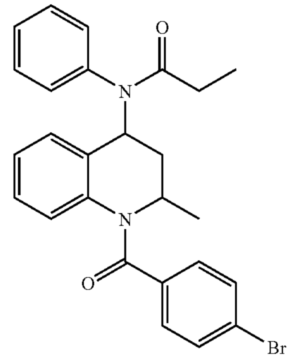 |
| A-100 | 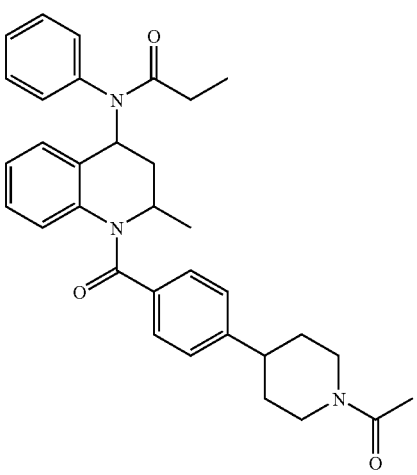 |

TABLE 1-continued

Compounds Derived from General Procedure A

| No. | Structure |
|---|---|
| A-101 | 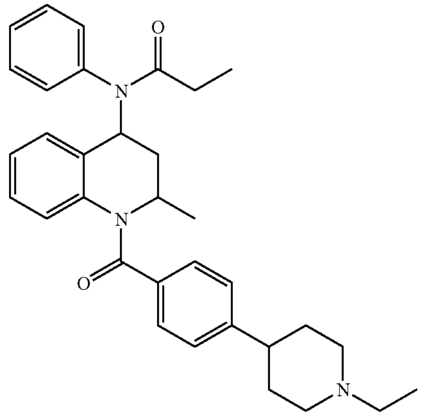 |
| A-102 | 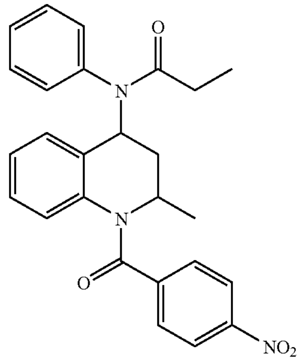 |
| A-103 | 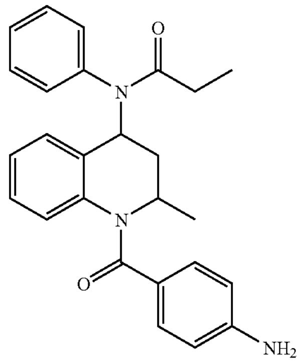 |
| A-104 | |
| A-105 | |
| A-106 | |

TABLE 1-continued

Compounds Derived from General Procedure A

| No. | Structure |
|---|---|
| A-107 | 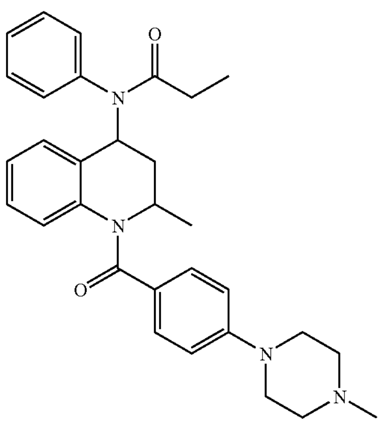 |
| A-108 | 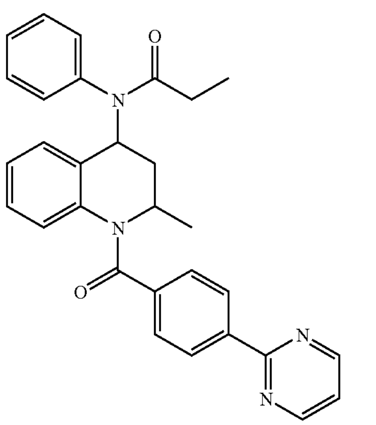 |
| A-109 | 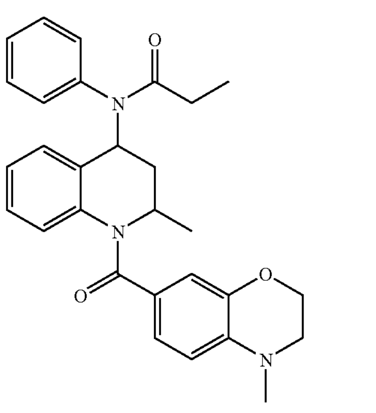 |
| A-110 | |
| A-111 | |
| A-112 | |

TABLE 1-continued
Compounds Derived from General Procedure A
| No. | Structure |
|---|---|
| A-113 | 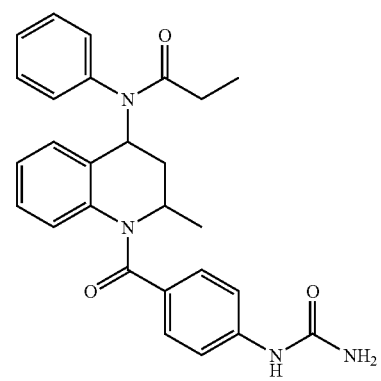 |
| A-114 | 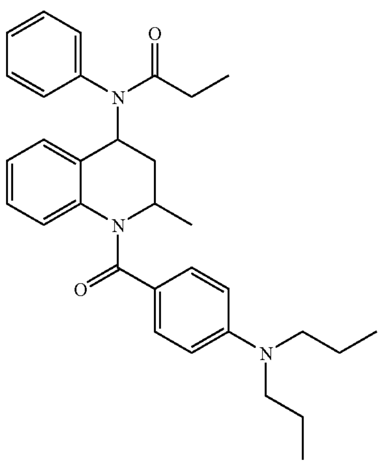 |
| A-115 | 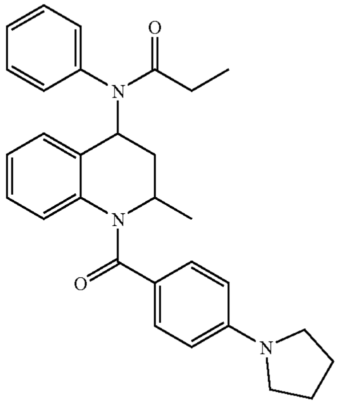 |
| A-116 | 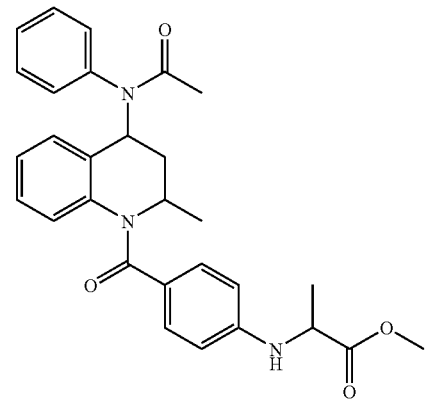 |
| A-117 | |
| A-118 | 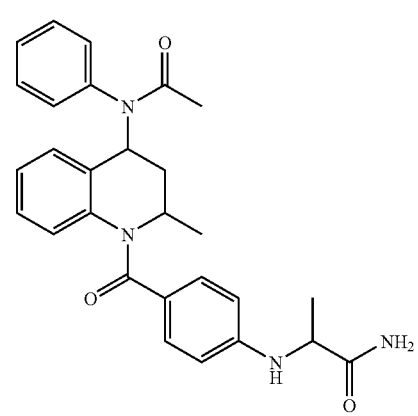 |

TABLE 1-continued

Compounds Derived from General Procedure A

| No. | Structure |
|---|---|
| A-119 | |
| A-120 | |
| A-121 | |
| A-122 | 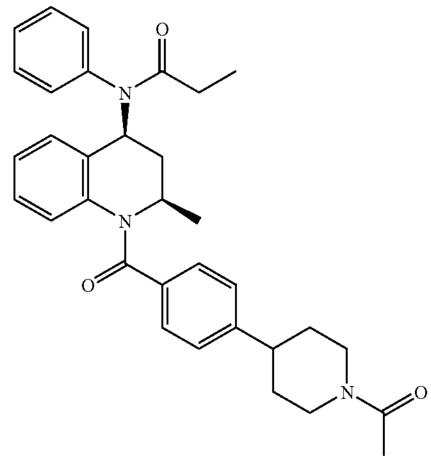 |
| A-123 | 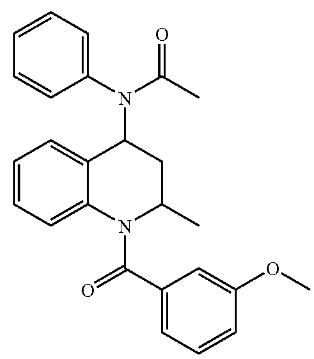 |
| A-124 | 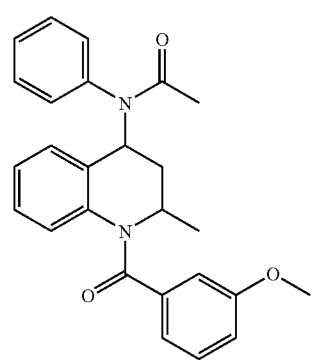 |
| A-125 | 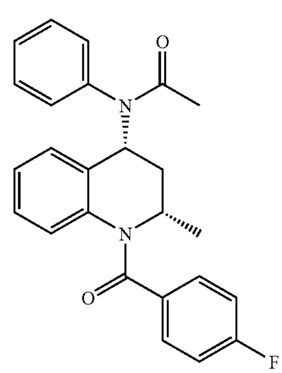 |

TABLE 1-continued

Compounds Derived from General Procedure A

| No. | Structure |
| --- | --- |
| A-126 | 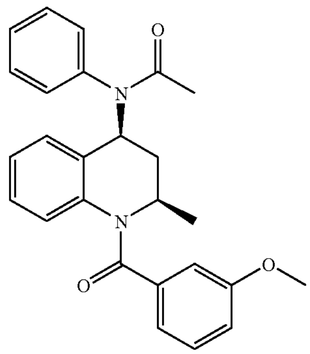 |
| A-127 | 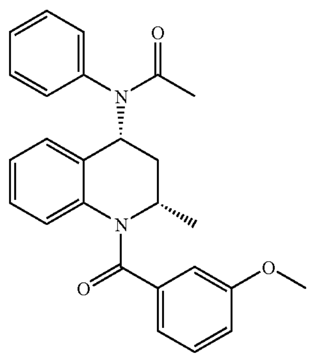 |
| A-128 | 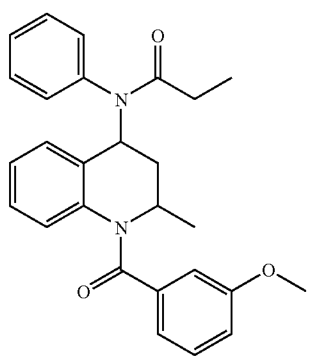 |
| A-129 | 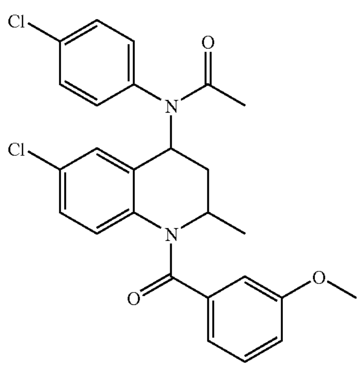 |
| A-130 | |
| A-131 | |
| A-132 | |
| A-133 | |

TABLE 1-continued

Compounds Derived from General Procedure A

| No. | Structure |
|---|---|
| A-134 | 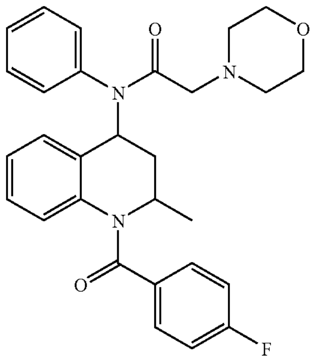 |
| A-135 | 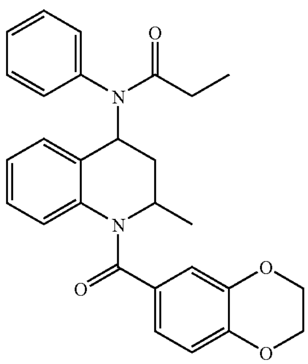 |
| A-136 | 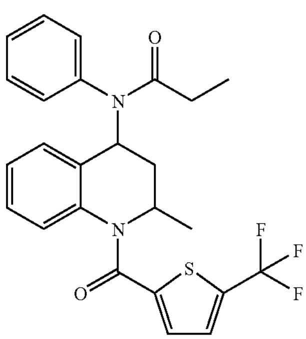 |
| A-137 | 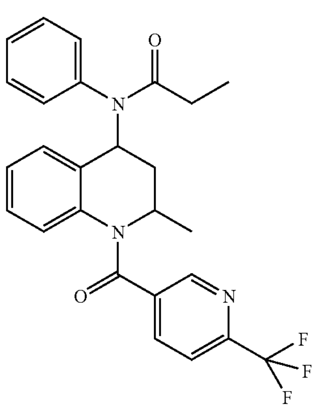 |
| A-138 | |
| A-139 | |
| A-140 | |

TABLE 1-continued

Compounds Derived from General Procedure A

| No. | Structure |
|---|---|
| A-141 | 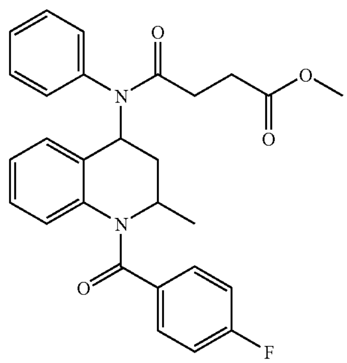 |
| A-142 | 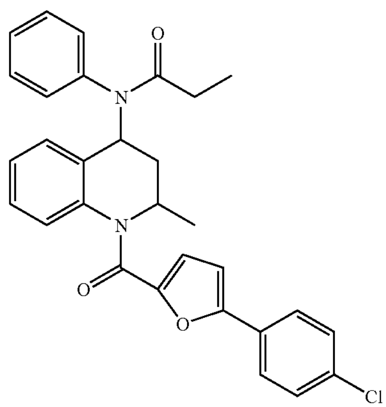 |
| A-143 | 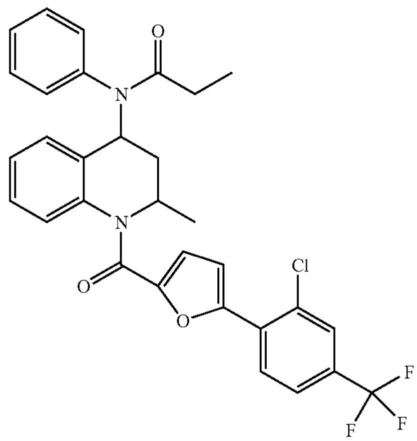 |
| A-144 | 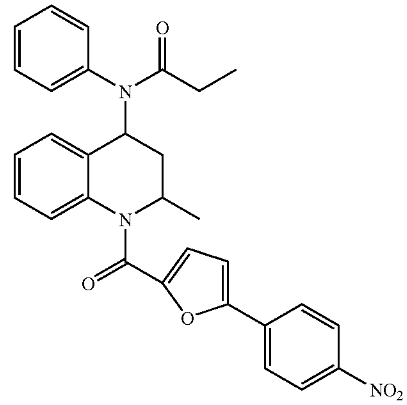 |
| A-145 | 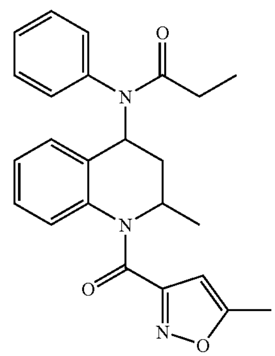 |
| A-146 | 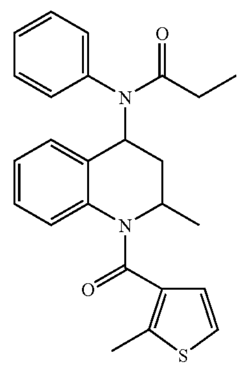 |
| A-147 | 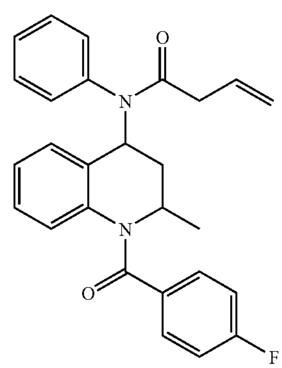 |

TABLE 1-continued
Compounds Derived from General Procedure A
| No. | Structure |
|---|---|
| A-148 | 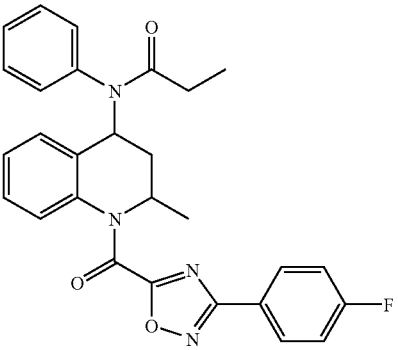 |
| A-149 | 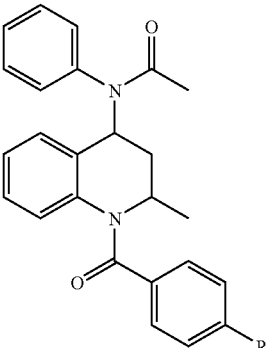 |
| A-150 | 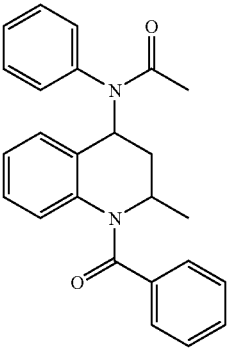 |
| A-151 | 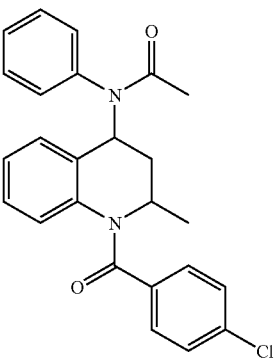 |
| A-152 | 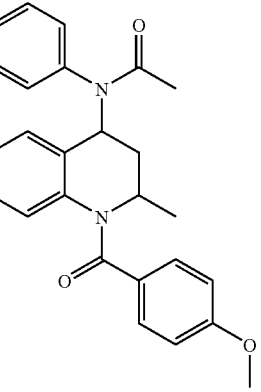 |
| A-153 | 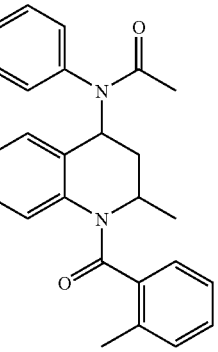 |
| A-154 | 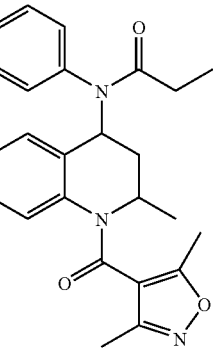 |
| A-155 | 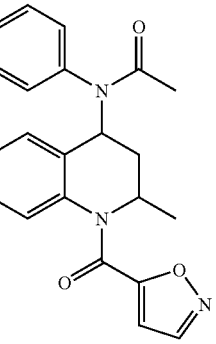 |

TABLE 1-continued

Compounds Derived from General Procedure A

| No. | Structure |
|---|---|
| A-156 | 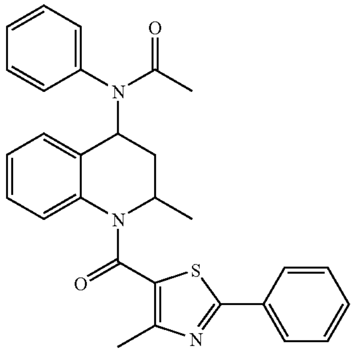 |
| A-157 | 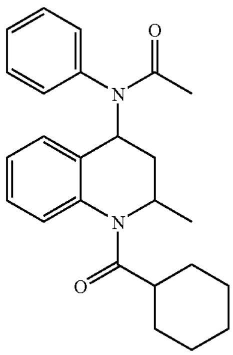 |
| A-158 | 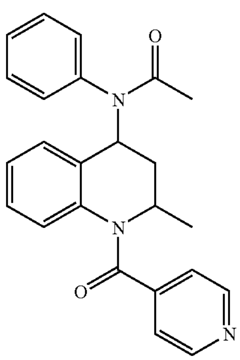 |
| A-159 | 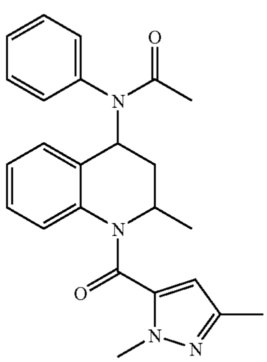 |
| A-160 | |
| A-161 | |
| A-162 | |
| A-163 | |

TABLE 1-continued

Compounds Derived from General Procedure A

| No. | Structure |
| --- | --- |
| A-164 | 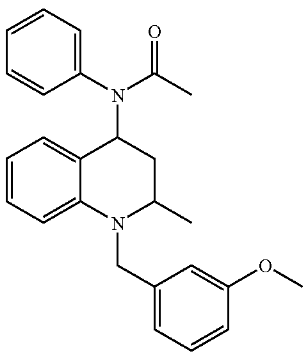 |
| A-165 | 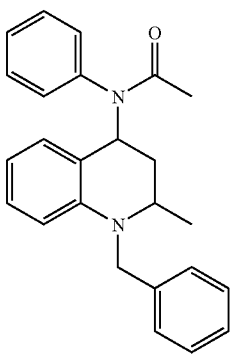 |
| A-166 | 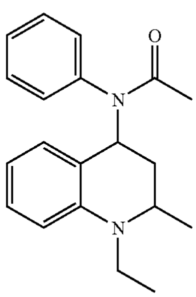 |
| A-167 | 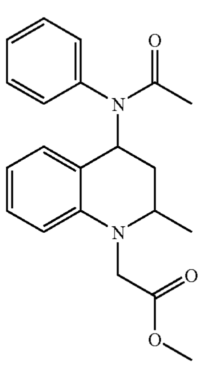 |
| A-168 | |
| A-169 | |
| A-170 | |
| A-171 | |

TABLE 1-continued

Compounds Derived from General Procedure A

| No. | Structure |
|---|---|
| A-172 | 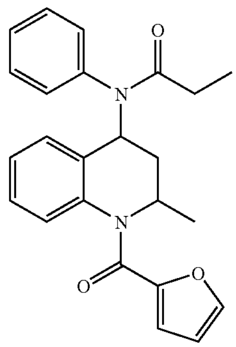 |
| A-173 | 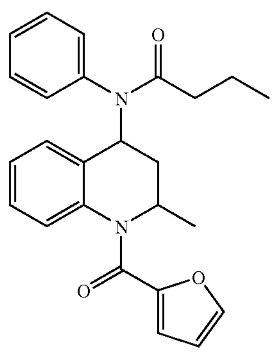 |
| A-174 | 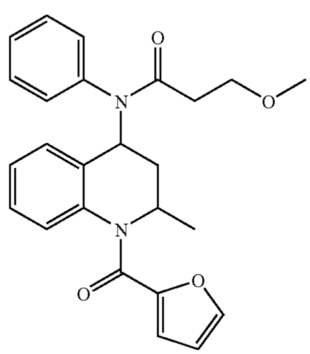 |
| A-175 | 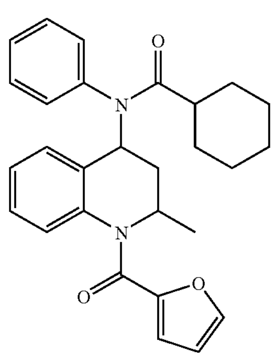 |
| A-176 | |
| A-177 | |
| A-178 | |
| A-179 | |

TABLE 1-continued

Compounds Derived from General Procedure A

| No. | Structure |
| --- | --- |
| A-180 | 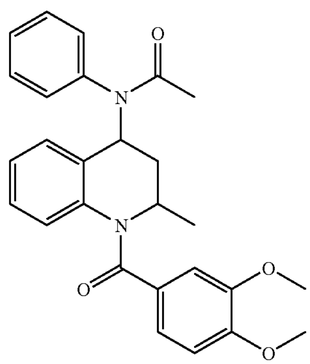 |
| A-181 | 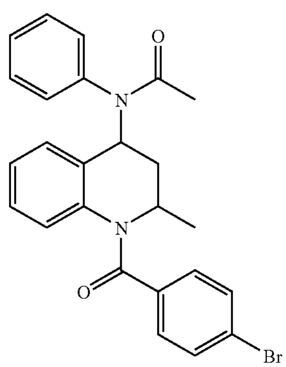 |
| A-182 | 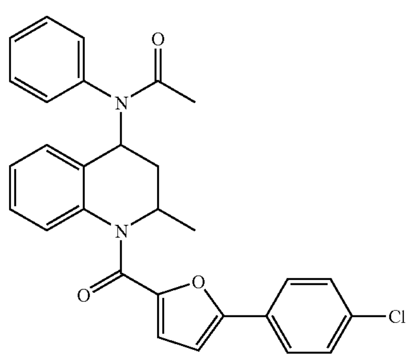 |
| A-183 | 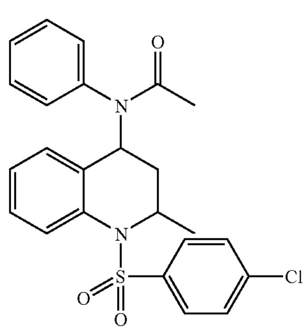 |
| A-184 | |
| A-185 | |
| A-186 | |
| A-187 | |

TABLE 1-continued
Compounds Derived from General Procedure A
| No. | Structure |
|---|---|
| A-188 | 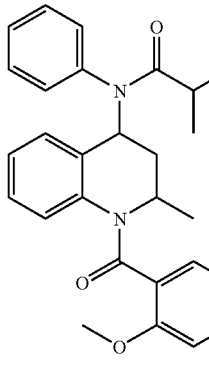 |
| A-189 | 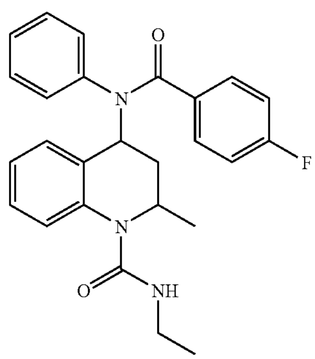 |
| A-190 | 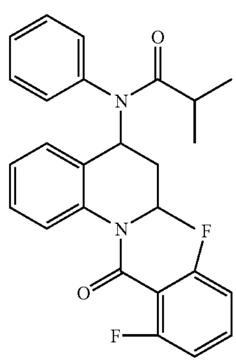 |
| A-191 | 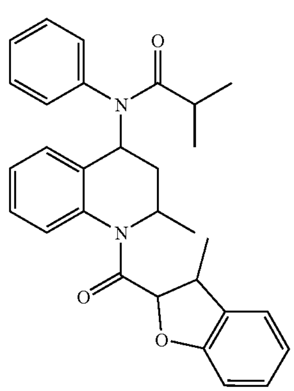 |
TABLE 1-continued
Compounds Derived from General Procedure A
| No. | Structure |
|---|---|
| A-192 | 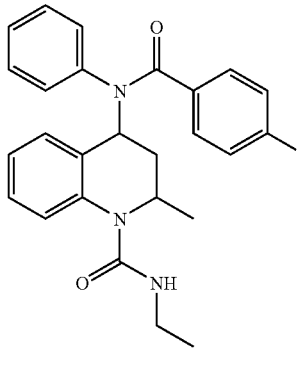 |
| A-193 | 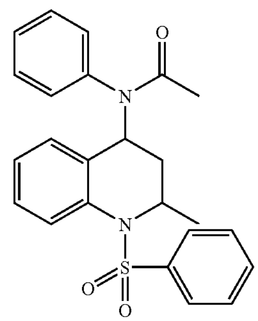 |
| A-194 | 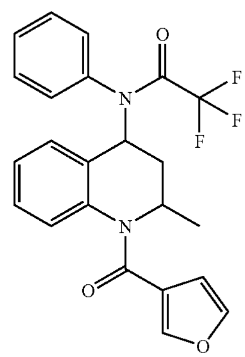 |
| A-195 | 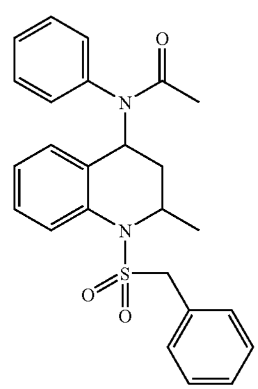 |

TABLE 1-continued
Compounds Derived from General Procedure A
| No. | Structure |
|---|---|
| A-196 | 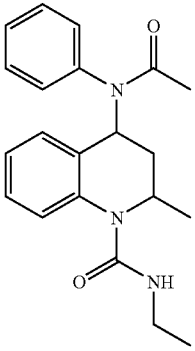 |
| A-197 | 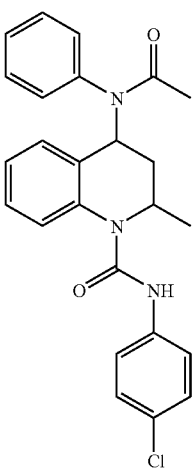 |
| A-198 | 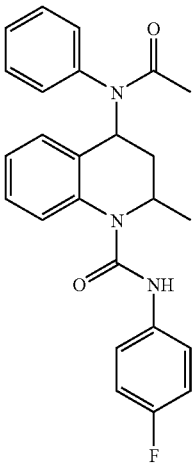 |
| A-199 | 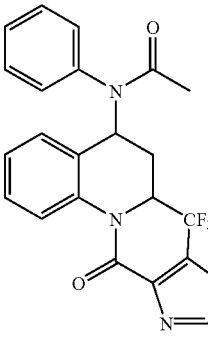 |
| A-200 | 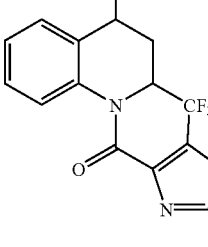 |
| A-201 | 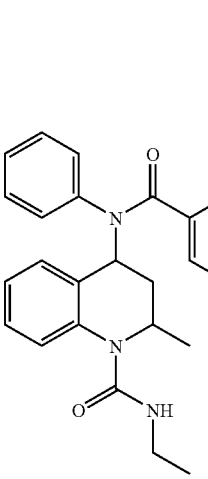 |
| A-202 | 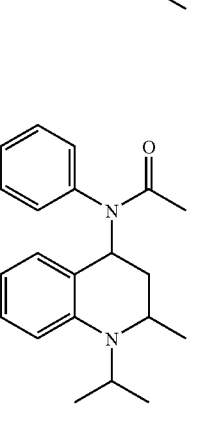 |

TABLE 1-continued
Compounds Derived from General Procedure A
| No. | Structure |
|---|---|
| A-203 | 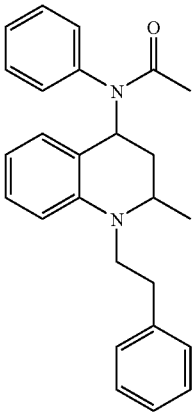 |
| A-204 | 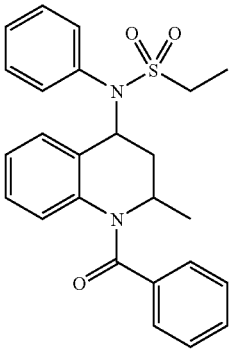 |
| A-205 | 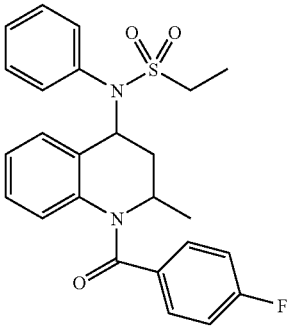 |
| A-206 | 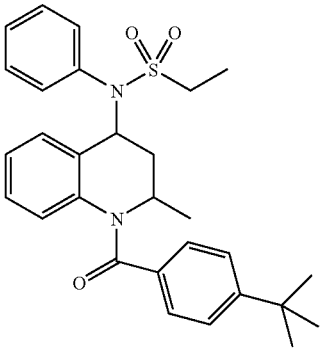 |
| A-207 | 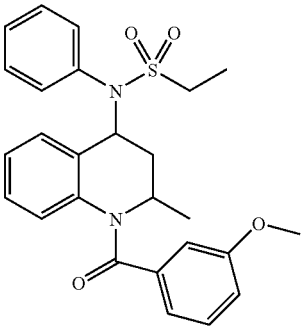 |
| A-208 | 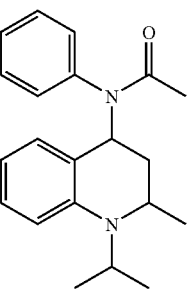 |
| A-209 | 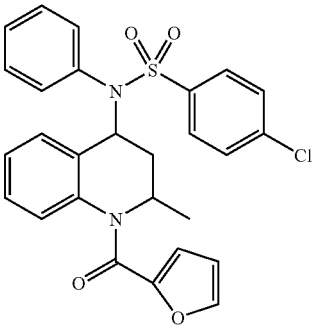 |
| A-210 | 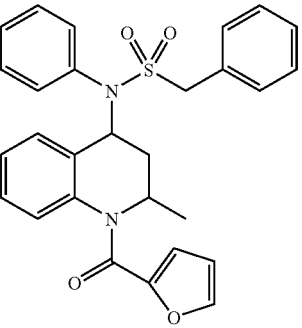 |

TABLE 1-continued

Compounds Derived from General Procedure A

| No. | Structure |
|---|---|
| A-211 | 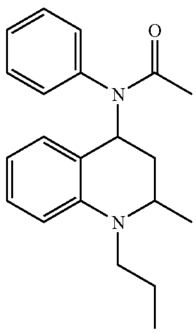 |
| A-212 | 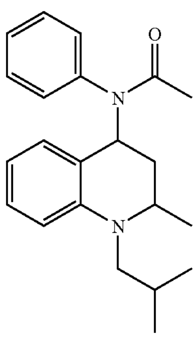 |
| A-213 | 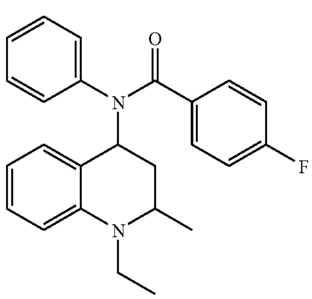 |
| A-214 | 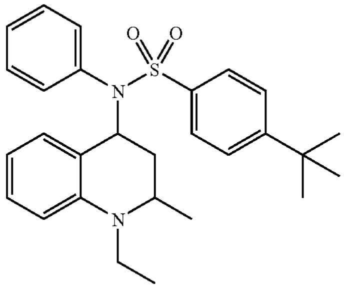 |
| A-215 | |
| A-216 | |
| A-217 | |
| A-218 | |

TABLE 1-continued

Compounds Derived from General Procedure A

| No. | Structure |
|---|---|
| A-219 | |
| A-220 | |
| A-221 | |
| A-222 | 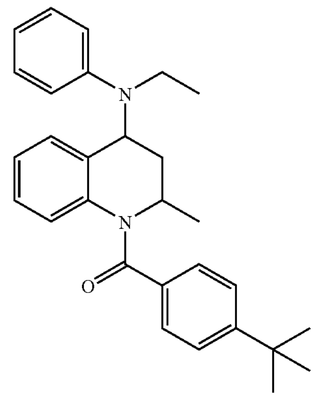 |
| A-223 | 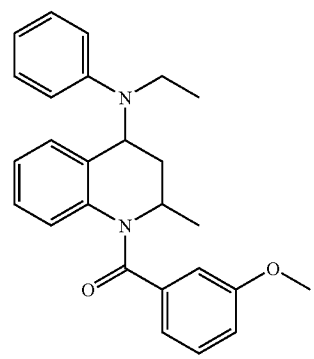 |
| A-224 | 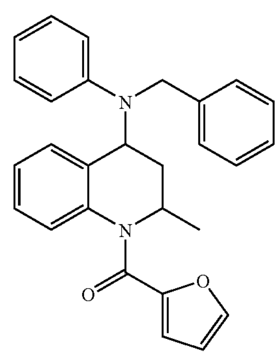 |
| A-225 | 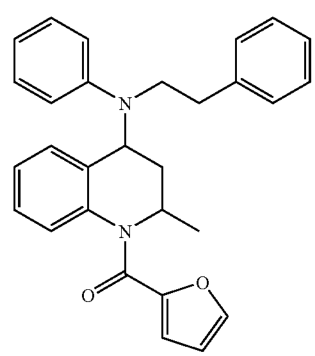 |

TABLE 1-continued
Compounds Derived from General Procedure A
| No. | Structure |
|---|---|
| A-226 | 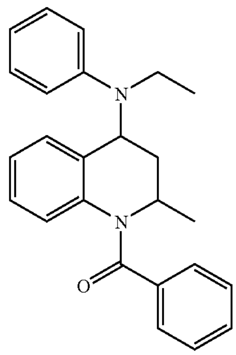 |
| A-227 | 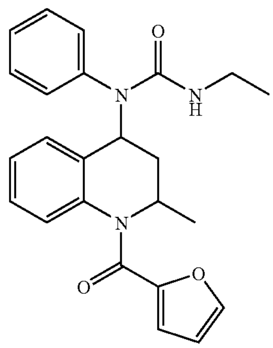 |
| A-228 | 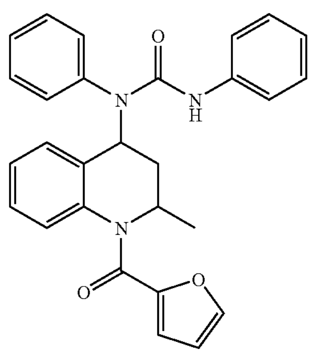 |
| A-229 | 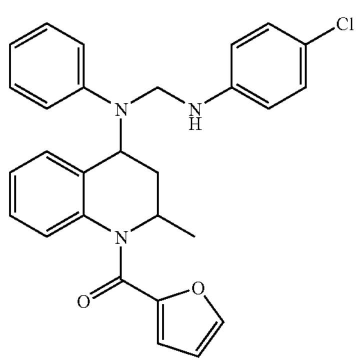 |
| A-230 | 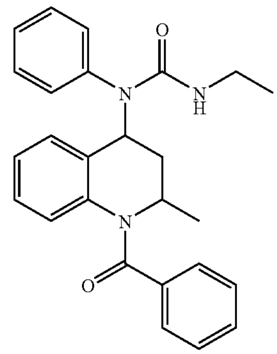 |
| A-231 | 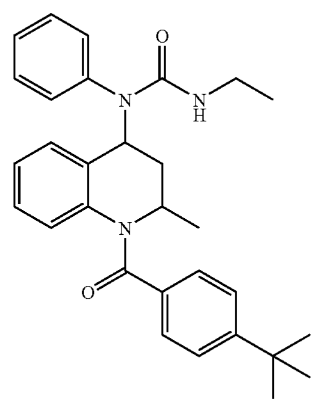 |
| A-232 | 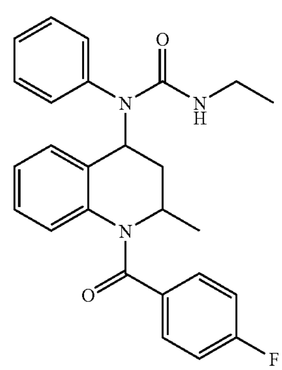 |
Scheme 11
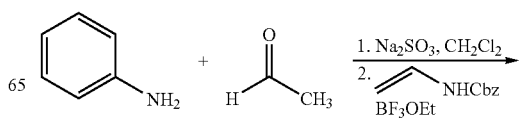

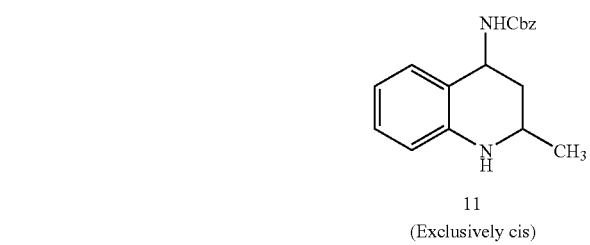

11
(Exclusively cis)

(±)-Cis-(2-methyl-1,2,3,4-tetrahydro-quinolin-4-yl)-carbamic Acid Benzyl Ester (11)

Aniline (3.64 mL, 39.97 mmol, 1.0 equ) was dissolved in methylene chloride (100 mL) and Na$_2$SO$_4$ (2 g) was added and cooled to −25° C. Acetaldehyde (2.23 mL, 39.97 mmol, 1.0 equ.) was added to the solution and stirred for 1 h at −25° C. Sodium sulfate was filtered off and N-vinyl-carbamic acid benzyl ester (7.07 g, 39.97 mmol, 1.0 equiv) was added to the filtrate at −25° C., followed by boron triflouride diethyl etherate (0.50 mL, 3.9 mmol, 0.1 equ). The reaction was allowed to stir at −25° C. for 1 h and then warmed to room temperature and stirred for 10 h. The reaction was evaporated in vacuo and the residue was purified by Biotage flash system (20% ethyl acetate/80% hexane) to yield 4.0 g, 33% of (±)-cis-(2-methyl-1,2,3,4-tetrahydro-quinolin-4-yl)-carbamic acid benzyl ester as a white solid.

H$^1$ NMR (300 MHz, CDCl$_3$) δ: 7.38 (m, 5H), 7.17 (d, 1H), 7.02 (t, 1H, C7-H), 6.68 (t, 1H), 6.47 (d, 1H), 5.17 (bs, 2H), 5.07 (m, 1H), 4.92 (d, 1H), 3.57 (m, 1H), 2.30 (m, 1H), 1.47 (q, 1H), 1.21 (d, 3H).

General Procedure B

Scheme 12

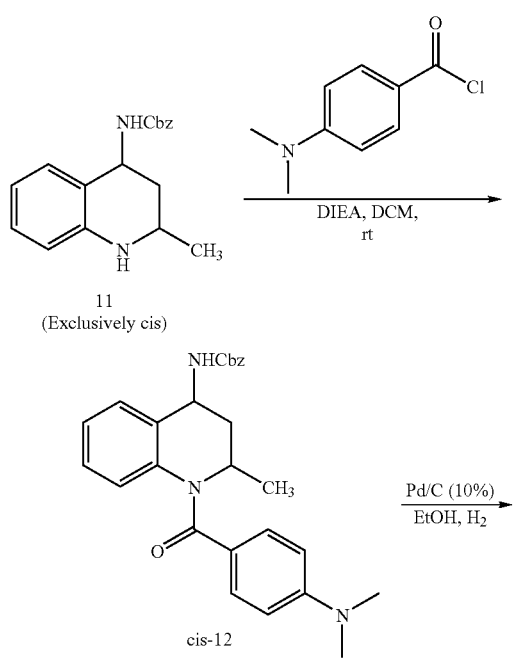

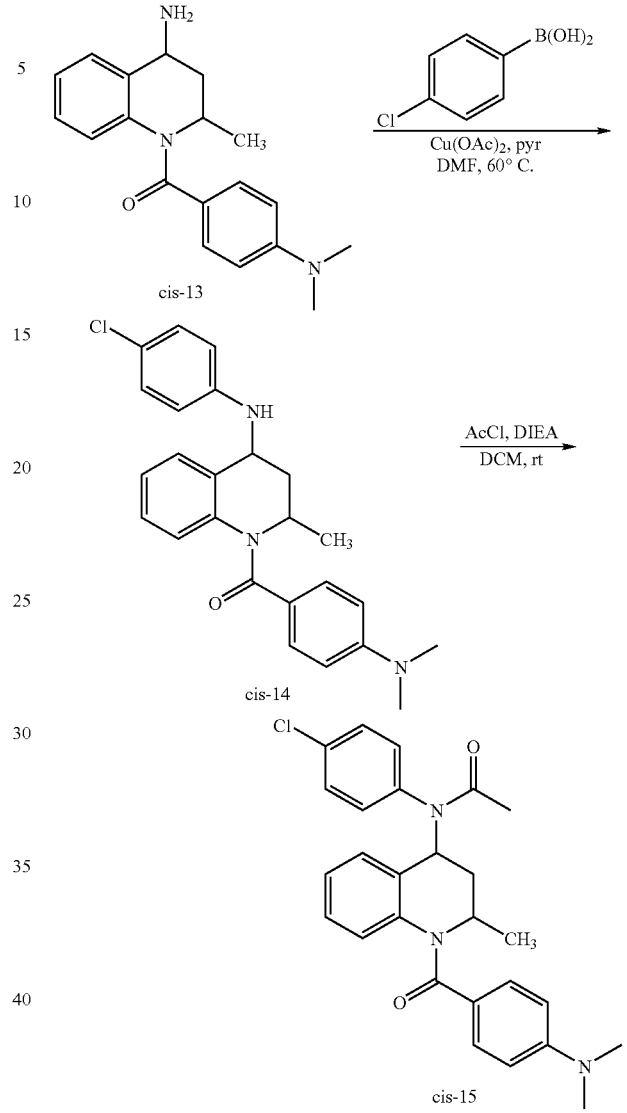

(±)-Cis-[1-(4-dimethylamino-benzoyl)-2-methyl-1,2,3,4-tetrahydro-quinolin-4-yl]-carbamic Acid Benzyl Ester (12)

To a solution of (±)-cis-(2-methyl-1,2,3,4-tetrahydro-quinolin-4-yl)-carbamic acid benzyl ester (500 mg, 1.68 mmol) in methylene chloride (20 mL) at room temperature was added diisopropylethylamine (542 mg, 749 uL, 4.2 mmol) followed by 4-dimethylaminobenzoyl chloride and stirred at from temperature until no starting material was present. The mixture was poured into water and extracted with ethyl acetate. The extracts were washed with 1 M (aq) NaOH and brine, dried over sodium sulfate, filtered dried and concentrated. The crude residue was purified by silica gel chromatography (100% hexanes to 70% hexanes/30% ethyl acetate gradient) to afford the amide (665 mg, 89%).

$^1$H-NMR (300 MHz, CDCl$_3$) δ: 1.24 (d, 3H), 1.36 (m, 1H), 2.75 (ddd, 1H), 2.91 (s, 6H), 4.79–4.92 (m, 3H), 5.22 (s, 2H), 6.43 (d, 2H), 6.65 (d, 1H), 6.90 (dd, 1H), 7.07–7.18 (m, 5H), 7.2–7.48 (m, 4H).

MS m/z: 444 (M+1).

(±)-Cis-1-(4-dimethylamino-benzoyl)-2-methyl-1,2,3,4-tetrahydro-4-aminoquinoline (13)

(±)-Cis-[1-(4-dimethylamino-benzoyl)-2-methyl-1,2,3,4-tetrahydro-quinolin-4-yl]-carbamic acid benzyl ester (665 mg, 1.49 mmol) was dissolved in ethanol (30 mL). The resulting solution was evacuated and backfilled with argon. A catalytic amount of palladium on carbon (10%) was added. The vessel was once again evacuated and this time was backfilled with hydrogen from a balloon. The reaction was then allowed to react at room temperature over night under a hydrogen atmosphere. Reaction was complete after 18 h. The mixture was carefully filtered and concentrated to 10% volume. The resulting concentrated solution was filtered through an Acrodisc (and concentrated to afford the crude amine (423 mg, 92%).

$^1$H-NMR (300 MHz, CDCl$_3$) δ: 1.19–1.40 (m, 4H), 2.76 (ddd, 1H), 2.95 (s, 6H), 4.08 (dd, 1H), 4.81 (m, 1H), 6.42 (d, 2H), 6.64 (d, 1H), 6.99 (dd, 1H), 7.08–7.23 (m, 5H), 7.52 (d, 1H).

MS m/z: 310 (M+1).

(±)-Cis-1-(4-dimethylamino-benzoyl)-2-methyl-1,2,3,4-tetrahydro-4-(N-4-chlorophenyl)aminoquinoline (14)

To a solution of (±)-cis-1-(4-dimethylamino-benzoyl)-2-methyl-1,2,3,4-tetrahydro-4-aminoquinoline (423 mg, 1.36 mmol) in DMF (15 mL, dry) was added 4-chlorophenylboronic acid (425 mg, 2.72 mmol), pyridine (322 mg, 330 uL, 4.08 mmol) and copper(II)acetate (494 mg, 2.72 mmol). The heterogeneous green mixture was stirred open to air for 1 h and then warmed to 60° C. and stirred over night (14 h). The mixture was then cooled to rt, poured into rapidly stirred ethyl acetate (150 mL); solids were removed by filtration. The extracts were washed several times with water and then once with brine.

The extracts were then dried over anhydrous sodium sulfate, filtered, and concentrated under reduced pressure. The crude residue was purified by silica gel chromatography (100% hexanes to 50/50 hexanes/ethyl acetate gradient) to afford the aniline product (120 mg, 22%) as a yellow oil.

$^1$H-NMR (300 MHz, CDCl$_3$) δ: 1.22 (d, 3H), 1.36 (ddd, 1H), 2.82 (ddd, 1H), 2.95 (s, 6H), 4.90 (br s, 1H), 4.41 (br d, 1H), 4.87 (ddd, 1H), 6.65 (d, 2H), 6.62–6.76 (m, 3H), 6.97–7.11 (m, 2H), 7.17–7.29 (m, 5H).

MS m/z: 420 (M+1)

(±)-Cis-N-(4-chloro-phenyl)-N-[1-(4-dimethylamino-benzoyl)-2-methyl-1,2,3,4-tetrahydro-quinolin-4-yl]-acetamide (15)

To a solution of (±)-cis-1-(4-dimethylamino-benzoyl)-2-methyl-1.,2,3,4-tetrahydro-4-(N-4-chlorophenyl)aminoquinoline (120 mg, 0.29 mmol) in methylene chloride (2 mL) was added diisopropylethylamine (37 mg, 0.051 mL, 0.29 mmol) followed by acetyl chloride (2 mL). The mixture was stirred at rt 4 h. The mixture was concentrated under reduced pressure, dissolved in ethyl acetate, washed with sat. aqueous sodium bicarbonate, brine and dried over sodium sulfate. The drying agent was removed by filtration under reduced pressure, concentrated and purified by silica gel chromatography (100% hexanes—25/75 hexanes/ethyl acetate gradient) to afford pure (±)-cis-N-(4-chloro-phenyl)-N-[1-(4-dimethylamino-benzoyl)-2-methyl-1,2,3,4-tetrahydro-quinolin-4-yl]-acetamide (45 mg, 34%).

$^1$H-NMR (300 MHz, CDCl$_3$) δ: 1.14–1.33 (m, 4H), 2.13 (s, 3H), 2.24–2.39 (m, 1H), 2.94 (s, 6H), 4.75 (ddd, 1H), 5.61 (br s, 1H), 6.44 (d, 2H), 6.63 (d, 1H), 6.96 (dd, 1H), 7.07–7.36 (m, 6H), 7.40 (d, 2H).

MS m/z: 420 (M+1)

(±)-Cis-N-[1-(3-methoxy-benzoyl)-2-methyl-1,2,3,4-tetrahydro-quinolin-4-yl]-N-o-tolyl-acetamide (B-1)

(±)-Cis-N-[1-(3-methoxy-benzoyl)-2-methyl-1,2,3,4-tetrahydro-quinolin-4-yl]-N-o-tolyl-acetamide was made following general procedure B, substituting 3-methoxybenzoyl chloride for 4-dimethylaminobenzoyl chloride and 2-tolylboronic acid for 4-chlorophenylboronic acid.

$^1$H-NMR (CDCl$_3$) δ: 1.14 (d, 3H), 1.26 (s, 1H), 1.58 (s, 3H), 1.97 (s, 3H), 2.08 (m, 1H), 3.63 (s, 3H), 4.80 (sextet, 1H), 5.55 (bs, 1H), 6.53 (d, 1H), 6.76 (s, 1H), 6.83 (t, 2H), 6.93 (t, 1H), 7.10 (t, 1H), 7.15–7.37 (m, 6H).

MS m/z: 429 (M+1)

N-(4-chloro-phenyl)-N-[1-(3-methoxy-benzoyl)-2-methyl-1,2,3,4-tetrahydro-quinolin-4-yl]-acetamide (B-2)

(±)-Cis-N-(4-chloro-phenyl)-N-[1-(3-methoxy-benzoyl)-2-methyl-1,2,3,4-tetrahydro-quinolin-4-yl]-acetamide was made following general procedure B, substituting 3-methoxybenzoyl chloride for 4-dimethylaminobenzoyl chloride.

(±)-Cis-N-(4-chloro-phenyl)-N-[1-(3-methoxy-benzoyl)-2-methyl-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-chloro-phenyl)-N-[1-(3-methoxy-benzoyl)-2-methyl-1,2,3,4-tetrahydro-quinolin-4-yl]-acetamide (B-9 & B-8, respectively)

$^1$H-NMR (CDCl$_3$) δ: 1.17 (d, 3H), 1.25 (t, 1H), 2.03 (s, 3H), 2.29 (m, 1H), 3.62 (s, 3H), 4.80 (sextet, 1H), 5.60 (bs, 1H), 6.54 (d, 1H), 6.74 (s, 1H), 6.80 (t, 1H), 6.93 (t, 1H), 7.08 (t, 1H), 7.14–7.30 (m, 5H), 7.38 (d, 2H).

MS m/z: 449 (M+1)

(±)-Cis-N-(4-chloro-phenyl)-N-[2-methyl-1-(thiophene-2-carbonyl)-1,2,3,4-tetrahydro-quinolin-4-yl]-acetamide (B-3)

(±)-Cis-N-(4-chloro-phenyl)-N-[2-methyl-1-(thiophene-2-carbonyl)-1,2,3,4-tetrahydro-quinolin-4-yl]-acetamide was made following general procedure B, substituting 2-thiophenecarbonyl chloride for 4-dimethylaminobenzoyl chloride.

(±)-Cis-N-(4-chloro-phenyl)-N-[2-methyl-1-(thiophene-2-carbonyl)-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-chloro-phenyl)-N-[2-methyl-1-(thiophene-2-carbonyl)-1,2,3,4-tetrahydro-quinolin-4-yl]-acetamide (B-7 & B-6, respectively).

$^1$H-NMR (300 MHz, CDCl$_3$) δ: 1.11–1.24 (m, 4H), 2.03 (s, 3H), 2.22–2.35 (m, 1H), 4.73 (ddd, 1H), 5.52 (br s, 1H), 6.69 (dd, 1H), 6.67 (dd, 1H), 6.89 (d, 1H), 7.08 (dd, 1H), 7.21 (d, 2H), 7.27–7.43 (m, 5H).

MS m/z: 425 (M+1).

(±)-Cis-N-(4-chloro-phenyl)-N-[2-methyl-1-(5-methyl-thiophene-2-carbonyl)-1,2,3,4-tetrahydro-quinolin-4-yl]-isobutyramide (B-4)

(±)-Cis-N-(4-chloro-phenyl)-N-[2-methyl-1-(5-methyl-thiophene-2-carbonyl)-1,2,3,4-tetrahydro-quinolin-4-yl]-isobutyramide was made following general procedure B, substituting 5-methyl-2-thiophenecarbonyl chloride for 4-dimethylaminobenzoyl chloride and isobutyryl chloride for acetyl chloride.

(±)-Cis-N-(4-chloro-phenyl)-N-[2-methyl-1-(5-methyl-thiophene-2-carbonyl)-1,2,3,4-tetrahydro-quinolin-4-yl]-isobutyramide was separated by chiral HPLC using a chiral cel OD column and eluting with 90% hexane/10% ethanol isocratic system to give (2R,4S)- and (2S,4R)-cis-N-(4-

Chloro-phenyl)-N-[2-methyl-1-(5-methyl-thiophene-2-carbonyl)-1,2,3,4-tetrahydro-quinolin-4-yl]-isobutyramide (B-11 & B-10 respectively).

$^1$H-NMR (CDCl$_3$) δ: 1.13 (d, 6H), 1.16 (d, 3H), 1.25 (m, 1H), 2.23 (m, 3H), 2.39 (s, 1H), 2.60 (septet, 1H), 4.66 (sextet, 1H), 5.50 (bs, 1H), 6.42 (s, 1H), 6.51 (s, 1H), 6.93 (d, 1H), 7.08 (t, 1H), 7.21 (d, 2H), 7.27 (d, 2H), 7.37 (bs, 2H).

MS m/z: 468 (M+1)

(±)-Cis-N-[1-(4-fluoro-benzoyl)-2-methyl-1,2,3,4-tetrahydro-quinolin-4-yl]-N-(4-fluoro-phenyl)-propionamide (B-5)

(±)-Cis-N-[1-(4-fluoro-benzoyl)-2-methyl-1,2,3,4-tetrahydro-quinolin-4-yl]-N-(4-fluoro-phenyl)-propionamide was made following general procedure B, substituting 4-fluorobenzoyl chloride for 4-dimethylaminobenzoyl chloride, 4-fluorophenylboronic acid for 4-chlorophenylboronic acid, and propionyl chloride for acetyl chloride.

$^1$H-NMR (CDCl$_3$) δ: 1.14 (t, 3H), 1.15 (d, 3H), 1.24 (m, 1H), 2.26 (m, 3H), 4.75 (sextet, 1H), 5.61 (bs, 1H), 6.46 (d, 1H), 6.87 (m, 3H), 7.10–7.26 (m, 8H).

MS m/z: 435 (M+1)

(±)-Cis-N-(4-chloro-3-methyl-phenyl)-N-[1-(4-fluoro-benzoyl)-2-methyl-1,2,3,4-tetrahydro-quinolin-4-yl]-propionamide (B-12)

(±)-Cis-N-(4-chloro-3-methyl-phenyl)-N-[1-(4-fluoro-benzoyl)-2-methyl-1,2,3,4-tetrahydro-quinolin-4-yl]-propionamide was made following general procedure B, substituting 4-fluorobenzoyl chloride for 4-dimethylaminobenzoyl chloride, propionyl chloride for acetyl chloride and 4-chloro-3-tolylboronic acid for 4-chlorophenylboronic acid.

$^1$H-NMR (CDCl$_3$) δ: 1.08 (t, 3H), 1.09 (d, 3H), 1.18 (m, 1H), 2.18 (m, 3H), 2.31 (s, 3H), 4.69 (sextet, 1H), 5.49 (bs, 1H), 6.42 (d, 1H), 6.79 (t, 2H), 6.86 (t, 1H), 6.96 (dd, 1H), 7.05–7.22 (m, 6H).

MS m/z: 465 (M+1).

(±)-Cis-N-[1-(4-Fluoro-benzoyl)-2-methyl-1,2,3,4-tetrahydro-quinolin-4-yl]-N-(4-trifluoromethyl-phenyl)-propionamide (B-13)

(±)-Cis-N-[1-(4-fluoro-benzoyl)-2-methyl-1,2,3,4-tetrahydro-quinolin-4-yl]-N-(4-trifluoro-methyl-phenyl)-propionamide was made following general procedure B, substituting 4-fluorobenzoyl chloride for 4-dimethylaminobenzoyl chloride, propionyl chloride for acetyl chloride and 4-trifluoromethylphenylboronic acid for 4-chlorophenylboronic acid.

$^1$H-NMR (CDCl$_3$) δ: 1.15 (t, 3H), 1.17 (d, 3H), 1.20 (m, 1H), 2.29 (m, 3H), 4.79 (sextet, 1H), 5.62 (bs, 1H), 6.49 (d, 1H), 6.87 (m, 3H), 7.19–7.28 (m, 6H), 7.41 (d, 1H), 7.69 (d, 1H).

MS m/z: 485 (M+1).

(±)-Cis-N-(4-chloro-phenyl)-N-[1-(4-methoxy-benzoyl)-2-methyl-1,2,3,4-tetrahydro-quinolin-4-yl]-propionamide (B-14)

(±)-Cis-N-(4-chloro-phenyl)-N-[1-(4-methoxy-benzoyl)-2-methyl-1,2,3,4-tetrahydro-quinolin-4-yl]-propionamide was made following general procedure B, substituting 4-methoxybenzoyl chloride for 4-dimethylaminobenzoyl chloride and propionyl chloride for acetyl chloride.

(±)-Cis-N-(4-chloro-phenyl)-N-[1-(4-methoxy-benzoyl)-2-methyl-1,2,3,4-tetrahydro-quinolin-4-yl]-propionamide was separated by chiral HPLC using a chiral cel OD column and eluting with 90% hexane/10% ethanol isocratic system to give (2R,4S)- and (2S,4R)-cis-N-(4-chloro-phenyl)-N-[1-(4-methoxy-benzoyl)-2-methyl-1,2,3,4-tetrahydro-quinolin-4-yl]-propionamide (B-18 & B-17, respectively).

$^1$H-NMR (CDCl$_3$) δ: 1.14 (t, 3H), 1.15 (d, 3H), 1.25 (t, 1H), 2.29 (m, 3H), 3.74 (s, 3H), 4.74 (sextet, 1H), 5.61 (bs, 1H), 6.53 (d, 1H), 6.68 (d, 2H), 6.93 (t, 1H), 7.14–7.28 (m, 6H), 7.38 (d, 2H).

MS m/z: 463 (M+1).

(±)-Cis-N-(4-chloro-phenyl)-N-[1-(4-methoxy-benzoyl)-2-methyl-1,2,3,4-tetrahydro-quinolin-4-yl]-acetamide (B-15)

(±)-Cis-N-(4-chloro-phenyl)-N-[1-(4-methoxy-benzoyl)-2-methyl-1,2,3,4-tetrahydro-quinolin-4-yl]-acetamide was made following general procedure B, substituting 4-methoxybenzoyl chloride for 4-dimethylaminobenzoyl chloride.

(±)-Cis-N-(4-chloro-phenyl)-N-[1-(4-methoxy-benzoyl)-2-methyl-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-Chloro-phenyl)-N-[1-(4-methoxy-benzoyl)-2-methyl-1,2,3,4-tetrahydro-quinolin-4-yl]-acetamide (B-34 & B-35, respectively).

$^1$H-NMR (CDCl$_3$) δ: 1.14 (d, 3H), 1.25 (t, 1H), 2.04 (s, 3H), 2.29 (m, 1H), 3.74 (s, 3H), 4.74 (sextet, 1H), 5.61 (bs, 1H), 6.53 (d, 1H), 6.68 (d, 2H), 6.93 (t, 1H), 7.14–7.28 (m, 6H), 7.38 (d, 2H).

MS m/z: 449 (M+1).

(±)-Cis-N-(4-chloro-phenyl)-N-[1-(4-hydroxy-benzoyl)-2-methyl-1,2,3,4-tetrahydro-quinolin-4-yl]-propionamide (B-16)

(±)-Cis-N-(4-chloro-phenyl)-N-[1-(4-hydroxy-benzoyl)-2-methyl-1,2,3,4-tetrahydro-quinolin-4-yl]-propionamide was made from (±)-cis-N-(4-chloro-phenyl)-N-[1-(4-methoxy-benzoyl)-2-methyl-1,2,3,4-tetrahydro-quinolin-4-yl]-propionamide. (±)-Cis-N-[1-(4-methoxy-benzoyl)-2-methyl-1,2,3,4-tetrahydro-quinolin-4-yl]-N-phenyl-propionamide (0.548 g, 0.001 mol) was dissolved in dichloromethane and a solution of BBr$_3$ (1.0 M in dichloromethane, 10 mL) was added; the reaction was allowed to stir at room temperature for 4 h or until no starting material remained. The reaction was washed with sat NaHCO$_3$ carefully and brine. The organics were dried over MgSO$_4$, filtered and concentrated down. The phenol was concentrated down and the residue was purified by Biotage flash chromatography using 100% EtOAc to give a white solid, 74% yield.

$^1$H-NMR (CDCl$_3$) δ: 1.09 (d, 3H), 1.11 (t, 3H), 1.19 (m, 1H), 2.26 (m, 3H), 4.74 (sextet, 1H), 5.54 (bs, 1H), 6.46 (d, 1H), 6.53 (d, 1H), 6.96 (t, 1H), 7.14–7.40 (m, 9H).

MS m/z: 415 (M+1).

(±)-Cis-N-[1-(4-fluoro-benzoyl)-2-methyl-1,2,3,4-tetrahydro-quinolin-4-yl]-N-p-tolyl-propionamide (B-21)

(±)-Cis-N-[1-(4-fluoro-benzoyl)-2-methyl-1,2,3,4-tetrahydro-quinolin-4-yl]-N-p-tolyl propionamide was made following general procedure B, substituting 4-fluorobenzoyl chloride for 4-dimethylaminobenzoyl chloride, propionyl chloride for acetyl chloride and 4-tolylboronic acid for 4-chlorophenylboronic acid.

$^1$H-NMR (300 MHz, CDCl$_3$) δ: 1.05–1.21 (m, 7H), 2.11–2.54 (m, 6H), 4.73 (ddd, 1H), 5.56 (br s, 1H), 6.37 d, 1H), 6.8–7.0 (m, 3H), 7.1–7.4 (m, 8H).

MS m/z: 431 (M+1).

(±)-Cis-N-(4-chloro-phenyl)-N-[1-(4-fluoro-benzoyl)-2-methyl-1,2,3,4-tetrahydro-quinolin-4-yl]-acetamide (B-22)

(±)-Cis-N-(4-chloro-phenyl)-N-[1-(4-fluoro-benzoyl)-2-methyl-1,2,3,4-tetrahydro-quinolin-4-yl]-acetamide was made following general procedure B, substituting 4-fluorobenzoyl chloride for 4-dimethylaminobenzoyl chloride.

(±)-Cis-N-(4-chloro-phenyl)-N-[1-(4-fluoro-benzoyl)-2-methyl-1,2,3,4-tetrahydro-quinolin-4-yl]-acetamide was separated by chiral HPLC using a chiral cel OD column and eluting with 95% hexane/5% ethanol isocratic system to give (2R,4S)- and (2S,4R)-cis-N-(4-chloro-phenyl)-N-[1-(4-fluoro-benzoyl)-2-methyl-1,2,3,4-tetrahydro-quinolin-4-yl]-acetamide (B-26 & B-27, respectively).

$^1$H-NMR (CDCl$_3$) δ: 1.1 (d, 3H), 1.1 (m, 1H), 2.0 (d, 3H), 2.3 (m, 1H), 4.7 (m, 1H), 5.6 (m, 1H), 6.5 (d, 1H), 6.7–7.0 (m, 3H), 7.1–7.4 (m, 8H).

MS m/z: 436 (M+1).

(±)-Cis-N-(4-chloro-phenyl)-N-[2-methyl-1-(5-methyl-thiophene-2-carbonyl)-1,2,3,4-tetrahydro-quinolin-4-yl]-acetamide (B-24)

(±)-Cis-N-(4-chloro-phenyl)-N-[2-methyl-1-(5-methyl-thiophene-2-carbonyl)-1,2,3,4-tetrahydro-quinolin-4-yl]-acetamide was made following general procedure B, substituting 5-methyl-2-thiophenecarbonyl chloride for 4-dimethylaminobenzoyl chloride.

(±)-Cis-N-(4-chloro-phenyl)-N-[2-methyl-1-(5-methyl-thiophene-2-carbonyl)-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-Chloro-phenyl)-N-[2-methyl-1-(5-methyl-thiophene-2-carbonyl)-1,2,3,4-tetrahydro-quinolin-4-yl]-acetamide (B-28 & B-25, respectively).

$^1$H-NMR (CDCl$_3$) δ: 1.1 (3H, d), 1.1 (1H, m), 2.0 (3H, d), 2.3 (1H, m), 2.4 (3H, s), 4.7 (1H, m), 5.6 (1H, m), 6.4 (1H, m), 6.6 (1H, m), 7.0 (1H, m), 7.1 (1H, m), 7.2–7.4 (6H, m).

MS m/z: 439 (M+1).

(±)-Cis-N-(4-chloro-phenyl)-N-[2-methyl-1-(5-methyl-thiophene-2-carbonyl)-1,2,3,4-tetrahydro-quinolin-4-yl]-propionamide (B-29)

(±)-Cis-N-(4-chloro-phenyl)-N-[2-methyl-1-(5-methyl-thiophene-2-carbonyl)-1,2,3,4-tetrahydro-quinolin-4-yl]-propionamide was made following general procedure B, substituting 5-methyl-2-thiophenecarbonyl chloride for 4-dimethylaminobenzoyl chloride and propionyl chloride for acetyl chloride.

$^1$H-NMR (CDCl$_3$) δ: 1.1–1.2 (7H, m), 2.1–2.3 (3H, m), 2.3 (3H, s), 4.8 (1H, m), 5.6 (1H, m), 6.2–6.4 (2H, m), 6.8–7.4 (8H, m).

MS m/z: 452 (M+2).

(±)-Cis-4-(4-{4-[(4-chloro-phenyl)-propionyl-amino]-2-methyl-3,4-dihydro-2H-quinoline-1-carbonyl}-phenoxy)-butyric acid ethyl ester (B-30)

(±)-Cis-4-(4-{4-[(4-chloro-phenyl)-propionyl-amino]-2-methyl-3,4-dihydro-2H-quinoline-1-carbonyl}-phenoxy)-butyric acid ethyl ester was prepared from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-chloro-phenyl)-N-[1-(4-hydroxy-benzoyl)-2-methyl-1,2,3,4-tetrahydroquinolin-4-yl]-propionamide (140 mg, 0.31 mmol) was dissolved in DMF (5 mL) at room temperature. Sodium hydride (60% in oil, 32 mg, 0.81 mmol) was added and the mixture allowed to stir 30 min. Ethyl 4-bromobutyrate (207 mg, 1.06 mmol) was added and the reaction was allowed to stir over night. Ethanol was added and the reaction was concentrated in vacuo. The crude residue was purified by silica gel chromatography (80/20 hexanes/ethyl acetate—50/50 hexanes ethyl acetate gradient) to afford the product (171 mg, 0.304 mmol, 98%).

$^1$H-NMR (CDCl$_3$) δ: 1.1–1.2 (7H, m), 1.3 (3H, t), 2.1 (2H, m), 2.3 (3H, m), 2.5 (2H, t), 3.9 (2H, t), 4.2 (2H, q), 4.8 (1H, m), 5.6 (1H, m), 6.5 (1H, d), 6.7 (2H, d), 6.9 (1H, t), 7.1–7.3 (6H, m), 7.4 (2H, m).

MS m/z: 563 (M+1).

(±)-Cis-4-(4-{4-[(4-chloro-phenyl)-propionyl-amino]-2-methyl-3,4-dihydro-2H-quinoline-1-carbonyl}-phenoxy)-butyric acid (B-31)

(±)-Cis-4-(4-{4-[(4-chloro-phenyl)-propionyl-amino]-2-methyl-3,4-dihydro-2H-quinoline-1-carbonyl}-phenoxy)-butyric acid was prepared from (±)-cis-4-(4-{4-[(4-chloro-phenyl)-propionyl-amino]-2-methyl-3,4-dihydro-2H-quinoline-1-carbonyl}-phenoxy)-butyric acid ethyl ester. Potassium carbonate (300 mg) was dissolved in water (5 mL) and (±)-cis-4-(4-{4-[(4-chloro-phenyl)-propionyl-amino]-2-methyl-3,4-dihydro-2H-quinoline-carbonyl}-phenoxy)-butyric acid ethyl ester (171 mg, 0.303 mmol) dissolved in methanol (5 mL) was added. The reaction was allowed to stir over night at room temperature. The methanol was removed in vacuo and hydrochloric acid (1 N) was added until acidic. Dichloromethane was added, extracted 2×; the combined organics were dried over magnesium sulfate, filtered and concentrated to afford the carboxylic acid (50 mg, 31%).

$^1$H-NMR (CDCl$_3$) δ: 1.1–1.2 (7H, m), 2.0 (2H, m), 2.3 (2H, m), 2.4 (3H, m), 3.3 (1H, s), 4.0 (2H, t), 4.8 (1H, m), 5.6 (1H, m), 6.5 (1H, d), 6.7 (2H, d), 6.9 (1H, t), 7.1–7.3 (3H, m), 7.4–7.6 (5H, m).

MS m/z: 535 (M+1).

(±)-Cis-N-(4-chloro-phenyl)-N-{2-methyl-1-[4-(1H-tetrazol-5-ylmethoxy)-benzoyl]-1,2,3,4-tetrahydro-quinolin-4-yl}-propionamide (B-32)

(±)-Cis-N-(4-chloro-phenyl)-N-{2-methyl-1-[4-(4H-tetrazol-5-ylmethoxy)-benzoyl]-1,2,3,4-tetrahydro-quinolin-4-yl}-propionamide was prepared from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-chloro-phenyl)-N-[1-(4-hydroxy-benzoyl)-2-methyl-1,2,3,4-tetrahydro-quinolin-4-yl]-propionamide (700 mg, 1.42 mmol) was dissolved in DMF (10 mL) at room temperature. Sodium hydride (60% in oil, 227 mg, 5.68 mmol) was added and the mixture allowed to stir 30 min. Bromoacetonitrile (850 mg, 7.11 mmol) was added and the reaction was allowed to stir over night. Ethanol was added and the reaction was concentrated in vacuo. The crude residue was purified by silica gel chromatography (30/70 ethyl acetate/dichloromethane) to afford the product (320 mg, 42%).

The nitrile (140 mg, 0.25 mmol) was dissolved in toluene, sodium azide (160 mg, 2.5 mmol) and triethylammonium hydrochloride (345 mg, 2.5 mmol) were added and the mixture was heated to 80° C. over night. Reaction was cooled to room temperature and water was added, followed by hydrochloric acid (1 N) until acidic. The aqueous solution was extracted three times with dichloromethane. The combined extracts were dried over magnesium sulfate, filtered, dried and concentrated. The crude product was triturated with ethyl ether/hexanes to yield a white solid (82 mg, 63%).

$^1$H-NMR (CDCl$_3$) δ: 1.0–1.2 (7H, m), 2.2–2.4 (3H, m), 4.8 (1H, m), 5.2 (2H, dd), 5.6 (1H, m), 6.7 (2H, m), 6.9 (1H, t), 7.1 (2H, d), 7.2–7.6 (7H, m).

MS m/z: 531 (M+1).

(±)-Cis-N-(4-chloro-phenyl)-N-[1-(4-isobutoxy-benzoyl)-2-methyl-1,2,3,4-tetrahydro-quinolin-4-yl]-acetamide (B-33)

(±)-Cis-N-(4-chloro-phenyl)-N-[1-(4-isobutoxy-benzoyl)-2-methyl-1,2,3,4-tetrahydro-quinolin-4-yl]-acetamide was made following general procedure B, substituting 4-isobutyloxybenzoyl chloride for 4-dimethylaminobenzoyl chloride.

$^1$H-NMR (CDCl$_3$) δ: 0.9–1.0 (8H, m), 1.2 (3H, d), 2.0 (3H, s), 2.3 (1H, m), 3.6 (2H, d), 4.7 (1H, m), 5.6 (1H, m), 6.5 (1H, d), 6.6 (2H, d), 6.9 (1H, m), 7.1–7.4 (8H, m).

MS m/z: 491 (M+1).

(±)-Cis-N-(4-chloro-phenyl)-N-{1-[4-(3-hydroxy-2,2-dimethyl-propoxy)-benzoyl]-2-methyl-1,2,3,4-tetrahydro-quinolin-4-yl}-acetamide (B-37)

(±)-Cis-N-(4-chloro-phenyl)-N-{1-[4-(3-hydroxy-2,2-dimethyl-propoxy)-benzoyl]-2-methyl-1,2,3,4-tetrahydro-quinolin-4-yl}-acetamide was prepared from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-chloro-phenyl)-N-[1-(4-hydroxy-benzoyl)-2-methyl-1,2,3,4-tetrahydro-quinolin-4-yl]-propionamide (210 mg, 0.484 mmol) was dissolved in DMF (10 mL) at room temperature. Potassium carbonate (1 g, 7.1 mmol) was added, followed by 3-bromo-2,2-dimethyl-propan-1-ol (813 mg, 4.84 mmol), the reaction was heated to 95° C. and stirred over night. The reaction mixture was cooled to room temperature, filtered and concentrated in vacuo. The crude product was purified by silica gel chromatography (95/5 dichloromethane/ethyl acetate—70/30 dichloromethane/ethyl acetate) to afford the pure ester (110 mg, 44%).

$^1$H-NMR (CDCl$_3$) δ: 1.0 (6H, s), 1.1 (3H, d), 1.1 (1H, m), 1.7 (1H, br), 2.0 (3H, s), 2.3 (1H, m), 3.5 (2H, s), 3.7 (2H, s), 4.8 (1H, m), 5.6 (1H, m), 6.5 (1H, d), 6.7 (2H, d), 6.9 (1H, t), 7.1–7.3 (7H, m), 7.4 (1H, d).

MS m/z: 521 (M+1).

(±)-Cis-3-(4-{4-[acetyl-(4-chloro-phenyl)-amino]-2-methyl-3,4-dihydro-2H-quinoline-1-carbonyl}-phenoxy)-2,2-dimethyl-propionic acid methyl ester (B-38)

(±)-Cis-3-(4-{4-[acetyl-(4-chloro-phenyl)-amino]-2-methyl-3,4-dihydro-2H-quinoline-1-carbonyl}-phenoxy)-2,2-dimethyl-propionic acid methyl ester was prepared from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-chloro-phenyl)-N-[1-(4-hydroxy-benzoyl)-2-methyl-1,2,3,4-tetrahydro-quinolin-4-yl]-propionamide (400 mg, 0.92 mmol) was dissolved in DMF (25 mL) at room temperature. Potassium carbonate (1 g, 7.1 mmol) was added, followed by 3-bromo-2,2-dimethyl-propionic acid methyl ester (400 mg, 0.92 mmol), the reaction was heated to 95° C. and stirred over night. The reaction mixture was cooled to room temperature, filtered and concentrated in vacuo. The crude product was purified by silica gel chromatography (95/5 dichloromethane/ethyl acetate—70/30 dichloromethane/ethyl acetate) to afford the pure ester (40 mg, 8%).

$^1$H-NMR (CDCl$_3$) δ: 1.1 (3H, d), 1.1 (1H, m), 1.3 (6H, s), 2.0 (3H, s), 2.3 (1H, m), 3.7 (3H, s), 3.9 (2H, dd), 4.8 (1H, m), 5.6 (1H, m), 6.5 (1H, d), 6.7 (2H, d), 6.9 (1H, t), 7.1–7.3 (7H, m), 7.4 (1H, d).

MS m/z: 549 (M+1).

(±)-Cis-(4-{acetyl-[1-(4-methoxy-benzoyl)-2-methyl-1,2,3,4-tetrahydro-quinolin-4-yl]-amino}-phenyl)-acetic acid (B-39)

(±)-Cis-(4-{acetyl-[1-(4-methoxy-benzoyl)-2-methyl-1,2,3,4-tetrahydro-quinolin-4-yl]-amino}-phenyl)-acetic acid was made from (±)-cis-N-(4-cyanomethyl-phenyl)-N-[1-(4-methoxy-benzoyl)-2-methyl-1,2,3,4-tetrahydro-quinolin-4-yl]-acetamide. (±)-Cis-N-(4-cyanomethyl-phenyl)-N-[1-(4-methoxy-benzoyl)-2-methyl-1,2,3,4-tetrahydro-quinolin-4-yl]-acetamide was made following general procedure B, substituting 4-methoxybenzoylchloride for 4-dimethylaminobenzoyl chloride and 4-(phenylboronic acid)-acetonitrile for 4-chlorophenylboronic acid. (±)-Cis-N-(4-cyanomethyl-phenyl)-N-[1-(4-methoxy-benzoyl)-2-methyl-1,2,3,4-tetrahydro-quinolin-4-yl]-acetamide was dissolved in ethanol (4 mL), potassium hydroxide (120 mg in 0.3 mL water) was added and the reaction was heated at 80° C. over night. The ethanol was removed in vacuo and hydrochloric acid (1 N) was added until acidic. Dichloromethane was added, extracted 2×; the combined organics were dried over magnesium sulfate, filtered and concentrated to afford the carboxylic acid (30 mg) after HPLC purification.

$^1$H-NMR (CDCl$_3$) δ: 1.1 (3H, d), 1.1 (1H, m), 2.0 (3H, s), 2.3 (1H, m), 3.6 (2H, s), 3.8 (3H, s), 4.8 (1H, m), 5.7 (1H, m), 6.5 (1H, m), 6.6 (2H, m), 6.9 (1H, m), 7.1–7.3 (8H, m).

MS m/z: 495 (M+23).

(±)-Cis-3-{acetyl-[1-(4-methoxy-benzoyl)-2-methyl-1,2,3,4-tetrahydro-quinolin-4-yl]-amino}-benzoic acid (B-40)

(±)-Cis-3-{acetyl-[1-(4-methoxy-benzoyl)-2-methyl-1,2,3,4-tetrahydro-quinolin-4-yl]-amino}-benzoic acid was made following the procedure for (±)-cis-(4-{acetyl-[1-(4-methoxy-benzoyl)-2-methyl-1,2,3,4-tetrahydro-quinolin-4-yl]-amino}-phenyl)-acetic acid, substituting 3-cyanophenyl-boronic acid for 4-(phenylboronic acid)-acetonitrile.

Basic nitrile hydrolysis using 1N NaOH in methanol and water afforded both the carboxylic acid and the primary amide, (±)-cis-3-{Acetyl-[1-(4-methoxy-benzoyl)-2-methyl-1,2,3,4-tetrahydro-quinolin-4-yl]-amino}-benzamide.

$^1$H-NMR (CDCl$_3$) δ: 1.1 (3H, d), 1.1 (1H, m), 2.0 (3H, s), 2.3 (1H, m), 3.8 (3H, s), 4.8 (1H, m), 5.6 (1H, m), 6.5 (1H, d), 6.6 (2H, d), 6.9 (2H, m), 7.1–7.5 (5H, m), 7.9–8.2 (2H, m).

MS m/z: 481 (M+23).

(±)-Cis-3-{Acetyl-[1-(4-methoxy-benzoyl)-2-methyl-1,2,3,4-tetrahydro-quinolin-4-yl]-amino}-benzamide (B-41)

$^1$H-NMR (CDCl$_3$) δ: 1.1 (3H, d), 1.1 (1H, m), 2.0 (3H, s), 2.3 (1H, m), 3.8 (3H, s), 4.8 (1H, m), 5.7 (1H, m), 6.5 (1H, m), 6.6 (2H, m), 6.9 (1H, m), 7.1–7.3 (4H, m), 7.4–7.6 (2H, m), 7.7–7.8 (2H, m).

MS m/z: 480 (M+23).

(±)-Cis-N-(4-Chloro-phenyl)-N-[1-(isoxazole-5-carbonyl)-2-methyl-1,2,3,4-tetrahydro-quinolin-4-yl]-propionamide (B-44)

(±)-Cis-N-(4-Chloro-phenyl)-N-[1-(isoxazole-5-carbonyl)-2-methyl-1,2,3,4-tetrahydro-quinolin-4-yl]-propionamide was made following general procedure B, substituting 5-isoxazolecarbonyl chloride for 4-dimethylaminobenzoyl chloride and propionyl chloride for acetyl chloride.

$^1$H-NMR (CDCl$_3$) δ: 1.14 (3H, d; overlapping 3H, t, and 1H, t), 2.30 (overlapping 2H, q; and 1H, m), 4.75 (1H, m), 5.45 (1H, m), 6.00 (1H, d), 6.80 (1H, d), 7.10–7.40 (7H, m), 8.05 (1H, s).

MS m/z: 424 (M+1).

(±)-Cis-N-(4-chloro-phenyl)-N-[1-(4-cyclopentyloxy-benzoyl)-2-methyl-1,2,3,4-tetrahydro-quinolin-4-yl]-acetamide (B-45)

(±)-Cis-N-(4—chloro-phenyl)-N-[1-(4-cyclopentyloxy-benzoyl)-2-methyl-1,2,3,4-tetrahydro-quinolin-4-yl]-acetamide was prepared from (±)-cis-N-(4-chloro-phenyl)-N-[1-(4-hydroxy-benzoyl)-2-methyl-1,2,3,4-tetrahydro-quinolin-4-yl]-propionamide. To a solution of (±)-cis-N-(4-Chloro-phenyl)-N-[1-(4-hydroxy-benzoyl)-2-methyl-1,2,3,4-tetrahydro-quinolin-4-yl]-acetamide in dimethylformamide was added cyclopentyl bromide, potassium carbonate (3.0 equiv), potassium iodide (catalytic) and heated to 65° C. overnight. Reaction mixture was filtered for removal of inorganic salts and concentrated. Crude mixture was purified by flash chromatography on silica gel using gradient elution ethyl acetate-methanol (2–20% methanol)

$^1$H-NMR (CDCl$_3$) δ: 1.15 (3H, d; overlapping 1H, t), 1.57 (2H, m), 1.79 (3×2H, m), 2.04 (3H, s), 2.30 (1H, m), 4.60–4.80 (1H, q, 1H, m), 5.60 (1H, m), 6.50 (1H, d), 6.62 (1H, d), 6.90 (1H, t), 7.10–7.30 (9H, m), 7.40 (1H, d).

MS m/z: 504 (M+1).

(±)-Cis-N-{1-[4-(4-Acetyl-piperazin-1-yl)-benzoyl]-2-methyl-1,2,3,4-tetrahydro-quinolin-4-yl}-N-(4-chloro-phenyl)-acetamide (B-46)

(±)-Cis-N-{1-[4-(4-Acetyl-piperazin-1-yl)-benzoyl]-2-methyl-1,2,3,4-tetrahydro-quinolin-4-yl}-N-(4-chloro-phenyl)-acetamide was made from (±)-cis-N-(4-chloro-phenyl)-N-[1-(4-hydroxy-benzoyl)-2-methyl-1,2,3,4-tetrahydro-quinolin-4-yl]-propionamide. (±)-Cis-N-(4-Chloro-phenyl)-N-[1-(4-hydroxy-benzoyl)-2-methyl-1,2,3,4-tetrahydro-quinolin-4-yl]-propionamide (1.07 g, 2.39 mmol) was dissolved in pyridine (5 mL) and trifluoro-methanesulfonic anhydride (703 uL, 2.5 mmol) was added. The reaction was stirred at room temperature 3 h. The reaction was partitioned between ether and water, and the aqueous was extracted three times with ether. The combined extracts were dried over sodium sulfate, filtered and concentrated. The crude triflate was purified by silica gel chromatography (70/30 hexanes/ethyl acetate—40/60 hexanes/ethyl acetate gradient) to afford (1.0 g 74%) of pure material.

To the triflate, Pd$_2$(dba)$_3$, BINAP, cesium carbonate, 18-crown-6 ether in toluene was added N-acetyl piperazine and reaction mixture was heated to reflux for 18 hours. Reaction mixture was cooled to room temperature and filtered through Celite® and concentrated. Crude mixture was purified by flash chromatography on silica gel using gradient elution ethyl acetate-methanol (2–20%).

$^1$H-NMR (CDCl$_3$) δ: 1.13 (3H, d; overlapping 1H, t), 2.02 (3H, s), 2.10 (3H, s), 2.35 (1H, m), 3.20(2×2H, m), 3.60 (2H, t), 3.70 (2H, t), 4.80 (1H, m), 5.65 (1H, m), 6.55 (1H, d), 6.70 (1H, d), 6.95 (1H, t), 7.10–7.40 (9H, m).

MS m/z: 546 (M+1).

(±)-Cis-N-(3-chloro-phenyl)-N-[1-(4-fluoro-benzoyl)-2-methyl-1,2,3,4-tetrahydro-quinolin-4-yl]-acetamide (B-50)

(±)-Cis-N-(3-chloro-phenyl)-N-[1-(4-fluoro-benzoyl)-2-methyl-1,2,3,4-tetrahydro-quinolin-4-yl]-acetamide was made following general procedure B, substituting 4-fluorobenzoylchloride for 4-dimethylaminobenzoyl chloride and 3-chlorophenylboronic acid for 4-chlorophenylboronic acid.

$^1$H-NMR (CDCl$_3$) δ: 1.16–1.26 (4H, m), 2.05 (3H, s), 2.25–2.39 (1H, m), 4.69–4.88 (1H, m), 5.47–5.68 (1H, broad), 6.49 (1H, d), 6.84–6.97 (4H, m), 7.18–7.42 (7H, m).

MS m/z 437 (M$^+$), 439 (M+2).

(±)Cis-N-[1-(4-fluoro-benzoyl)-2-methyl-1,2,3,4-tetrahydro-quinolin-4-yl]-N-(4-phenoxy-phenyl)-acetamide (B-51)

(±)-Cis-N-[1-(4-fluoro-benzoyl)-2-methyl-1,2,3,4-tetrahydro-quinolin-4-yl]-N-(4-phenoxy-phenyl)-acetamide was made following general procedure B, substituting 4-fluorobenzoylchloride for 4-dimethylaminobenzoyl chloride and 4-phenoxyphenylboronic acid for 4-chlorophenylboronic acid.

$^1$H-NMR (CDCl$_3$) δ: 1.16–1.18 (4H, m), 2.06 (3H, s), 2.34–2.38 (1H, m), 4.74–4.82 (1H, m), 5.29 (1H, br), 6.47 (1H, d), 6.83–7.40 (16H, m).

MS m/z: 496 (M+1).

(±)-Cis-N-[1-(3-methoxy-benzoyl)-2-methyl-1,2,3,4-tetrahydro-quinolin-4-yl]-N-pyridin-2-yl-acetamide (B-52)

(±)-Cis-N-[1-(3-methoxy-benzoyl)-2-methyl-1,2,3,4-tetrahydro-quinolin-4-yl]-N-pyridin-2-yl-acetamide was made following general procedure B, substituting 3-methoxy benzoyl chloride for 4-dimethylaminobenzoyl chloride and synthesis of the N-pyridinyl instead of the 4-chlorophenyl was accomplished using the following procedure.

Pd$_2$(dba)$_3$ (0.05 equ.), and rac-BINAP (0.1 equ.) were added to a flask with degassed toluene and stirred for 1 h. To the above solution was added 2-bromopyridine (1.1 equ.) and NaO$^t$Bu (1.1 equ.) and stirred for 30 min. (±)-Cis-(4-amino-2-methyl-3,4-dihydro-2H-quinolin-1-yl)-(3-methoxy-phenyl)-methanone was dissolved in degassed toluene and added to the solution and heated to 100° C. for 17 h. The reaction was diluted with ether and filtered through celite and concentrated down. The compound was purified by Biotage with 20% EtOAc/80% Hexane to 30% EtOAc/70% Hexane to 50% EtOAc/50% Hexane to give 43% of the product. (±)-Cis-(3-methoxy-phenyl)-[2-methyl-4-(pyridin-2-ylamino)-3,4-dihydro-2H-quinolin-1-yl]-methanone was acetylated with acetyl chloride as previously described to give (±)-cis-N-[1-(3-methoxy-benzoyl)-2-methyl-1,2,3,4-tetrahydro-quinolin-4-yl]-N-pyridin-2-yl-acetamide.

$^1$H-NMR (CDCl$_3$) δ: 1.16 (d, 3H), 1.24 (t, 1H), 2.02 (s, 3H), 2.43 (m, 1H), 3.61 (s, 3H), 4.81 (sextet, 1H), 5.65 (bs, 1H), 6.52 (d, 1H), 6.75 (s, 1H), 6.79 (d, 2H), 6.90 (t, 1H), 7.07 (t, 1H), 7.14 (t, 1H), 7.25–7.33 (m, 2H), 7.49 (d, 1H), 7.77 (t, 1H), 8.56 (s, 1H).

MS m/z: 416.0 (M+1).

(±)-Cis-N-cyclohexyl-N-[1-(3-methoxy-benzoyl)-2-methyl-1,2,3,4-tetrahydro-quinolin-4-yl]-acetamide (B-53)

(±)-Cis-N-cyclohexyl-N-[1-(3-methoxy-benzoyl)-2-methyl-1,2,3,4-tetrahydro-quinolin-4-yl]-acetamide was made following general procedure B, substituting 3-methoxy benzoyl chloride for 4-dimethylaminobenzoyl chloride and synthesis of the N-cyclohexyl instead of the 4-chlorophenyl was accomplished using the following procedure.

(±)-Cis-(4-amino-2-methyl-3,4-dihydro-2H-quinolin-1-yl)-(3-methoxy-phenyl)-methanone (1.0 equ.), and cyclohexanone (1.0 equ.) were dissolved in ethanol and a catalytic amount of acetic acid was added. The reaction was stirred for 30 minutes and NaBH$_4$ (1.0 equ.) was added and stirred for an additional 2 h at room temperature. Additional NaBH$_4$ was added (1.0 equ.) and stirred for an additional 12 h. The reaction was concentrated down and partitioned between CH$_2$Cl$_2$ and 1N NaOH. The organics were separated and dried over Na$_2$SO$_4$, filtered and concentrated down. The compound was purified by Biotage with 30% EtOAc/70% hexane to 50% EtOAc/50% hexane give 96% of the product. Cis-(±)-N-(4-cyclohexylamino-2-methyl-3,4-dihydro-2H-quinolin-1-yl)-(3-methoxy-phenyl)-methanone was acetylated with acetyl chloride as previously described to give cis-(±)-N-cyclohexyl-N-[1-(3-methoxy-benzoyl)-2-methyl-1,2,3,4-tetrahydro-quinolin-4-yl]-acetamide.

¹H-NMR (CDCl₃) δ: 1.1–1.45 (m, 6H), 1.5–1.75 (m, 3H), 1.85–2.1 (m, 3H), 2.3 (s, 3H), 2.4 (m, 1H), 2.7 (m, 1H), 3.5 (q, 1H), 3.63 (s, 3H), 3.7 (m, 1H), 4.3 (dd, 1H), 4.90 (sextet, 1H), 6.6 (t, 1H), 6.7 (d, 1H)<6.8 (s, 1H), 6.85 (m, 2H), 7.0 (m, 3H).

MS m/z: 421 (M+1).

(±)-Cis-N-(5-chloro-pyridin-2-yl)-N-[1-(3-methoxy-benzoyl)-2-methyl-1,2,3,4-tetrahydro-quinolin-4-yl]-acetamide (B-54)

(±)-Cis-N-(5-chloro-pyridin-2-yl)-N-[1-(3-methoxy-benzoyl)-2-methyl-1,2,3,4-tetrahydro-quinolin-4-yl]-acetamide was made following general procedure B, substituting 3-methoxy benzoyl chloride for 4-dimethylaminobenzoyl chloride and addition of the N-4-chloropyridinyl instead of the 4-chlorophenyl was accomplished using the following procedure To a flask was added Pd₂(dba)₃ (molar 0.05 equ.), and rac-BINAP (0.1 equ.) in degassed toluene and stirred for 1 h. To the above solution was added 2,5-dichloropyridinepyridine (1.1 equ.) and NaOᵗBu (1.1 equ.) and stirred for 30 min. The corresponding amine, (±)-cis-(4-amino-2-methyl-3,4-dihydro-2H-quinolin-1-yl)-(3-methoxy-phenyl)-methanone was dissolved in degassed toluene and added to the solution and heated to 60° C. for 40 h. The reaction was diluted with ether and filtered through celite and concentrated down. The compound was purified by Biotage with 20% EtOAc/80% Hexane to give 45% of the product. (±)-Cis-[4-(5-chloro-pyridin-2-ylamino)-2-methyl-3,4-dihydro-2H-quinolin-1-yl]-(3-methoxy-phenyl)-methanone was acetylated with propionyl chloride as previously described to give (±)-cis-N-(5-chloro-pyridin-2-yl)-N-[1-(3-methoxy-benzoyl)-2-methyl-1,2,3,4-tetrahydro-quinolin-4-yl]-acetamide.

¹H-NMR (CDCl₃) δ: 1.14 (t, 3H), 1.15 (d, 3H), 1.22 (m, 1H), 2.31 (m, 3H), 4.79 (sextet, 1H), 5.64 (bs, 1H), 6.44 (d, 1H), 6.81–6.92 (m, 3H), 7.10–7.22 (m, 4H), 7.43 (d, 1H), 7.72 (dd, 1H), 8.50 (d, 1H).

MS m/z: 452 (M+1).

(±)-Cis-N-(4-chloro-phenyl)-N-[1-(4-methoxy-benzoyl)-2,5-dimethyl-1,2,3,4-tetrahydro-quinolin-4-yl]-acetamide (B-55)

(±)-Cis-N-(4-chloro-phenyl)-N-[1-(4-methoxy-benzoyl)-2,5-dimethyl-1,2,3,4-tetrahydro-quinolin-4-yl]-acetamide was made following general procedure B, substituting 3-toluidine for aniline and 4-methoxybenzoyl chloride for 4-dimethylaminobenzoyl chloride. The reaction was non-selective and also (±)-cis-N-(4-chloro-phenyl)-N-[1-(4-methoxy-benzoyl)-2,7-dimethyl-1,2,3,4-tetrahydro-quinolin-4-yl]-acetamide was obtained in a 1:1 mixture with the product.

¹H-NMR (CDCl₃) δ: 1.07 (d, 3H), 1.25 (t, 1H), 1.91 (s, 3H), 2.15 (m, 1H), 2.43 (s, 3H), 3.76 (s, 3H), 4.26 (sextet, 1H), 6.28 (d, 1H), 6.33 (t, 1H), 6.58 (t, 1H), 6.62 (d, 2H), 6.77 (t, 1H), 6.88 (d, 3H), 7.28 (m, 2H), 7.44 (d, 1H).

MS m/z: 463.0 (M+1)

(±)-Cis-N-(4-chloro-phenyl)-N-[1-(4-methoxy-benzoyl)-2,7-dimethyl-1,2,3,4-tetrahydro-quinolin-4-yl]-acetamide (B-56)

(±)-Cis-N-(4-chloro-phenyl)-N-[1-(4-methoxy-benzoyl)-2,7-dimethyl-1,2,3,4-tetrahydro-quinolin-4-yl]-acetamide was made following general procedure B, substituting 3-toluidine for aniline and 4-methoxybenzoyl chloride for 4-dimethylaminobenzoyl chloride. The reaction was non-selective and also (±)-cis-N-(4-chloro-phenyl)-N-[1-(4-methoxy-benzoyl)-2,5-dimethyl-1,2,3,4-tetrahydro-quinolin-4-yl]-acetamide was obtained in a 1:1 mixture with the titled compound.

(±)-Cis-N-(4-chloro-phenyl)-N-[1-(4-methoxy-benzoyl)-2,7-dimethyl-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-chloro-phenyl)-N-[1-(4-methoxy-benzoyl)-2,7-dimethyl-1,2,3,4-tetrahydro-quinolin-4-yl]-acetamide (B-58 & B-57, respectively).

¹H-NMR (CDCl₃) δ: 1.13 (d, 3H), 1.26 (t, 1H), 2.03 (s, 3H), 2.05 (s, 3H), 2.27 (m, 1H), 3.76 (s, 3H), 4.75 (sextet, 1H), 5.59 (bs, 1H), 6.35 (s, 1H), 6.68 (d, 2H), 6.95 (d, 1H), 7.18 (m, 1H), 7.20 (d, 2H), 7.37 (d, 2H).

MS m/z: 463.5 (M+1)

(±)-Cis-N-(4-chloro-phenyl)-N-[1-(4-fluoro-benzoyl)-6-methoxy-2-methyl-1,2,3,4-tetrahydro-quinolin-4-yl]-propionamide (B-59)

(±)-Cis-N-(4-chloro-phenyl)-N-[1-(4-fluoro-benzoyl)-6-methoxy-2-methyl-1,2,3,4-tetrahydro-quinolin-4-yl]-propionamide was made following general procedure B, substituting 4-anisidine for aniline, 4-fluorobenzoyl chloride for 4-dimethylaminobenzoyl chloride and propionyl chloride for acetyl chloride.

¹H-NMR (300 MHz, CDCl₃) δ: 1.08–1.22 (m, 7H), 2.09–2.38 (m, 3H), 3.79 (s, 3H), 4.77 (ddd, 1H), 5.58 (br s, 1H), 6.41–6.50 (m, 2H), 6.82–6.94 (m, 3H), 7.16–7.32 (m, 4H), 7.35–7.44 (m, 2H).

MS m/z=481 (M+1).

(±)-Cis-N-(4-chloro-phenyl)-N-[1-(4-fluoro-benzoyl)-6-hydroxy-2-methyl-1,2,3,4-tetrahydro-quinolin-4-yl]-propionamide (B-60)

(±)-Cis-N-(4-chloro-phenyl)-N-[1-(4-fluoro-benzoyl)-6-hydroxy-2-methyl-1,2,3,4-tetrahydro-quinolin-4-yl]-propionamide was made from (±)-cis-N-(4-chloro-phenyl)-N-[1-(4-fluoro-benzoyl)-6-methoxy-2-methyl-1,2,3,4-tetrahydro-quinolin-4-yl]-propionamide using the procedure described previously for the preparation of (±)-cis-N-(4-chloro-phenyl)-N-[1-(4-hydroxy-benzoyl)-2-methyl-1,2,3,4-tetrahydro-quinolin-4-yl]-propionamide.

¹H-NMR (300 MHz, CDCl₃) δ: 1.04–1.18 (m, 7H), 2.07–2.41 (m, 5H), 4.76 (ddd, 1H), 5.50 (br s, 1H), 6.27 (d, 1H), 6.36 (d, 1H), 6.65 (s, 1H), 6.70–6.91 (m, 3H), 7.03–7.44 (m, 4H).

MS m/z: 467 (M+1).

(±)-Cis-N-(4-chloro-phenyl)-N-[1-(4-fluoro-benzoyl)-2,7-dimethyl-1,2,3,4-tetrahydro-quinolin-4-yl]-propionamide (B-61)

(±)-Cis-N-(4-chloro-phenyl)-N-[1-(4-fluoro-benzoyl)-2,7-dimethyl-1,2,3,4-tetrahydro-quinolin-4-yl]-propionamide was made following general procedure B, substituting 3-toluidine for aniline, 4-fluorobenzoyl chloride for 4-dimethylaminobenzoyl chloride, and propionyl chloride for acetyl chloride.

¹H-NMR (300 MHz, CDCl₃) δ: 1.10 (m, 7H), 2.04 (s, 3H), 2.14–2.32 (m, 3H), 4.74 (ddd, 1H), 5.57 (br s, 1H), 6.26 (s, 1H), 6.81–6.98 (m, 4H), 7.11–7.33 (m, 4H), 7.31–7.43 (m, 2H).

MS m/z: 465 (M+1).

(±)-Cis-[4-[(4-Chloro-phenyl)-propionyl-amino]-1-(4-fluoro-benzoyl)-2-methyl-1,2,3,4-tetrahydro-quinolin-6-yloxy]-acetic acid methyl ester (B-62)

(±)-Cis-[4-[(4-Chloro-phenyl)-propionyl-amino]-1-(4-fluoro-benzoyl)-2-methyl-1,2,3,4-tetrahydro-quinolin-6-yloxy]-acetic acid methyl ester was made from (±)-cis-N-(4-chloro-phenyl)-N-[1-(4-fluoro-benzoyl)-6-hydroxy-2-methyl-1,2,3,4-tetrahydro-quinolin yl]-propionamide following the phenol alkylation procedure used to make (±)-cis-4-(4-{4-[(4-chloro-phenyl)-propionyl-amino]-2-methyl-3,4-dihydro-2H-quinoline-1-carbonyl}-phenoxy)-butyric acid ethyl ester. Methyl bromoacetate was substituted for ethyl-4-bromobutyrate.

$^1$H-NMR (300 MHz, CDCl$_3$) δ: 1.07–1.22 (m, 7H), 2.10–2.38 (m, 3H), 3.80 (s, 2H), 4.58 (s, 3H), 4.75 (m, 1H), 5.54 (br s, 1H), 6.39 (m, 2H), 6.81–6.94 (m, 3H), 7.18–7.35 (m, 5H, 7.36–7.44 (m, 2H).

MS m/z: 539 (M+1).

(±)-Cis-N-(4-Chloro-phenyl)-N-[6-(2-diethylamino-ethoxy)-1-(4-fluoro-benzoyl)-2-methyl-1,2,3,4-tetrahydro-quinolin-4-yl]-propionamide (B-63)

(±)-Cis-N-(4-Chloro-phenyl)-N-[6-(2-diethylamino-ethoxy)-1-(4-fluoro-benzoyl)-2-methyl-1,2,3,4-tetrahydro-quinolin-4-yl]-propionamide was made from (±)-cis-N-(4-chloro-phenyl)-N-[1-(4-fluoro-benzoyl)-6-hydroxy-2-methyl-1,2,3,4-tetrahydro-quinolin-4-yl]-propionamide following the phenol alkylation procedure used to make (±)-cis-4-(4-{4-[(4-chloro-phenyl)-propionyl-amino]-2-methyl-3,4-dihydro-2H-quinoline-1-carbonyl}-phenoxy)-butyric acid ethyl ester. (2-Bromo-ethyl)-diethyl-amine was substituted for ethyl-4-bromobutyrate.

$^1$H-NMR (300 MHz, CDCl$_3$) δ: 0.95–1.11 (m, 13H), 2.09–2.38 (m, 3H), 2.51–2.77 (m, 4H), 2.79–2.92 (m, 2H), 3.86–4.08 (m, 2H), 4.76 (ddd, 1H), 5.58 (br s, 1H), 6.34–6.51 (m, 2H), 6.78–6.94 (m, 3H), 7.14–7.31 (m, 4H), 7.37–7.42 (m, 2H).

MS m/z: 566 (M+1).

(±)-Cis-2-[4-[(4-chloro-phenyl)-propionyl-amino]-1-(4-fluoro-benzoyl)-2-methyl-1,2,3,4-tetrahydro-quinolin-6-yloxy]-2-methyl-propionic acid ethyl ester (B-64)

(±)-Cis-2-[4-[(4-chloro-phenyl)-propionyl-amino]-1-(4-fluoro-benzoyl)-2-methyl-1,2,3,4-tetrahydro-quinolin-6-yloxy]-2-methyl-propionic acid ethyl ester was made from (±)-cis-N-(4-chloro-phenyl)-N-[1-(4-fluoro-benzoyl)-6-hydroxy-2-methyl-1,2,3,4-tetrahydro-quinolin-4-yl]-propionamide following the phenol alkylation procedure used to make (±)-cis-4-(4-{4-[(4-chloro-phenyl)-propionyl-amino]-2-methyl-3,4-dihydro-2H-quinoline-1-carbonyl}-phenoxy)-butyric acid ethyl ester. 2-Bromo-2-methyl-propionic acid ethyl ester was substituted for ethyl-4-bromobutyrate.

$^1$H-NMR (300 MHz, CDCl$_3$) δ: 1.13–1.28 (m, 10H), 1.56 (s, 3H), 1.58 (s, 3H), 2.16–2.29 (m, 3H), 4.73 (ddd, H), 5.56 (br s, 1H), 6.31–6.39 (m, 2H), 6.76–6.88 (m, 3H), 7.16–7.22 (m, 4H), 7.38–7.41 (m, 2H).

MS m/z: 581 (M+1).

(±)-Cis-[4-[(4-chloro-phenyl)-propionyl-amino]-1-(4-fluoro-benzoyl)-2-methyl-1,2,3,4-tetrahydro-quinolin-6-yloxy]-acetic acid (B-65)

(±)-Cis-[4-[(4-chloro-phenyl)-propionyl-amino]-1-(4-fluoro-benzoyl)-2-methyl-1,2,3,4-tetrahydro-quinolin-6-yloxy]-acetic acid was prepared from (±)-cis-[4-[(4-chloro-phenyl)-propionyl-amino]-1-(4-fluoro-benzoyl)-2-methyl-1,2,3,4-tetrahydro-quinolin-6-yloxy]-acetic acid methyl ester. To a solution of (±)-cis-[4-[(4-chloro-phenyl)-propionyl-amino]-1-(4-fluoro-benzoyl)-2-methyl-1,2,3,4-tetrahydro-quinolin-6-yloxy]-acetic acid methyl ester (83 mg, 0.155 mmol) in methanol (3 mL) was added sodium hydroxide (1 M in water, 310 uL, 0.310 mmol). The reaction was stirred at room temperature 3 h and concentrated under reduced pressure to remove methanol. The pH of the remaining aqueous solution was adjusted to 6 with 1 M hydrochloric acid. The suspension was extracted twice with ethyl acetate. The combined extracts were washed with brine, dried over sodium sulfate, filtered and concentrated to afford the carboxylic acid (76 mg, 94%).

$^1$H-NMR (300 MHz, CDCl$_3$) δ: 1.09–1.26 (m, 7H), 2.08–2.18 (m, 3H), 4.58 (AB q, 2H), 4.79 (ddd, 1H), 5.57 (br s, 1H), 6.40 (m, 2H), 6.86 (m, 3H), 7.09–7.30 (m, 4H), 7.35–7.46 (m, 2H), 8.18 (br s, 1H).

MS m/z: 523 (M−1).

(±)-Cis-2-[4-[(4-chloro-phenyl)-propionyl-amino]-1-(4-fluoro-benzoyl)-2-methyl-1,2,3,4-tetrahydro-quinolin-6-yloxy]-2-methyl-propionic acid (B-66)

(±)-Cis-2-[4-[(4-chloro-phenyl)-propionyl-amino]-1-(4-fluoro-benzoyl)-2-methyl-1,2,3,4-tetrahydro-quinolin-6-yloxy]-2-methyl-propionic acid was prepared from (±)-cis-2-[4-[(4-chloro-phenyl)-propionyl-amino]-1-(4-fluoro-benzoyl)-2-methyl-1,2,3,4-tetrahydro-quinolin-6-yloxy]-2-methyl-propionic acid ethyl ester. The saponification conditions detailed in the procedure for the synthesis of (±)-cis-[4-[(4-chloro-phenyl)-propionyl-amniino]-1-(4-fluoro-benzoyl)-2-methyl-1,2,3,4-tetrahydro-quinolin-6-yloxy]-acetic acid were used.

$^1$H-NMR (300 MHz, CDCl$_3$) δ: 1.04–1.21 (m, 7H), 1.54–1.66 (m, 6H), 2.12–2.37 (m, 3H), 4.77 (ddd, 1H), 5.53 (br s, 1H), 6.37 (d, 1H), 6.48 (d, 1H), 6.66–6.92 (m, 1H), 7.12–7.26 (m, 4H), 7.43 (m, 2H), 9.00 (br s, 1H).

MS m/z: 553 (M+1).

(±)-Cis-N-[6-carbamoylmethoxy-1-(4-fluoro-benzoyl)-2-methyl-1,2,3,4-tetrahydro-quinolin-4-yl]-N-(4-chloro-phenyl)-propionamide (B-67)

(±)-Cis-N-[6-carbamoylmethoxy-1-(4-fluoro-benzoyl)-2-methyl-1,2,3,4-tetrahydro-quinolin-4-yl]-N-(4-chloro-phenyl)-propionamide was prepared from (±)-cis-4-[(4-chloro-phenyl)-propionyl-amino]-1-(4-fluoro-benzoyl)-2-methyl-1,2,3,4-tetrahydro-quinolin-6-yloxy]-acetic acid methyl ester. To solid (±)-cis-[4-[(4-chloro-phenyl)-propionyl-amino]-1-(4-fluoro-benzoyl)-2-methyl-1,2,3,4-tetrahydro-quinolin-6-yloxy]-acetic acid methyl ester (76 mg, 0.14 mmol) was added a solution of ammonia in methanol (2 M, 10 mL). The resulting solution was stirred over night at room temperature and concentrated. The resulting crude amide was purified by silica gel chromatography (100% hexanes—100% ethyl acetate gradient) to afford pure product (59 mg, 76%).

$^1$H-NMR (300 MHz, CDCl$_3$) δ: 1.10–1.23 (m, 7H), 2.16–2.39 (m, 3H), 4.44 (s, 2H), 4/77 (ddd, 1H), 5.56 (br s, 1H), 6.25 (br s, 1H), 6.40–6.62 (m, 3H), 7.16–7.26 (m, 4H), 7.35–7.48 (m, 2H).

MS m/z: 524 (M+1).

(±)-Cis-N-[6-Bromo-1-(4-fluoro-benzoyl)-2-methyl-1,2,3,4-tetrahydro-quinolin-4-yl]-N-(4-chloro-phenyl)-propionamide (B-69)

(±)-Cis-N-[6-bromo-1-(4-fluoro-benzoyl)-2-methyl-1,2,3,4-tetrahydro-quinolin-4-yl]-N-(4-chloro-phenyl)-propionamide was made following general procedure B, substituting 4-bromoaniline for aniline and 4-fluorobenzoyl chloride for 4-dimethylaminobenzoyl chloride and propionyl chloride for acetyl chloride.

¹H-NMR (CDCl₃) δ: 1.1–1.2 (7H, m), 2.1–2.3 (3H, m), 4.8 (1H, m), 5.6 (1H, m), 6.4 (1H, d), 6.9 (3H, t), 7.1 (1H, m), 7.2 (4H, m), 7.4 (3H, m).

MS m/z: 531 (M+2).

(±)-Cis-N-(4-chloro-phenyl)-N-[1-(4-fluoro-benzoyl)-2-methyl-6-morpholin-4-yl-1,2,3,4-tetrahydro-quinolin-4-yl]-propionamide (B-70)

(±)-Cis-N-(4-chloro-phenyl)-N-[1-(4-fluoro-benzoyl)-2-methyl-6-morpholin-4-yl-1,2,3,4-tetrahydro-quinolin-4-yl]-propionamide was made from (±)-cis-N-[6-bromo-1-(4-fluoro-benzoyl)-2-methyl-1,2,3,4-tetrahydro-quinolin-4-yl]-N-(4-chloro-phenyl)-propionamide.

(±)-Cis-N-[6-bromo-1-(4-fluoro-benzoyl)-2-methyl-1,2,3,4-tetrahydro-quinolin-4-yl]-N-(4-chloro-phenyl)-propionamide was dissolved in toluene, followed by Pd₂(dba)₃, BINAP, sodium tert-butoxide, and morpholine. The reaction mixture was heated to 90° C. for 24 hours. The reaction mixture was cooled to room temperature and filtered through Celite® and concentrated. Crude mixture was purified by flash chromatography on silica gel using a gradient elution of hexane-ethylacetate (10–50%).

¹H-NMR (CDCl₃) δ: 1.1–1.2 (7H, m), 2.1–2.3 (3H, m), 3.1 (4H, t), 3.8 (4H, t), 4.8 (1H, m), 5.6 (1H, m), 6.3 (1H, d), 6.4 (1H, m), 6.7 (1H, s), 6.9 (3H, m), 7.1–7.4 (5H, m).

MS m/z: 536 (M+1).

(±)-Cis-(4-chloro-phenyl)-N-[6-diethylamino-1-(4-fluoro-benzoyl)-2-methyl-1,2,3,4-tetrahydro-quinolin-4-yl]-propionamide (B-71)

(±)-Cis-N-(4-chloro-phenyl)-N-[6-diethylamino-1-(4-fluoro-benzoyl)-2-methyl-1,2,3,4-tetrahydro-quinolin-4-yl]-propionamide was made in the same way as (±)-cis-N-(4-chloro-phenyl)-N-[1-(4-fluoro-benzoyl)-2-methyl-6-morpholin-4-yl-1,2,3,4-tetrahydro-quinolin-4-yl]-propionamide except diethylamine was substituted for morpholine. The reaction was non-selective and yielded (±)-cis-N-[6-diethylamino-1-(4-fluoro-benzoyl)-2-methyl-1,2,3,4-tetrahydro-quinolin-4-yl]-N-(4-diethylamino-phenyl)-propionamide in addition to the titled compound.

¹H-NMR (CDCl₃) δ: 1.1–1.3 (13H, m), 1.6 (1H, m), 2.1–2.3 (3H, m), 3.3 (4H, m), 4.7 (1H, m), 5.6 (1H, m), 6.2 (1H, m), 6.3 (1H, m), 6.5 (1H, s), 6.9 (2H, m), 7.3 (4H, m), 7.4 (2H, m).

MS m/z: 523 (M+2).

(±)-Cis-N-[6-diethylamino-1-(4-fluoro-benzoyl)-2-methyl-1,2,3,4-tetrahydro-quinolin-4-yl]-N(4-diethylamino-phenyl)-propionamide (B-72)

(±)-Cis-N-[6-diethylamino-1-(4-fluoro-benzoyl)-2-methyl-1,2,3,4-tetrahydro-quinolin-4-yl]-N(4-diethylamino-phenyl)-propionamide was made in the same way as (±)-cis-N-(4-chloro-phenyl)-N-[1-(4-fluoro-benzoyl)-2-methyl-6-morpholin-4-yl-1,2,3,4-tetrahydro-quinolin-4-yl]-propionamide except diethylamine was substituted for morpholine. The reaction was non-selective and yielded (±)-cis-N-(4-chloro-phenyl)-N-[6-diethylamino-1-(4-fluoro-benzoyl)-2-methyl-1,2,3,4-tetrahydro-quinolin-4-yl]-propionamide in addition to the titled compound.

¹H-NMR (CDCl₃) δ: 1.1–1.3 (19H, m), 2.3 (3H, m), 3.3 (8H, m), 4.7 (1H, m), 5.6 (1H, m), 6.1 (1H, m), 6.2 (1H, m), 6.6 (3H, m), 6.9 (1H, m), 7.1 (3H, m), 7.3 (2H, m).

MS m/z: 560 (M+2).

(±)-Cis-3-[4-[(4-chloro-phenyl)-propionyl-amino]-1-(4-fluoro-benzoyl)-2-methyl-1,2,3,4-tetrahydro-quinolin-6-yl]-acrylic acid (B-73)

(±)-Cis-3-[4-[(4-chloro-phenyl)-propionyl-amino]-1-(4-fluoro-benzoyl)-2-methyl-1,2,3,4-tetrahydro-quinolin-6-yl]-acrylic acid was made from (±)-cis-N-[6-bromo-1-(4-fluoro-benzoyl)-2-methyl-1,2,3,4-tetrahydro-quinolin-4-yl]-N-(4-chloro-phenyl)-propionamide. To a solution of (±)-cis-N-[6-bromo-1-(4-fluoro-benzoyl)-2-methyl-1,2,3,4-tetrahydro-quinolin-4-yl]-N-(4-chloro-phenyl)-propionamide (250 mg, 0.47 mmol), TEA (0.2 ml, 1.4 mmol), palladium acetate (11 mg, 0.047 mmol), 1,3-Bis (diphenylphosphino)propane (39 mg, 0.094 mmol), in 10 ml DMF was added 0.13 ml methyl acrylate (1.41 mmol). The resulting reaction mixture was heated to 80° C. overnight. The mixture was filtered through celite and the filtrate was concentrated under vacuum. The residue was purified by silica gel chromatography, eluting with ethyl acetate-hexane (2:3) to give (±)-cis-3-[4-[(4-chloro-phenyl)-propionyl-amino]-1-(4-fluoro-benzoyl)-2-methyl-1,2,3,4-tetrahydro-quinolin-6-yl]-acrylic acid methyl ester (110 mg, 44%).

To a solution of (±)-cis-3-[4-[(4-chloro-phenyl)-propionyl-amino]-1-(4-fluoro-benzoyl)-2-methyl-1,2,3,4-tetrahydro-quinolin-6-yl]-acrylic acid methyl ester (110 mg, 0.21 mmol) in 4 ml methanol was added 50 mg K₂CO₃, (0.36 mmol, in 2 ml water). The resulting reaction mixture was stirred at room temperature overnight. The methanol was removed under vacuum. 1M HCl was added until the mixture was acidic. Dichloromethane (25 ml) was added. Organic layer was dried with magnesium sulfate. Dichloromethane was removed under vacuum. The residue was purified by HPLC to give 10 mg title compound ¹H-NMR (CDCl₃) δ: 1.0–1.2 (7H, m), 2.4 (2H, m), 2.5 (1H, m), 3.3 (1H, br), 4.8 (1H, m), 5.6 (1H, m), 6.4 (1H, d), 6.6 (1H, d), 7.0 (2H, t), 7.2–7.6 (9H, m).

MS m/z: 522 (M+2).

(±)-Cis-N-(4-chloro-phenyl)-N-[1-(3-methoxy-benzoyl)-2,8-dimethyl-1,2,3,4-tetrahydro-quinolin-4-yl]-acetamide (B-74)

(±)-Cis-N-(4-chloro-phenyl)-N-[1-(3-methoxy-benzoyl)-2,8-dimethyl-1,2,3,4-tetrahydro-quinolin-4-yl]-acetamide was made following general procedure B, substituting 2-toluidine for aniline and 3-methoxybenzoyl chloride for 4-dimethylaminobenzoyl chloride.

¹H-NMR (CDCl₃) δ: 1.11 (3H, d; overlapping 1H, t), 1.76 (3H, s), 2.00 (3H, s), 2.35 (1H, m), 3.55 (3H, s), 5.00 (1H, m), 5.60 (1H, m), 6.65 (1H, s), 6.80 (1H, t), 6.85 (1H, t), 6.95 (1H, t), 7.15 (1H, t), 7.25 (1H, t), 7.25–7.55 (6H, m)

MS m/z: 429 (M+1).

(±)-Cis-N-(4-Chloro-phenyl)-N-[1-(3-methoxy-benzoyl)-2,6-dimethyl-1,2,3,4-tetrahydro-quinolin-4-yl]-acetamide (B-75)

(±)-Cis-N-(4-chloro-phenyl)-N-[1-(3-methoxy-benzoyl)-2,6-dimethyl-1,2,3,4-tetrahydro-quinolin-4-yl]-acetamide was made following general procedure B, substituting 4-toluidine for aniline and 3-methoxybenzoyl chloride for 4-dimethylaminobenzoyl chloride.

¹H-NMR (CDCl₃) δ: 1.12 (3H, d; overlapping 1H, t), 2.02 (3H, s), 2.33–2.35 (3H, s; overlapping 1H, m), 3.63 (3H, s), 4.80 (1H, m), 5.60 (1H, m), 6.44 (1H, d), 6.70–6.85 (3H, complex), 7.05 (1H, t), 7.15 (1H, s), 7.25–7.55 (6H, complex).

MS m/z: 429 (M+1).

(±)-Cis-N-(4-chloro-phenyl)-N-[1-(3-methoxy-benzoyl)-2-methyl-6-trifluoromethyl-1,2,3,4-tetrahydro-quinolin-4-yl]-acetamide (B-76)

(±)-Cis-N-(4-chloro-phenyl)-N-[1-(3-methoxy-benzoyl)-2-methyl-6-trifluoromethyl-1,2,3,4-tetrahydro-quinolin-4-yl]-acetamide was made following general procedure B, substituting 4-trifluoromethylaniline for aniline and 3-methoxybenzoyl chloride for 4-dimethylaminobenzoyl chloride.

¹H-NMR (CDCl₃) δ: 1.15 (3H, d; overlapping 1H, t), 2.03 (3H, s), 2.38 (1H, m), 3.63 (3H, s), 4.80 (1H, m), 5.60 (1H, m), 6.60 (1H, d), 6.70 (1H, d), 6.80 (1H, dd), 7.15 (1H, t), 7.25–7.40 (6H, m), 7.60 (1H, s).

MS m/z: 483 (M+1).

(±)-Cis-N-(4-chloro-phenyl)-N-[6-methoxy-1-(3-methoxy-benzoyl)-2-methyl-1,2,3,4-tetrahydro-quinolin-4-yl]-acetamide (B-77)

(±)-Cis-N-(4-chloro-phenyl)-N-[6-methoxy-1-(3-methoxy-benzoyl)-2-methyl-1,2,3,4-tetrahydro-quinolin-4-yl]-acetamide was made following general procedure B, substituting 4-methoxyaniline for aniline and 3-methoxybenzoyl chloride for 4-dimethylaminobenzoyl chloride.

¹H-NMR (CDCl₃) δ: 1.12 (3H, d; overlapping 1H, t), 2.02 (3H, s), 2.35 (1H, m), 3.63 (3H, s), 3.76 (3H, s), 4.80 (1H, m), 5.60 (1H, m), 6.44 (1H, s), 6.70–6.95 (4H, complex), 7.15 (1H, t), 7.25–7.55 (6H, m).

MS m/z: 445 (M+1).

(±)-Cis-N-(4-chloro-phenyl)-N-[2-methyl-1-(thiophene-2-carbonyl)-6-trifluoromethyl-1,2,3,4-tetrahydro-quinolin-4-yl]-acetamide (B-78)

(±)-Cis-N-(4-chloro-phenyl)-N-[2-methyl-1-(thiophene-2-carbonyl)-6-trifluoromethyl-1,2,3,4-tetrahydro-quinolin-4-yl]-acetamide was made following general procedure B, substituting 4-trifluoromethylaniline for aniline and 2-thiophene carbonyl chloride for 4-dimethylaminobenzoyl chloride.

¹H-NMR (CDCl₃) δ: 1.14 (3H, d; overlapping 1H, t), 2.02 (3H, s), 2.35 (1H, m), 4.80 (1H, m), 5.65 (1H, m), 6.65 (1H, d), 6.80 (1H, d), 7.00 (1H, d), 7.20 (overlapping 2×1H, d), 7.24–7.42 (3H, m), 7.60 (1H, s).

MS m/z: 539 (M+1).

(±)-Cis-N-(4-chloro-phenyl)-N-[2-methyl-1-(5-methyl-thiophene-2-carbonyl)-6-trifluoromethyl-1,2,3,4-tetrahydro-quinolin-4-yl]-acetamide (B-79)

(±)-Cis-N-(4-chloro-phenyl)-N-[2-methyl-1-(5-methyl-thiophene-2-carbonyl)-6-trifluoromethyl-1,2,3,4-tetrahydro-quinolin-4-yl]-acetamide was made following general procedure B, substituting 4-trifluoromethylaniline for aniline and 5-methyl-2-thiophene carbonyl chloride for 4-dimethylaminobenzoyl chloride.

¹H-NMR (CDCl₃) δ: 1.14 (3H, d; overlapping 1H, t), 2.02 (3H, s), 2.35 (1H, m), 2.40 (3H, s), 4.80 (1H, m), 5.65 (1H, m), 6.45 (1H, d), 6.55 (1H, d), 7.00 (1H, d), 7.20 (overlapping 2×1H, d), 7.24–7.42 (3H, m), 7.55 (1H, s).

MS m/z: 554 (M+1).

(±)-Cis-N-(4-chloro-phenyl)-N-[1-(4-fluoro-benzoyl)-2-methyl-7-trifluoromethyl-1,2,3,4-tetrahydro-quinolin-4-yl]-propionamide (B-80)

(±)-Cis-N-(4-chloro-phenyl)-N-[1-(4-fluoro-benzoyl)-2-methyl-7-trifluoromethyl-1,2,3,4-tetrahydro-quinolin-4-yl]-propionamide was made following general procedure B, substituting 3-trifluoromethylaniline for aniline, 4-fluorobenzoyl chloride for 4-dimethylaminobenzoyl chloride and propionyl chloride for acetyl chloride. A mixture of the and 7 position isomer was obtained.

¹H-NMR (CDCl₃) δ: 1.15 (3H, d; overlapping 1H, t), 2.20–2.40 (2H, q; 1H, m), 4.80 (1H, m), 5.65 (1H, m), 6.70 (1H, s), 6.95 (2×1H, t), 7.10–7.60 (8H, m)

MS m/z: 519 (M+1).

(±)-Cis-N-[7-bromo-1-(4-dimethylamino-benzoyl)-2-methyl-1,2,3,4-tetrahydro-quinolin-4-yl]-N-(4-chloro-phenyl)-acetamide (B-81)

(±)-Cis-N-[7-bromo-1-(4-dimethylamino-benzoyl)-2-methyl-1,2,3,4-tetrahydro-quinolin-4-yl]-N-(4-chloro-phenyl)-acetamide was made following general procedure B, substituting 3-bromoaniline for aniline. A mixture of the 5 and 7 position isomer was obtained.

(±)-Cis-N-(4-chloro-phenyl)-N-[1-(4-dimethylamino-benzoyl)-7-isopropyl-2-methyl-1,2,3,4-tetrahydro-quinolin-4-yl]-acetamide (B-82)

(±)-Cis-N-(4-chloro-phenyl)-N-[1-(4-dimethylamino-benzoyl)-7-isopropyl-2-methyl-1,2,3,4-tetrahydro-quinolin-4-yl]-acetamide was made following general procedure B, substituting 3-isopropylaniline for aniline. A mixture of the 5 and 7 position isomer was obtained.

¹H-NMR (CDCl₃) δ: 0.89 (2×3H, t), 1.15 (3H, d; overlapping 1H, t), 2.01 (3H, s), 2.33 (1H, m), 2.60 (1H, m), 2.87(2×3H, s), 4.80 (11H, m), 5.65 (1H, m), 6.40 (overlapping 1H, s, 2H, d), 6.90 (1H, d), 7.10 (1H, d), 7.15–7.35 (5H, m) 7.40 (1H, d).

MS m/z: 505 (M+1).

(±)-Cis-N-(4-chloro-phenyl)-N-[1-(4-dimethylamino-benzoyl)-2-methyl-7-morpholin-4-yl-1,2,3,4-tetrahydro-quinolin-4-yl]-acetamide (B-83)

(±)-Cis-N-(4-chloro-phenyl)-N-[1-(4-dimethylamino-benzoyl)-2-methyl-7-morpholin-4-yl-1,2,3,4-tetrahydro-quinolin-4-yl]-acetamide was made from (±)-cis-N-[7-bromo-1-(4-dimethylamino-benzoyl)-2-methyl-1,2,3,4-tetrahydro-quinolin-4-yl]-N-(4-chloro-phenyl)-acetamide. (±)-Cis-N-[7-bromo-1-(4-dimethylamino-benzoyl)-2-methyl-1,2,3,4-tetrahydro-quinolin-4-yl]-N-(4-chloro-phenyl)-acetamide was dissolved in toluene, followed by Pd₂(dba)₃, BINAP, sodium tert-butoxide, and morpholine. The reaction mixture was heated to 90° C. for 24 hours. The reaction mixture was cooled to room temperature and filtered through Celite® and concentrated. Crude mixture was purified by flash chromatography on silica gel using gradient elution hexane-ethylacetate (10–50%).

¹H-NMR (CDCl₃) δ: 1.11 (3H, d; overlapping 1H, t), 1.99 (3H, s), 2.33 (1H, m), 2.60–2.80 (2×2H, m), 2.89(2×3H, s), 3.70(2×2H, m), 4.70 (1H, m), 5.60 (1H, m), 6.10 (1H, s), 6.44 (2×1H, d), 7.00–7.40 (8H, m).

MS m/z: 548 (M+1).

(±)-Cis-N-[7-diethylamino-1-(4-dimethylamino-benzoyl)-2-methyl-1,2,3,4-tetrahydro-quinolin-4-yl]-N-(4-diethylamino-phenyl)-acetamide (B-84)

(±)-Cis-N-[7-diethylamino-1-(4-dimethylamino-benzoyl)-2-methyl-1,2,3,4-tetrahydro-quinolin-4-yl]-N-(4-diethylamino-phenyl)-acetamide was made in the same way as (±)-cis-N-(4-chloro-phenyl)-N-[1-(4-dimethylamino-benzoyl)-2-methyl-7-morpholin-4-yl-1,2,3,4-tetrahydro-quinolin-4-yl]-acetamide except diethylamine was substituted for morpholine. The reaction was non-selective and yielded (±)-cis-N-(4-chloro-phenyl)-N-[7-diethylamino-1-(4-dimethylamino-benzoyl)-2-methyl-1,2,3,4-tetrahydro-quinolin-4-yl]-acetamide in addition to the titled compound.

¹H-NMR (CDCl₃) δ: 0.78 (2×3H, t), 1.15 (overlapping 3H, d; 1H, t), 1.98 (3H, s), 2.33 (1H, m), 2.87(2×3H, s), 2.90–3.10(2×2H, q), 4.70 (1H, m), 5.60 (1H, m), 5.90 (1H, s), 6.46 (3×1H, d), 7.00–7.40 (7H, m).

MS m/z: 557 (M+1).

(±)-Cis-N-(4-chloro-phenyl)-N-[7-diethylamino-1-(4-dimethylamino-benzoyl)-2-methyl-1,2,3,4-tetrahydro-quinolin-4-yl]-acetamide (B-85)

(±)-Cis-N-(4-chloro-phenyl)-N-[7-diethylamino-1-(4-dimethylamino-benzoyl)-2-methyl-1,2,3,4-tetrahydro-quinolin-4-yl]-acetamide was made in the same way as (±)-cis-N-(4-chloro-phenyl)-N-[1-(4-dimethylamino-benzoyl)-2-methyl-7-morpholin-4-yl-1,2,3,4-tetrahydro-quinolin-4-yl]-acetamide except diethylamine was substituted for morpholine.

The reaction was non-selective and yielded (±)-cis-N-[7-diethylamino-1-(4-dimethylamino-benzoyl)-2-methyl-1,2,3,4-tetrahydro-quinolin-4-yl]-N-(4-diethylamino-phenyl)-acetamide in addition to the titled compound.

$^1$H-NMR (CDCl$_3$) δ: 0.78 (2×3H, t), 1.15 (overlapping 2×3H, t; 3H, d; 1H, t), 2.00 (3H, s), 2.33 (1H, m), 2.76(2×3H, s), 2.80–3.00(2×2H, q), 3.24(2×2H, q), 4.60 (1H, m), 5.60 (1H, m), 5.90 (1H, s), 6.46 (2×1H, d), 6.60 (1H, m), 6.90 (2×1H, d), 7.00–7.20 (6H, m).

MS m/z: 609 (M+1).

(±)-Cis-N-(4-chloro-phenyl)-N-[1-(4-fluoro-benzoyl)-5-methoxy-2-methyl-1,2,3,4-tetrahydro-quinolin-4-yl]-propionamide (B-86)

(±)-Cis-N-(4-chloro-phenyl)-N-[1-(4-fluoro-benzoyl)-5-methoxy-2-methyl-1,2,3,4-tetrahydro-quinolin-4-yl]-propionamide was prepared following general procedure B, substituting 3-anisidine for aniline, 4-fluorobenzoyl chloride for 4-dimethylaminobenzoyl chloride and propionyl chloride for acetyl chloride.

$^1$H-NMR (CDCl$_3$) δ: 1.09–1.14 (6H, m), 1.50–1.66 (1H, m), 1.97–2.34 (3H, m), 3.83 (3H, s), 4.65 (1H, q), 5.70–5.80 (1H, br), 6.08 (1H, d), 6.68 (1H, d). 6.81–6.89 (3H, m), 7.14–7.18 (4H, m), 7.33–7.36 (2H, m).

MS m/z: 481 (M+1).

(±)-Cis-2,2-dimethyl-propionic acid 4-[acetyl-(4-chloro-phenyl)-amino]-1-(4-dimethylamino-benzoyl)-2-methyl-1,2,3,4-tetrahydro-quinolin-7-yl ester (B-87)

(±)-Cis-2,2-dimethyl-propionic acid 4-[acetyl-(4-chloro-phenyl)-amino]-1-(4-dimethylamino-benzoyl)-2-methyl-1,2,3,4-tetrahydro-quinolin-7-yl ester was prepared following general procedure B, substituting 2,2-dimethyl-propionic acid 3-amino-phenyl ester for aniline.

$^1$H-NMR (CDCl$_3$) δ: 1.11–1.25 (13H, m), 2.02 (3H, s), 2.20–2.40 (1H, m), 2.92 (6H, s), 4.60–4.72 (1H, m), 5.45–5.55 (1H, br), 6.26 (1H, s), 6.46 (2H, d), 6.85 (1H, d), 7.09–7.39 (7H, m).

MS m/z: 562 (M+1).

(±)-Cis-N-(4-chloro-phenyl)-N-[1-(4-dimethylamino-benzoyl)-7-hydroxy-2-methyl-1,2,3,4-tetrahydro-quinolin-4-yl]-acetamide (B-88)

(±)-Cis-N-(4-chloro-phenyl)-N-[1-(4-dimethylamino-benzoyl)-7-hydroxy-2-methyl-1,2,3,4-tetrahydro-quinolin-4-yl]-acetamide was made from (±)-cis-2,2-dimethyl-propionic acid 4-[acetyl-(4-chloro-phenyl)-amino]-1-(4-dimethylamino-benzoyl)-2-methyl-1,2,3,4-tetrahydro-quinolin-7-yl ester. (±)-Cis-2,2-dimethyl-propionic acid 4-[acetyl-(4-chloro-phenyl)-amino]-1-(4-dimethylamino-benzoyl)-2-methyl-1,2,3,4-tetrahydro-quinolin-7-yl ester (100 mg, 0.178 mmol) was dissolved in tetrahydrofuran and sodium hydroxide (1 M, 356 uL, 0.356 mmol) was added. The mixture was stirred at room temperature 4 hours, then heated at reflux 2 h. The mixture was cooled to rt, acidified, concentrated and purified by silica gel chromatography (20 mg, 23%).

$^1$H-NMR (MeOD) δ: 1.06–1.08 (4H, m), 2.00 (3H, s), 2.35–2.45 (1H, m), 2.93 (6H, s), 4.65–4.68 (1H, m), 5.42–5.50 (1H, br), 6.07 (1H, s), 6.53 (2H, d), 6.63 (1H, d), 7.10–7.20 (3H, m), 7.35–7.48 (4H, m).

MS m/z: 478 (M+1).

(±)-Cis-[4-[acetyl-(4-chloro-phenyl)-amino]-1-(4-dimethylamino-benzoyl)-2-methyl-1,2,3,4-tetrahydro-quinolin-7-yloxy]-acetic Acid Ethyl Ester (B-89)

(±)-Cis-[4-[acetyl-(4-chloro-phenyl)-amino]-1-(4-dimethylamino-benzoyl)-2-methyl-1,2,3,4-tetrahydro-quinolin-7-yloxy]-acetic acid ethyl ester was prepared from (±)-cis-N-(4-chloro-phenyl)-N-[1-(4-dimethylamino-benzoyl)-7-hydroxy-2-methyl-1,2,3,4-tetrahydro-quinolin-4-yl]-acetamide, following the alkylation conditions described for the synthesis of (±)-cis-4-(4-{4-[(4-chloro-phenyl)-propionyl-amino]-2-methyl-3,4-dihydro-2H-quinoline-1-carbonyl}-phenoxy)-butyric acid ethyl ester, substituting ethyl bromoacetate for ethyl 4-bromobutyrate.

$^1$H-NMR (MeOD) δ: 1.10–1.38 (7H, m), 2.00 (3H, s), 2.39–2.45 (1H, m), 2.94 (6H, s), 4.04–4.20 (2H, m), 4.29 (2H, s), 4.60–4.75 (1H, m), 5.40–5.50 (1H, br), 6.16 (1H, s), 6.54 (2H, d), 6.79 (1H, d), 7.08 (2H, d), 7.20–7.48 (5H, m).

MS m/z: 564 (M+1).

(±)-Cis-2-[4-[acetyl-(4-chloro-phenyl)-amino]-1-(4-dimethylamino-benzoyl)-2-methyl-1,2,3,4-tetrahydro-quinolin-7-yloxy]-acetamide (B-90)

(±)-Cis-2-[4-[acetyl-(4-chloro-phenyl)-amino]-1-(4-dimethylamino-benzoyl)-2-methyl-1,2,3,4-tetrahydro-quinolin-7-yloxy]-acetamide was prepared from (±)-cis-[4-[acetyl-(4-chloro-phenyl)-amino]-1-(4-dimethylamino-benzoyl)-2-methyl-1,2,3,4-tetrahydro-quinolin-7-yloxy]-acetic acid ethyl ester, via the same amidation procedure used in the synthesis of (±)-cis-N-[6-carbamoylmethoxy-1-(4-fluoro-benzoyl)-2-methyl-1,2,3,4-tetrahydro-quinolin-4-yl]-N-(4-chloro-phenyl)-propionamide.

$^1$H-NMR (MeOD) δ: 1.09–1.15 (4H, m), 2.00 (3H, s), 2.39–2.45 (1H, m), 2.94 (6H, s), 4.04–4.20 (2H, m), 4.60–4.75 (1H, m), 5.40–5.50 (1H, br), 6.14 (1H, s), 6.53 (2H, d), 6.81 (1H, d), 7.09 (2H, d), 7.20–7.48 (5H, m).

MS m/z: 535 (M+1).

(±)-Cis-[4-[acetyl-(4-chloro-phenyl)-amino]-1-(4-dimethylamino-benzoyl)-2-methyl-1,2,3,4-tetrahydro-quinolin-7-yloxy]-acetic acid (B-91)

(±)-Cis-[4-[acetyl-(4-chloro-phenyl)-amino]-1-(4-dimethylamino-benzoyl)-2-methyl-1,2,3,4-tetrahydro-quinolin-7-yloxy]-acetic acid was prepared from (±)-cis-[4-[acetyl-(4-chloro-phenyl)-amino]-1-(4-dimethylamino-benzoyl)-2-methyl-1,2,3,4-tetrahydro-quinolin-7-yloxy]-acetic acid ethyl ester following the saponification procedure described above for the synthesis of (±)-cis-[4-[(4-chloro-phenyl)-propionyl-amino]-1-(4-fluoro-benzoyl)-2-methyl-1,2,3,4-tetrahydro-quinolin-6-yloxy]-acetic acid.

$^1$H-NMR (MeOD) δ: 1.08–1.10 (4H, m), 1.98 (3H, s), 2.39–2.45 (1H, m), 2.93 (6H, s), 4.20 (2H, s), 4.61–4.70 (1H, m), 5.40–5.50 (1H, br), 6.17 (1H, s), 6.53 (2H, d), 6.79 (1H, d), 7.08 (2H, d), 7.28–7.48 (5H, m).

MS m/z: 536 (M+1).

(±)-Cis-N-(4-chloro-phenyl)-N-[1-(4-dimethylamino-benzoyl)-7-(2-hydroxy-2-methyl-propoxy)-2-methyl-1,2,3,4-tetrahydro-quinolin-4-yl]-acetamide (B-92)

(±)-Cis-N-(4-chloro-phenyl)-N-[1-(4-dimethylamino-benzoyl)-7-(2-hydroxy-2-methyl-propoxy)-2-methyl-1,2,3,4-tetrahydro-quinolin-4-yl]-acetamide was prepared from (±)-cis-[4-[acetyl-(4-chloro-phenyl)-amino]-1-(4-dimethylamino-benzoyl)-2-methyl-1,2,3,4-tetrahydro-quinolin-7- yloxy]-acetic acid ethyl ester was using the same alkylation procedure described for the synthesis of (±)-cis-N-{1-[4-(2-hydroxy-2-methyl-propoxy)-benzoyl]-2-methyl-1,2,3,4-tetrahydro-quinolin-4-yl}-N-phenyl-propionamide.

$^1$H-NMR (CDCl$_3$) δ: 1.01–1.20 (4H, m), 1.30 (6H, s), 2.01 (3H, s), 2.20–2.40 (1H, m), 2.92 (6H, s), 3.70 (2H, s), 4.65–4.72 (1H, m), 5.45–5.55 (1H, br), 6.13 (1H, s), 6.45 (2H, d), 6.65 (1H, d), 7.12–7.46 (7H, m).

MS m/z: 551 (M+1).

(±)-Cis-N-(4-chloro-phenyl)-N-[1-(4-dimethylamino-benzoyl)-7-ethoxy-2-methyl-1,2,3,4-tetrahydro-quinolin-4-yl]-acetamide (B-93)

(±)-Cis-N-(4-chloro-phenyl)-N-[1-(4-dimethylamino-benzoyl)-7-ethoxy-2-methyl-1,2,3,4-tetrahydro-quinolin-4-yl]-acetamide was made from (±)-cis-N-(4-chloro-phenyl)-N-[1-(4-dimethylamino-benzoyl)-7-hydroxy-2-methyl-1,2,3,4-tetrahydro-quinolin-4-yl]-acetamide using the same alkylation procedure described for the synthesis of (±)-cis-4-(4-{4-[(4-chloro-phenyl)-propionyl-amino]-2-methyl-3,4-dihydro-2H-quinoline-1-carbonyl}-phenoxy)-butyric acid ethyl ester, substituting ethyl iodide for ethyl-4-bromobutyrate.

$^1$H-NMR (CDCl$_3$) δ: 1.01–1.20 (7H, m), 2.01 (3H, s), 2.20–2.40 (1H, m), 2.92 (6H, s), 3.60 (2H, q), 4.65–4.72 (1H, m), 5.45–5.55 (1H, br), 6.15 (1H, s), 6.44 (2H, d), 6.69 (1H, d), 7.11–7.46 (7H, m).

MS m/z: 506 (M+1).

(±)-Cis-4-[4-[acetyl-(4-chloro-phenyl)-amino]-1-(4-dimethylamino-benzoyl)-2-methyl-1,2,3,4-tetrahydro-quinolin-7-yloxy]-butyric acid ethyl ester (B-94)

(±)-Cis-4-[4-[acetyl-(4-chloro-phenyl)-amino]-1-(4-dimethylamino-benzoyl)-2-methyl-1,2,3,4-tetrahydro-quinolin-7-yloxy]-butyric acid ethyl ester was made from (±)-cis-N-(4-chloro-phenyl)-N-[1-(4-dimethylamino-benzoyl)-7-hydroxy-2-methyl-1,2,3,4-tetrahydro-quinolin-4-yl]-acetamide using the same alkylation procedure described for the synthesis of (±)-cis-4-(4-{4-[(4-chloro-phenyl)-propionyl-amino]-2-methyl-3,4-dihydro-2H-quinoline-1-carbonyl}-phenoxy)-butyric acid ethyl ester.

$^1$H-NMR (CDCl$_3$) δ: 1.09–1.11 (4H, m), 1.23 (3H, t), 1.81–1.85 (2H, m), 2.01 (3H, s), 2.30–2.33 (3H, m), 2.92 (6H, s), 3.50–3.54 (1H, m), 3.72–3.76 (1H, m), 4.09 (2H, q), 4.66–4.73 (1H, m), 5.57–5.63 (1H, m), 6.14 (1H, s), 6.46 (2H, d), 6.68 (1H, d), 7.11–7.39 (7H, m).

MS m/z: 593 (M+1).

(±)-Cis-4-[4-[acetyl-(4-chloro-phenyl)-amino]-1-(4-dimethylamino-benzoyl)-2-methyl-1,2,3,4-tetrahydro-quinolin-7-yloxy]-butyric acid (B-95)

(±)-Cis-4-[4-[acetyl-(4-chloro-phenyl)-amino]-1-(4-dimethylamino-benzoyl)-2-methyl-1,2,3,4-tetrahydro-quinolin-7-yloxy]-butyric acid was made from (±)-cis-4-[4-[acetyl-(4-chloro-phenyl)-amino]-1-(4-dimethylamino-benzoyl)-2-methyl-1,2,3,4-tetrahydro-quinolin-7-yloxy]-butyric acid ethyl ester following the saponification conditions described for the synthesis of (±)-cis-[4-[(4-chloro-phenyl)-propionyl-amino]-1-(4-fluoro-benzoyl)-2-methyl-1,2,3,4-tetrahydro-quinolin-6-yloxy]-acetic acid.

$^1$H-NMR (CDCl$_3$) δ: 1.08–1.11 (4H, m), 1.80–1.86 (2H, m), 1.99 (3H, s), 2.28–2.35 (3H, m), 2.89 (6H, s) 3.37–3.46 (1H, m), 3.66–3.73 (1H, m), 4.64–4.72 (1H, m), 5.54–5.63 (1H, m), 6.07 (1H, s), 6.52 (2H, d), 6.67 (1H, d), 7.08–7.36 (7H, m).

MS m/z: 564 (M+1).

(±)-Cis-N-(4-chloro-phenyl)-N-[1-(4-dimethylamino-benzoyl)-2,7-dimethyl-1,2,3,4-tetrahydro-quinolin-4-yl]-acetamide (B-96)

(±)-Cis-N-(4-chloro-phenyl)-N-[1-(4-dimethylamino-benzoyl)-2,7-dimethyl-1,2,3,4-tetrahydro-quinolin-4-yl]-acetamide was made following general procedure B, substituting 3-toluidine for aniline. Both the 5 and 7-position isomers were obtained in this procedure.

$^1$H-NMR (CDCl$_3$) δ: 1.11 (3H, d), 1.45–1.59 (4H, m), 2.02–2.07 (3H, m), 2.24–2.28 (1H, m), 2.92 (6H, s) 4.67–4.74 (1H, m), 5.52–5.59 (1H, m), 6.43–6.45 (3H, m), 6.95 (1H, d), 7.13–7.22 (6H, m), 7.35–7.43 (1H, m).

MS m/z: 307 (M).

(±)-Cis-N-(4-chloro-phenyl)-N-[1-(4-fluoro-benzoyl)-2-phenethyl-1,2,3,4-tetrahydro-quinolin-4-yl]-propionamide (B-97)

(±)-Cis-N-(4-chloro-phenyl)-N-[1-(4-fluoro-benzoyl)-2-phenethyl-1,2,3,4-tetrahydro-quinolin-4-yl]-propionamide was made following general procedure B, substituting 4-fluorobenzoyl chloride for 4-dimethylaminobenzoyl chloride, 3-phenyl-propionaldehyde for acetaldehyde and propionyl chloride for acetyl chloride.

$^1$H-NMR (CDCl$_3$) δ: 1.16 (dt, 3H), 1.25 (m, 1H), 1.54 (m, 1H), 1.97 (m, 1H), 2.30 (m, 3H), 2.56 (t, 2H), 4.85 (sextet, 1H), 5.66 (bs, 1H), 6.44 (d, 1H), 6.86 (t, 2H), 6.93 (m, 2H), 7.03 (d, 2H), 7.12–7.29 (m, 8H), 7.37 (d, 2H).

MS m/z: 542 (M+1).

(±)-Cis-N-(4-chloro-phenyl)-N-[2-(2-cyano-ethyl)-1-(4-fluoro-benzoyl)-1,2,3,4-tetrahydro-quinolin-4-yl]-propionamide (B-98)

(±)-Cis-N-(4-chloro-phenyl)-N-[2-(2-cyano-ethyl)-1-(4-fluoro-benzoyl)-1,2,3,4-tetrahydro-quinolin-4-yl]-propionamide was made following general procedure B, substituting 4-fluorobenzoyl chloride for 4-dimethylaminobenzoyl chloride, 4-oxobutyrylnitrile for acetaldehyde and propionyl chloride for acetyl chloride.

$^1$H-NMR (300 MHz, CDCl$_3$) δ: 1.19–1.23 (m, 4H), 1.65–1.79 (m, 2H), 2.07–2.57 (m, 5H), 4.90 (ddd, 1H), 5.61 (br s, 1H), 6.61 (d, 1H), 6.86 (m, 2H), 6.95 (dd, 1H), 7.14–7.43 (m, 8H).

MS m/z=490 (M+1).

(±)-Cis-N-[2-ethyl-1-(3-methoxy-benzoyl)-1,2,3,4-tetrahydro-quinolin-4-yl]-N-phenyl-acetamide (B-99)

(±)-Cis-N-[2-ethyl-1-(3-methoxy-benzoyl)-1,2,3,4-tetrahydro-quinolin-4-yl]-N-phenyl-acetamide was made following general procedure B, substituting 3-methoxybenzoyl chloride for 4-dimethylaminobenzoyl chloride, propionyl aldehyde for acetaldehyde and phenylboronic acid for 4-chlorophenylboronic acid.

$^1$H-NMR (CDCl$_3$) δ: 0.8 (3H, t), 1.3 (2H, m), 1.6 (1H, m), 2.0 (3H, s), 2.3 (1H, m), 3.7 (3H, s), 4.7 (1H, m), 5.7 (1H, m), 6.5 (1H, d), 6.7 (1H, s), 6.8 (2H, m), 6.9–7.4 (9H, m)

MS m/z: 429 (M+1).

(±)-Cis-N-[1-(3-methoxy-benzoyl)-2-phenyl-1,2,3,4-tetrahydro-quinolin-4-yl]-N-phenyl-acetamide (B-100)

(±)-Cis-N-[1-(3-methoxy-benzoyl)-2-phenyl-1,2,3,4-tetrahydro-quinolin-4-yl]-N-phenyl-acetamide was made following general procedure B, substituting 3-methoxybenzoyl chloride for 4-dimethylaminobenzoyl chloride, benzaldehyde for acetaldehyde and phenylboronic acid for 4-chlorophenylboronic acid.

$^1$H-NMR (CDCl$_3$) δ: 1.5 (1H, m), 2.0 (3H, s), 2.5 (1H, m), 3.6 (3H, s), 5.7 (1H, t) 5.8 (1H, m), 6.6 (1H, d), 6.9 (2H, m), 6.9–7.4 (15H, m).

MS m/z: 494 (M−18).

(±)-Cis-4-(acetyl-phenyl-amino)-1-(4-fluoro-benzoyl)-1,2,3,4-tetrahydro-quinoline-2-carboxylic acid ethyl ester (B-101)

(±)-Cis-4-(acetyl-phenyl-amino)-1-(4-fluoro-benzoyl)-1,2,3,4-tetrahydro-quinoline-2-carboxylic acid ethyl ester was made following general procedure B, substituting 4-fluorobenzoyl chloride for 4-dimethylaminobenzoyl chloride, ethyl glyoxylate for acetaldehyde and phenylboronic acid for 4-chlorophenylboronic acid.

$^1$H-NMR (CDCl$_3$) δ: 1.2 (3H, t), 1.2 (1H, m), 2.0 (3H, s), 2.5 (1H, m), 4.1 (2H, q), 5.0 (1H, t), 5:7 (1H, m), 6.6 (1H, d), 6.8–7.0 (4H, d), 7.1–7.4 (8H, m).

MS m/z: 461 (M+1).

(±)-Cis-4-(acetyl-phenyl-amino)-1-(4-fluoro-benzoyl)-1,2,3,4-tetrahydro-quinoline-2-carboxylic acid (B-102)

(±)-Cis-4-(acetyl-phenyl-amino)-1-(4-fluoro-benzoyl)-1,2,3,4-tetrahydro-quinoline-152-carboxylic acid was made from (±)-cis-4-(acetyl-phenyl-amino)-1-(3-methoxy-benzoyl)-1,2,3,4-tetrahydro-quinoline-2-carboxylic acid ethyl ester by basic hydrolysis with 1N sodium hydroxide, ethanol and water.

$^1$H-NMR (CDCl$_3$) δ: 1.2 (1H, m), 2.0 (3H, s), 2.6 (1H, m), 5.0 (1H, t), 5.6 (1H, m), 6.6 (1H, d), 6.9–7.0 (3H, m), 7.2 (2H, m), 7.3–7.5 (7H, m).

MS m/z: 433 (M+1).

(±)-Cis-N-(4-chloro-phenyl)-N-[1-(4-fluoro-benzoyl)-2-propyl-1,2,3,4-tetrahydro-quinolin-4-yl]-propionamide (B-103)

(±)-Cis-N-(4-chloro-phenyl)-N-[1-(4-fluoro-benzoyl)-2-propyl-1,2,3,4-tetrahydro-quinolin-4-yl]-propionamide was made following general procedure B, substituting 4-fluorobenzoyl chloride for 4-dimethylaminobenzoyl chloride, butyryl aldehyde for acetaldehyde and propionyl chloride for acetyl chloride.

$^1$H-NMR (CDCl$_3$) δ: 0.8 (3H, t), 1.1–1.2 (7H, m), 1.4 (1H, m), 2.1–2.3 (3H, m), 4.8 (1H, m), 5.6 (1H, m), 6.7 (1H, d), 6.9–7.1 (4H, m), 7.2–7.5 (7H, m).

MS m/z: 479 (M+1).

(±)-Cis-propionic acid 4-[(4-chloro-phenyl)-propionyl-amino]-1-(4-fluoro-benzoyl)-1,2,3,4-tetrahydro-quinolin-2-ylmethyl ester (B-104)

(±)-Cis-propionic acid 4-[(4-chloro-phenyl)-propionyl-amino]-1-(4-fluoro-benzoyl)-1,2,3,4-tetrahydro-quinolin-2-ylmethyl ester was prepared following general procedure B, substituting propionic acid 2-oxo-ethyl ester for acetaldehyde, 4-fluorobenzoyl chloride for 4-dimethylaminobenzoyl chloride and propionyl chloride for acetyl chloride.

$^1$H-NMR (CDCl$_3$) δ: 0.8 (3H, t), 1.1 (3H, t), 1.1 (1H, m), 2.1 (2H, m), 2.2 (3H, s), 3.8 (1H, m), 4.2 (1H, m), 5.0 (1H, m), 5.4 (1H, m), 6.4 (1H, d), 6.8 (3H, m), 7.1–7.4 (8H, m).

MS m/z: 523 (M+1).

(±)-Cis-N-(4-chloro-phenyl)-N-[1-(4-fluoro-benzoyl)-2-hydroxymethyl-1,2,3,4-tetrahydro-quinolin-4-yl]-propionamide (B-105)

(±)-Cis-N-(4-chloro-phenyl)-N-[1-(4-fluoro-benzoyl)-2-hydroxymethyl-1,2,3,4-tetrahydro-quinolin-4-yl]-propionamide was prepared from (±)-cis-propionic acid 4-[(4-chloro-phenyl)-propionyl-amino]-1-(4-fluoro-benzoyl)-1,2,3,4-tetrahydro-quinolin-2-ylmethyl ester using the saponification conditions utilized in the synthesis of (±)-cis-[4-[(4-chloro-phenyl)-propionyl-amino]-1-(4-fluoro-benzoyl)-2-methyl-1,2,3,4-tetrahydro-quinolin-6-yloxy]-acetic acid.

$^1$H-NMR (CDCl$_3$) δ: 1.1 (3H, t), 1.3 (1H, m), 1.8 (1H, m), 2.1 (2H, m), 3.4 (1H, t), 3.6 (2H, m), 4.2 (1H, m), 6.2 (1H, m), 6.4 (1H, d), 6.7 (2H, t), 6.8–7.0 (5H, m), 7.1–7.3 (4H, m).

MS m/z: 367 (M−99).

(±)-Cis-N-(4-chloro-phenyl)-N-[2-diethylaminomethyl-1-(4-fluoro-benzoyl)-1,2,3,4-tetrahydro-quinolin-4-yl]-propionamide (B-106)

(±)-Cis-N-(4-chloro-phenyl)-N-[2-diethylaminomethyl-1-(4-fluoro-benzoyl)-1,2,3,4-tetrahydro-quinolin-4-yl]-propionamide was made following general procedure B, substituting diethylamino-acetaldehyde for acetaldehyde, 4-fluorobenzoyl chloride for 4-dimethylaminobenzoyl chloride, and propionyl chloride for acetyl chloride.

$^1$H-NMR (CDCl$_3$) δ: 0.8 (6H, m), 1.1 (3H, t), 1.1 (1H, m), 1.8 (2H, m), 2.2–2.5 (6H, m), 2.6 (1H, m), 4.8 (1H, m), 5.7 (1H, m), 6.4 (1H, d), 6.9 (3H, m), 7.1–7.4 (8H, m).

MS m/z: 523 (M+2).

(±)-Cis-N-(4-chloro-phenyl)-N-[1-(4-fluoro-benzoyl)-2-methoxymethyl-1,2,3,4-tetrahydro-quinolin-4-yl]-propionamide (B-107)

(±)-Cis-N-(4-chloro-phenyl)-N-[1-(4-fluoro-benzoyl)-2-methoxymethyl-1,2,3,4-tetrahydro-quinolin-4-yl]-propionamide was prepared following general procedure B, substituting methoxyacetaldehyde for acetaldehyde, 4-fluorobenzoyl chloride for 4-dimethylamino-benzoyl chloride, and propionyl chloride for acetyl chloride.

$^1$H-NMR (CDCl$_3$) δ: 1.1 (3H, t), 1.3 (1H, m), 1.8 (1H, m), 2.1 (1H, m), 3.4 (4H, m), 3.6 (2H, m), 4.2 (1H, m), 6.3 (1H, m), 6.5 (1H, d), 6.7 (1H, m), 6.8–7.0 (4H, m), 7.1–7.4 (6H, m).

MS m/z: 381 (M−99).

(±)-Cis-N-(4-chloro-phenyl)-N-[1-(4-fluoro-benzoyl)-2-phenyl-1,2,3,4-tetrahydro-quinolin-4-yl]-propionamide (B-108)

(±)-Cis-N-(4-chloro-phenyl)-N-[1-(4-fluoro-benzoyl)-2-phenyl-1,2,3,4-tetrahydro-quinolin-4-yl]-propionamide was made following general procedure B, substituting benzaldehyde for acetaldehyde, 4-fluorobenzoyl chloride for 4-dimethylaminobenzoyl chloride, and propionyl chloride for acetyl chloride.

$^1$H-NMR (CDCl$_3$) δ: 1.1–1.2 (3H, m), 1.2–1.4 (1H, m), 2.2–2.4 (2H, m), 2.4–2.6 (1H, m), 5.6 (1H, t), 5.8 (1H, m), 6.6 (1H, d), 6.8 (2H, m), 7.0 (1H, m), 7.2–7.4 (13H, m).

MS m/z: 513 (M+1).

(±)-Cis-N-(4-chloro-phenyl)-N-[1-(4-fluoro-benzoyl)-6-methoxy-2-trifluoromethyl-1,2,3,4-tetrahydro-quinolin-4-yl]-propionamide (B-109)

(±)-Cis-N-(4-chloro-phenyl)-N-[1-(4-fluoro-benzoyl)-6-methoxy-2-trifluoromethyl-1,2,3,4-tetrahydro-quinolin-4-yl]-propionamide was prepared following general procedure B, substituting N-(4-chloro-phenyl)-N-vinyl-propionamide for N-vinyl carbamic acid benzyl ester and trifluoroacetaldehyde for acetaldehyde in the synthesis of 11 and 4-fluorobenzoyl chloride for 4-dimethylaminobenzoyl chloride and propionyl chloride for acetyl chloride.

$^1$H-NMR (CDCl$_3$) δ: 1.1–1.2 (3H, m), 1.6 (1H, br), 2.2–2.4 (3H, m), 3.8 (3H, s), 5.5 (1H, m), 5.6 (1H, m), 6.5 (1H, s), 6.8 (1H, s), 6.9 (2H, t), 7.1–7.3 (4H, m), 7.4 (2H, d).

MS m/z: 535 (M+1).

(±)-Cis-N-(4-chloro-phenyl)-N-[6-methoxy-1-(3-methoxy-benzoyl)-2-trifluoromethyl-1,2,3,4-tetrahydro-quinolin-4-yl]-propionamide (B-110)

(±)-Cis-N-(4-chloro-phenyl)-N-[6-methoxy-1-(3-methoxy-benzoyl)-2-trifluoromethyl-1,2,3,4-tetrahydro-quinolin-4-yl]-propionamide was made following the procedure for the synthesis of (±)-N-(4-chloro-phenyl)-N-[1-(4-fluoro-benzoyl)-6-methoxy-2-trifluoromethyl-1,2,3,4-tetrahydro-quinolin-4-yl]-propionamide, substituting 3-methoxybenzoyl chloride for 4-fluorobenzoyl chloride.

$^1$H-NMR (CDCl$_3$) δ: 1.1–1.2 (3H, m), 1.6 (1H, br), 2.2–2.4 (3H, m), 3.7 (3H, s), 3.8 (3H, s), 5.5 (1H, m), 5.6 (1H, m), 6.5 (2H, m), 6.6 (1H, m), 6.8 (3H, m), 7.1 (1H, t), 7.2 (2H, d), 7.4 (2H, d).

MS m/z: 547 (M+1).

(±)-Cis-N-(4-chloro-phenyl)-N-[1-(furan-2-carbonyl)-6-methoxy-2-trifluoromethyl-1,2,3,4-tetrahydro-quinolin-4-yl]-propionamide (B-111)

(±)-Cis-N-(4-chloro-phenyl)-N-[1-(furan-2-carbonyl)-6-methoxy-2-trifluoromethyl-1,2,3,4-tetrahydro-quinolin-4-yl]-propionamide propionamide was made following the procedure for the synthesis of (±)-cis-N-(4-chloro-phenyl)-N-[1-(4-fluoro-benzoyl)-6-methoxy-2-trifluoromethyl-1,2,3,4-tetrahydro-quinolin-4-yl]-propionamide, substituting 2-furoyl chloride chloride for 4-fluorobenzoyl chloride.

$^1$H-NMR (CDCl$_3$) δ: 1.1–1.2 (3H, m), 1.6 (1H, br), 2.2–2.4 (3H, m), 3.8 (3H, s), 5.4 (2H, m), 6.0 (1H, m), 6.3 (1H, m), 6.8 (1H, m), 6.9 (1H, s), 7.0 (1H, m), 7.2 (2H, m), 7.4 (3H, m).

MS m/z: 507 (M+1).

(±)-Cis-N-[2-benzyl-1-(4-fluoro-benzoyl)-1,2,3,4-tetrahydro-quinolin-4-yl]-N-(4-chloro-phenyl)-propionamide (B-112)

(±)-Cis-N-[2-benzyl-1-(4-fluoro-benzoyl)-1,2,3,4-tetrahydro-quinolin-4-yl]-N-(4-chloro-phenyl)-propionamide was made following general procedure B, substituting phenylacetaldehyde for acetaldehyde, 4-fluorobenzoyl chloride for 4-dimethylamionbenzoyl chloride, and propionyl chloride for acetyl chloride.

$^1$H-NMR (CDCl$_3$) δ: 1.14 (3H, t), 2.05–2.52 (5H, m), 3.18–3.24 (1H, m), 4.89–4.93 (1H, m) 5.45–5.55 (1H, br), 6.46 (1H, d), 6.83–7.37 (16H, m).

MS m/z: 528 (M+1).

(±)-Cis-N-(4-chloro-phenyl)-N-[2-methyl-1-(3-methyl-isoxazole-5-carbonyl)-1,2,3,4-tetrahydro-quinolin-4-yl]-acetamide (B-113)

(±)-Cis-N-(4-chloro-phenyl)-N-[2-methyl-1-(3-methyl-isoxazole-5-carbonyl)-1,2,3,4-tetrahydro-quinolin-4-yl]-acetamide was made following general procedure B, substituting 3-methylisoxazole-5-carbonyl chloride for 4-dimethylamionbenzoyl chloride.

(±)-Cis-N-(4-chloro-phenyl)-N-[2-methyl-1-(3-methyl-isoxazole-5-carbonyl)-1,2,3,4-tetrahydro-quinolin-4-yl]-acetamide was separated by chiral HPLC using a chiral cel OD column and eluting with 90% hexane/10% ethanol isocratic system to give (2R,4S)- and (2S,4R)-cis-N-(4-chloro-phenyl)-N-[2-methyl-1-(3-methyl-isoxazole-5-carbonyl)-1,2,3,4-tetrahydro-quinolin-4-yl]-acetamide (B-42 & B-36, respectively)

$^1$H-NMR (CDCl$_3$) δ: 1.1 (3H, d), 1.1 (1H, m), 2.0 (3H, s), 2.2 (3H, s), 2.3 (1H, m), 4.7 (1H, m), 5.4 (1H, m), 5.8 (1H, s), 6.8 (1H, d), 7.1–7.4 (7H, m).

MS m/z: 424 (M+1).

Compounds B-114–B-147 can be prepared by the schemes set forth in Scheme 13 and 14 and by the general procedures B and others described herein. Those skilled in the art will be able to recognize, or be able to ascertain, using no more than routine experimentation, many equivalents to the specific embodiments of the invention described herein.

TABLE 2

Compounds Derived from General Procedure B

| No. | Structure |
|---|---|
| B-1 | (structure shown) |

TABLE 2-continued
Compounds Derived from General Procedure B
| No. | Structure |
|---|---|
| B-2 | 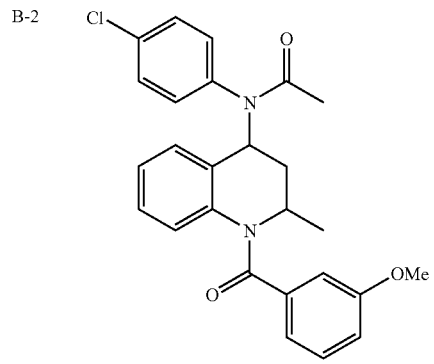 |
| B-3 | 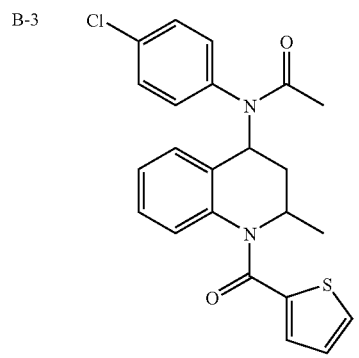 |
| B-4 | 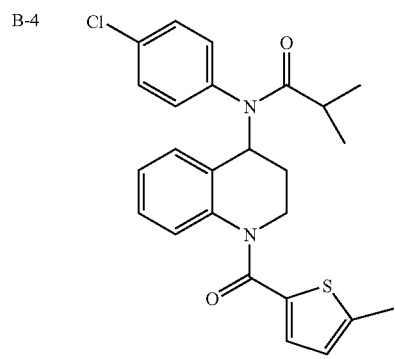 |
| B-5 | 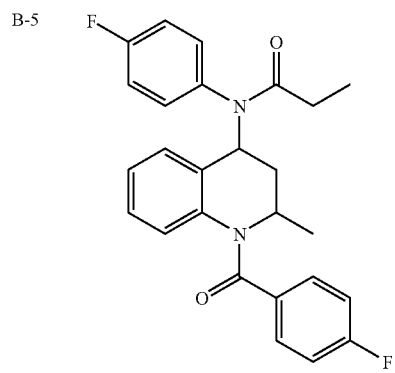 |

TABLE 2-continued
Compounds Derived from General Procedure B
| No. | Structure |
|---|---|
| B-6 | 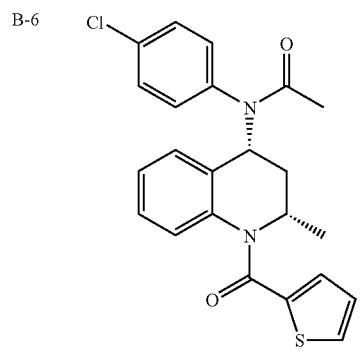 |
| B-7 | 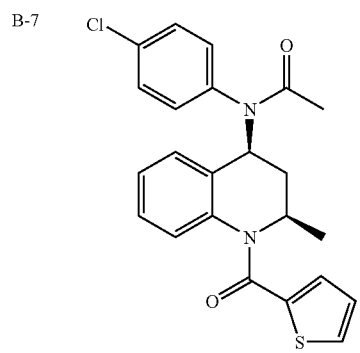 |
| B-8 | 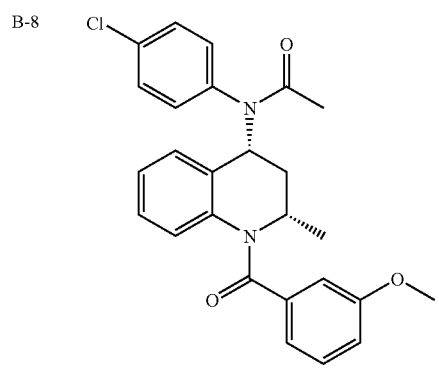 |
| B-9 | 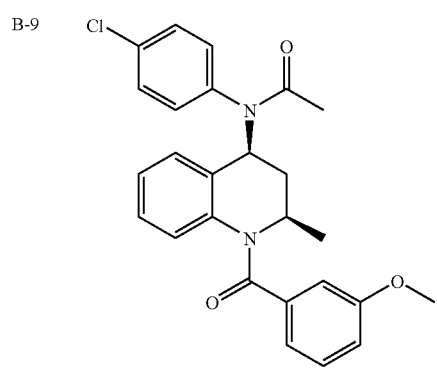 |

TABLE 2-continued

Compounds Derived from General Procedure B

| No. | Structure |
|---|---|
| B-10 | 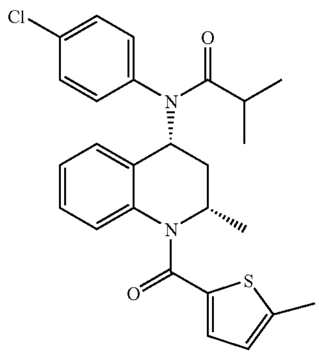 |
| B-11 | 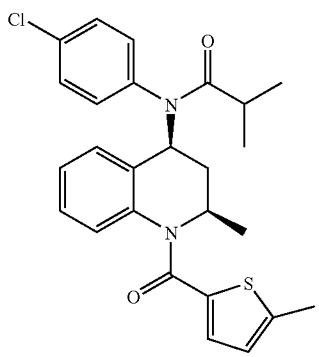 |
| B-12 | 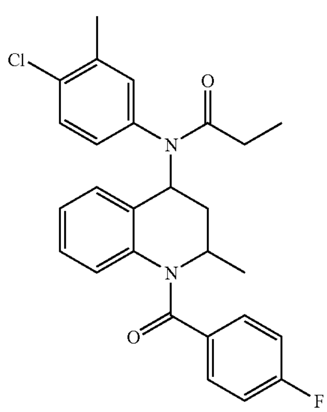 |
| B-13 | 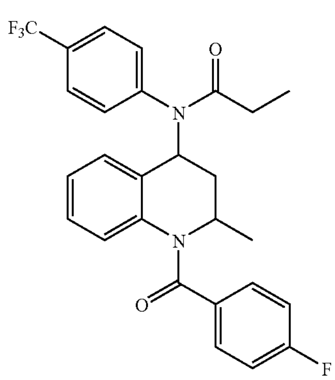 |

TABLE 2-continued
Compounds Derived from General Procedure B
| No. | Structure |
|---|---|
| B-14 | 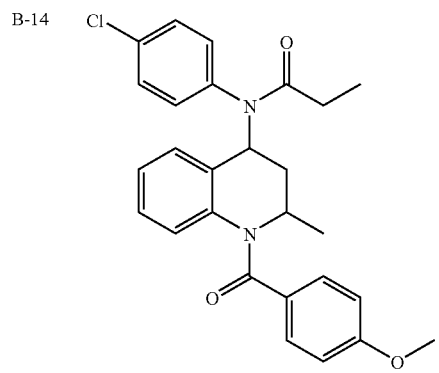 |
| B-15 | 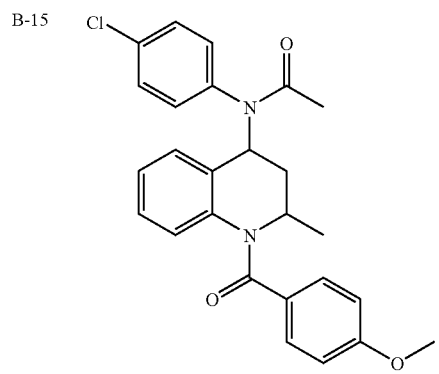 |
| B-16 | 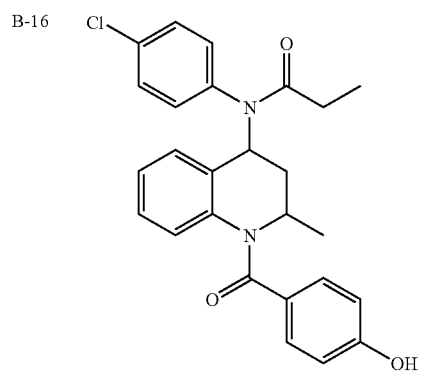 |
| B-17 | 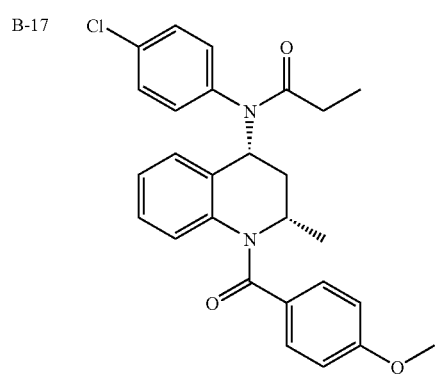 |

TABLE 2-continued
Compounds Derived from General Procedure B
| No. | Structure |
|---|---|
| B-18 | 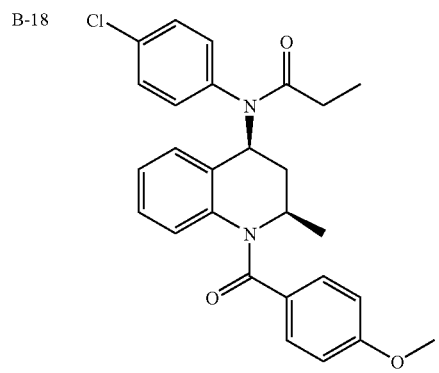 |
| B-19 | 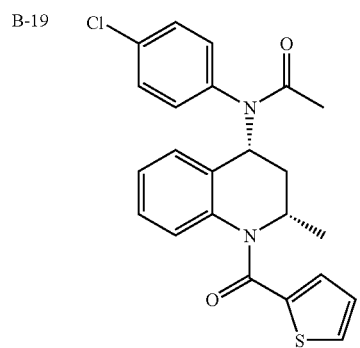 |
| B-20 | 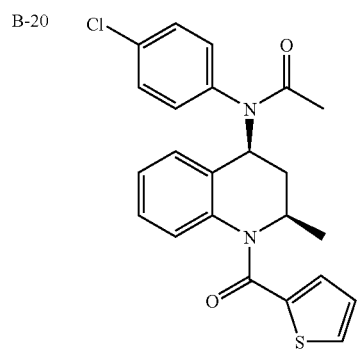 |
| B-21 | 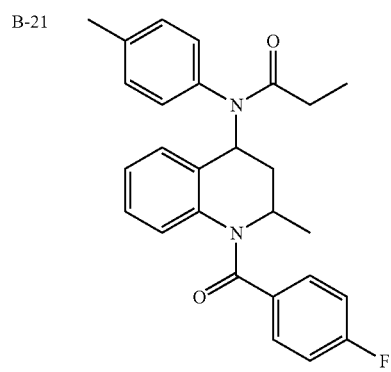 |

TABLE 2-continued

Compounds Derived from General Procedure B

| No. | Structure |
|---|---|
| B-22 | 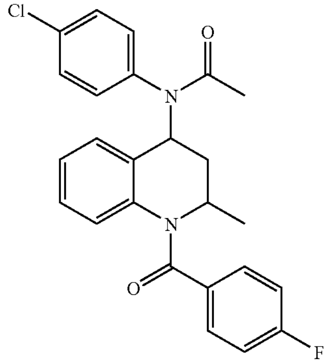 |
| B-23 | 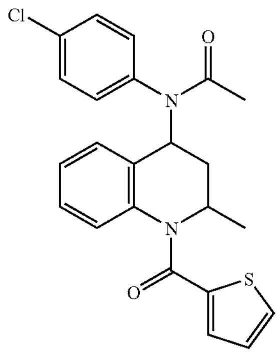 |
| B-24 | 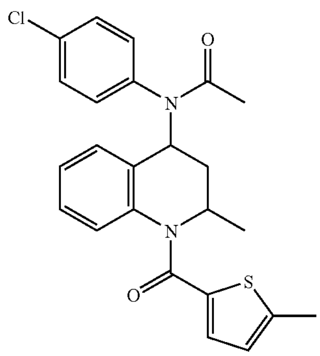 |
| B-25 | 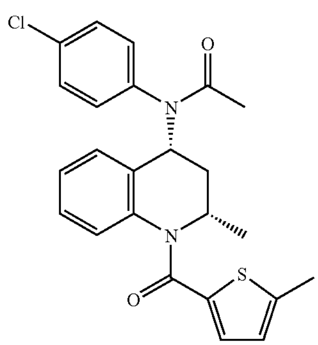 |

TABLE 2-continued
Compounds Derived from General Procedure B
| No. | Structure |
|---|---|
| B-26 | 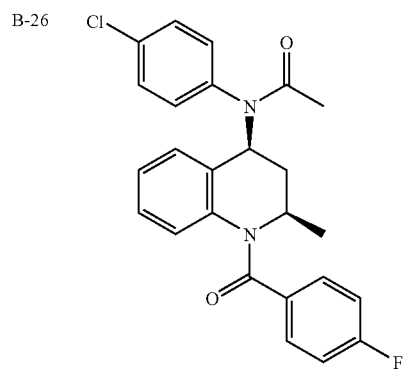 |
| B-27 | 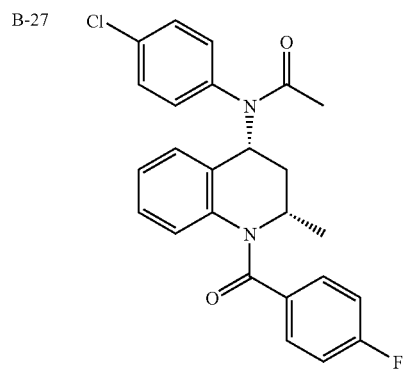 |
| B-28 | 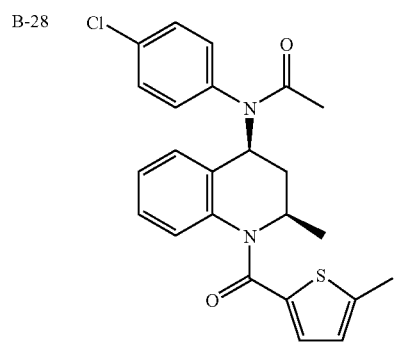 |
| B-29 | 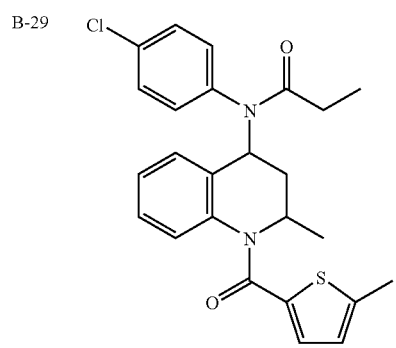 |

TABLE 2-continued
Compounds Derived from General Procedure B
| No. | Structure |
|---|---|
| B-30 | 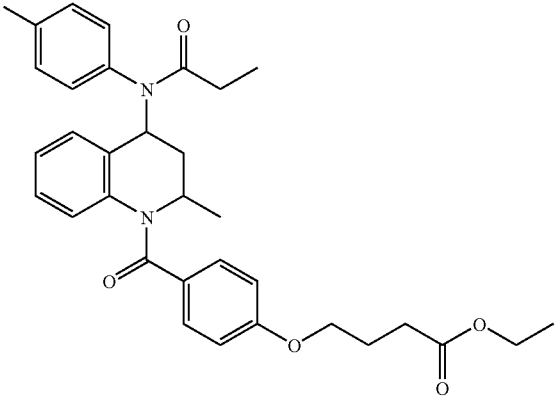 |
| B-31 | 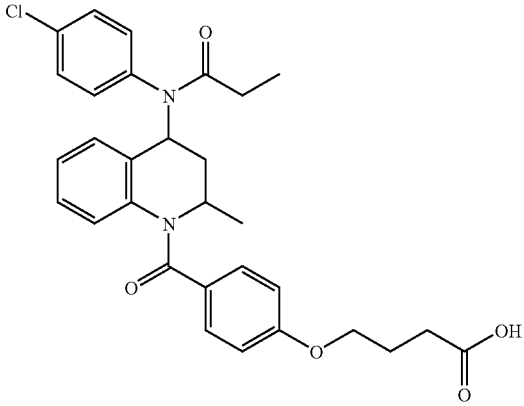 |
| B-32 | 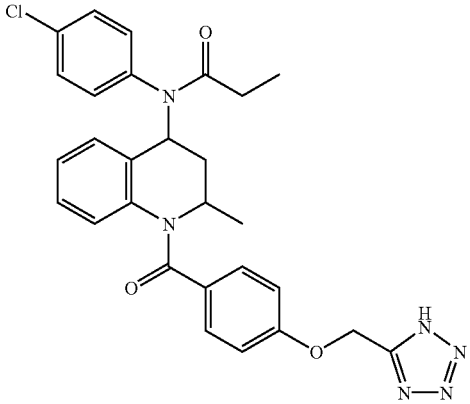 |

TABLE 2-continued
Compounds Derived from General Procedure B
| No. | Structure |
|-----|-----------|
| B-33 | 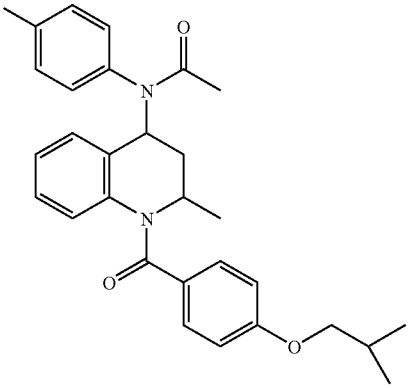 |
| B-34 | 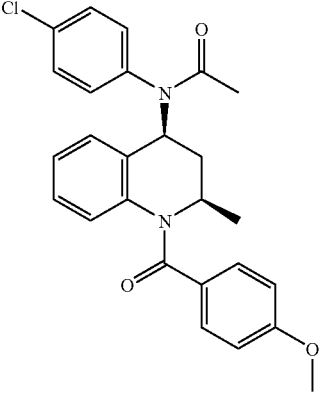 |
| B-35 | 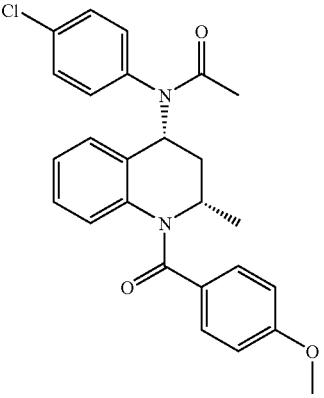 |

TABLE 2-continued
Compounds Derived from General Procedure B
| No. | Structure |
|---|---|
| B-36 | 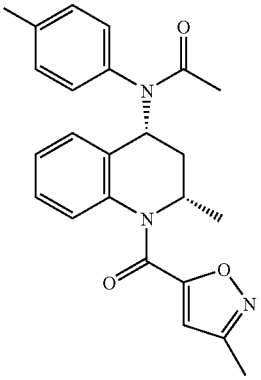 |
| B-37 | 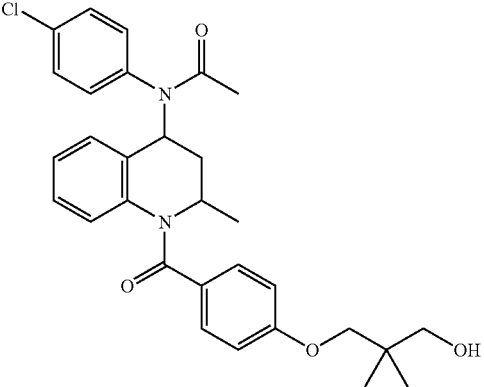 |
| B-38 | 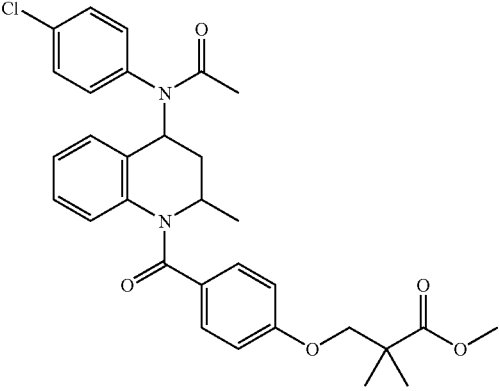 |

TABLE 2-continued
Compounds Derived from General Procedure B
| No. | Structure |
| --- | --- |
| B-39 | 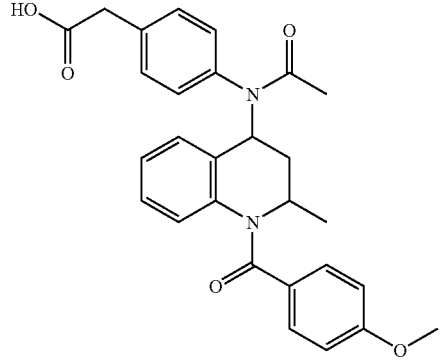 |
| B-40 | 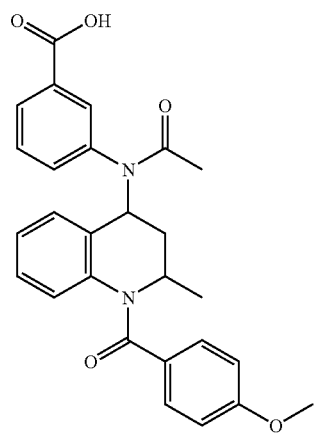 |
| B-41 | 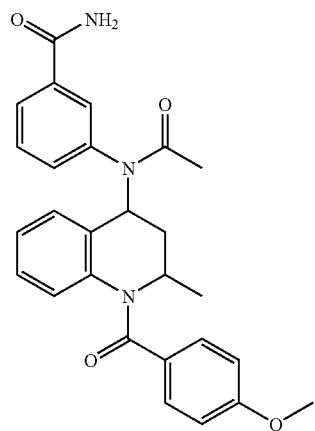 |

TABLE 2-continued
Compounds Derived from General Procedure B
| No. | Structure |
|---|---|
| B-42 | 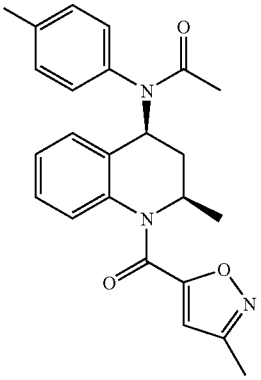 |
| B-43 | 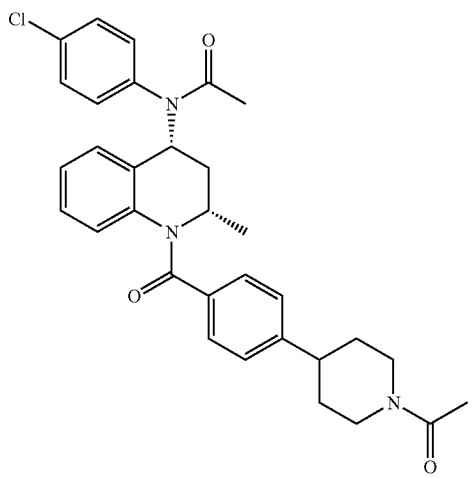 |
| B-44 | 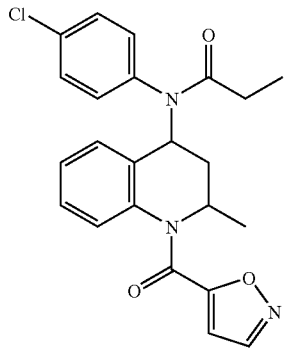 |

TABLE 2-continued
Compounds Derived from General Procedure B
| No. | Structure |
|---|---|
| B-45 | 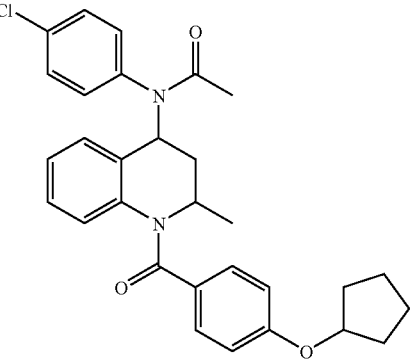 |
| B-46 | 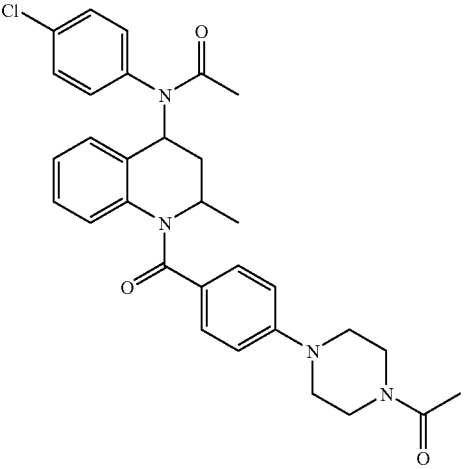 |
| B-47 | 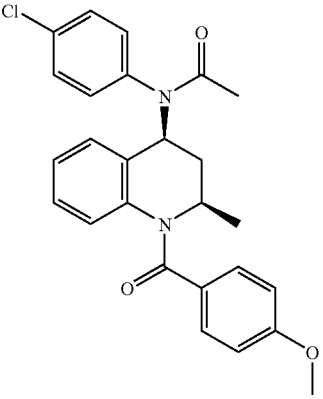 |

TABLE 2-continued
Compounds Derived from General Procedure B
| No. | Structure |
|---|---|
| B-48 | 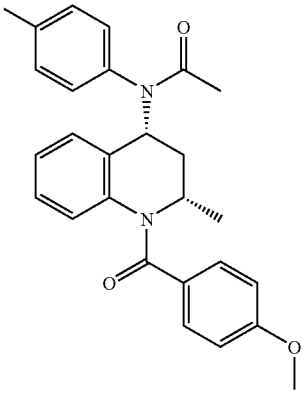 |
| B-49 | 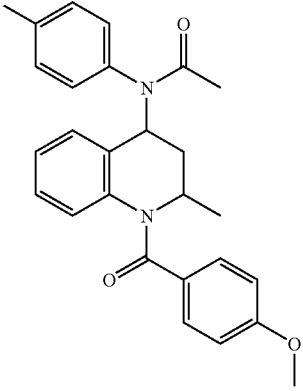 |
| B-50 | 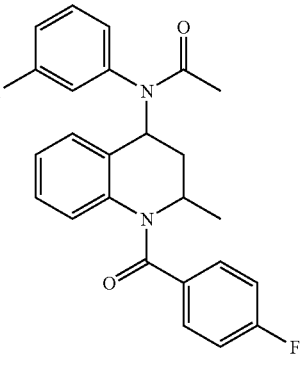 |
| B-51 | 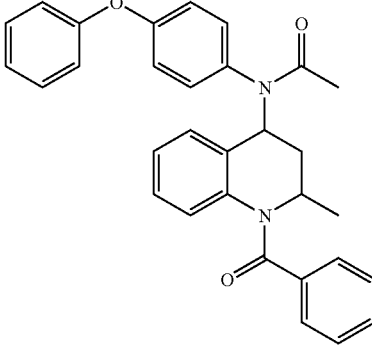 |

TABLE 2-continued
Compounds Derived from General Procedure B
| No. | Structure |
|---|---|
| B-52 | 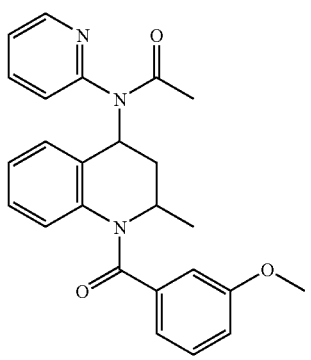 |
| B-53 | 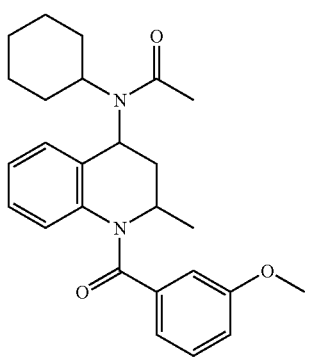 |
| B-54 | 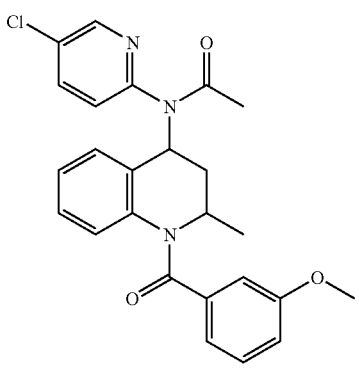 |
| B-55 | 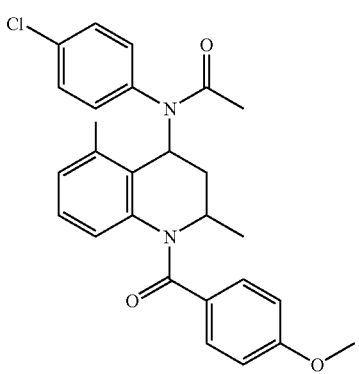 |

TABLE 2-continued
Compounds Derived from General Procedure B
| No. | Structure |
|---|---|
| B-56 | 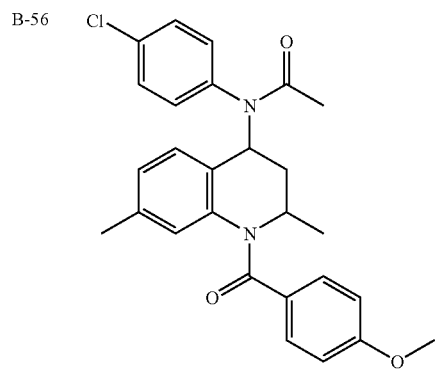 |
| B-57 | 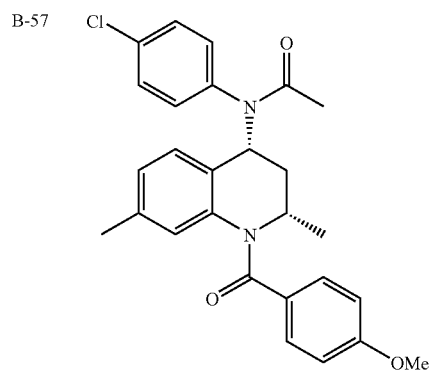 |
| B-58 | 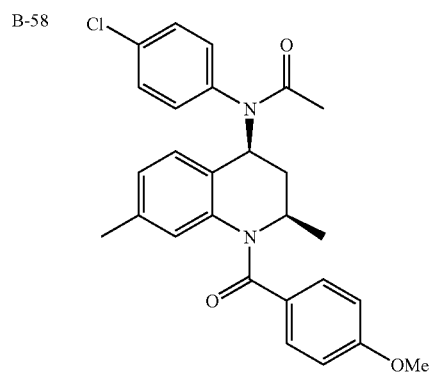 |
| B-59 | 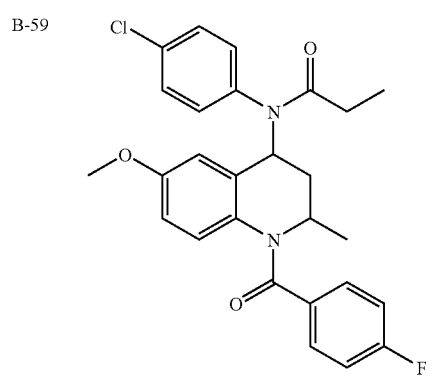 |

TABLE 2-continued

Compounds Derived from General Procedure B

| No. | Structure |
|---|---|
| B-60 | 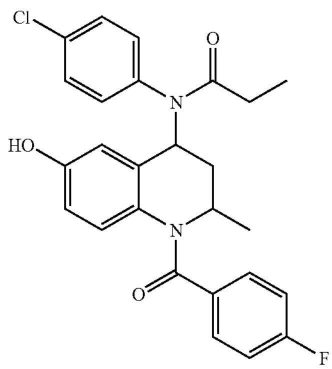 |
| B-61 | 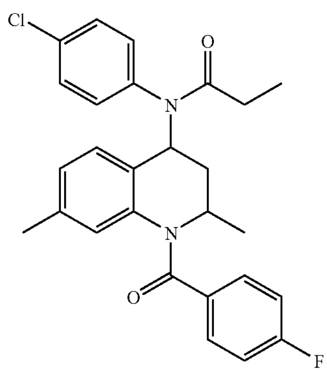 |
| B-62 | 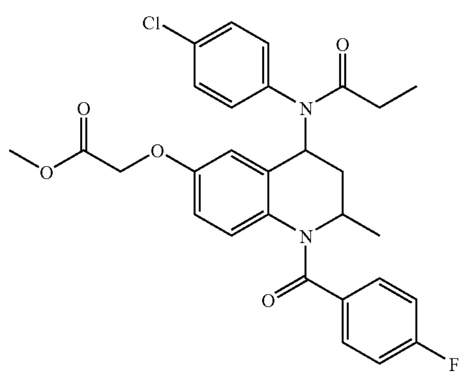 |
| B-63 | 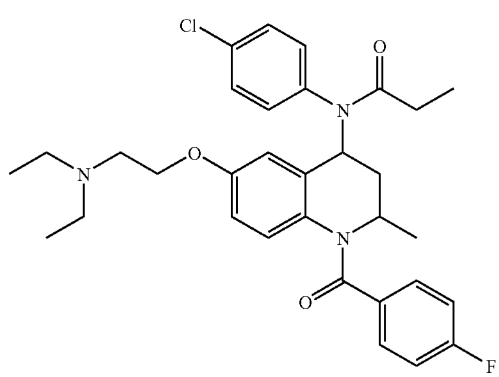 |

TABLE 2-continued
Compounds Derived from General Procedure B
| No. | Structure |
| --- | --- |
| B-64 | 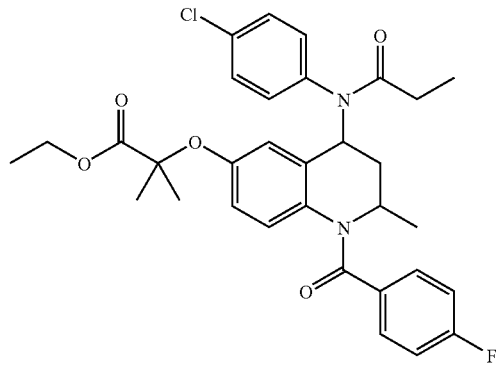 |
| B-65 | 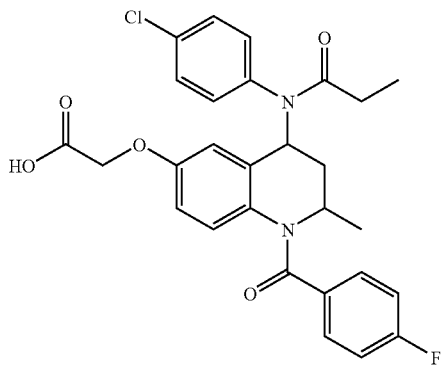 |
| B-66 | 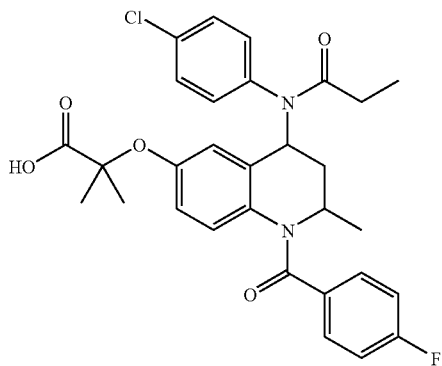 |
| B-67 | 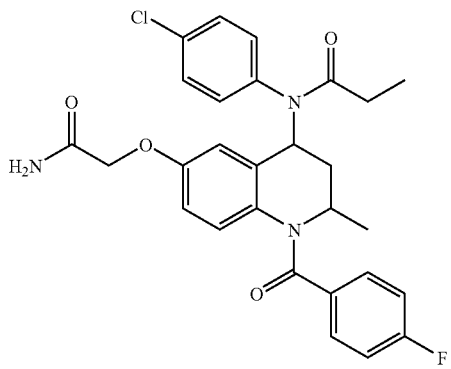 |

TABLE 2-continued

Compounds Derived from General Procedure B

| No. | Structure |
| --- | --- |
| B-68 | 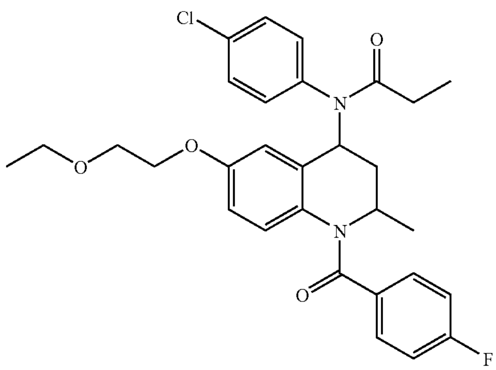 |
| B-69 | 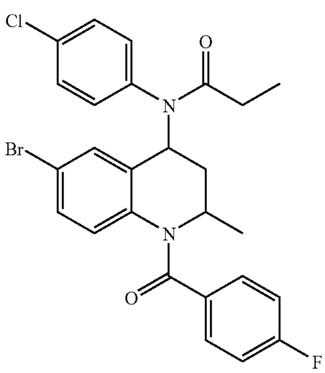 |
| B-70 | 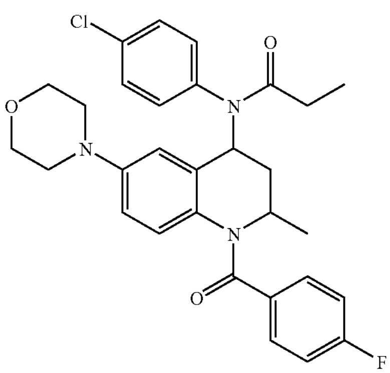 |
| B-71 | 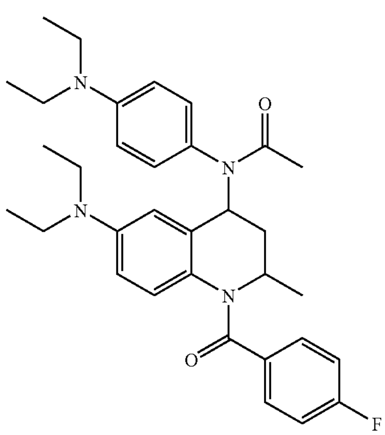 |

TABLE 2-continued

Compounds Derived from General Procedure B

| No. | Structure |
|---|---|
| B-72 | 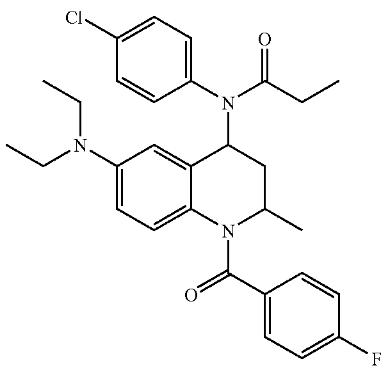 |
| B-73 | 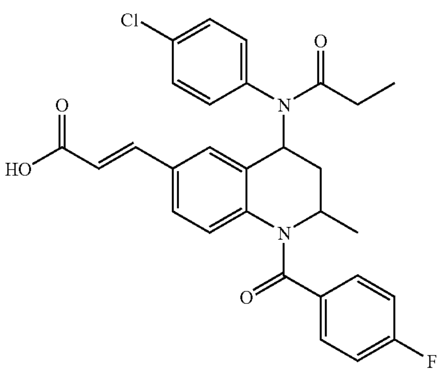 |
| B-74 | 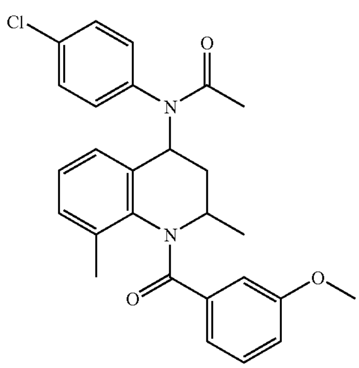 |
| B-75 | 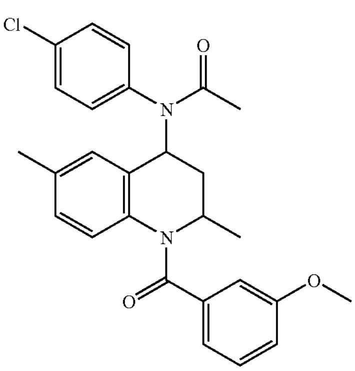 |

TABLE 2-continued
Compounds Derived from General Procedure B
| No. | Structure |
|---|---|
| B-76 | 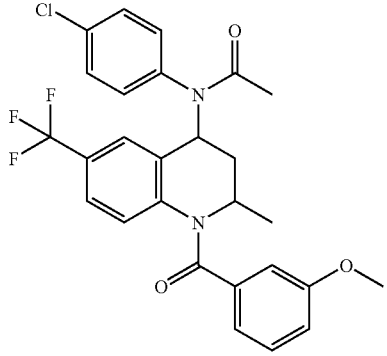 |
| B-77 | 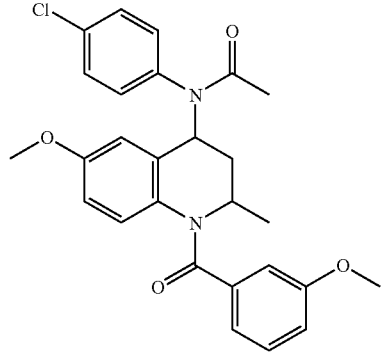 |
| B-78 | 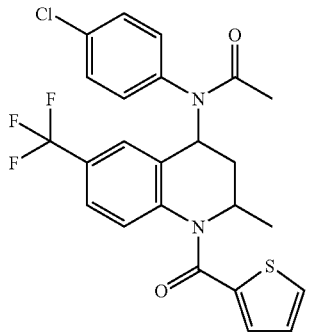 |
| B-79 | 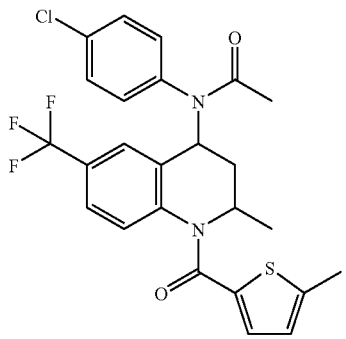 |

TABLE 2-continued
Compounds Derived from General Procedure B
| No. | Structure |
|---|---|
| B-80 | 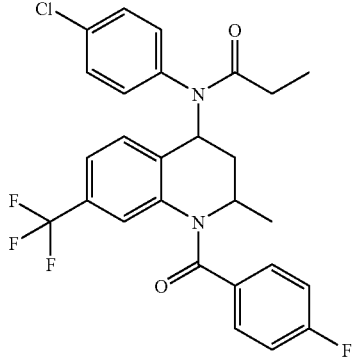 |
| B-81 | 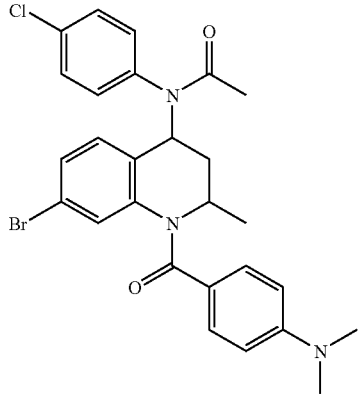 |
| B-82 | 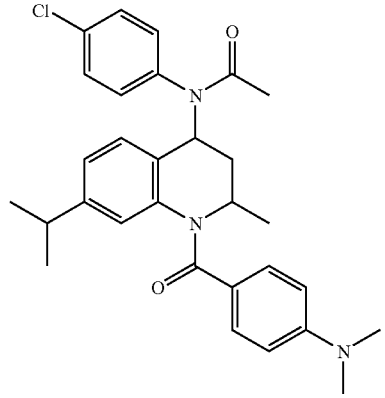 |

TABLE 2-continued
Compounds Derived from General Procedure B
| No. | Structure |
|---|---|
| B-83 | 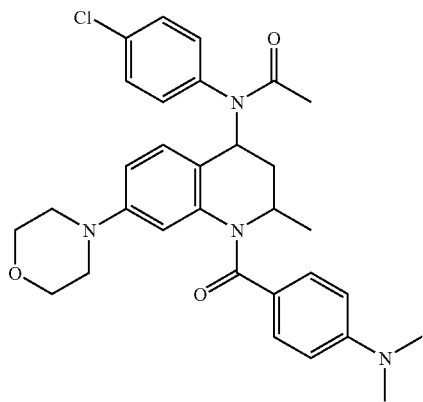 |
| B-84 | 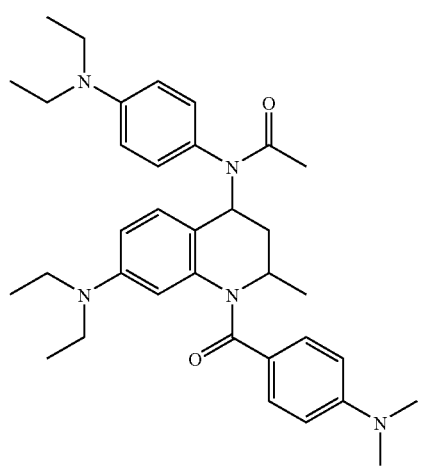 |
| B-85 | 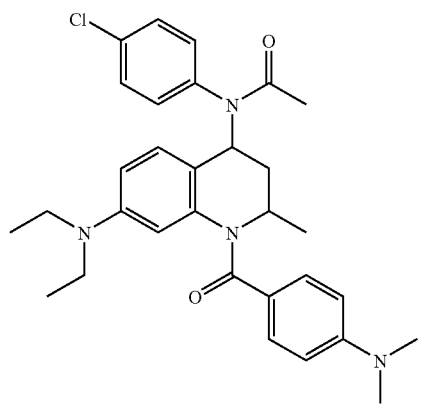 |

TABLE 2-continued
Compounds Derived from General Procedure B
| No. | Structure |
|---|---|
| B-86 | 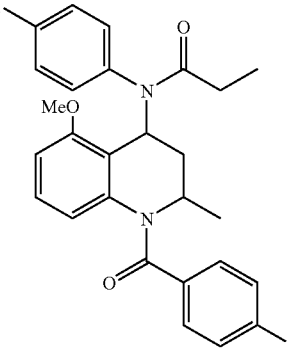 |
| B-87 | 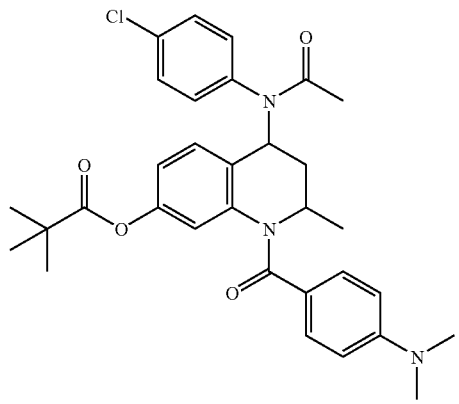 |
| B-88 | 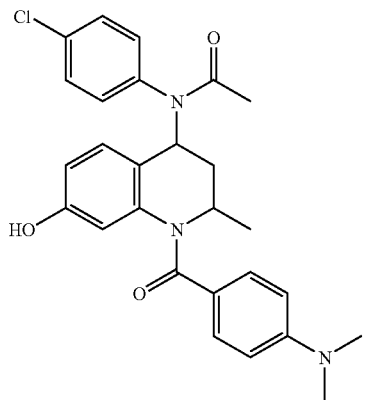 |

TABLE 2-continued
Compounds Derived from General Procedure B
| No. | Structure |
|---|---|
| B-89 | 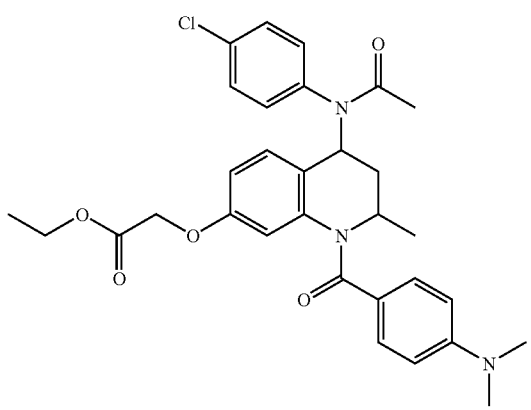 |
| B-90 | 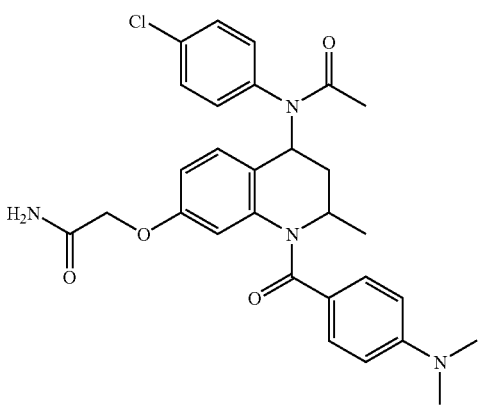 |
| B-91 | 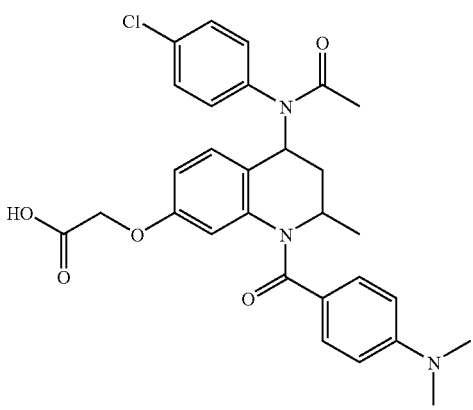 |

TABLE 2-continued
Compounds Derived from General Procedure B
| No. | Structure |
|---|---|
| B-92 | 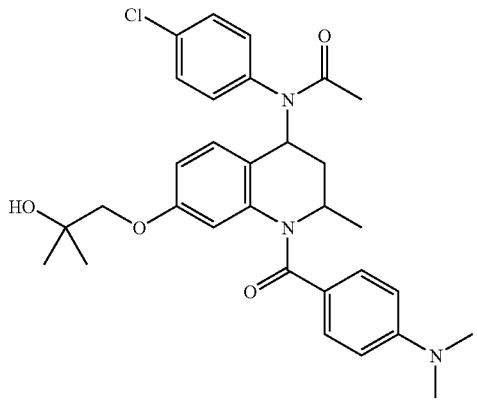 |
| B-93 | 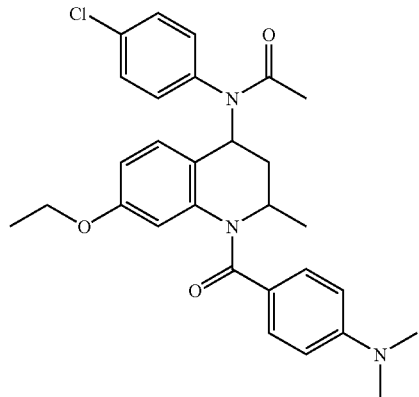 |
| B-94 | 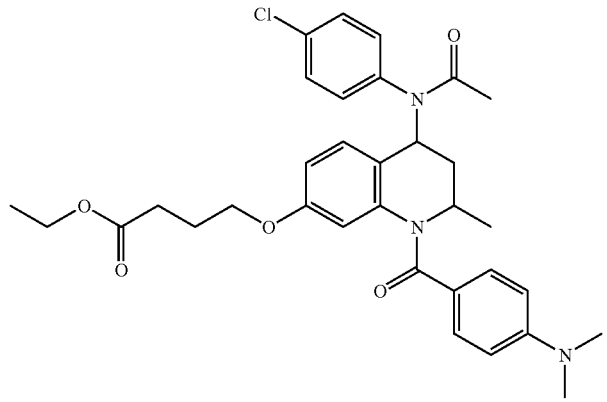 |

TABLE 2-continued

Compounds Derived from General Procedure B

| No. | Structure |
|-----|-----------|
| B-95 | 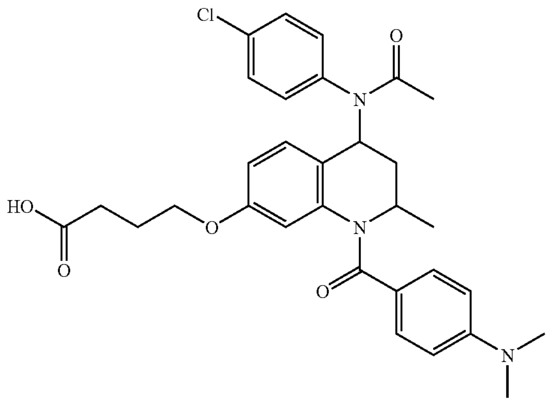 |
| B-96 | 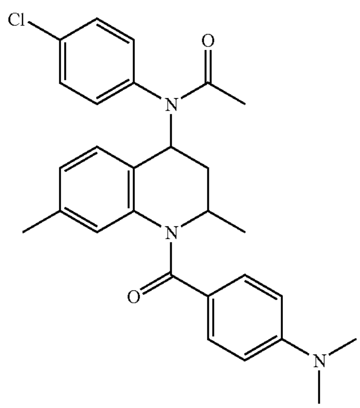 |
| B-97 | 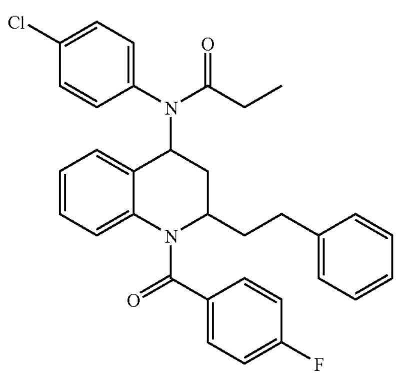 |
| B-98 | 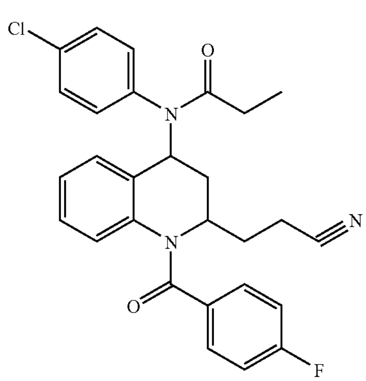 |

TABLE 2-continued
Compounds Derived from General Procedure B
| No. | Structure |
|-----|-----------|
| B-99 | 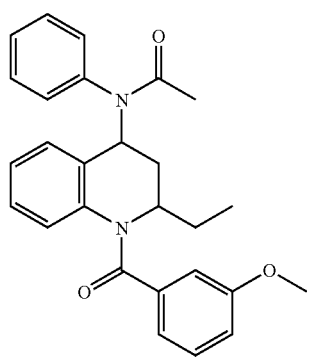 |
| B-100 | 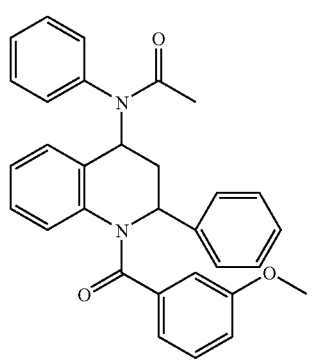 |
| B-101 | 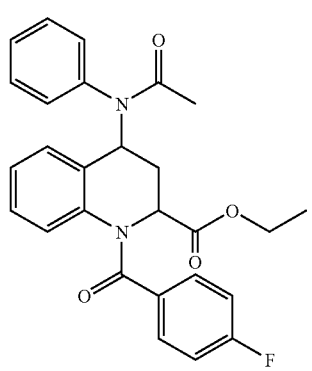 |
| B-102 | 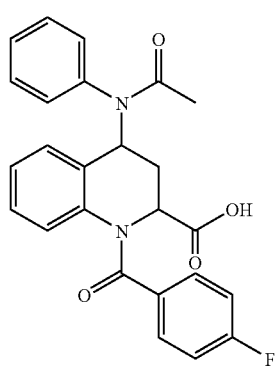 |

TABLE 2-continued
Compounds Derived from General Procedure B
| No. | Structure |
|-----|-----------|
| B-103 | 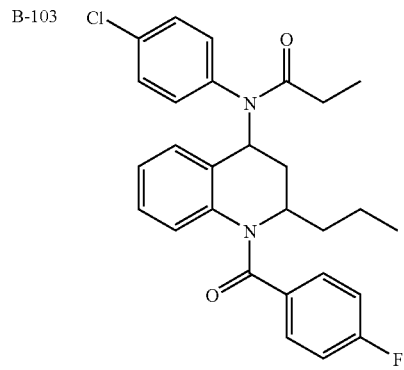 |
| B-104 | 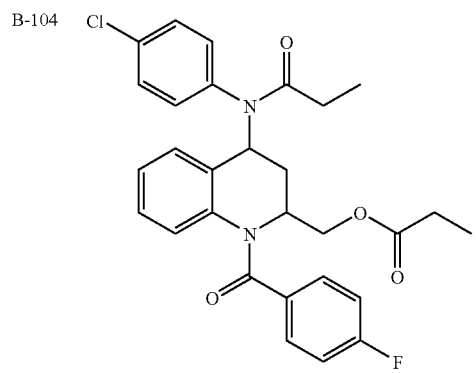 |
| B-105 | 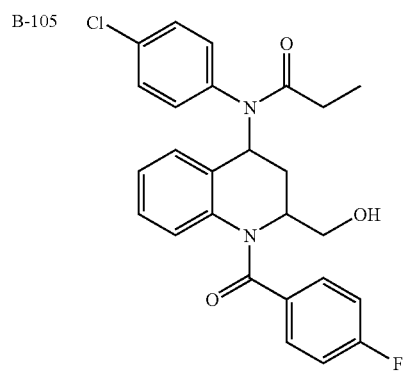 |
| B-106 | 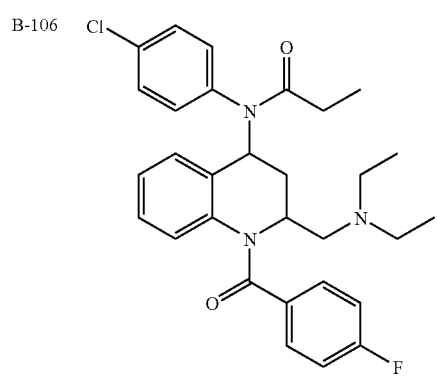 |

TABLE 2-continued
Compounds Derived from General Procedure B
| No. | Structure |
|---|---|
| B-107 | 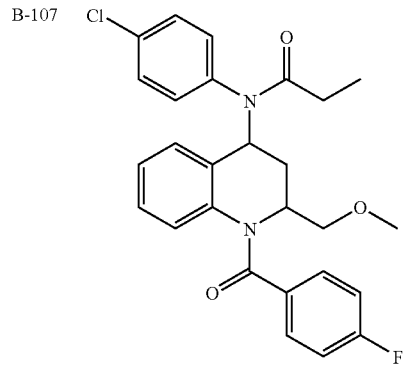 |
| B-108 | 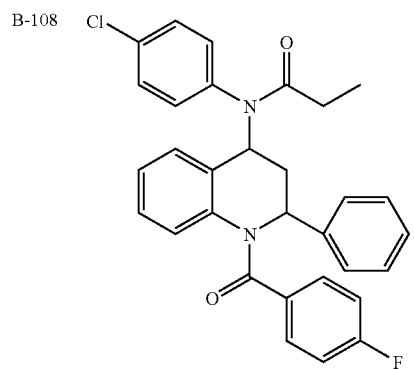 |
| B-109 | 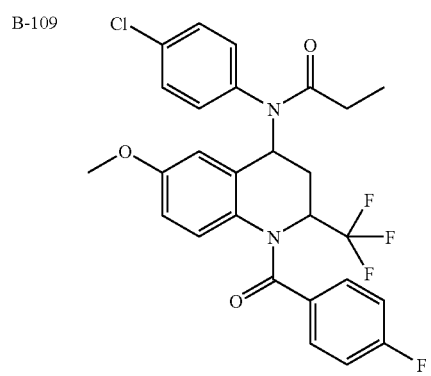 |
| B-110 | 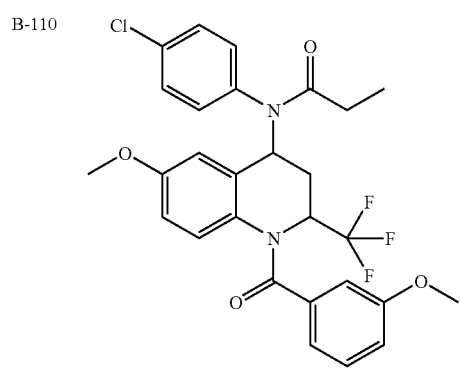 |

TABLE 2-continued
Compounds Derived from General Procedure B
| No. | Structure |
|---|---|
| B-111 | 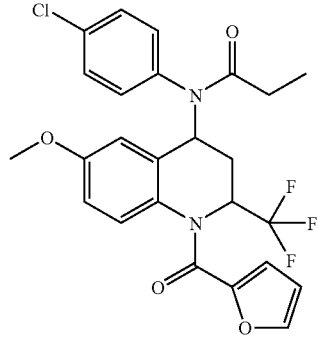 |
| B-112 | 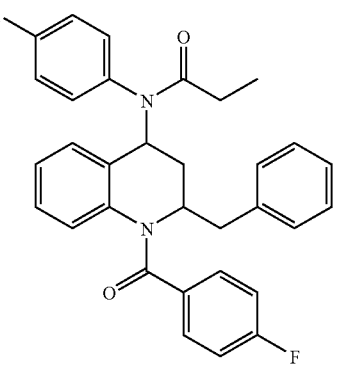 |
| B-113 | 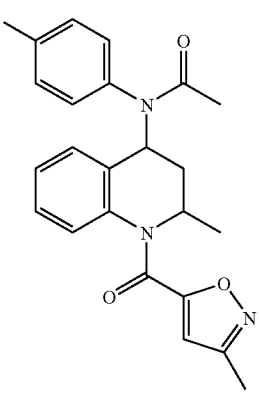 |
| B-114 | 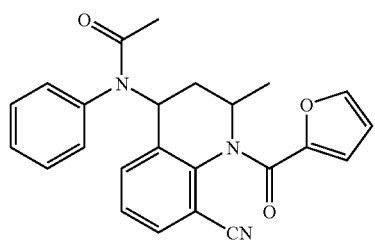 |

TABLE 2-continued
Compounds Derived from General Procedure B
| No. | Structure |
|---|---|
| B-115 | 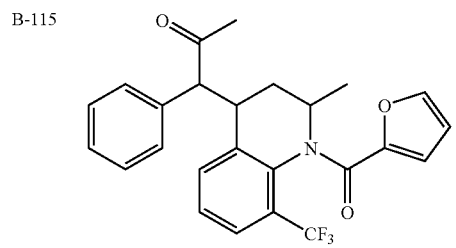 |
| B-116 | 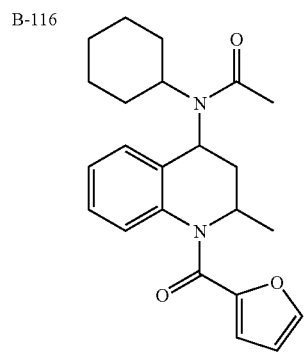 |
| B-117 | 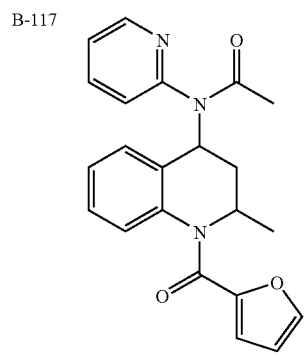 |
| B-118 | 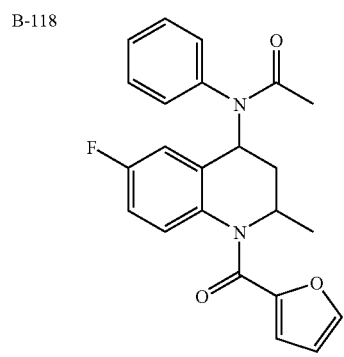 |

TABLE 2-continued
Compounds Derived from General Procedure B
| No. | Structure |
|-----|-----------|
| B-119 | 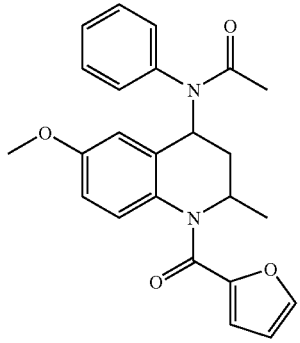 |
| B-120 | 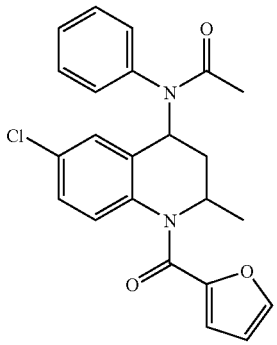 |
| B-121 | 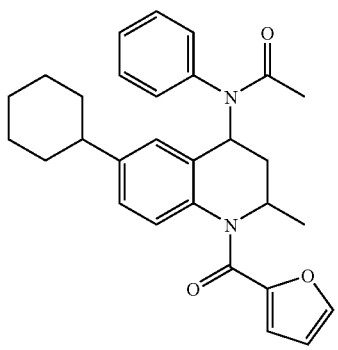 |
| B-122 | 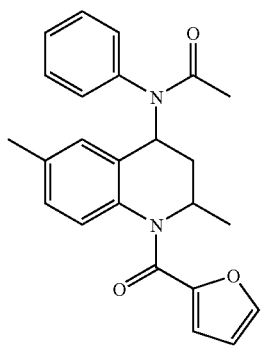 |

TABLE 2-continued
Compounds Derived from General Procedure B
| No. | Structure |
|---|---|
| B-123 | 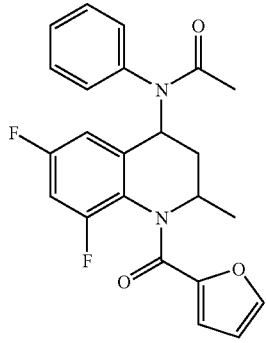 |
| B-124 | 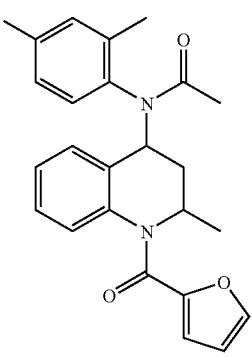 |
| B-125 | 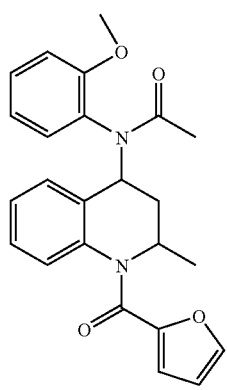 |
| B-126 | 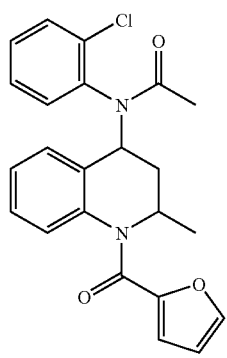 |

TABLE 2-continued
Compounds Derived from General Procedure B
| No. | Structure |
| --- | --- |
| B-127 | 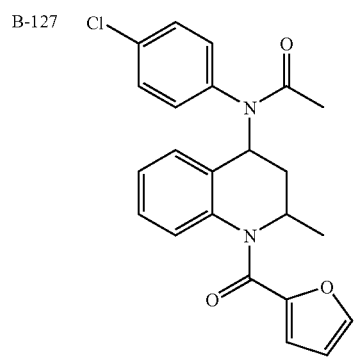 |
| B-128 | 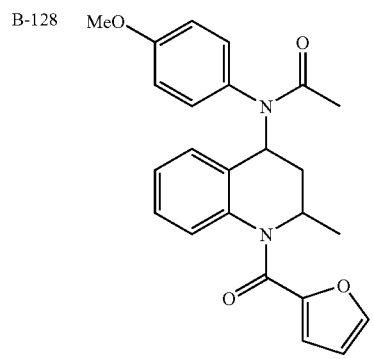 |
| B-129 | 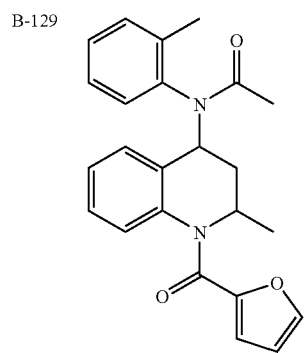 |
| B-130 | 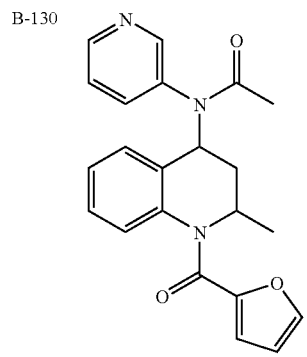 |

TABLE 2-continued

Compounds Derived from General Procedure B

| No. | Structure |
|---|---|
| B-131 | 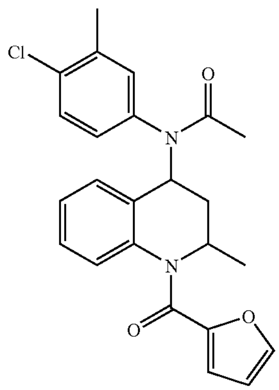 |
| B-132 | 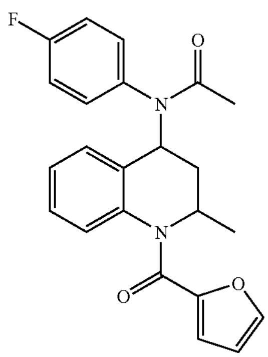 |
| B-133 | 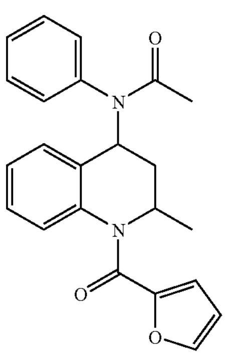 |
| B-134 | 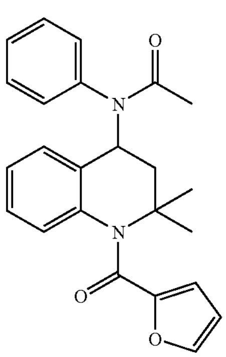 |

TABLE 2-continued
Compounds Derived from General Procedure B
| No. | Structure |
| --- | --- |
| B-135 | 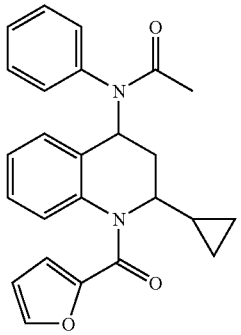 |
| B-136 | 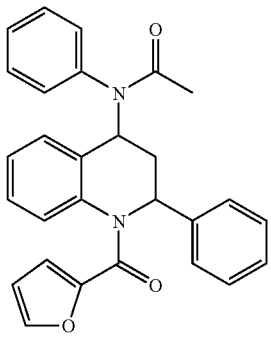 |
| B-137 | 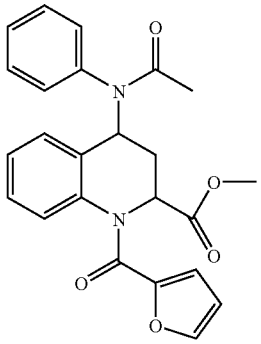 |
| B-138 | 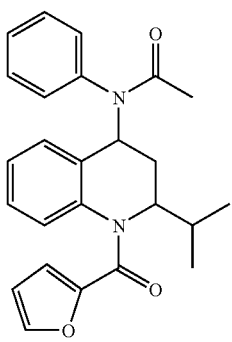 |

TABLE 2-continued
Compounds Derived from General Procedure B
| No. | Structure |
| --- | --- |
| B-139 | 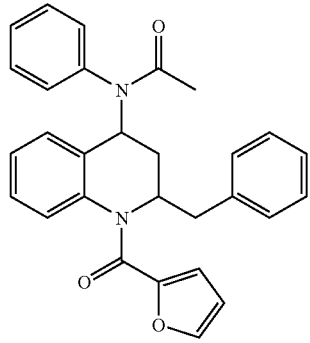 |
| B-140 | 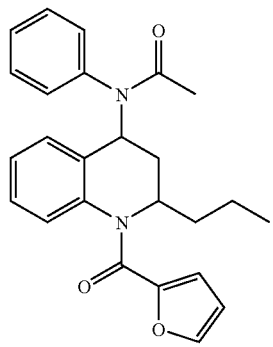 |
| B-141 | 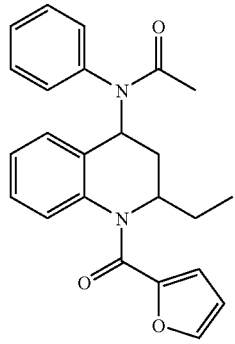 |
| B-142 | 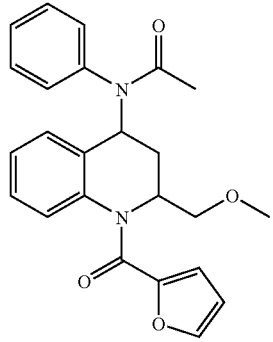 |

TABLE 2-continued

Compounds Derived from General Procedure B

| No. | Structure |
|---|---|
| B-143 | 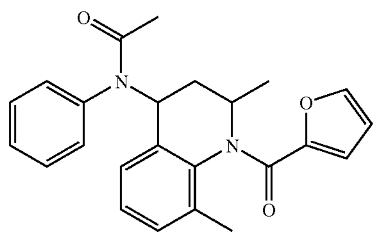 |
| B-144 | 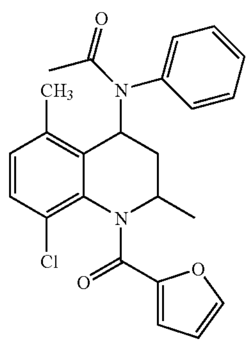 |
| B-145 | 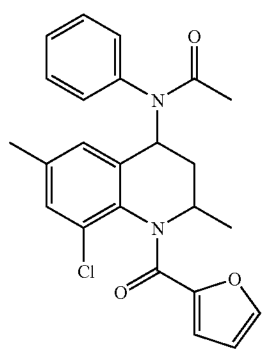 |
| B-146 | 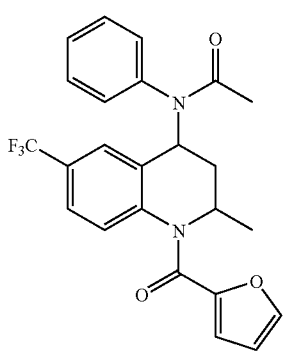 |

TABLE 2-continued

Compounds Derived from General Procedure B

| No. | Structure |
|---|---|
| B-147 | 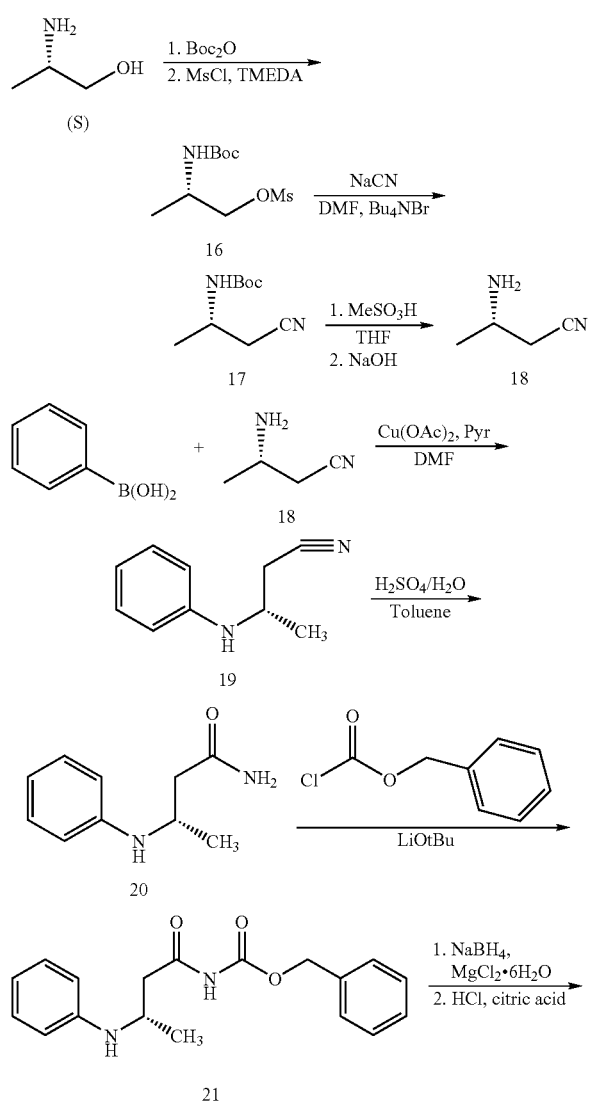 |

Methanesulfonic Acid 2-(S)-tert-butoxycarbonylamino-propyl Ester (16)

To a room temperature solution of S-2-amino-propan-1-ol (28.23 g, 0.375 mol) in ethyl acetate (300 mL) was added BOC anhydride (86.13 g, 0.395 mol) dissolved in 30 mL of ethyl acetate via an addition funnel (exothermic). The solution turns cloudy then clear. The reaction mixture was stirred for approximately 30 minutes. Tetramethylethylenediamine (TMEDA) (59.6 mL, 0.395 mol) was added and the reaction mixture was cooled to approximately 0° C. Methanesulfonyl chloride (30.6 mL, 0.395 mol) was added to the reaction mixture over a 30-minute period. After stirring for 2.5 hour at 0° C., during which time a white precipitate formed. The reaction mixture was filtered and the filtrate was concentrated to ½ volume and poured into hexanes (800 mL) and rapidly stirred. The mixture was cooled in an ice-bath for 2 h and then filtered to give 82 g (86%) of methanesulfonic acid 2-(S)-tert-butoxycarbonylamino-propyl ester.

$^1$H NMR (300 MHz, CDCl$_3$) δ1.23 (d, 3H), 1.44 (s, 9H), 3.03 (s, 2H), 3.96 (m, 1H), 4.15 (dd, 1H), 4.23 (dd, 1H), 4.58 (bs, 1H).

(S)-(2-Cyano-1-methyl-ethyl)-carbamic acid tert-butyl ester (17)

Sodium cyanide (48.92 g, 0.421 mol) was added to dimethylformamide (DMF) (420 mL) and the mixture was stirred at 35° C. for 30 minutes. Tetrabutylammonium bromide (5.22 g, 0.016 mol) was added and the reaction mixture was stirred for an additional 2 h at 35° C. Methanesulfonic acid 2-(S)-tert-butoxycarbonylamino-propyl ester (82.03 g, 0.324 mol) was added and the reaction mixture was stirred at 35° C. overnight. Add an additional 5.22 g of tetrabutylammonium bromide (0.016 mol) was added and stirred overnight at 35° C. The mixture was then partitioned between 1200 mL water and 1600 mL of ethyl acetate. The resulting organic and aqueous phases were separated and extracted sequentially 2 times with 800 mL of ethyl acetate. The combined extracts were washed 3 times with 500 mL of water and a saturated solution of sodium chloride in water. The organic layer was dried over magnesium sulfate, filtered and concentrated to afford a solid in 84% of (S)-(2-cyano-1-methyl-ethyl)-carbamic acid tert-butyl ester.

(S)-3-Amino-butyronitrile (18)

To a solution of (S)-(2-cyano-1-methyl-ethyl)-carbamic acid tert-butyl ester (50.29 g, 0.273 mol) dissolved in THF (550 mL) was added methanesulfonic acid (44 mL, 0.682 mol) and stirred for 20 minutes. The reaction mixture was heated to 65° C. for approximately 3 h (make sure the reaction is vented during this time). The mixture was allowed to cool to ambient temperature. The resulting solids were isolated by filtration to afford the title compound. The solids were suspended in dichloromethane, and 300 mL of sat. $Na_2CO_3$ and the pH was adjusted to 13 with 6M NaOH (20 mL). Extract 2×500 mL dichloromethane. Combine the organics and wash with a saturated solution of sodium chloride in water. The organic layer was dried over sodium sulfate, filtered and concentrated to give (S)-3-amino-butyronitrile in 64% yield.

$^1$H NMR (300 MHz, $CDCl_3$), 1.23 (d, 3H), 1.46 (bs, 2H), 2.34 (dd, 1H), 2.43 (dd, 1H), 3.34 (sextet, 1H).

(S)-3-Phenylamino-butyronitrile (19)

(S)-3-Amino-butyronitrile (2.51 g, 0.030 mol) was dissolved in 40 mL of DMF, phenyl boronic acid (4.73 g, 0.0389 mol), $Cu(OAc)_2$ (7.06 g, 0.0389 mol) and pyridine (6.29 mL, 0.077 mol) were added and the reaction was heated to 65° C. open to the air until no starting material was apparent by LCMS (It is very important that this reaction not be run under argon or nitrogen, it needs the air to catalyze the reaction. Also, the reaction should be stirred very vigourously to allow the air to mix with the reaction.) Once the starting material was gone (~18 h), the reaction was allowed to cool to room temperature and poured into ethyl acetate and filter. Wash the precipitate well with ethyl acetate. The filtrate is washed 2 times with $H_2O$ and dried over $Na_2SO_4$, filtered and concentrated. Isco chromatography (100% hexane to 30% ethyl acetate/70% hexane gradient) afforded the N-phenyl nitrile in 2.13 g (41%) as a white solid.

$^1$H NMR (300 MHz, $CDCl_3$) δ 1.44 (d, 3H), 2.61 (d, 2H), 3.64 (bs, 1H), 3.90 (bs, 1H), 6.60 (d, 2H), 6.77 (t, 1H), 7.18–7.26 (m, 2H)

(S)-3-Phenylamino-butyramide (20)

To a solution of (S)-3-phenylamino-butyronitrile (6.06 g, 0.0378 mol) in toluene (150 mL) was added a cooled solution of conc. sulfuric acid in $H_2O$ (20.12 mL $H_2SO_4$/3 mL)—(The ratio of toluene to acid/$H_2O$ is very important and should be followed strictly). Stir the biphasic mixture at room temperature for 0.5 h and warm to 35° C. and stir for 22 h. The reaction was cooled to room temperature and quenched with 13 g of $Na_2CO_3$ in water (add slowly some foaming). Separate the organic and extract 2×EtOAc. Combine all the organics and wash the organics with brine, dry over $MgSO_4$, filter and concentrate to give the desired product in 2.11 g (90%)

$^1$H NMR (300 MHz, $CDCl_3$) δ: 1.29 (d, 3H), 2.40 (dd, 1H), 2.48 (dd, 1H), 3.73 (bs, 1H), 3.92 (sextet, 1H), 5.52 (bs, 1H), 6.00 (bs, 1H), 6.66 (d, 2H), 6.74 (t, 1H), 7.19 (m, 2H)

(S)-(3-Phenylamino-butyryl)-carbamic acid benzyl ester (21)

A clean, dry and nitrogen gas purged flask was charged with (S)-3-phenylamino-butyramide (3.25 g, 0.018 mmol) in THF (65 mL) and the mixture was cooled to –10° C. Benzyl chloroformate (3.12 mL, 0.022 mmol) was then added followed by the slow addition of 1.0 M lithium tert-butoxide in THF solution (18 mL). The lithium tert-butoxide solution was added at such a rate that the internal temperature remained below 0° C. Fifteen minutes after the completion of base addition, the reaction (starting material gone by TLC) was quenched by adding EtOAc (65 mL) and 1.0 M hydrochloric acid (10 mL). The aqueous phase was then basified with 1N NaOH. The aqueous phase was extracted 3× EtOAc. The organics were collected together and with saturated aqueous sodium chloride solution (130 mL). The phases were separated, the organic layer was dried ($MgSO_4$), filtered, and concentrated. Flash chromatography using a Biotage system (10% EtOAc/90% hexane to 20% EtOAc/80% Hexane) afforded the title compound in 82% yield.

$^1$H NMR (300 MHz, $CDCl_3$) δ: 1.30 (d, 3H), 2.87 (dd, 1H), 3.04 (dd, 1H), 3.80 (bs, 1H), 4.02 (m, 1H), 5.17 (s, 2H), 6.62 (d, 2H), 6.73 (t, 1H), 7.17 (t, 2H), 7.37 (s, 5H), 8.13 (bs, 1H).

(2S, 4R)-(2-Methyl-1,2,3,4-tetrahydro-quinolin-4-yl)-carbamic acid benzyl ester (22)

A clean, dry flask was charged with (S)-(3-phenylamino-butyryl)-carbamic acid benzyl ester (0.821 g, 2.63 mmol) followed by reagent grade ethanol (20 mL) and cooled to –10° C. Sodium borohydride (0.070 g, 1.84 mmol) was added to the solution in one portion. Nitrogen gas purging is maintained for 5 minutes. A solution of 3.3 M aqueous magnesium chloride solution (0.561 g $MgCl_2$ $6H_2O$ in 1.5 mL water) was added at such a rate that the internal temperature did not exceed –5° C. Once addition was completed, the reaction solution was warmed to 0° C. for 30 min. The reaction was quenched with methylene chloride (10 mL), and 1 M hydrochloric acid/citric acid solution (10.52 mL 1 N HCl, and 1.38 g citric acid). This bilayer was stirred at room temperature for six hours. The reaction mixture was diluted with ethyl acetate (200 mL) and neutralized with sat. aqueous $NaHCO_3$ solution (pH=10). The organics were collected together and washed with sat. NaCl solution and dried over $Na_2SO_4$, filtered and concentrated. Flash chromatography using an Isco system (100% hexane to 50% EtOAc/50% hexane gradient) afforded the title compound (0.733 g). (91%).

$^1$H-NMR (300 MHz, $CDCl_3$) δ: 7.38 (m, 5H), 7.17 (d, 1H), 7.02 (t, 1H), 6.68 (t, 1H, C6-H), 6.47 (d, 1H), 5.17 (bs, 2H), 5.07 (m, 1H), 4.92 (d, 1H), 3.78 (bs, 1H), 3.57 (m, 1H), 2.30 (m, 1H), 1.47 (q, 1H), 1.21 (d, 3H).

General Procedure C

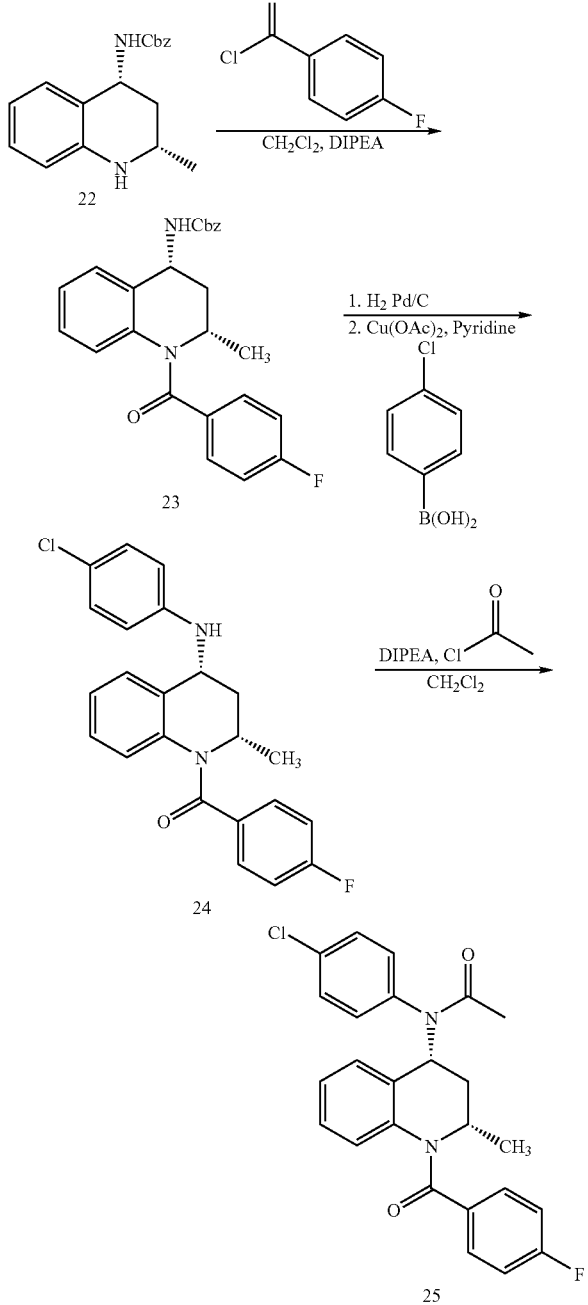

(2S,4R)-N-(4-Chloro-phenyl)-N-[1-(4-fluoro-benzoyl)-2-methyl-1,2,3,4-tetrahydro-quinolin-4-yl]-acetamide (25)

To a solution of (2S, 4R)-(2-methyl-1,2,3,4-tetrahydro-quinolin-4-yl)-carbamic acid benzyl ester (1.0 g, 3.38 mmol) in methylene chloride (50 mL) at room temperature was added diisopropylethylamine (650 uL, 3.72 mmol) followed by 4-fluoropropyl chloride. The reaction was stirred over night at room temperature. The mixture was poured into water and extracted with ethyl acetate. The extracts were washed with 1 M (aq) NaOH and brine, dried over magnesium sulfate, filtered dried and concentrated. The crude residue was purified by silica gel chromatography (75% hexanes/25% ethyl acetate) to afford the pure amide (720 mg, 51%).

(2S,4R)-[1-(4-fluorobenzoyl)-2-methyl-1,2,3,4-tetrahydro-quinolin-4-yl]-carbamic acid benzyl ester (720 mg, 1.73 mmol) was dissolved in ethanol (30 mL). The vessel in which resided the resulting solution was evacuated and backfilled with argon. A catalytic amount of Palladium on Carbon (10%) was added. The vessel was once again evacuated and this time was backfilled with hydrogen and shaken in a Parr bottle at 40 psi hydrogen. Reaction was complete after 4 h. The mixture was carefully filtered and concentrated to 10% volume. The resulting concentrated solution was filtered through an Celite (and concentrated to afford the crude amine.

To a solution of (2S, 4R)-(4-amino-2-methyl-3,4-dihydro-2H-quinolin-1-yl)-(4-fluoro-phenyl)-methanone (1.0 g, 3.5 mmol) in DMF (20 mL, dry) was added 4-chlorophenylboronic acid (1.1 g, 7.0 mmol), pyridine (850 uL, 10.5 mmol) and copper(II)acetate (1.27 g, 7.0 mmol). The heterogeneous green mixture was stirred open to air for 1 h and then warmed to 60° C. and stirred over night (14 h). The mixture was then cooled to rt, poured into rapidly stirred ethyl acetate (150 mL); solids were removed by filtration through Celite®. The extracts were washed several times with water and then once with brine. The extracts were then dried over anhydrous magnesium sulfate, filtered, and concentrated under reduced pressure. The crude residue was purified by silica gel chromatography (95% methylene chloride/5% ethyl acetate) to afford the aniline product (250 mg, 18%) as a yellow oil.

To a solution of (2S, 4R)-[4-(4-chloro-phenylamino)-2-methyl-3,4-dihydro-2H-quinolin-1-yl]-(4-fluoro-phenyl)-methanone (250 mg, 0.636 mmol) in methylene chloride (5 mL) was added diisopropylethylamine (120 uL, 0.70 mmol) followed by acetyl chloride (90 uL, 1.27 mmol). The mixture was stirred at rt 4 h. The mixture was concentrated under reduced pressure, dissolved in ethyl acetate, washed with sat. aqueous sodium bicarbonate, brine and dried over magnesium sulfate, filtered, and concentrated under reduced pressure. The residue was purified by silica gel chromatography (25/75 hexanes/ethyl acetate gradient) to afford pure N-(4-chloro-phenyl)-N-[1-(4-fluoro-benzoyl)-2-methyl-1,2,3,4-tetrahydro-quinolin-4-yl]-acetamide (200 mg, 71%).

$^1$H-NMR (CDCl$_3$) δ: 1.1 (3H, d), 1.1 (1H, m), 2.0 (3H, d), 2.3 (1H, m), 4.7 (1H, m), 5.6 (1H, m), 6.5 (1H, d), 6.7–7.0 (3H, m), 7.1–7.4 (8H, m).

MS m/z: 436 (M+1).

(2S,4R)-N-(4-Chloro-phenyl)-N-[2-methyl-1-(4-morpholin-4-yl-benzoyl)-1,2,3,4-tetrahydro-quinolin-4-yl]-acetamide (C-1)

(2S,4R)-N-(4-Chloro-phenyl)-N-[2-methyl-1-(4-morpholin-4-yl-benzoyl)-1,2,3,4-tetrahydro-quinolin-4-yl]-acetamide was made following general procedure C, substituting 4-bromobenzoyl chloride for 4-fluorobenzoyl chloride. Further elaboration to the morpholine was done following the same procedure as described for (±)-N-(4-chloro-phenyl)-N-[1-(4-fluoro-benzoyl)-2-methyl-6-morpholin-4-yl-1,2,3,4-tetrahydro-quinolin-4-yl]-propionamide.

$^1$H-NMR (CDCl$_3$) δ: 1.13 (d, 3H), 1.22 (t, 1H), 2.03 (s, 3H), 2.29 (s, 1H), 3.31 (t, 4H), 3.80 (t, 4H), 4.75 (sextet, 1H), 5.61 (bs, 1H), 6.58 (d, 1H), 6.64 (d, 2H), 6.94 (t, 1H), 7.15 (d, 2H), 7.18 (t, 1H), 7.21 (d, 2H), 7.28–7.39 (m, 3H).

MS m/z: 505.4 (M+1).

(2S,4R)-4-(4-{4-[Acetyl-(4-chloro-phenyl)-amino]-2-methyl-3,4-dihydro-2H-quinoline-1-carbonyl}-phenoxy)-butyric acid (C-2)

(2S,4R)-4-(4-{4-[Acetyl-(4-chloro-phenyl)-amino]-2-methyl-3,4-dihydro-2H-quinoline-1-carbonyl}-phenoxy)-butyric acid was prepared was made following general procedure C, substituting 4-methoxybenzoyl chloride for 4-fluorobenzoyl chloride. Further elaboration to the acid was done following the same procedure as described for (±)-4-(4-{4-[(4-chloro-phenyl)-propionyl-amino]-2-methyl-3,4-dihydro-2H-quinoline-1-carbonyl}-phenoxy)-butyric acid.

$^1$H-NMR (CDCl$_3$) δ: 1.1 (3H, d), 1.1 (1H, m), 2.0 (3H, s), 2.1 (2H, m), 2.3 (1H, m), 2.5 (2H, m), 3.9 (2H, m), 4.7 (1H, m), 5.6 (1H, m),), 6.5 (1H, d), 6.7 (2H, d), 6.9 (1H, t), 7.1–7.3 (7H, m), 7.4 (1H, d).

MS m/z: 522 (M+2).

(2S,4R)-N-(4-Chloro-phenyl)-N-[1-(4-dimethylamino-benzoyl)-2-methyl-1,2,3,4-tetrahydro-quinolin-4-yl]-acetamide (C-3)

(2S,4R)-N-(4-Chloro-phenyl)-N-[1-(4-dimethylaminobenzoyl)-2-methyl-1,2,3,4-tetrahydro-quinolin-4-yl]-acetamide was prepared following general procedure C, substituting 4-dimethylaminobenzoyl chloride for 4-fluorobenzoyl chloride.

$^1$H-NMR (300 MHz, CDCl$_3$) δ: 1.14–1.33 (m, 4H), 2.13 (s, 3H), 2.24–2.39 (m, 1H), 2.94 (s, 6H), 4.75 (ddd, 1H), 5.61 (br s, 1H), 6.44 (d, 2H), 6.63 (d, 1H), 6.96 (dd, 1H), 7.07–7.36 (m, 6H), 7.40 (d, 2H).

MS m/z: 420 (M+1).

(2S,4R)-N-(4-Chloro-phenyl)-N-[1-(4-isopropoxy-benzoyl)-2-methyl-1,2,3,4-tetrahydro-quinolin-4-yl]-acetamide (C-4)

(2S,4R)-N-(4-Chloro-phenyl)-N-[1-(4-isopropoxy-benzoyl)-2-methyl-1,2,3,4-tetrahydro-quinolin-4-yl]-acetamide was prepared following general procedure C, substituting 4-isopropoxybenzoyl chloride for 4-fluorobenzoyl chloride.

$^1$H-NMR (300 MHz, CDCl$_3$) δ: 1.14 (d, 3H), 1.23–1.31 (m, 7H), 2.03 (s, 3H), 2.23–2.35 (m, 1H), 4.48 (sept., 1H), 4.74 (ddd, 1H), 5.61 (br s, 1H), 6.55 (d, 1H), 6.64 (d, 2H), 6.92 (dd, 1H), 7.09–7.24 (m, 5H), 7.29 (d, 1H), 7.34–7.41 (m, 2H).

MS m/z: 477 (M+1).

(2S,4R)-N-(4-Chloro-phenyl)-N-[2-methyl-1-(6-morpholin-4-yl-pyridine-3-carbonyl)-1,2,3,4-tetrahydro-quinolin-4-yl]-acetamide (C-5)

(2S,4R)-N-(4-Chloro-phenyl)-N-[2-methyl-1-(6-morpholin-4-yl-pyridine-3-carbonyl)-1,2,3,4-tetrahydro-quinolin-4-yl]-acetamide was prepared following general procedure C, substituting 2-chloronicotinoyl chloride for 4-fluorobenzoyl chloride. Prior to removal of the benzyl carbamate, the chloronicotinamide was converted to the 2-morpholinonicotinamide as follows. A solution of the (2S,4R)-[1-(6-chloro-nicotinoyl)-2-methyl-1,2,3,4-tetrahydro-quinolin-4-yl]-carbamic acid benzyl ester (525 mg, 1.20 mol) was dissolved in morpholine (5 mL). The resulting solution was heated at 70° C. over night. Upon completion of reaction (12 h), the solution was concentrated under reduced pressure; the crude residue was dissolved in ethyl acetate and washed with water and brine to remove remaining morpholine. The extracts were dried over sodium sulfate, filtered and concentrated to afford the crude morpholinonicotinate (639 mg, >100%). The resulting product was carried on to fully elaborated (2S,4R)-N-(4-chloro-phenyl)-N-[2-methyl-1-(6-morpholin-4-yl-pyridine-3-carbonyl)-1,2,3,4-tetrahydro-quinolin-4-yl]-acetamide as described in general procedure C.

$^1$H-NMR (300 MHz, CDCl$_3$) δ: 1.11–1.22 (m, 4H), 2.03 (s, 3H), 2.24–2.38 (m, 1H), 3.48–3.56 (m, 4H), 3.74–3.80 (m, 4H), 4.73 (ddd, 1H), 5.56 (br s, 1H), 6.30 (d, 1H), 6.66 (d, 1H), 7.02 (dd, 1H), 7.12 (dd, 1H), 7.16–7.25 (m, 3H), 7.32 (d, 1H), 7.40 (d, 2H), 8.24 (br s, 1H).

MS m/z: 505 (M+1).

(2S,4R)-N-(4-Chloro-phenyl)-N-[1-(3-ethyl-isoxazole-5-carbonyl)-2-methyl-1,2,3,4-tetrahydro-quinolin-4-yl]-acetamide (C-6)

(2S,4R)-N-(4-Chloro-phenyl)-N-[1-(3-ethyl-isoxazole-5-carbonyl)-2-methyl-1,2,3,4-tetrahydro-quinolin-4-yl]-acetamide was prepared following general procedure C, substituting 3-ethylisoxazole carbonyl chloride for 4-fluorobenzoyl chloride.

$^1$H-NMR (300 MHz, CDCl$_3$) δ: 1.06–1.23 (m, 7H), 2.02 (s, 3H), 2.21–2.37 (m, 1H), 2.52–2.66 (m, 2H), 4.72 (ddd, 1H), 5.34–5.56 (br s, 1H), 5.88 (s, 1H), 6.80 (d, 1H), 7.11 (dd, 1H), 7.20 (d, 2H), 7.28–7.43 (m, 4H).

MS m/z: 438 (M+1).

(2S,4R)-N-[1-(3-Benzyl-isoxazole-5-carbonyl)-2-methyl-1,2,3,4-tetrahydro-quinolin-4-yl]-N-(4-chloro-phenyl)-acetamide (C-7)

(2S,4R)-N-[1-(3-Benzyl-isoxazole-5-carbonyl)-2-methyl-1,2,3,4-tetrahydro-quinolin-4-yl]-N-(4-chloro-phenyl)-acetamide was prepared following general procedure C, substituting 3-benzylisoxazole carbonyl chloride for 4-fluorobenzoyl chloride.

$^1$H-NMR (300 MHz, CDCl$_3$) δ: 1.06–1.43 (m, 4H), 2.01 (s, 3H), 2.16–2.35 (m, 1H), 3.81–4.01 (m, 2H), 4.70 (ddd, 1H), 5.40 (br s, 1H), 5.83 (s, 1H), 6.75 (d, 1H), 7.02 (dd, 1H), 7.10 (m, d, 2H), 7.14–7.22 (m, 2H), 7.22–7.34 (m, 5H), 7.38 (d, 2H).

MS m/z: 500 (M+1).

(2S,4R)-N-(4-Chloro-phenyl)-N-[1-(3-methoxymethyl-isoxazole-5-carbonyl)-2-methyl-1,2,3,4-tetrahydro-quinolin-4-yl]-acetamide (C-8)

(2S,4R)-N-(4-Chloro-phenyl)-N-[1-(3-methoxymethyl-isoxazole-5-carbonyl)-2-methyl-1,2,3,4-tetrahydro-quinolin-4-yl]-acetamide was prepared following general procedure C, substituting 3-methoxymethyl ether isoxazole carbonyl chloride for 4-fluorobenzoyl chloride.

$^1$H-NMR (300 MHz, CDCl$_3$) δ: 1.11–1.24 (m, 4H), 2.02 (s, 3H), 2.22–2.39 (m, 1H), 3.28 (s, 3H), 4.42 (s, 2H), 4.73 (ddd, 1H), 5.46 (br s, 1H), 6.09 (s, 1H), 6.79 (d, 1H), 7.10 (d, 1H), 7.10 (d, 2H), 7.27–7.42 (m, 4H).

MS m/z: 454 (M+1).

(2S,4R)-4-(4-{4-[Acetyl-(4-chloro-phenyl)-amino]-2-methyl-3,4-dihydro-2H-quinoline-1-carbonyl}-phenoxy)-piperidine-1-carboxylic Acid Ethyl Ester (C-9)

(2S,4R)-4-(4-{4-[Acetyl-(4-chloro-phenyl)-amino]-2-methyl-3,4-dihydro-2H-quinoline-1-carbonyl}-phenoxy)-piperidine-1-carboxylic acid ethyl ester was prepared following general procedure C, substituting 4-(4-chlorocarbonyl-phenoxy)-piperidine-1-carboxylic acid ethyl ester for 4-fluorobenzoyl chloride.

$^1$H-NMR (CDCl$_3$) δ: 1.1 (3H, d), 1.1 (1H, m), 1.2 (3H, t), 1.7 (2H, m), 1.9 (2H, m), 2.0 (3H, s), 2.3 (1H, m), 3.3 (2H, m), 3.7 (2H, m), 4.1 (2H, q), 4.4 (1H, m), 4.8 (1H, m), 5.6 (1H, m), 6.5 (1H, d), 6.7 (2H, d), 6.9 (1H, t), 7.1–7.3 (7H, m), 7.4 (1H, d).

MS m/z: 590 (M).

(2S,4R)-2-(4-{4-[Acetyl-(4-chloro-phenyl)-amino]-2-methyl-3,4-dihydro-2H-quinoline-1-carbonyl}-phenoxy)-acetamide (C-10)

(2S,4R)-2-(4-{4-[Acetyl-(4-chloro-phenyl)-amino]-2-methyl-3,4-dihydro-2H-quinoline-1-carbonyl}-phenoxy)-acetamide was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. Further elaboration to the amide was done following the same procedure as described for (±)-N-[1-(4-carbamoylmethoxy-benzoyl)-2-methyl-1,2,3,4-tetrahydro-quinolin-4-yl]-N-phenyl-propionamide $^1$H-NMR (CDCl$_3$) δ: 1.1 (3H, m), 1.8 (1H, s), 2.0 (3H, s), 2.3 (1H, m), 4.4 (2H, s), 4.7 (1H, m), 5.6 (1H, br), 5.9 (2H, brs) 6.5 (2H, d), 6.7 (2H, d), 6.9 (1H, t), 7.2–7.4 (7H, m).

MS m/z: 492 (M+1).

(2S,4R)-N-(4-Chloro-phenyl)-N-{2-methyl-1-[4-(2-morpholin-4-yl-ethoxy)-benzoyl]-1,2,3,4-tetrahydro-quinolin-4-yl}-acetamide (C-11)

(2S,4R)-N-(4-Chloro-phenyl)-N-{2-methyl-1-[4-(2-morpholin-4-yl-ethoxy)-benzoyl]-1,2,3,4-tetrahydro-quinolin-4-yl}-acetamide was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. Further elaboration to the morpholine was done following the same procedure as described for (±)-N-{2-methyl-1-[4-(2-morpholin-4-yl-ethoxy)-benzoyl]-1,2,3,4-tetrahydro-quinolin-4-yl}-N-phenyl-propionamide.

$^1$H-NMR (CDCl$_3$) δ: 1.1 (3H, d), 1.1 (1H, m), 2.0 (3H, s), 2.3 (1H, m), 2.6 (4H, m), 2.8 (2H, m), 3.7 (4H, m), 4.1 (2H, m), 4.7 (1H, m), 5.6 (1H, m), 6.5 (1H, d), 6.7 (2H, d), 6.9 (1H, t), 7.1–7.3 (7H, m), 7.4 (1H, d).

MS m/z: 549 (M+2).

(2S,4R)-(4-{4-[Acetyl-(4-chloro-phenyl)-amino]-2-methyl-3,4-dihydro-2H-quinoline-1-carbonyl}-phenoxy)-acetic acid (C-13)

(2S,4R)-(4-{4-[Acetyl-(4-chloro-phenyl)-amino]-2-methyl-3,4-dihydro-2H-quinoline-1-carbonyl}-phenoxy)-acetic acid was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. Further elaboration to the acid was done following the same procedure as described for {(±)-4-[2-methyl-4-(phenyl-propionyl-amino)-3,4-dihydro-2H-quinoline-1-carbonyl]-phenoxy}-acetic.

$^1$H-NMR (CDCl$_3$) δ: 1.1 (3H, d), 1.1 (1H, m), 2.0 (3H, s), 2.3 (1H, m), 4.3 (2H, s), 4.6 (1H, m), 5.6 (1H, m), 6.4–6.9 (5H, m), 7.0–7.4 (7H, m).

MS m/z: 494 (M+2).

(2S,4R)-N-(4-Chloro-phenyl)-N-{2-methyl-1-[4-(1H-tetrazol-5-ylmethoxy)-benzoyl]-1,2,3,4-tetrahydro-quinolin-4-yl}-acetamide (C-14)

(2S,4R)-N-(4-Chloro-phenyl)-N-{2-methyl-1-[4-(1H-tetrazol-5-ylmethoxy)-benzoyl]-1,2,3,4-tetrahydro-quinolin-4-yl}-acetamide was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. Further elaboration to the tetrazole was done following the same procedure as described for (±)-N-(4-chloro-phenyl)-N-{2-methyl-1-[4-(1H-tetrazol-5-ylmethoxy)-benzoyl]-1,2,3,4-tetrahydro-quinolin-4-yl}-propionamide.

$^1$H-NMR (CDCl$_3$) δ: 1.1 (3H, d), 1.1 (1H, m), 2.0 (3H, s), 2.3 (1H, m), 4.8 (1H, m), 5.2 (2H, dd), 5.6 (1H, m), 6.4 (1H, m), 6.5 (1H, d), 7.0 (2H, m), 7.1–7.4 (8H, m).

MS m/z: 517 (M+1).

(2S,4R)-N-{1-[4-(1-Acetyl-piperidin-4-yloxy)-benzoyl]-2-methyl-1,2,3,4-tetrahydro-quinolin-4-yl}-N-(4-chloro-phenyl)-acetamide (C-15)

(2S,4R)-N-{1-[4-(1-Acetyl-piperidin-4-yloxy)-benzoyl]-2-methyl-1,2,3,4-tetrahydro-quinolin-4-yl}-N-(4-chloro-phenyl)-acetamide was prepared from (2S,4R)-4-(4-{4-[acetyl-(4-chloro-phenyl)-amino]-2-methyl-3,4-dihydro-2H-quinoline-1-carbonyl}-phenoxy)-piperidine-1-carboxylic acid ethyl ester, followed by removal of the ethoxy carbamate using basic hydrolysis and then acetylation.

$^1$H-NMR (CDCl$_3$) δ: 1.1 (3H, d), 1.1 (1H, m), 1.6–2.1 (4H, m), 2.0 (6H, s), 2.3 (1H, m), 3.4 (1H, m), 3.5–3.8 (3H, m), 4.4 (1H, m), 4.7 (1H, m), 5.6 (1H, m), 6.5 (1H, d), 6.7 (2H, d), 6.9 (1H, t), 7.1–7.3 (7H, m), 7.4 (1H, d).

MS m/z: 560 (M+1).

(2S,4R)-N-(4-Chloro-phenyl)-N-{2-methyl-1-[4-(pyridin-4-ylmethoxy)-benzoyl]-1,2,3,4-tetrahydro-quinolin-4-yl}-acetamide (C-16)

(2S,4R)-N-(4-Chloro-phenyl)-N-{2-methyl-1-[4-(pyridin-4-ylmethoxy)-benzoyl]-1,2,3,4-tetrahydro-quinolin-4-yl}-acetamide (2S,4R)-N-(4-Chloro-phenyl)-N-{2-methyl-1-[4-(1H-tetrazol-5-ylmethoxy)-benzoyl]-1,2,3,4-tetrahydro-quinolin-4-yl}-acetamide was made from (2S,4R)-N-(4-chloro-phenyl)-N-[1-(4-methoxy-benzoyl)-2-methyl-1,2,3,4-tetrahydro-quinolin-4-yl]-acetamide. (2S,4R)-N-(4-Chloro-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride. (2S,4R)-N-(4-Chloro-phenyl)-N-[1-(4-methoxy-benzoyl)-2-methyl-1,2,3,4-tetrahydro-quinolin-4-yl]-acetamide was dissolved in dichloromethane and a solution of BBr$_3$ (1.0 M in dichloromethane, 10 mL) was added; the reaction was allowed to stir at room temperature for until no starting material remained. The reaction was washed with sat NaHCO$_3$ carefully and brine. The organics were dried over MgSO$_4$, filtered and concentrated down. The residue was purified by Biotage flash chromatography using 100% EtOAc to give a white solid.

The phenol was dissolved in DMF (5 mL) at room temperature. Sodium hydride (60% in oil) was added and the mixture allowed to stir 30 min. 4-Bromomethyl-pyridine was added and the reaction was allowed to stir over night. Ethanol was added and the reaction was concentrated in vacuo. The residue was partitioned between ethyl acetate and water, then extracted three times with ethyl acetate, dried over MgSO$_4$, filtered and concentrated down. The crude residue was purified by silica gel chromatography (2/98 methanol/dichloromethane—5/95 methanol/dichloromethane gradient) to afford the product.

¹H-NMR (CDCl₃) δ: 1.1 (3H, d), 1.1 (1H, m), 2.0 (3H, s), 2.3 (1H, m), 4.7 (1H, m), 5.0 (2H, s), 5.6 (1H, in), 6.5 (1H, d), 6.7 (2H, d), 6.9 (1H, t), 7.0–7.4 (10H, in), 8.6 (2H, d).

MS m/z: 526 (M+1).

(2S,4R)-4-(3-{4-[Acetyl-(4-chloro-phenyl)-ainino]-2-methyl-3,4-dihydro-2H-quinoline-1-carbonyl}-phenoxy)-butyric acid (C-17)

(2S,4R)-4-(3-{4-[Acetyl-(4-chloro-phenyl)-amino]-2-methyl-3,4-dihydro-2H-quinoline-1-carbonyl}-phenoxy)-butyric acid was prepared following general procedure C, substituting 3-methoxybenzoyl chloride for 4-fluorobenzoyl chloride. Further elaboration to the acid was done following the same procedure as described for (±)-4-(4-{4-[(4-chloro-phenyl)-propionyl-amino]-2-methyl-3,4-dihydro-2H-quinoline-1-carbonyl}-phenoxy)-butyric acid.

¹H-NMR (CDCl₃) δ: 1.1 (3H, d), 1.1 (1H, m), 1.8–2.0 (2H, m), 2.0 (3H, s), 2.3 (1H, m), 2.4 (2H, m), 3.8 (2H, m), 4.8 (1H, m), 5.7 (1H, m), 6.4 (1H, m), 6.5 (1H, d), 6.8 (1H, m), 7.0 (1H, t), 7.1–7.4 (7H, m), 7.5 (1H, m).

MS m/z: 521 (M+1).

(2S,4R)-N-(4-Chloro-phenyl)-N-[1-(4-hydroxy-benzoyl)-2-methyl-1,2,3,4-tetrahydro-quinolin-4-yl]-acetamide (C-18)

(2S,4R)-N-(4-Chloro-phenyl)-N-[1-(4-hydroxy-benzoyl)-2-methyl-1,2,3,4-tetrahydro-quinolin-4-yl]-acetamide was prepared was made following general procedure C, substituting 3-methoxybenzoyl chloride for 4-fluorobenzoyl chloride. Further elaboration to the phenol was done following the same procedure as described for (±)-N-[1-(4-hydroxy-benzoyl)-2-methyl-1,2,3,4-tetrahydro-quinolin-4-yl]-N-phenyl-propionamide.

¹H-NMR (CDCl₃) δ: 1.1 (3H, d), 1.1 (1H, m), 2.0 (3H, s), 2.3 (1H, m), 4.7 (1H, m), 5.6 (1H, m), 6.4 (2H, d), 6.5 (1H, d), 6.9 (3H, m), 7.1–7.3 (4H, m), 7.4 (2H, m), 8.0 (1H, br).

MS m/z: 435 (M+1).

(2S, 4R)-4-(4-{4-[Acetyl-(4-chloro-phenyl)-amino]-2-methyl-3,4-dihydro-2H-quinoline-1-carbonyl}-phenyl)-piperidine-1-carboxylic acid ethyl ester (C-19)

(2S,4R)-4-(4-{4-[Acetyl-(4-chloro-phenyl)-amino]-2-methyl-3,4-dihydro-2H-quinoline-1-carbonyl}-phenyl)-piperidine-1-carboxylic acid ethyl ester was prepared following general procedure C, substituting 4-(4-chlorocarbonyl-phenyl)-piperidine-1-carboxylic acid ethyl ester for 4-fluorobenzoyl chloride.

¹H-NMR (CDCl₃) δ: 1.1 (4H, m), 1.3 (3H, m), 1.5 (2H, m), 1.7 (2H, m), 2.0 (3H, s), 2.3 (1H, m), 2.6 (1H, m), 2.8 (2H, t), 4.1 (2H, m), 4.2 (2H, m), 4.8 (1H, m), 5.6 (1H, br), 6.5 (1H, d), 6.9 (1H, m), 7.0 (2H, d), 7.1 (2H, d), 7.3 (5H, m), 7.4 (2H, m).

MS m/z: 474 (M+1).

(2S,4R)-N-(4-Chloro-phenyl)-N-[1-(3-ethoxy-benzoyl)-2-methyl-1,2,3,4-tetrahydro-quinolin-4-yl]-acetamide (C-20)

(2S,4R)-N-(4-Chloro-phenyl)-N-[1-(3-ethoxy-benzoyl)-2-methyl-1,2,3,4-tetrahydro-quinolin-4-yl]-acetamide was prepared following general procedure C, substituting 3-ethoxybenzoyl chloride for 4-fluorobenzoyl chloride.

¹H-NMR (CDCl₃) δ: 1.2 (3H, m), 1.3 (4H, m), 2.0 (3H, s), 2.2 (1H, m), 3.9 (2H, m), 4.8 (1H, m), 5.6 (1H, br), 6.5 (1H, d), 6.7 (1H, d), 6.8 (2H, d), 6.9 (1H, m), 7.0 (1H, m), 7.1–7.3 (4H, m), 7.4 (2H, d).

MS m/z: 463 (M+1).

(2S,4R)-(4-{4-[Acetyl-(4-chloro-phenyl)-amino]-2-methyl-3,4-dihydro-2H-quinoline-1-carbonyl}-phenyl)-carbamic acid ethyl ester (C-22)

(2S,4R)-(4-{4-[Acetyl-(4-chloro-phenyl)-amino]-2-methyl-3,4-dihydro-2H-quinoline-1-carbonyl}-phenyl)-carbamic acid ethyl ester was prepared following general procedure C, substituting (4-chlorocarbonyl-phenyl)-carbamic acid ethyl ester for 4-fluorobenzoyl chloride.

¹H-NMR (CDCl₃) δ: 1.1 (3H, m), 1.3 (4H, m), 2.0 (3H, s), 2.3 (1H, m), 4.2 (2H, m), 4.8 (1H, m), 5.6 (1H, br), 6.5 (1H, d), 6.9 (1H, m), 7.1–7.3 (8H, m), 7.4 (2H, d).

MS m/z: 506 (M+1).

(2S,4R)-N-(4-Chloro-phenyl)-N-[2-methyl-1-(4-oxazol-5-yl-benzoyl)-1,2,3,4-tetrahydro-quinolin-4-yl]-acetamide (C-24)

(2S,4R)-N-(4-Chloro-phenyl)-N-[2-methyl-1-(4-oxazol-5-yl-benzoyl)-1,2,3,4-tetrahydro-quinolin-4-yl]-acetamide was prepared following general procedure C, substituting 4-oxazol-5-yl-benzoyl chloride for 4-fluorobenzoyl chloride.

¹H-NMR (CDCl₃) δ: 1.2 (3H, m), 1.3 (1H, m), 2.1 (3H, s), 2.3 (1H, m), 4.8 (1H, m), 5.6 (1H, br), 6.5 (1H, d), 6.9 (1H, m), 7.1–7.3 (8H, m), 7.4 (1H, d), 7.5 (2H, d), 7.9 (1H, s).

MS m/z: 486 (M+1).

(2S,4R)-N-(3,4-Dichloro-phenyl)-N-[1-(4-methoxy-benzoyl)-2-methyl-1,2,3,4-tetrahydro-quinolin-4-yl]-acetamide (C-25)

(2S,4R)-N-(3,4-Dichloro-phenyl)-N-[1-(4-methoxy-benzoyl)-2-methyl-1,2,3,4-tetrahydro-quinolin-4-yl]-acetamide was made following general procedure C, substituting 3,4-dichlorophenylboronic acid for 4-chlorophenylboronic acid and 4-methoxybenzoyl chloride for 4-fluorobenzoyl chloride.

¹H-NMR (CDCl₃) δ: 1.2 (3H, m), 1.3 (1H, m), 2.0 (3H, s), 2.3 (1H, m), 3.7 (3H, s), 4.8 (1H, m), 5.6 (1H, br), 6.6 (1H, d), 6.7 (2H, d), 7.0 (1H, m), 7.2 (3H, m), 7.3 (2H, d), 7.4 (1H, s), 7.5 (1H, d).

MS m/z: 483 (M+1).

(2S,4R)-N-(2,3-Dihydro-benzo[1,4]dioxin-6-yl)-N-[1-(4-methoxy-benzoyl)-2-methyl-1,2,3,4-tetrahydro-quinolin-4-yl]-acetamide (C-26)

(2S,4R)-N-(2,3-Dihydro-benzo[1,4]dioxin-6-yl)-N-[1-(4-methoxy-benzoyl)-2-methyl-1,2,3,4-tetrahydro-quinolin-4-yl]-acetamide was made following general procedure C, substituting 2,3-dihydro-benzo[1,4]dioxine-6-carboxylic acid for 4-chlorophenylboronic acid and 4-methoxyphenyl-benzoyl chloride for 4-fluorobenzoyl chloride.

¹H-NMR (CDCl₃) δ: 1.2 (3H, m), 1.3 (1H, m), 2.0 (3H, s), 2.4 (1H, m), 3.7 (3H, s), 4.3 (4H, s), 4.8 (1H, m), 5.6 (1H, br), 6.5 (1H, d), 6.68 (2H, d), 6.7–6.9 (3H, m), 7.10–7.3 (5H, m).

MS m/z: 474 (M+2).

(2S,4R)-N-[1-(4-Methoxy-benzoyl)-2-methyl-1,2,3,4-tetrahydro-quinolin-4-yl]-N-p-tolyl-acetamide (C-27)

(2S,4R)-N-[1-(4-Methoxy-benzoyl)-2-methyl-1,2,3,4-tetrahydro-quinolin-4-yl]-N-p-tolyl-acetamide was prepared following general procedure C, substituting 4-methoxybenzoyl chloride for 4-fluorobenzoyl chloride and 4-toluene boronic acid for 4-chlorophenylboronic acid ¹H-NMR (CDCl₃) δ: 1.15 (3H, d; overlapping 1H, t), 2.01 (3H, s), 2.33–2.36 (overlapping 1H, m, 1H, s), 3.73 (3H, s), 4.70 (1H, m), 5.65 (1H, m), 6.50 (1H, d), 6.68 (2×1H, d), 6.95 (1H, t), 7.00–7.40 (8H, m).

MS m/z: 429 (M+1).

(2S,4R)-N-(4-Chloro-phenyl)-N-[2-methyl-1-(4-pyrrolidin-1-yl-benzoyl)-1,2,3,4-tetrahydro-quinolin-4-yl]-acetamide (C-28)

(2S,4R)-N-(4-Chloro-phenyl)-N-[2-methyl-1-(4-pyrrolidin-1-yl-benzoyl)-1,2,3,4-tetrahydro-quinolin-4-yl]-acetamide was prepared following general procedure C, substituting 4-pyrrolidin-1-yl-benzoyl chloride for 4-fluorobenzoyl chloride.

$^1$H-NMR (CDCl$_3$) δ: 1.11–1.15 (4H, m), 1.94–1.98 (4H, m), 2.03 (3H, s), 2.24–2.34 (1H, m), 3.21–3.25 (4H, m), 4.68–4.75 (1H, m), 5.61–5.65 (1H, br), 6.30 (2H, d), 6.63 (1H, d), 6.92–7.52 (9H, m).

MS m/z: 488 (M+1).

(2S,4R)-N-(4-Chloro-phenyl)-N-[1-(1-isopropyl-1H-benzotriazole-5-carbonyl)-2-methyl-1,2,3,4-tetrahydro-quinolin-4-yl]-acetamide (C-29)

(2S,4R)-N-(4-Chloro-phenyl)-N-[1-(1-isopropyl-1H-benzotriazole-5-carbonyl)-2-methyl-1,2,3,4-tetrahydro-quinolin-4-yl]-acetamide was made following general procedure C, substituting 1-isopropyl-1H-benzotriazole-5-carbonyl chloride for 4-fluorobenzoyl chloride.

$^1$H-NMR (CDCl$_3$) δ: 1.19–1.27 (4H, m), 1.68 (6H, d), 2.04 (3H, s), 2.30–2.40 (1H, m), 4.83 (1H, q), 4.98 (1H, q) 5.45–5.55 (1H, br), 6.48 (1H, d), 6.83 (1H, t), 7.10–7.41 (8H, m), 8.13 (1H, br).

MS m/z: 503 (M+1).

(2S,4R)-N-(4-Chloro-phenyl)-N-{1-[4-(1-hydroxy-1-methyl-ethyl)-benzoyl]-2-methyl-1,2,3,4-tetrahydro-quinolin-4-yl}-acetamide (C-30)

(2S,4R)-N-(4-Chloro-phenyl)-N-{1-[4-(1-hydroxy-1-methyl-ethyl)-benzoyl]-2-methyl-1,2,3,4-tetrahydro-quinolin-4-yl}-acetamide was prepared from (2S, 4R)-N-[1-(4-acetyl-benzoyl)-2-methyl-1,2,3,4-tetrahydro-quinolin-4-yl]-N-(4-chloro-phenyl)-acetamide. (2S,4R)-N-[1-(4-Acetyl-benzoyl)-2-methyl-1,2,3,4-tetrahydro-quinolin-4-yl]-N-(4-chloro-phenyl)-acetamide (112 mg, 124 mmol) was dissolved in THF (5 mL) and cooled to 0° C. Methyl magnesium bromide (1.4 M in ether, 2 mL, 2.4 mmol) was added and the mixture stirred at 0° C. for 2 h. The reaction was warmed to rt and stirred an additional 2 h. The reaction was poured into saturated aqueous ammonium chloride. The phases were separated and the aqueous was extracted with ethyl acetate. The extracts were washed with brine, dried over magnesium sulfate, filtered, dried and concentrated. The crude alcohol was purified by silica gel chromatography to afford pure product (20 mg, 24%).

$^1$H-NMR (CDCl$_3$) δ: 1.12–1.21 (4H, m), 1.48 (6H, d), 2.02 (3H, s), 2.25–2.34 (1H, m), 4.70–4.80 (1H, m), 5.45–5.54 (1H, br), 6.50 (1H, d), 6.88 (1H, t), 7.11–7.38 (10H, m).

MS m/z: 478 (M+1).

(2S,4R)-N-(4-Chloro-phenyl)-N-[1-(3-ethoxy-isoxazole-5-carbonyl)-2-methyl-1,2,3,4-tetrahydro-quinolin-4-yl]-acetamide (C-31)

(2S,4R)-N-(4-Chloro-phenyl)-N-[1-(3-ethoxy-isoxazole-5-carbonyl)-2-methyl-1,2,3,4-tetrahydro-quinolin-4-yl]-acetamide was prepared following general procedure C, substituting 3-ethoxy-isoxazole-5-carbonyl chloride for 4-fluorobenzoyl chloride.

$^1$H-NMR (CDCl$_3$) δ: 1.16 (3H, d), 1.33 (3H, t), 1.69 (1H, br s), 2.00 (3H, s), 2.21–2.38 (1H, m), 4.21 (2H, q), 4.66–4.73 (1H, m), 5.65 (1H, s), 6.86 (1H, t), 7.13–7.39 (8H, m).

MS m/z: 454 (M).

(2S,4R)-3-(4-{4-[Acetyl-(4-chloro-phenyl)-amino]-2-methyl-3,4-dihydro-2H-quinoline-1-carbonyl}-phenyl)-propionic acid (C-32)

(2S,4R)-3-(4-{4-[Acetyl-(4-chloro-phenyl)-amino]-2-methyl-3,4-dihydro-2H-quinoline-1-carbonyl}-phenyl)-propionic acid was prepared from (2S,4R)-3-(4-{4-[acetyl-(4-chloro-phenyl)-amino]-2-methyl-3,4-dihydro-2H-quinoline-1-carbonyl}-phenyl)-acrylic acid. A solution of (2S,4R)-3-(4-{4-[acetyl-(4-chloro-phenyl)-amino]-2-methyl-3,4-dihydro-2H-quinoline-1-carbonyl}-phenyl)-acrylic acid (50 mg, 0.102 mmol) in EtOH (2 ml) and CH$_2$Cl$_2$ (10 drops for solubility) was subjected to Pd—C (10%, ca. 50 mg) and 1 atm H$_2$ gas. After 1 hour, the mixture was filtered, concentrated and subjected to silica gel chromatography (2% MeOH in EtOAc to 10% MeOH in EtOAc), to afford the title compound (50 mg, 99%).

$^1$H-NMR (CDCl$_3$ 300 MHz) δ 1.09 (3H, d), 1.17–1.18 (1H, m), 2.00 (3H, s), 2.20–2.35 (1H, m), 2.46–2.60 (2H, m), 2.80–2.90 (2H, m), 4.65–4.80 (1H, m), 5.40–5.71 (1H, m), 6.48 (1H, d), 6.89 (1H, t), 7.0 (2H, d), 7.12 (2H, d), 7.20–7.48 (5H, m), 7.72 (1H, d).

MS m/z: 322 (M–C$_8$H$_7$NO).

(2S,4R)-3-(4-{4-[Acetyl-(4-chloro-phenyl)-amino]-2-methyl-3,4-dihydro-2H-quinoline-1-carbonyl}-phenyl)-acrylic acid (C-33)

(2S,4R)-3-(4-{4-[Acetyl-(4-chloro-phenyl)-amino]-2-methyl-3,4-dihydro-2H-quinoline-1-carbonyl}-phenyl)-acrylic acid was prepared following general procedure C, substituting 3-(4-chlorocarbonyl-phenyl)-acrylic acid methyl ester for 4-fluorobenzoyl chloride. The ester was hydrolyzed as follows. To a solution of (2S,4R)-3-(4-{4-[acetyl-(4-chloro-phenyl)-amino]-2-methyl-3,4-dihydro-2H-quinoline-1-carbonyl}-phenyl), acrylic acid methyl ester (112 mg, 0.239 mmol) in THF/MeOH (2 ml, 2 ml) was added LiOH (4 ml: 1.0 M in H$_2$O). Upon consumption of the starting unit (1 hour), the mixture was neutralized with aq. HCl (1.0 M), partioned with EtOAc (10 ml) and separated. The organic layer was separated and concentrated whereby the resulting oil was subjected to silica gel chromatography (2% MeOH in EtOAc to 10% MeOH in EtOAc) to afford the title compound (110 mg, 99%).

$^1$H-NMR (MeOD, 300 MHz) δ 0.85–0.95 (1H, m), 1.12 (3H, d), 2.04 (3H, s), 2.40–2.53 (1H, m), 4.70–4.80 (1H, m), 5.50–5.71 (1H, m), 6.46 (1H, d), 6.57 (1H, d), 6.96 (1H, t), 7.20–7.55 (8H, m), 7.60 (2H, d), 7.81 (1H, d).

MS m/z: 320 (M–C$_8$H$_7$NO).

(2S,4R)-N-[1-(4-Methoxy-benzoyl)-2-methyl-1,2,3,4-tetrahydro-quinolin-4-yl]-N-(4-methoxy-phenyl)-acetamide (C-34)

(2S,4R)-N-[1-(4-Methoxy-benzoyl)-2-methyl-1,2,3,4-tetrahydro-quinolin-4-yl]-N-(4-methoxy-phenyl)-acetamide was prepared following general procedure C, substituting 4-methoxybenzoyl chloride for 4-fluorobenzoyl chloride and 4-methoxyphenylboronic acid for 4-chlorophenylboronic acid.

$^1$H-NMR (CDCl$_3$ 300 MHz) δ 1.12 (3H, d), 1.20–1.23 (1H, m), 2.09 (3H, s), 2.30–2.42 (1H, m), 3.71 (3H, s), 3.81 (3H, s) 4.70–4.81 (1H, m), 5.50–5.80 (1H, m), 6.52 (1H, d), 6.67 (2H, d), 6.80–6.94 (4H, m), 7.10–7.40 (5H, m).

MS m/z: 280 (M–C$_9$H$_{10}$NO$_2$).

(2S,4R)-N-(4-Isopropyl-phenyl)-N-[1-(4-methoxy-benzoyl)-2-methyl-1,2,3,4-tetrahydro-quinolin-4-yl]-acetamide (C-35)

(2S,4R)-N-(4-Isopropyl-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride and 4-isopropylphenylboronic acid for 4-chlorophenylboronic acid.

$^1$H-NMR (CDCl$_3$ 300 MHz) δ 1.21 (6H, d), 1.20–1.23 (1H, m), 1.23 (3H, d), 2.09 (3H, s), 2.30–2.42 (1H, m), 2.80–2.95 (1H, m), 3.74 (3H, s), 4.65–4.83 (1H, m), 5.50–5.80 (1H, m), 6.53 (1H, d), 6.67 (2H, d), 6.72 (2H, d), 6.92 (1H, t), 7.02–7.12 (3H, m), 7.21 (2H, d), 7.38 (1H, d).

MS m/z: 280 (M–C$_{11}$H$_{14}$NO).

(2S,4R)-N-(4-Bromo-phenyl)-N-[1-(4-methoxy-benzoyl)-2-methyl-1,2,3,4-tetrahydro-quinolin-4-yl]-acetamide (C-36)

(2S,4R)-N-(4-Bromo-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride and 4-bromophenylboronic acid for 4-chlorophenylboronic acid.

$^1$H-NMR (CDCl$_3$ 300 MHz) δ 1.12 (3H, d), 1.20–1.24 (1H, m), 2.05 (3H, s), 2.20–2.38 (1H, m), 3.72 (3H, s), 4.66–4.81 (1H, m), 5.50–5.75 (1H, m), 6.52 (1H, d), 6.67 (2H, d), 6.92 (1H, t), 7.10–7.18 (5H, m), 7.26 (1H, t), 7.48–7.58 (2H, m).

MS m/z: 493 (M+1).

(2S,4R)-4-{Acetyl-[1-(4-methoxy-benzoyl)-2-methyl-1,2,3,4-tetrahydro-quinolin-4-yl]-amino}-benzoic Acid (C-37)

(2S,4R)$_4$-{Acetyl-[1-(4-methoxy-benzoyl)-2-methyl-1,2,3,4-tetrahydro-quinolin-4-yl]-amino}-benzoic acid was made from (2S,4R)-4-{acetyl-[1-(4-methoxy-benzoyl)-2-methyl-1,2,3,4-tetrahydro-quinolin-4-yl]-amino}-benzoic acid methyl ester. (2S,4R)-4-{acetyl-[1-(4-methoxy-benzoyl)-2-methyl-1,2,3,4-tetrahydro-quinolin-4-yl]-amino}-benzoic acid methyl ester prepared following general procedure C, substituting 4-methoxybenzoyl chloride for 4-fluorobenzoyl chloride and 4-phenylboronic acid methyl ester for 4-chlorophenylboronic acid. (2S,4R)-4-{acetyl-[1-(4-methoxy-benzoyl)-2-methyl-1,2,3,4-tetrahydro-quinolin-4-yl]-amino}-benzoic acid methyl ester was converted to the acid using the following procedure. To a solution of 4-{acetyl-[1-(4-methoxy-benzoyl)-2-methyl-1,2,3,4-tetrahydro-quinolin-4-yl]-amino}-benzoic acid methyl ester (10 mg, 0.038 mmol) in 4 ml methanol was added 100 mg K$_2$CO$_3$ (0.72 mmol, in 0.5 ml water). The resulting reaction mixture was stirred at room temperature overnight. The methanol was removed under vacuum. 1M HCl was added until the mixture is acidic. Dichloromethane (20 ml) and 5 ml water was added. Organic layer was dried with magnesium sulfate. Dichloromethane was removed under vacuum to give the title compound (15 mg, 86%)

$^1$H-NMR (CDCl$_3$) δ: 1.1 (3H, d), 1.1 (1H, m), 2.0 (3H, s), 2.3 (1H, m), 3.8 (3H, s), 4.8 (1H, m), 5.6 (1H, m), 6.5 (1H, d), 6.6 (2H, d), 6.9 (1H, t), 7.1–7.4 (6H, m), 8.1 (2H, d).

MS m/z: 460 (M+2).

(2S,4R)-N-(3-Aminomethyl-phenyl)-N-[1-(4-methoxy-benzoyl)-2-methyl-1,2,3,4-tetrahydro-quinolin-4-yl]-acetamide (C-38)

(2S,4R)-N-(3-Aminomethyl-phenyl)-N-[1-(4-methoxy-benzoyl)-2-methyl-1,2,3,4-tetrahydro-quinolin-4-yl]-acetamide was prepared from (2S, 4R)-N-(3-cyano-phenyl)-N-[1-(4-methoxy-benzoyl)-2-methyl-1,2,3,4-tetrahydro-quinolin-4-yl]-acetamide. (2S,4R)-N-(3-cyano-phenyl)-N-[1-(4-methoxy-benzoyl)-2-methyl-1,2,3,4-tetrahydro-quinolin-4-yl]-acetamide was prepared following standard procedure C, substituting 3-cyanophenylboronic acid for 4-fluorobenzoyl chloride. To a mixture of (2S, 4R)-N-(3-cyano-phenyl)-N-[1-(4-methoxy-benzoyl)-2-methyl-1,2,3,4-tetrahydro-quinolin-4-yl]-acetamide (48 mg, 0.1 mmol) in 2 ml ethanol was added cobalt chloride (14 mg, 0.11 mmol). Sodium borohydride (12 mg, 0.33 mmol) was added at 0° C., and the temperature was held at 0° for 30 min. The mixture was then warmed to rt, and stirred overnight. The reaction was quenched by adding saturated aqueous ammonium chloride. The separated aqueous layer was extracted with ethyl acetate. The combined extracts were washed with water and brine, dried over magnesium sulfate, filtered and concentrated under reduced pressure. The crude oil was purified by HPLC to give the title compound (10 mg, 10%).

$^1$H-NMR (CDCl$_3$) δ: 1.1–1.2 (4H, m), 2.0 (3H, s), 2.3 (1H, m), 3.4 (2H, br), 3.8 (3H, s), 4.3 (1H, d), 4.8 (2H, d), 5.6 (1H, br), 6.4 (1H, m), 6.6 (2H, m), 6.9 (1H, m), 7.1–7.4 (8H, m).

MS m/z: 444 (M+1)

(2S,4R)-N-(4-Butyl-phenyl)-N-[1-(4-methoxy-benzoyl)-2-methyl-1,2,3,4-tetrahydro-quinolin-4-yl]-acetamide (C-39)

(2S,4R)-N-(4-Butyl-phenyl)-N-[1-(4-methoxy-benzoyl)-2-methyl-1,2,3,4-tetrahydro-quinolin-4-yl]-acetamide was prepared following general procedure C, substituting 4-methoxybenzoyl chloride for 4-fluorobenzoyl chloride and 4-butylphenylboronic acid for 4-chlorophenylboronic acid.

$^1$H-NMR (CDCl$_3$) δ: 0.9 (3H, m), 1.2 (3H, d), 1.4 (3H, m), 1.6 (2H, m), 2.0 (3H, s), 2.4 (1H, m), 2.6 (2H, m), 3.8 (3H, s), 4.8 (1H, m), 5.6 (1H, br), 6.5 (1H, d), 6.7 (2H, d), 7.0 (1H, m), 7.1–7.2 (7H, m), 7.4 (1H, d).

MS m/z: 471 (M+1).

Compounds C-40–C-147 can be prepared by the schemes set forth in Schemes 15–16 and by the general procedures C and others described herein. Those skilled in the art will be able to recognize, or be able to ascertain, using no more than routine experimentation, many equivalents to the specific embodiments of the invention described herein.

TABLE 3
Compounds Derived from General Procedure C
| No. | Structure |
|---|---|
| C-1 | 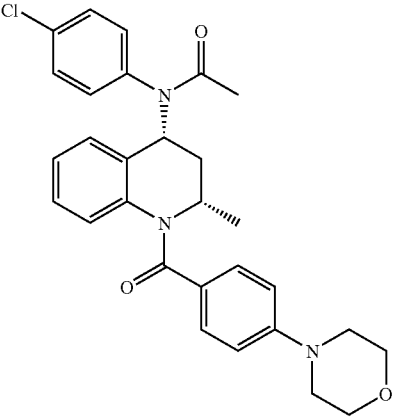 |
| C-2 | 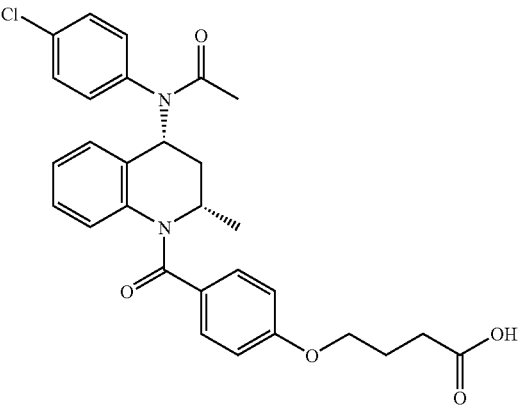 |
| C-3 | 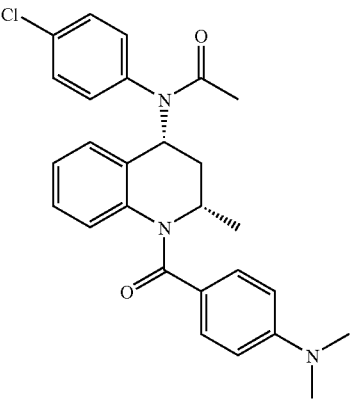 |

TABLE 3-continued
Compounds Derived from General Procedure C
| No. | Structure |
|---|---|
| C-4 | 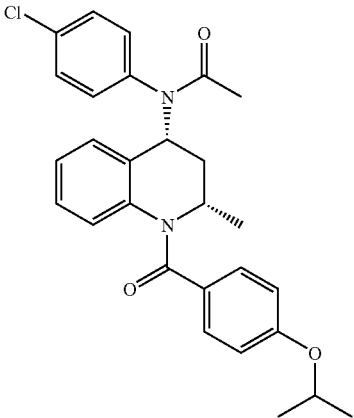 |
| C-5 | 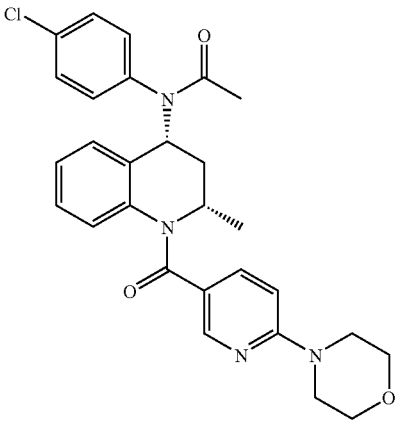 |
| C-6 | 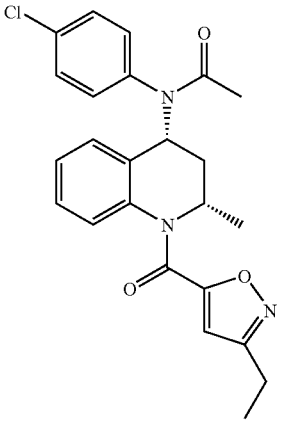 |

TABLE 3-continued

Compounds Derived from General Procedure C

| No. | Structure |
|---|---|
| C-7 | 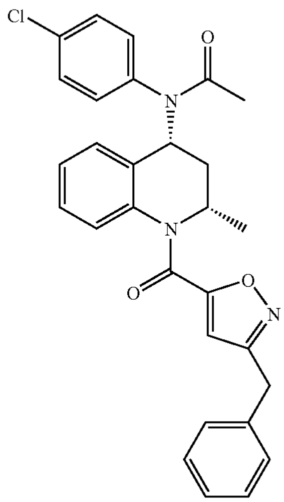 |
| C-8 | 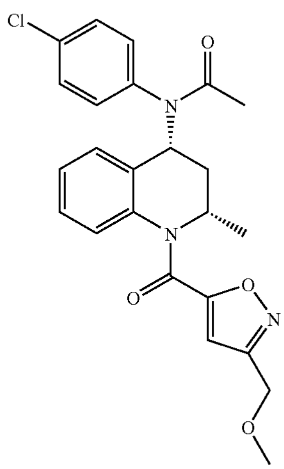 |
| C-9 | 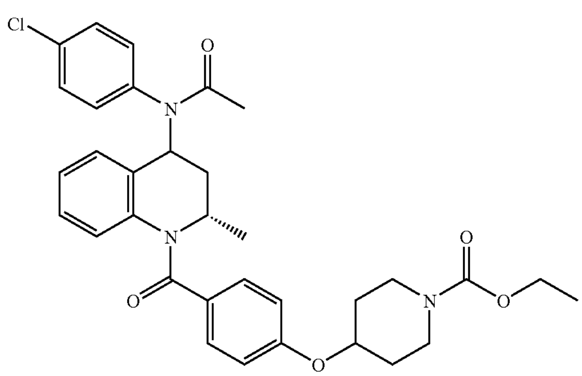 |

TABLE 3-continued

Compounds Derived from General Procedure C

| No. | Structure |
|---|---|
| C-10 | 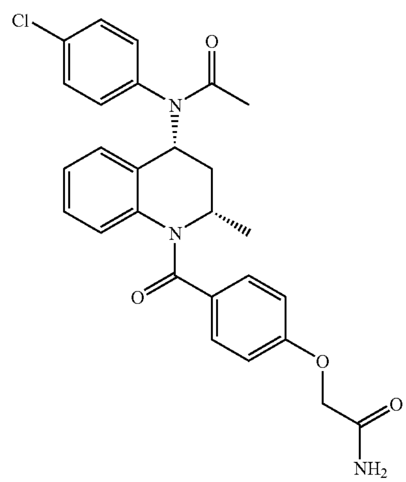 |
| C-11 | 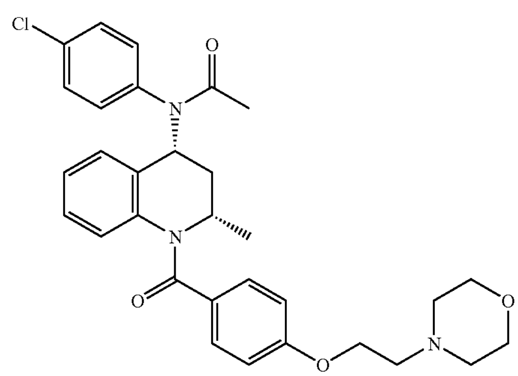 |
| C-12 | 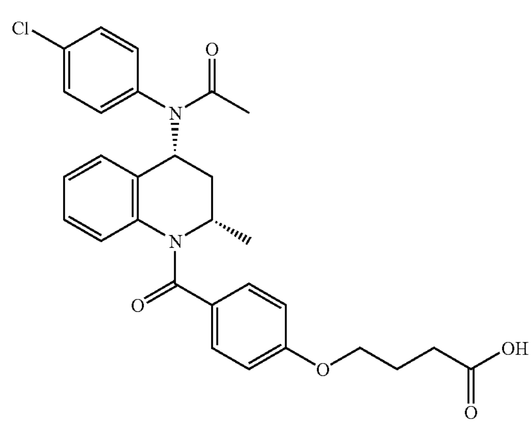 |

TABLE 3-continued

Compounds Derived from General Procedure C

| No. | Structure |
|---|---|
| C-13 | 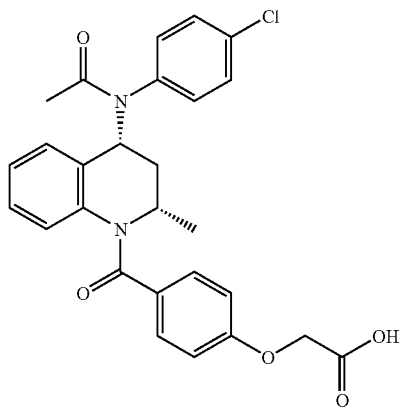 |
| C-14 | 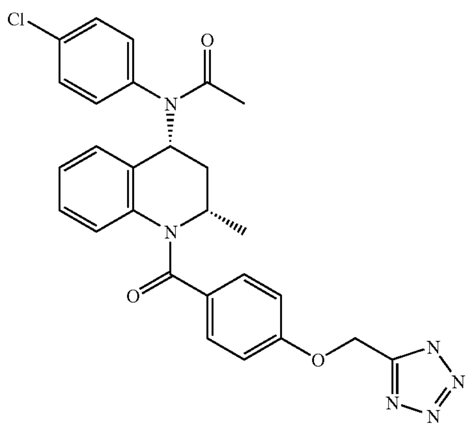 |
| C-15 | 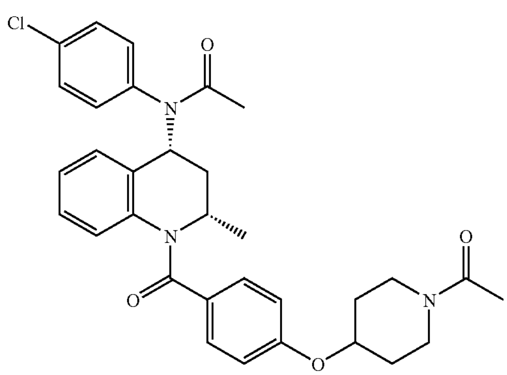 |

TABLE 3-continued
Compounds Derived from General Procedure C
| No. | Structure |
|---|---|
| C-16 | 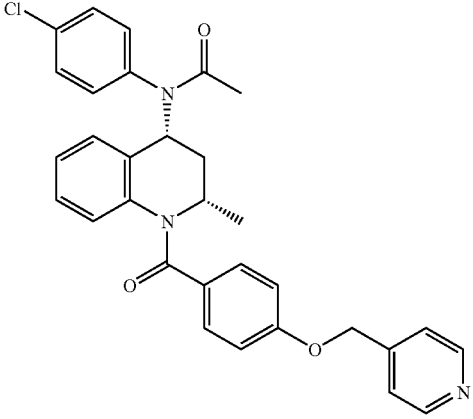 |
| C-17 | 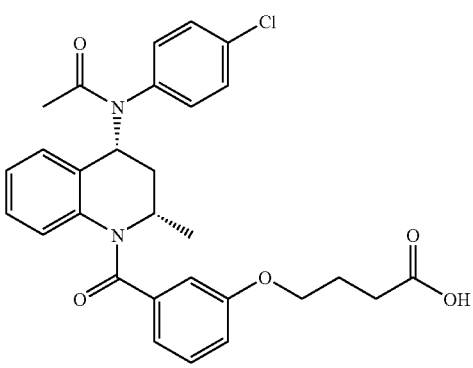 |
| C-18 | 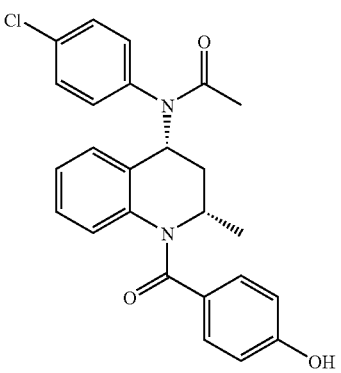 |

TABLE 3-continued
Compounds Derived from General Procedure C
| No. | Structure |
|---|---|
| C-19 | 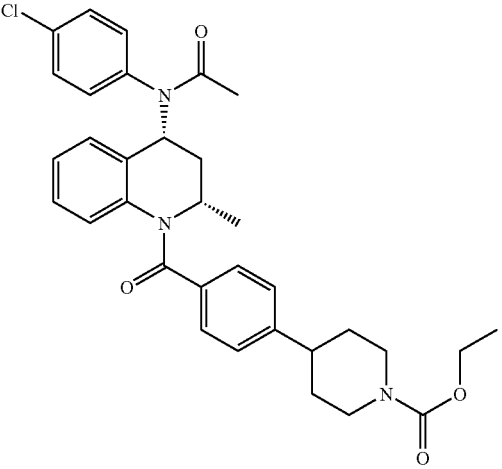 |
| C-20 | 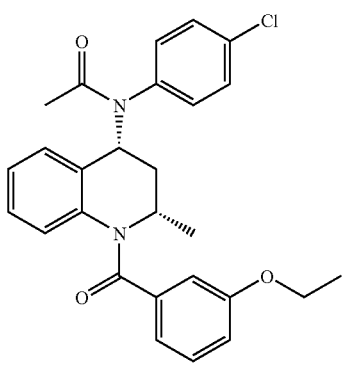 |
| C-21 | 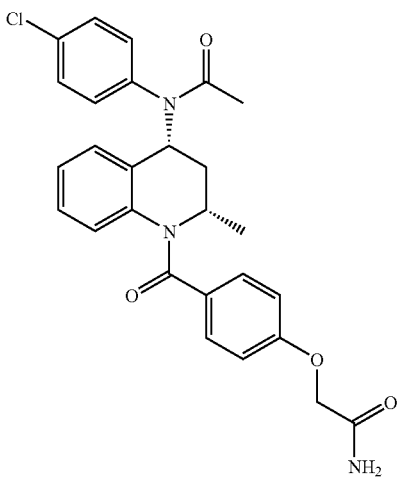 |

TABLE 3-continued
Compounds Derived from General Procedure C
| No. | Structure |
|---|---|
| C-22 | 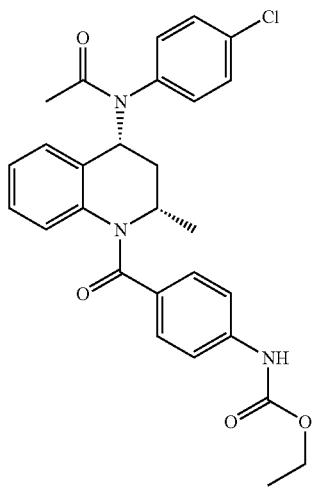 |
| C-23 | 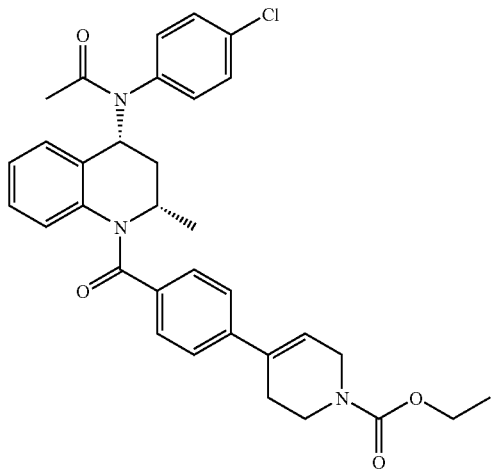 |
| C-24 | 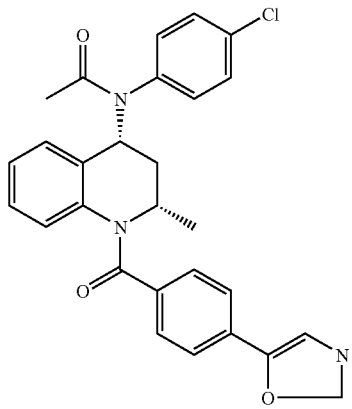 |

TABLE 3-continued
Compounds Derived from General Procedure C
| No. | Structure |
|---|---|
| C-25 | 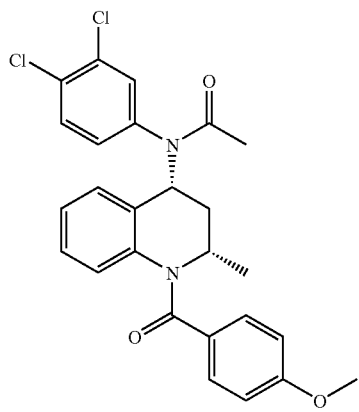 |
| C-26 | 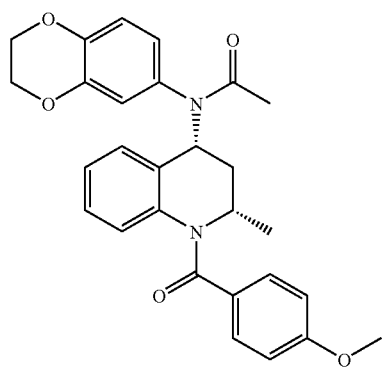 |
| C-27 | 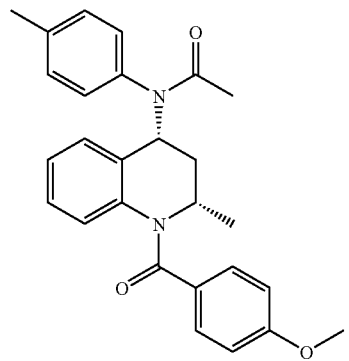 |

TABLE 3-continued
Compounds Derived from General Procedure C
| No. | Structure |
| --- | --- |
| C-28 | 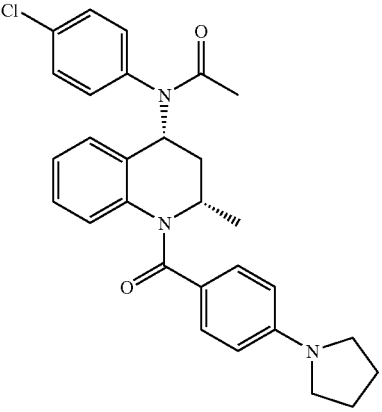 |
| C-29 | 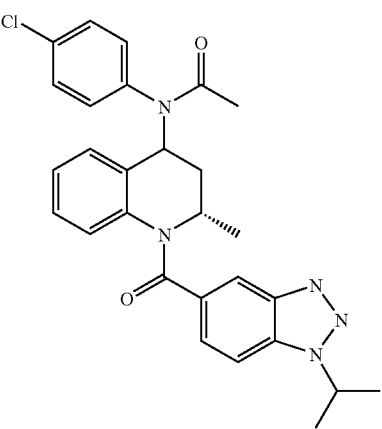 |
| C-30 | 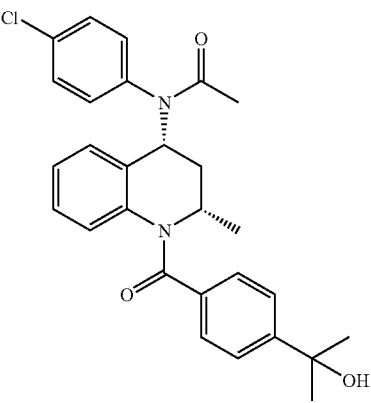 |

TABLE 3-continued
Compounds Derived from General Procedure C
| No. | Structure |
|---|---|
| C-31 | 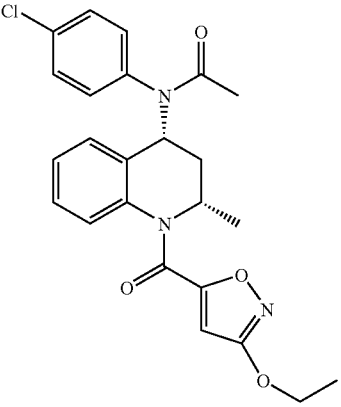 |
| C-32 | 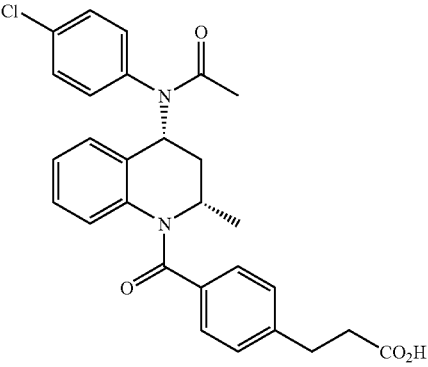 |
| C-33 | 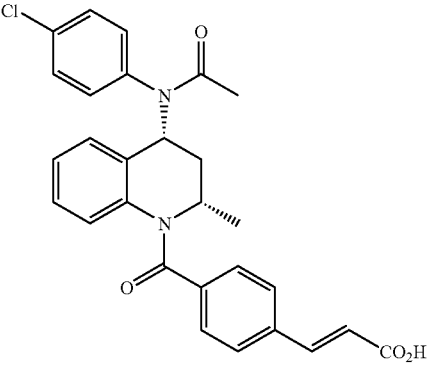 |

TABLE 3-continued
Compounds Derived from General Procedure C
| No. | Structure |
|---|---|
| C-34 | 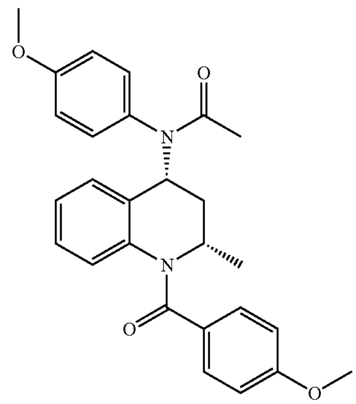 |
| C-35 | 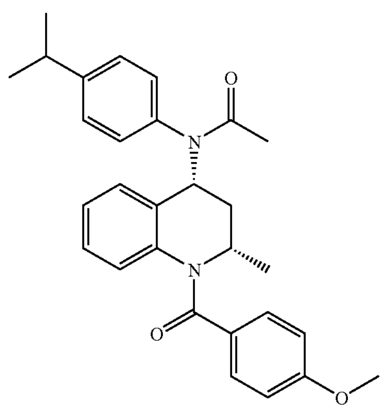 |
| C-36 | 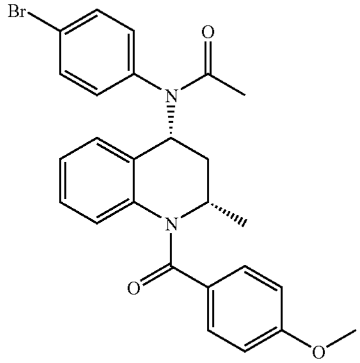 |

TABLE 3-continued
Compounds Derived from General Procedure C
| No. | Structure |
|---|---|
| C-37 | 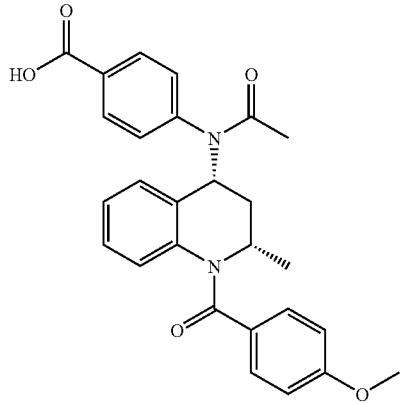 |
| C-38 | 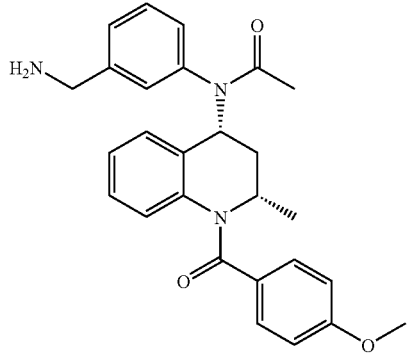 |
| C-39 | 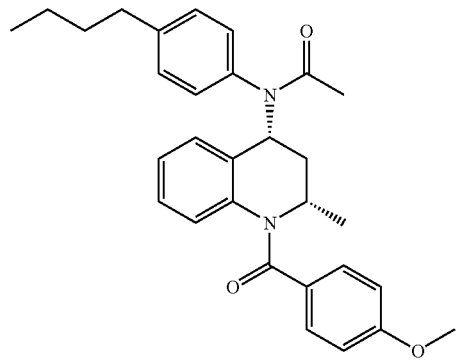 |

TABLE 3-continued
Compounds Derived from General Procedure C
| No. | Structure |
|---|---|
| C-40 | 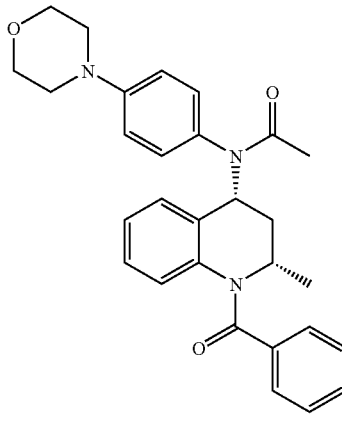 |
| C-41 | 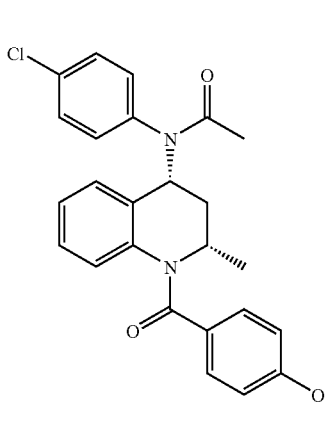 |
| C-42 | 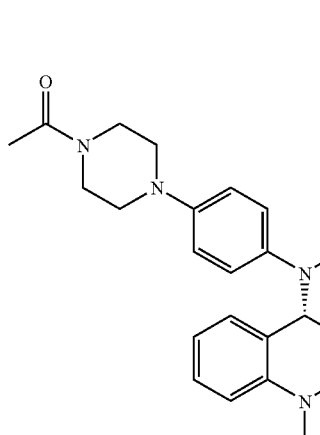 |

TABLE 3-continued
Compounds Derived from General Procedure C
| No. | Structure |
|---|---|
| C-43 | 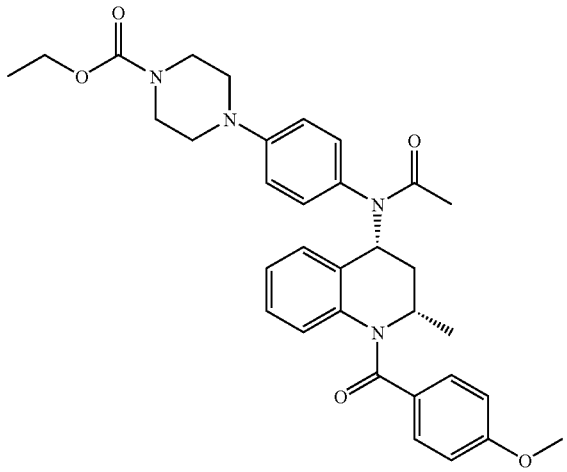 |
| C-44 | 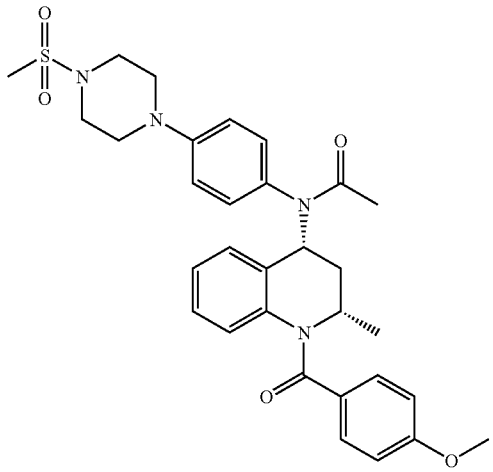 |
| C-45 | 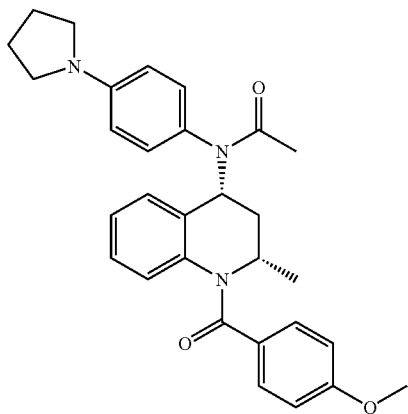 |

TABLE 3-continued

Compounds Derived from General Procedure C

| No. | Structure |
|---|---|
| C-46 | 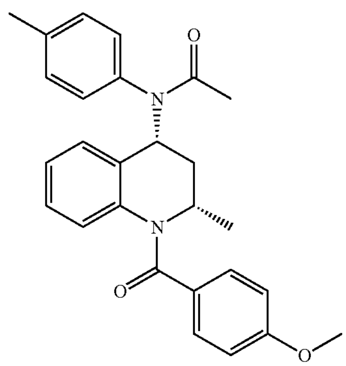 |
| C-47 | 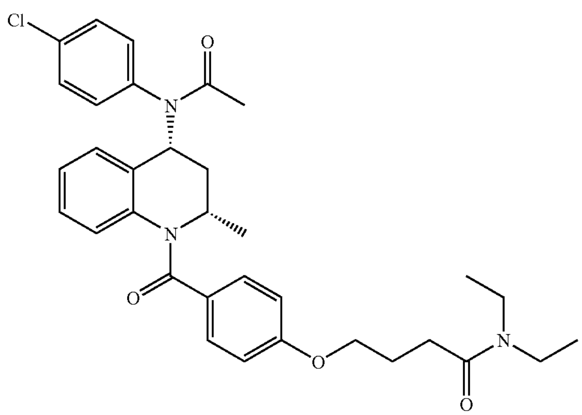 |
| C-48 | 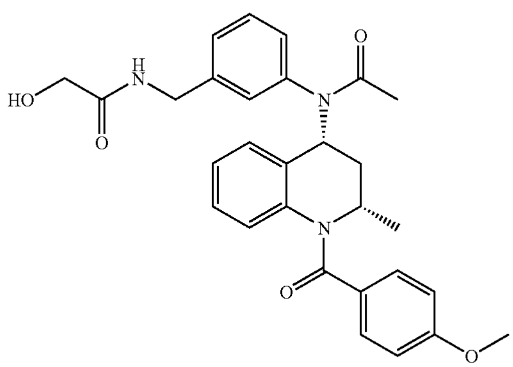 |
| C-49 | 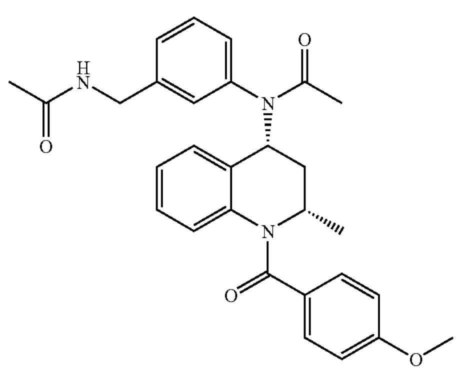 |

TABLE 3-continued

Compounds Derived from General Procedure C

| No. | Structure |
|-----|-----------|
| C-50 | 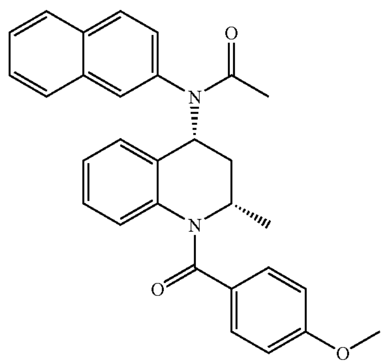 |
| C-51 | 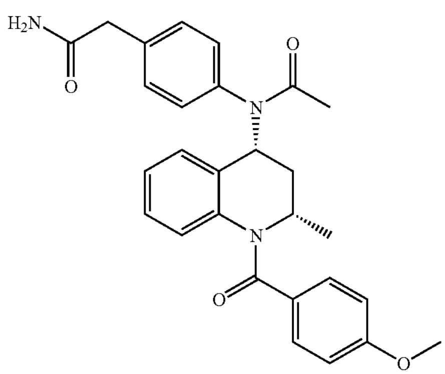 |
| C-52 | 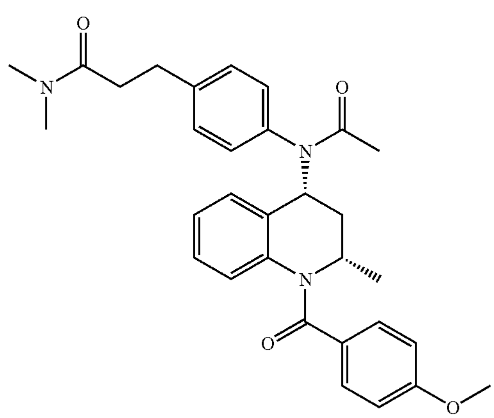 |
| C-53 | 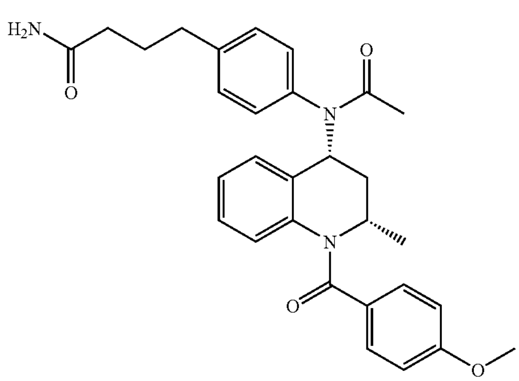 |

TABLE 3-continued
Compounds Derived from General Procedure C
| No. | Structure |
|---|---|
| C-54 | 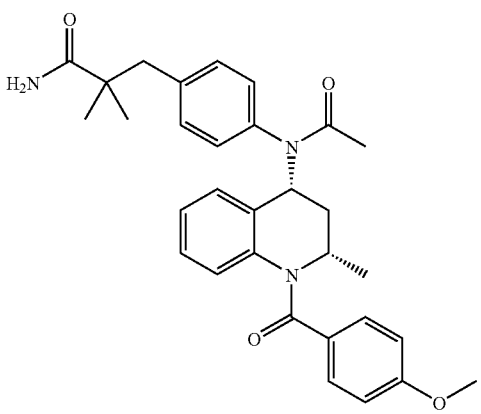 |
| C-55 | 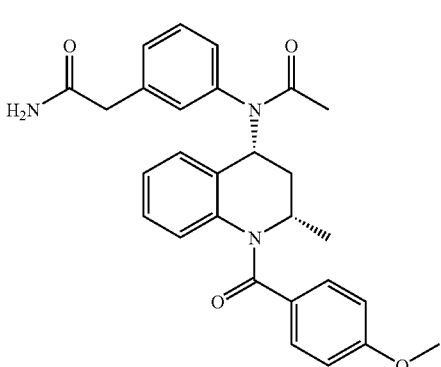 |
| C-56 | 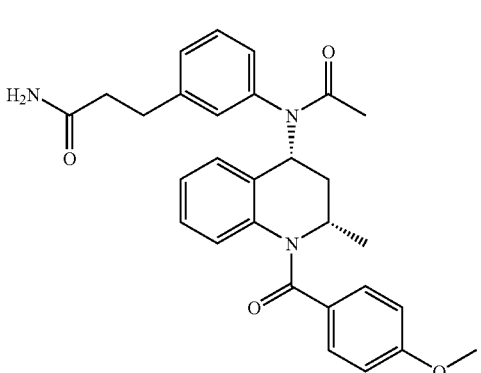 |
| C-57 | 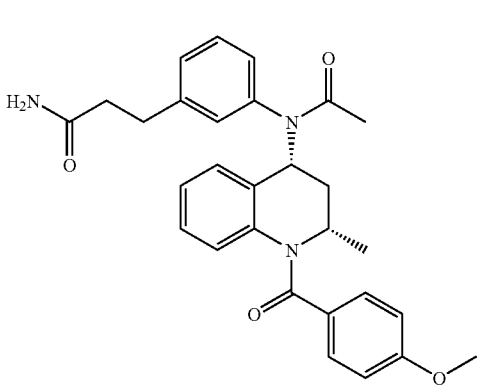 |

TABLE 3-continued
Compounds Derived from General Procedure C
| No. | Structure |
|---|---|
| C-58 | 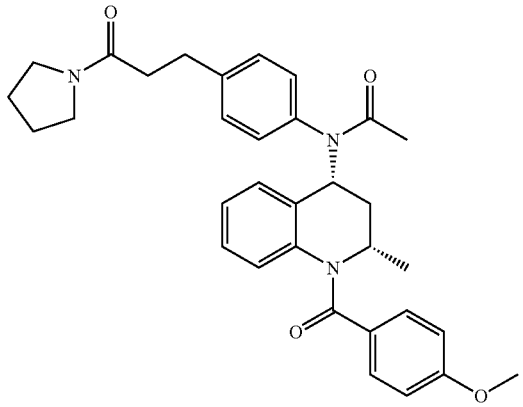 |
| C-59 | 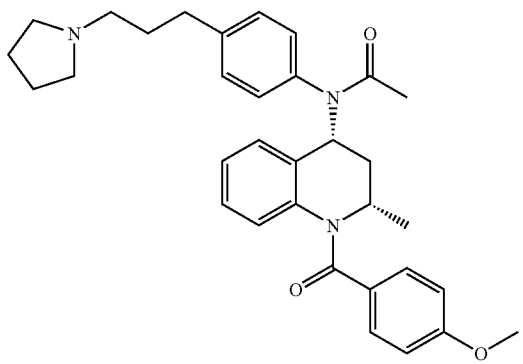 |
| C-60 | 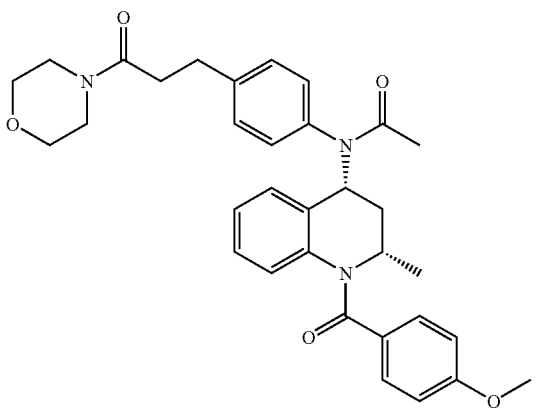 |

TABLE 3-continued
Compounds Derived from General Procedure C
| No. | Structure |
|---|---|
| C-61 | 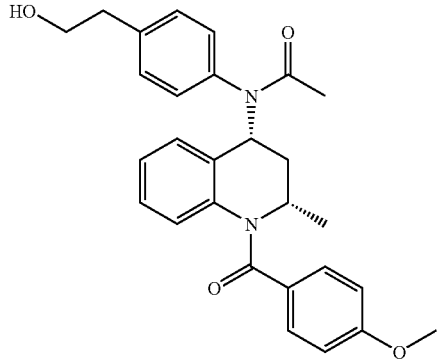 |
| C-62 | 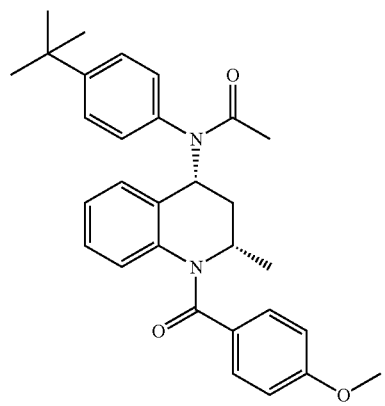 |
| C-63 | 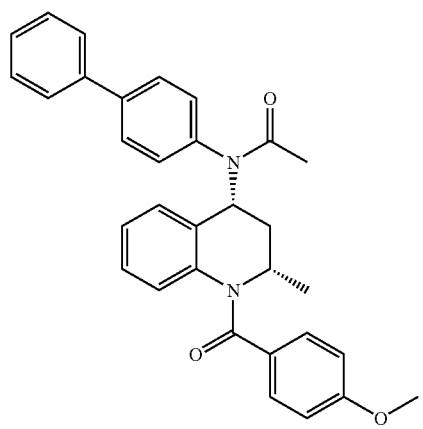 |

TABLE 3-continued

Compounds Derived from General Procedure C

| No. | Structure |
|---|---|
| C-64 | 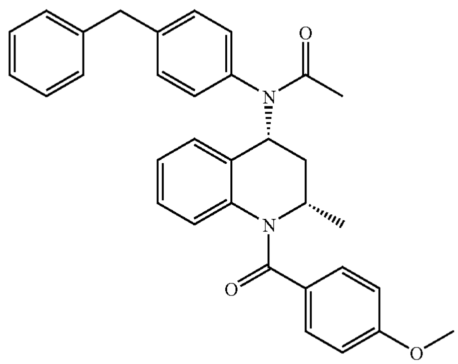 |
| C-65 | 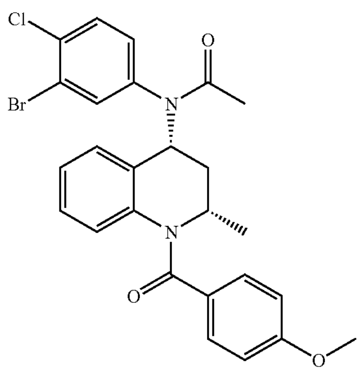 |
| C-66 | 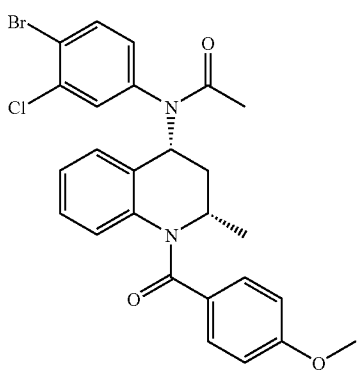 |
| C-67 | 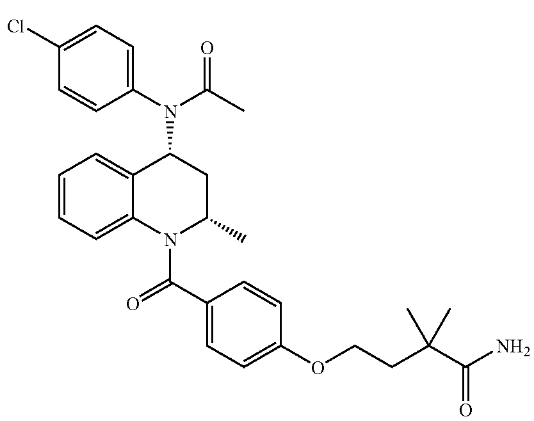 |

TABLE 3-continued

Compounds Derived from General Procedure C

| No. | Structure |
|-----|-----------|
| C-68 | 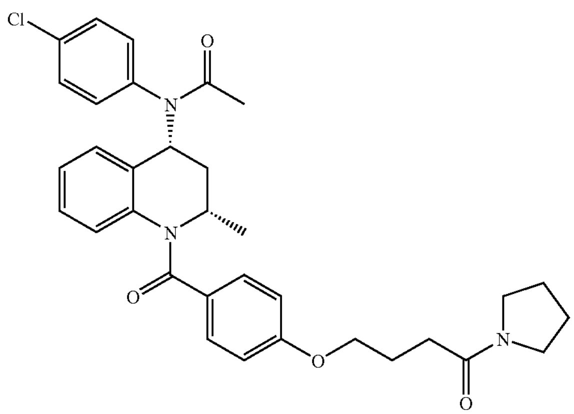 |
| C-69 | 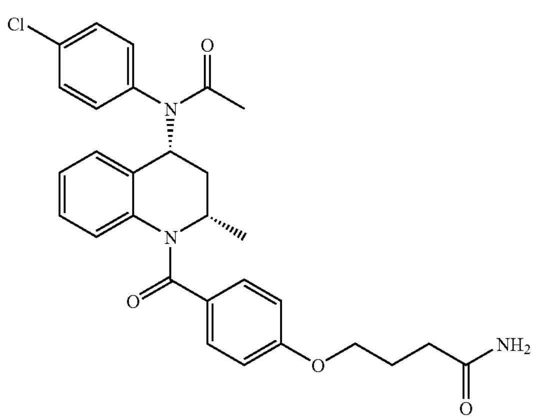 |
| C-70 | 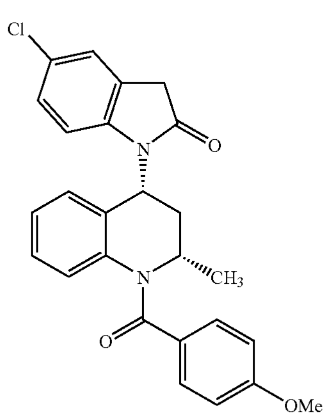 |

TABLE 3-continued
Compounds Derived from General Procedure C
| No. | Structure |
|---|---|
| C-71 | 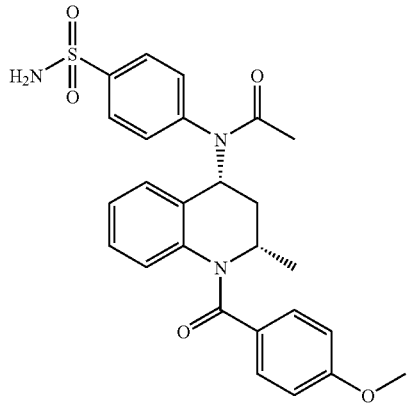 |
| C-72 | 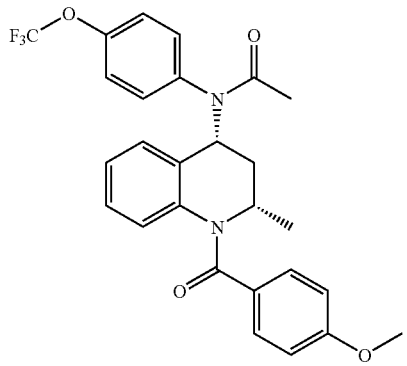 |
| C-73 | 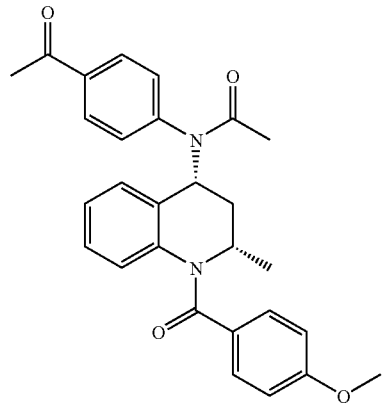 |

TABLE 3-continued

Compounds Derived from General Procedure C

| No. | Structure |
|---|---|
| C-74 | 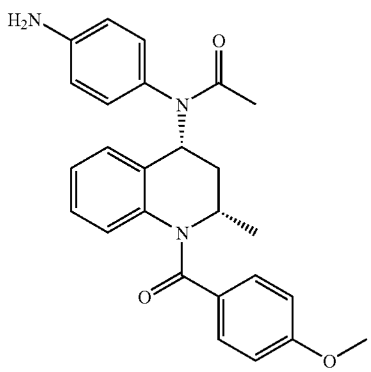 |
| C-75 | 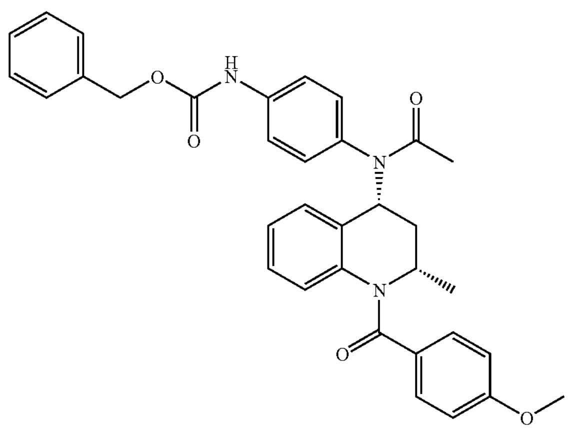 |
| C-76 | 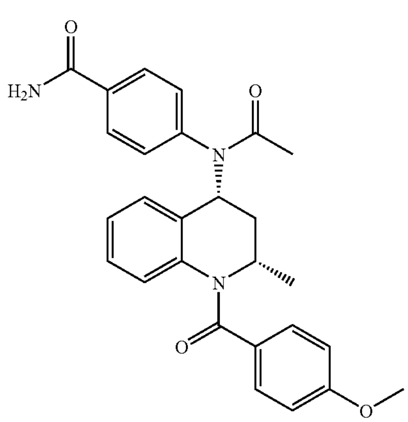 |

TABLE 3-continued
Compounds Derived from General Procedure C
| No. | Structure |
|---|---|
| C-77 | 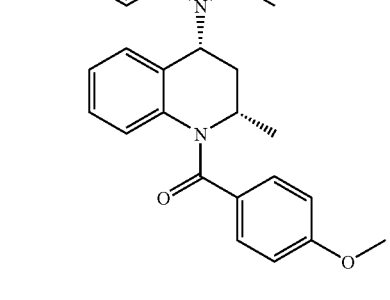 |
| C-78 | 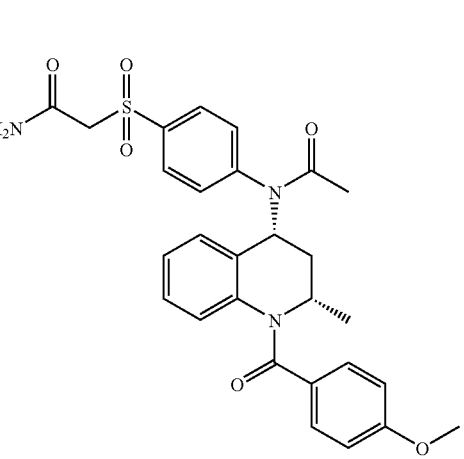 |
| C-79 | 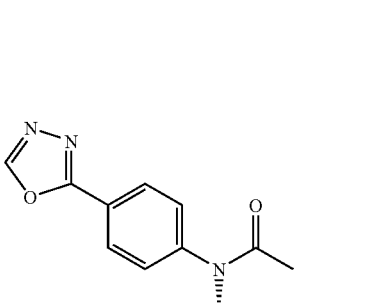 |

TABLE 3-continued
Compounds Derived from General Procedure C
| No. | Structure |
|---|---|
| C-80 | 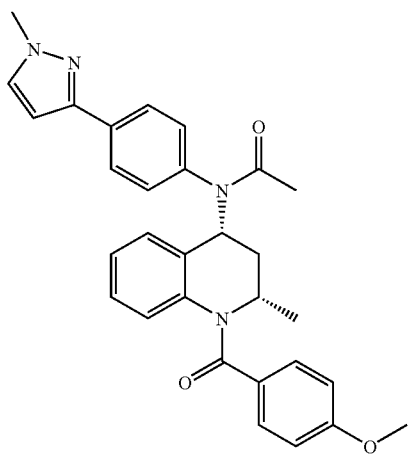 |
| C-81 | 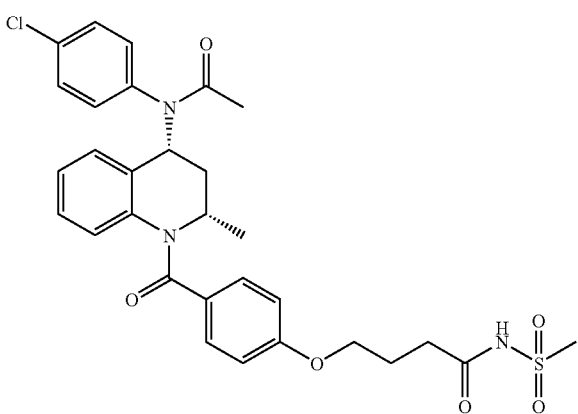 |
| C-82 | 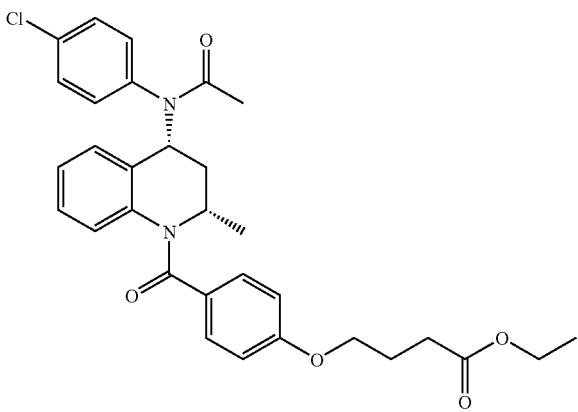 |

TABLE 3-continued
Compounds Derived from General Procedure C
| No. | Structure |
|---|---|
| C-83 | 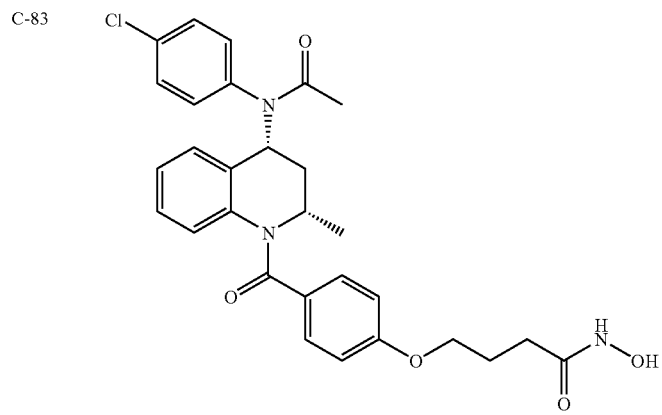 |
| C-84 | 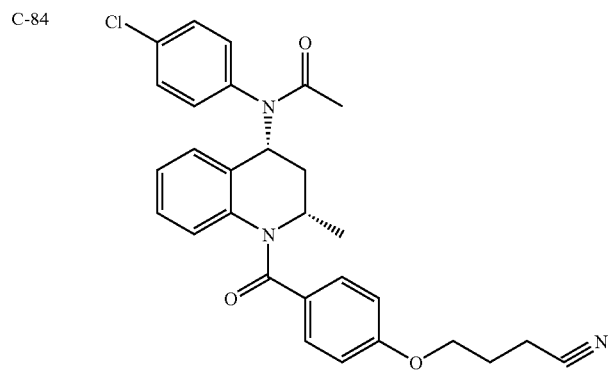 |
| C-85 | 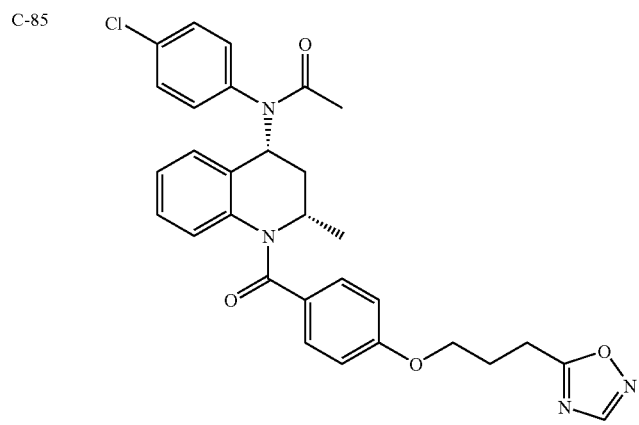 |

TABLE 3-continued

Compounds Derived from General Procedure C

| No. | Structure |
|---|---|
| C-86 | 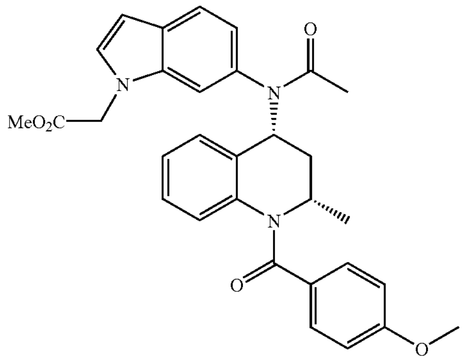 |
| C-87 | 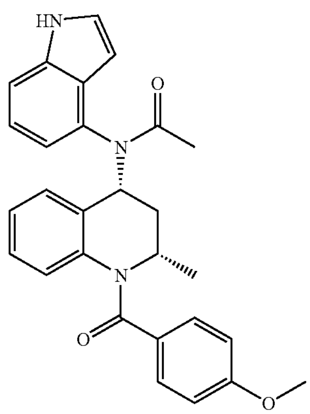 |
| C-88 | 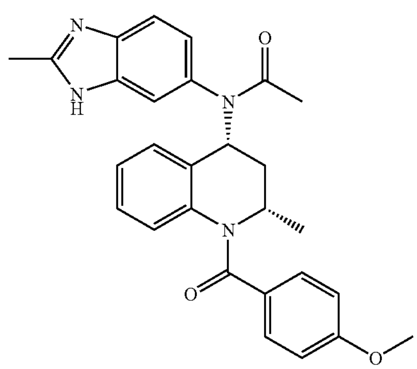 |
| C-89 | 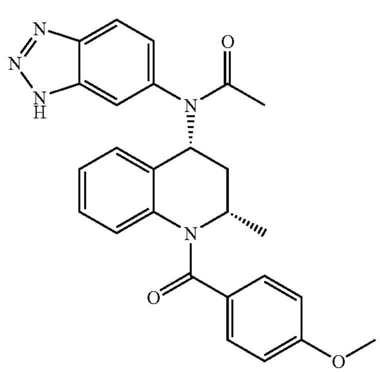 |

TABLE 3-continued
Compounds Derived from General Procedure C
| No. | Structure |
|-----|-----------|
| C-90 | 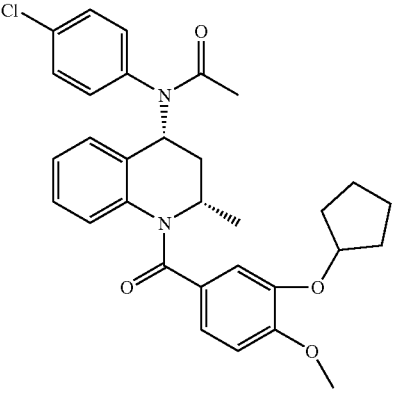 |
| C-91 | 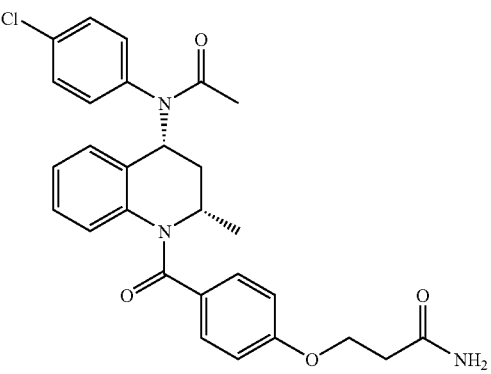 |
| C-92 | 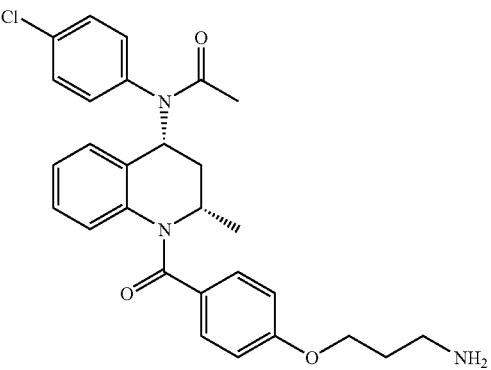 |

TABLE 3-continued
Compounds Derived from General Procedure C
| No. | Structure |
|---|---|
| C-93 | 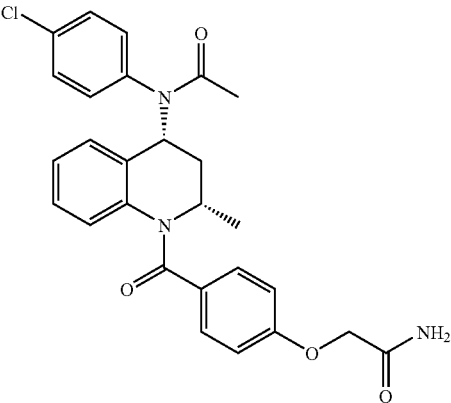 |
| C-94 | 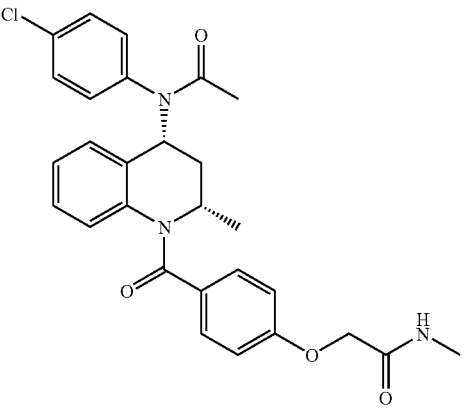 |
| C-95 | 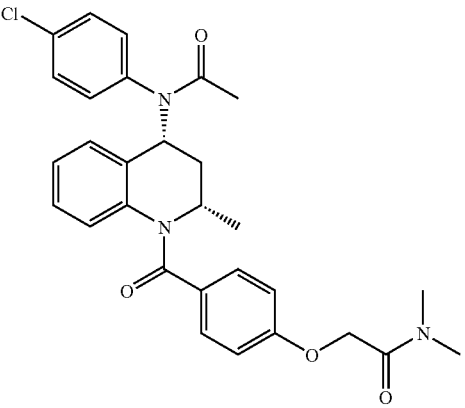 |

TABLE 3-continued

Compounds Derived from General Procedure C

| No. | Structure |
|---|---|
| C-96 | 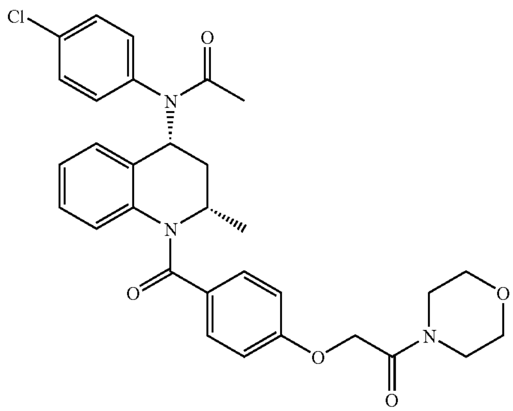 |
| C-97 | 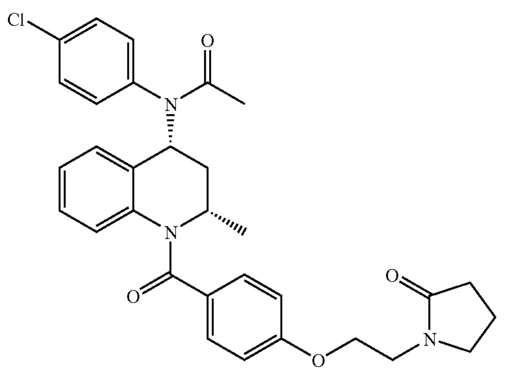 |
| C-98 | 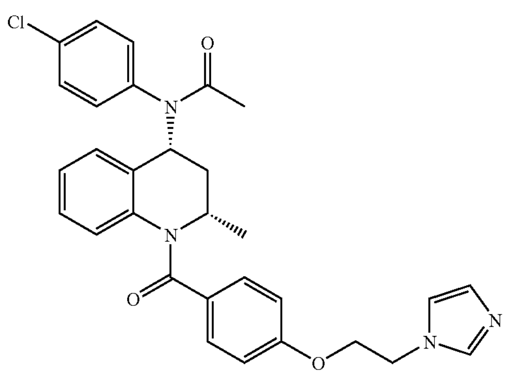 |
| C-99 | 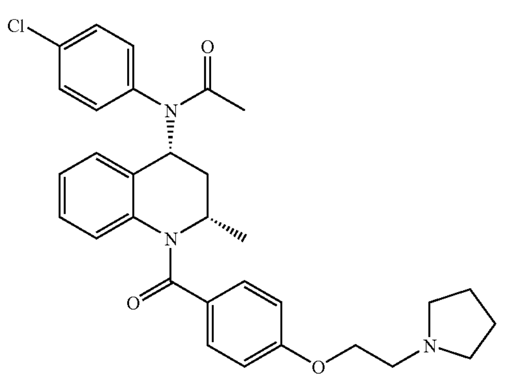 |

TABLE 3-continued

Compounds Derived from General Procedure C

| No. | Structure |
|---|---|
| C-100 | (4-chlorophenyl)-N-acetyl on 4-position of 2-methyl-1-(2,3-dihydrobenzofuran-5-ylcarbonyl)-1,2,3,4-tetrahydroquinoline |
| C-101 | (4-chlorophenyl)-N-acetyl on 4-position of 2-methyl-1-(4-(difluoromethoxy)benzoyl)-1,2,3,4-tetrahydroquinoline |
| C-102 | (4-chlorophenyl)-N-acetyl on 4-position of 2-methyl-1-(4-ethoxybenzoyl)-1,2,3,4-tetrahydroquinoline |
| C-103 | (4-chlorophenyl)-N-acetyl on 4-position of 2-methyl-1-(4-(3-(pyrrolidin-1-yl)propoxy)benzoyl)-1,2,3,4-tetrahydroquinoline |

TABLE 3-continued
Compounds Derived from General Procedure C
| No. | Structure |
|-----|-----------|
| C-104 | 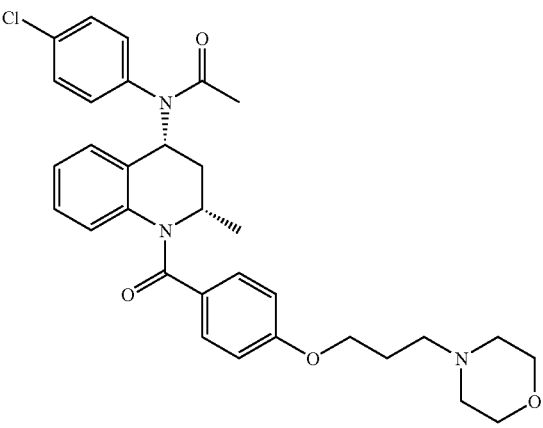 |
| C-105 | 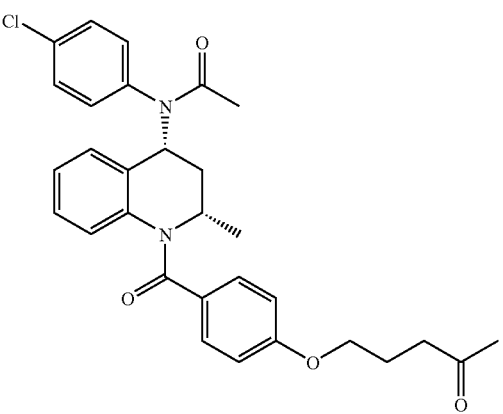 |
| C-106 | 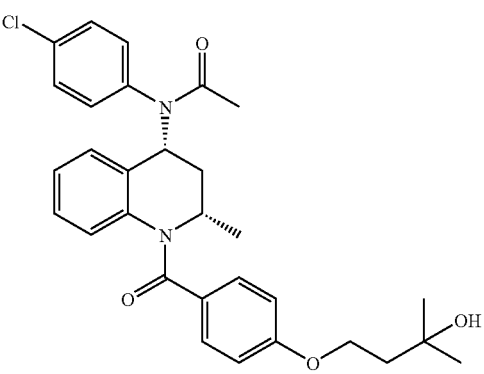 |

TABLE 3-continued
Compounds Derived from General Procedure C
| No. | Structure |
|---|---|
| C-107 | 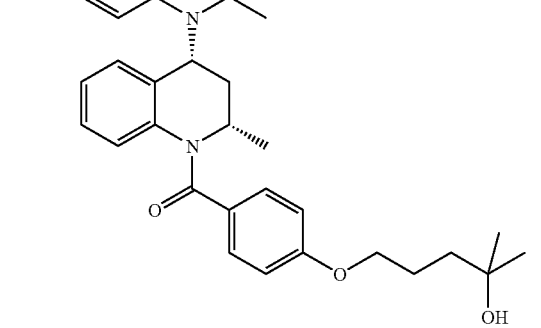 |
| C-108 | 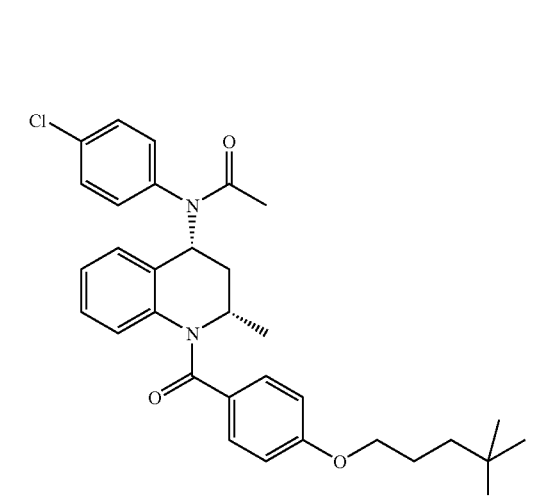 |
| C-109 | 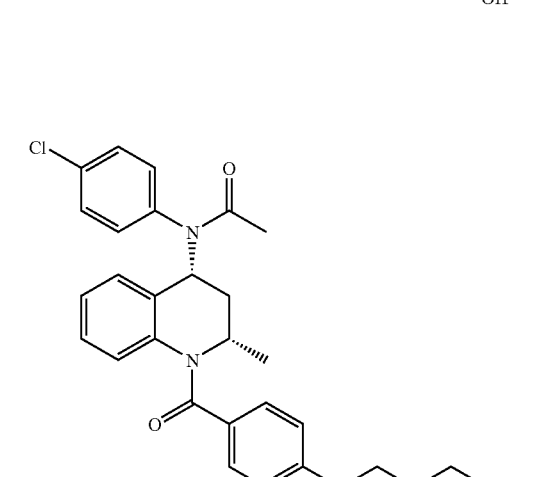 |

TABLE 3-continued
Compounds Derived from General Procedure C
| No. | Structure |
|---|---|
| C-110 | 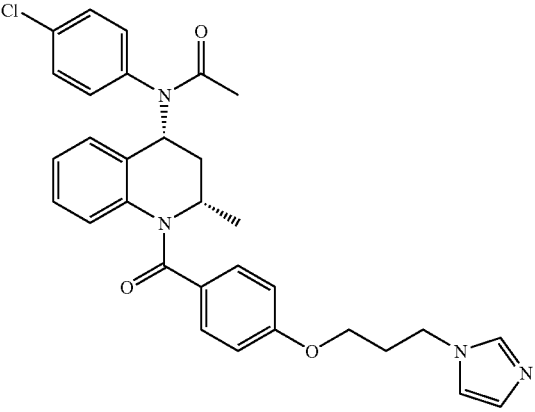 |
| C-111 | 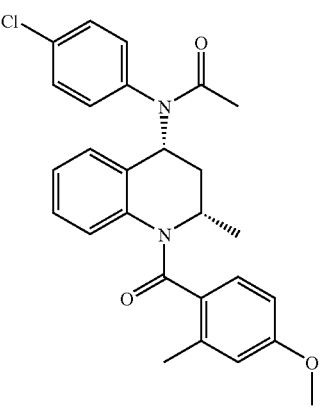 |
| C-112 | 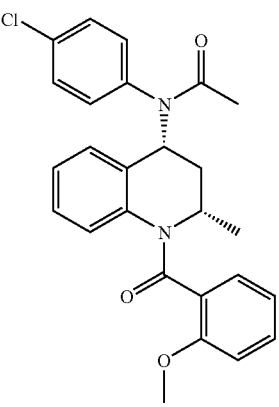 |

TABLE 3-continued
Compounds Derived from General Procedure C
| No. | Structure |
|---|---|
| C-113 | 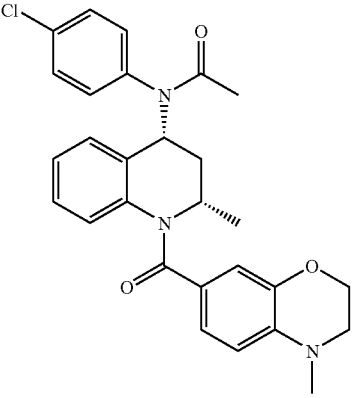 |
| C-114 | 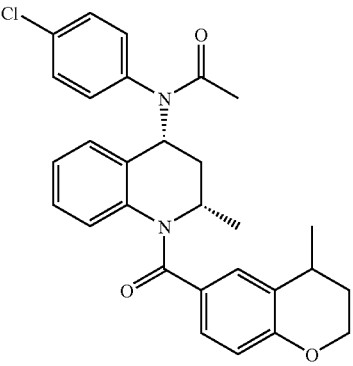 |
| C-115 | 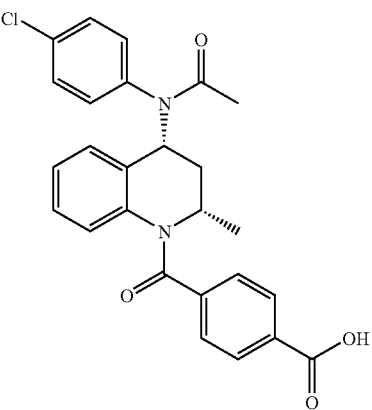 |

TABLE 3-continued
Compounds Derived from General Procedure C
| No. | Structure |
|-----|-----------|
| C-116 | 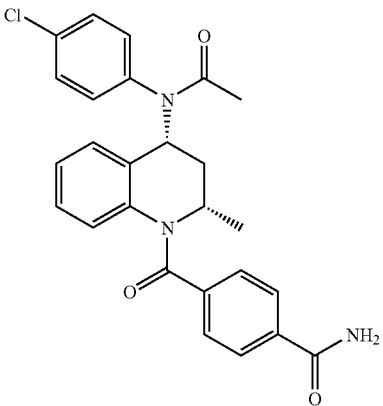 |
| C-117 | 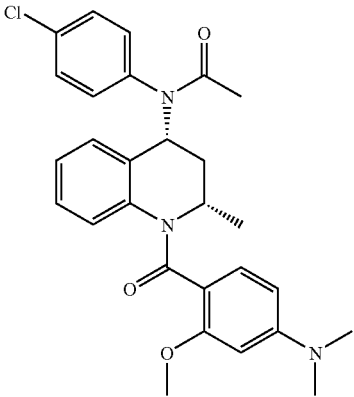 |
| C-118 | 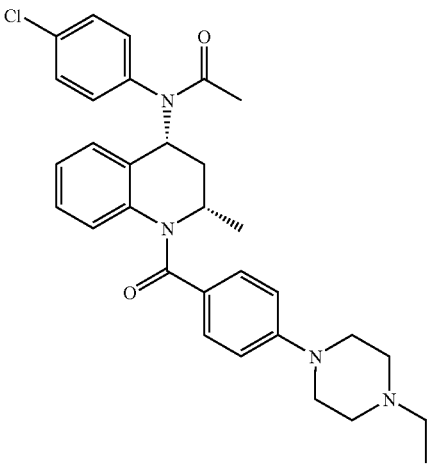 |

TABLE 3-continued
Compounds Derived from General Procedure C
| No. | Structure |
|---|---|
| C-119 | 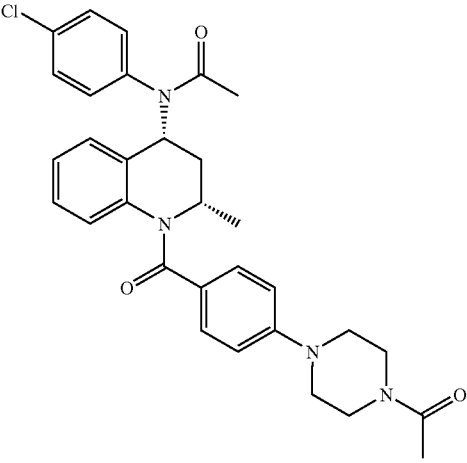 |
| C-120 | 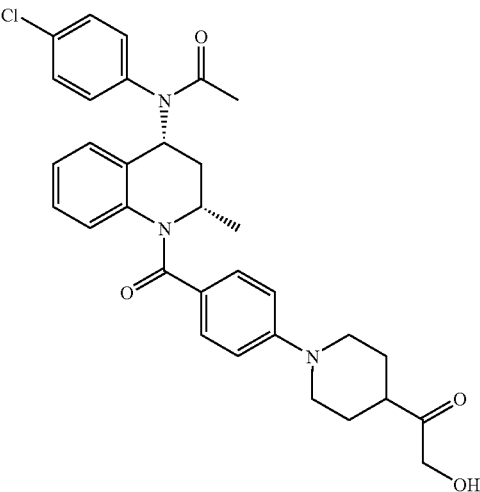 |
| C-121 | 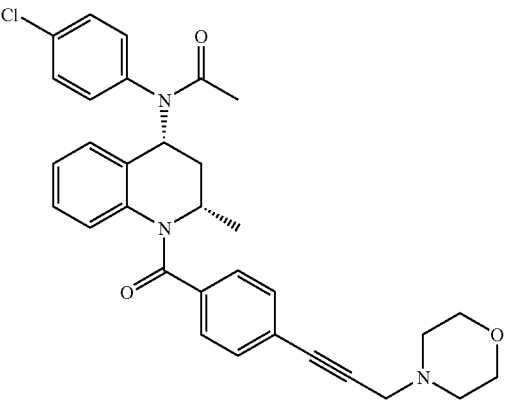 |

TABLE 3-continued

Compounds Derived from General Procedure C

| No. | Structure |
|---|---|
| C-122 | 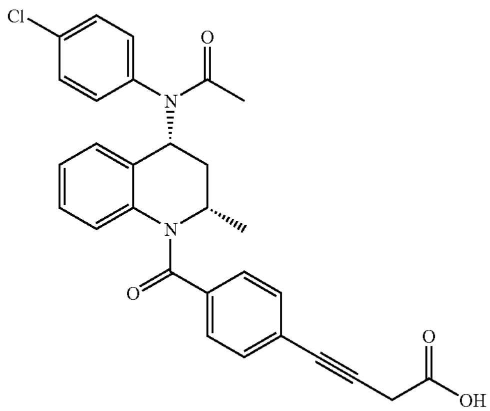 |
| C-123 | 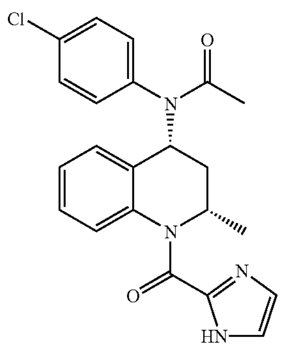 |
| C-124 | 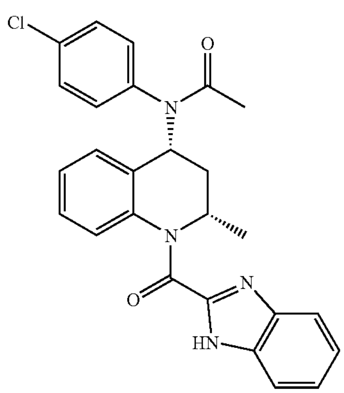 |
| C-125 | 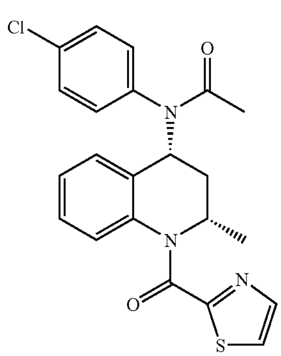 |

TABLE 3-continued
Compounds Derived from General Procedure C
| No. | Structure |
|---|---|
| C-126 | 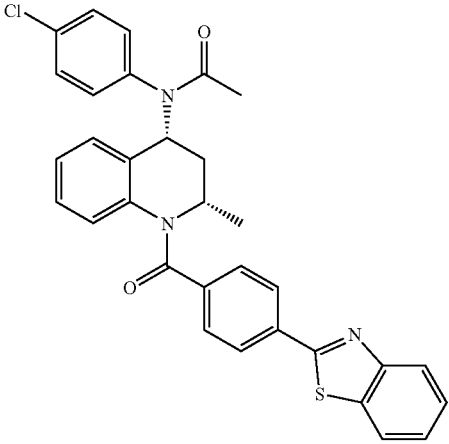 |
| C-127 | 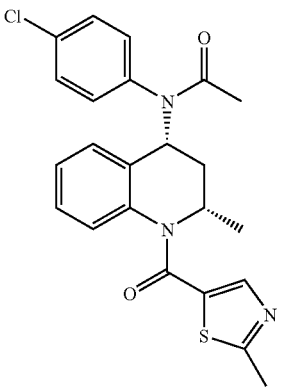 |
| C-128 | 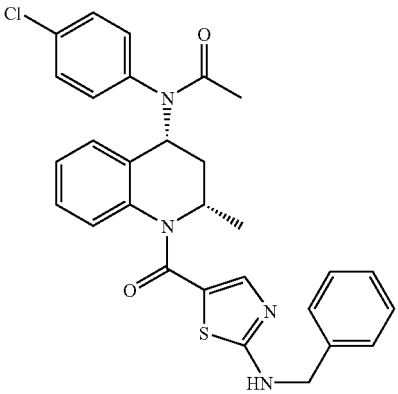 |

TABLE 3-continued
Compounds Derived from General Procedure C
| No. | Structure |
|---|---|
| C-129 | 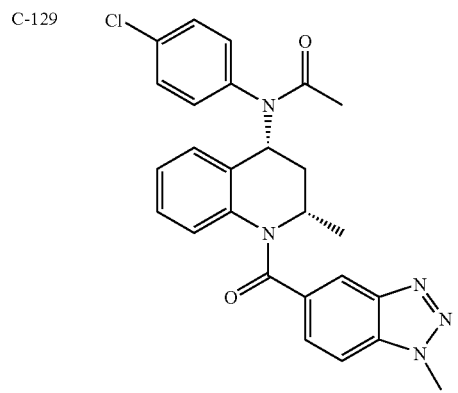 |
| C-130 | 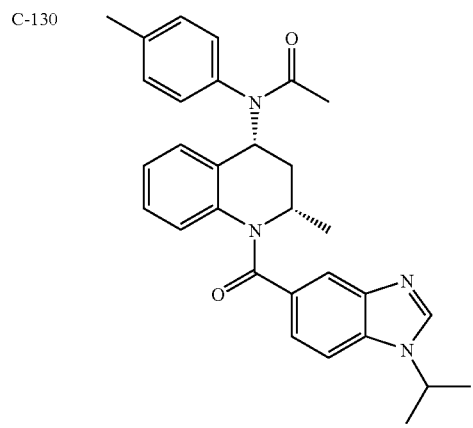 |
| C-131 | 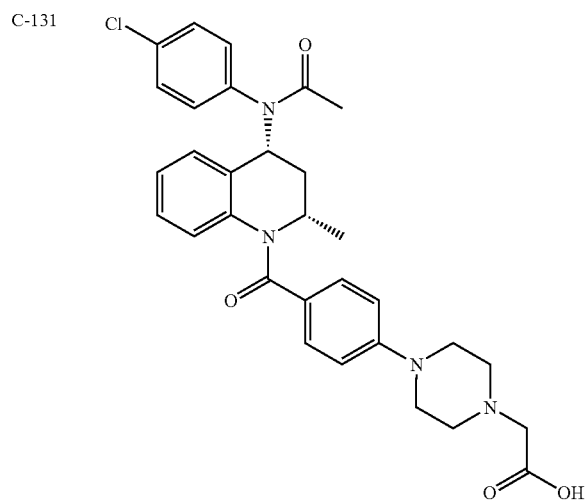 |

TABLE 3-continued
Compounds Derived from General Procedure C
| No. | Structure |
|---|---|
| C-132 | 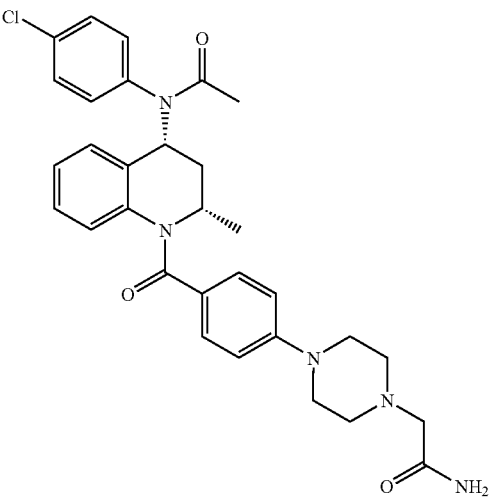 |
| C-133 | 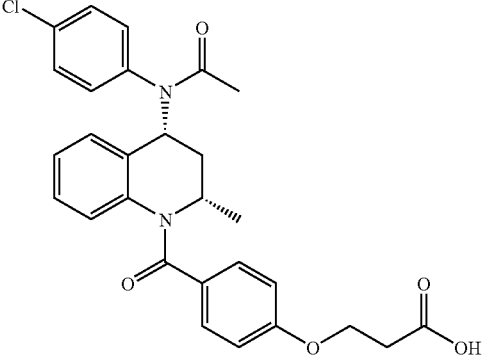 |
| C-134 | 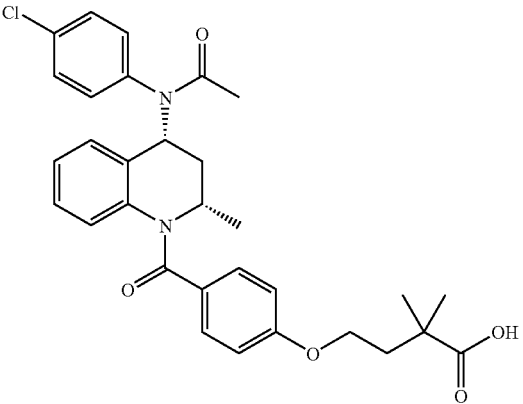 |

TABLE 3-continued
Compounds Derived from General Procedure C
| No. | Structure |
|---|---|
| C-135 | 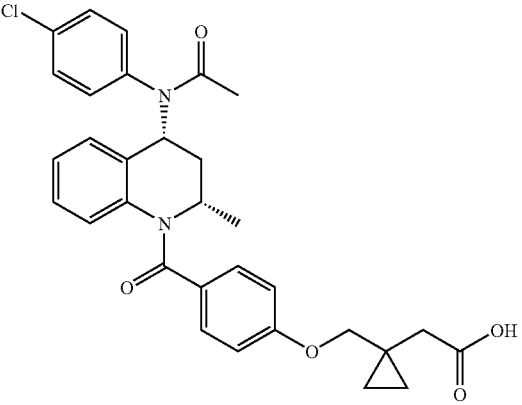 |
| C-136 | 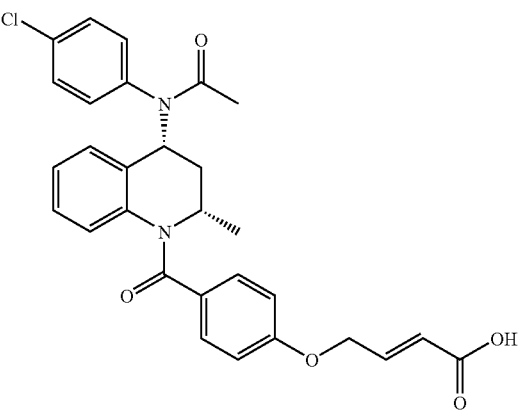 |
| C-137 | 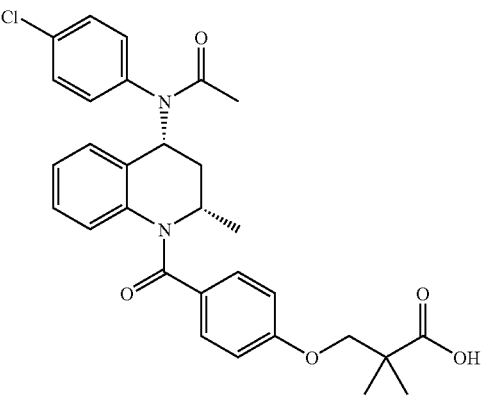 |

TABLE 3-continued
Compounds Derived from General Procedure C
| No. | Structure |
|---|---|
| C-138 | 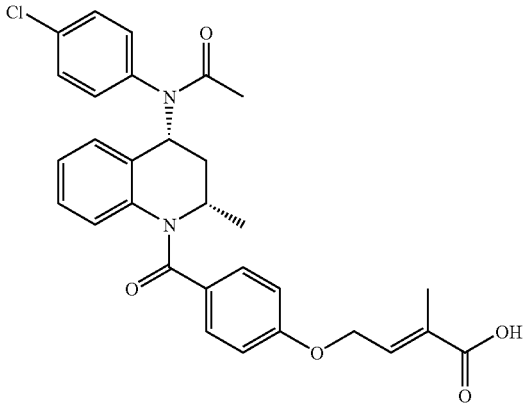 |
| C-139 | 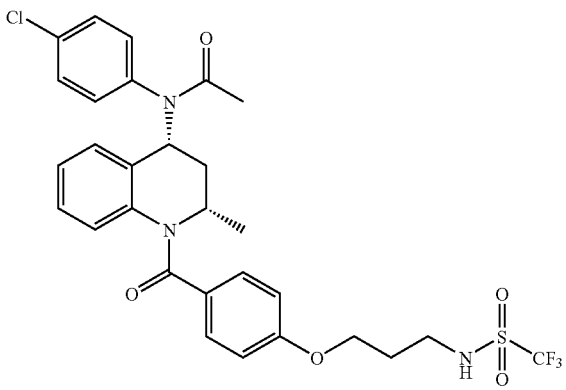 |
| C-140 | 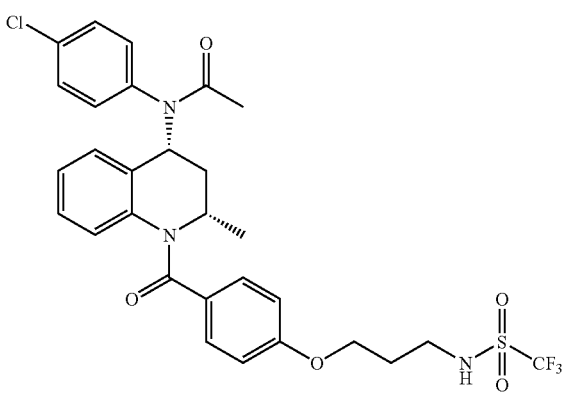 |

TABLE 3-continued
Compounds Derived from General Procedure C
| No. | Structure |
|---|---|
| C-141 | 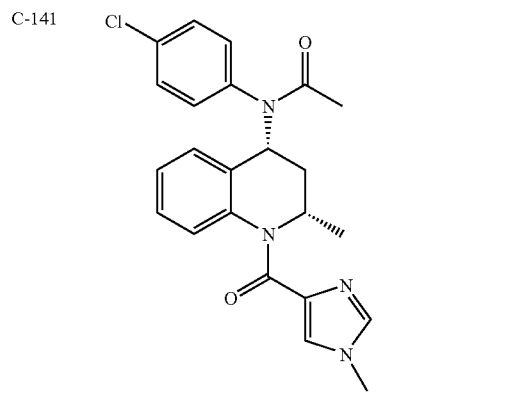 |
| C-142 | 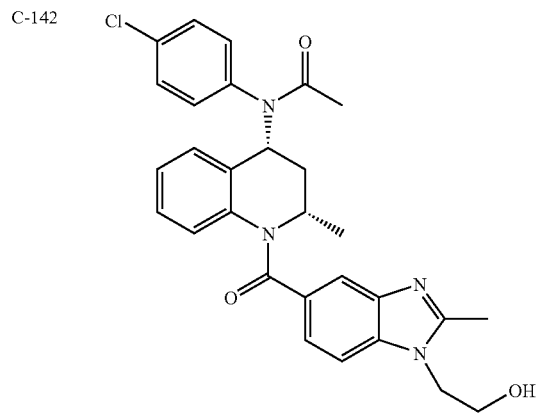 |
| C-143 | 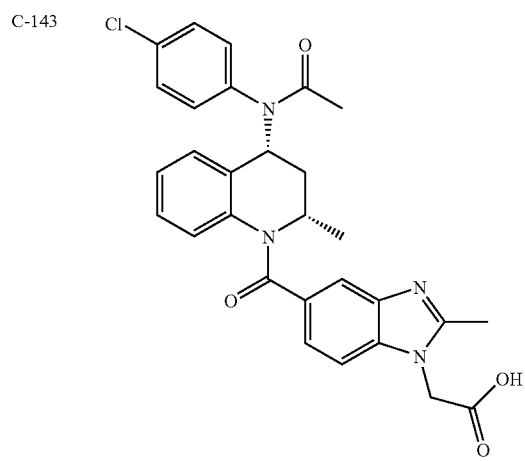 |

TABLE 3-continued
Compounds Derived from General Procedure C
| No. | Structure |
|---|---|
| C-144 | 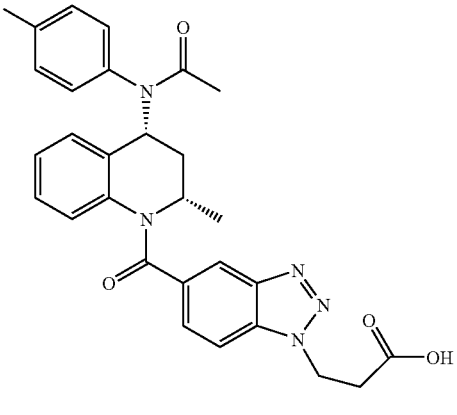 |
| C-145 | 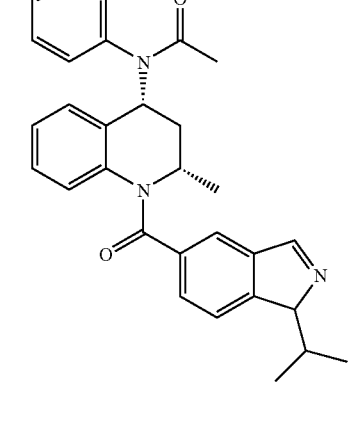 |
| C-146 | 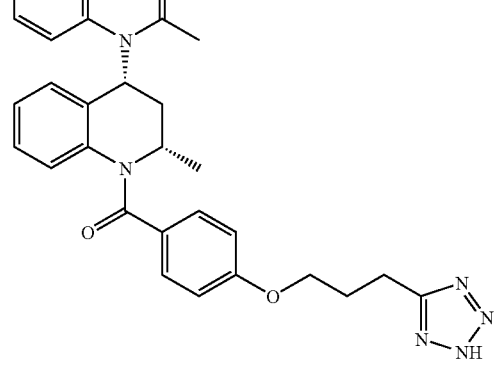 |

General Procedure D

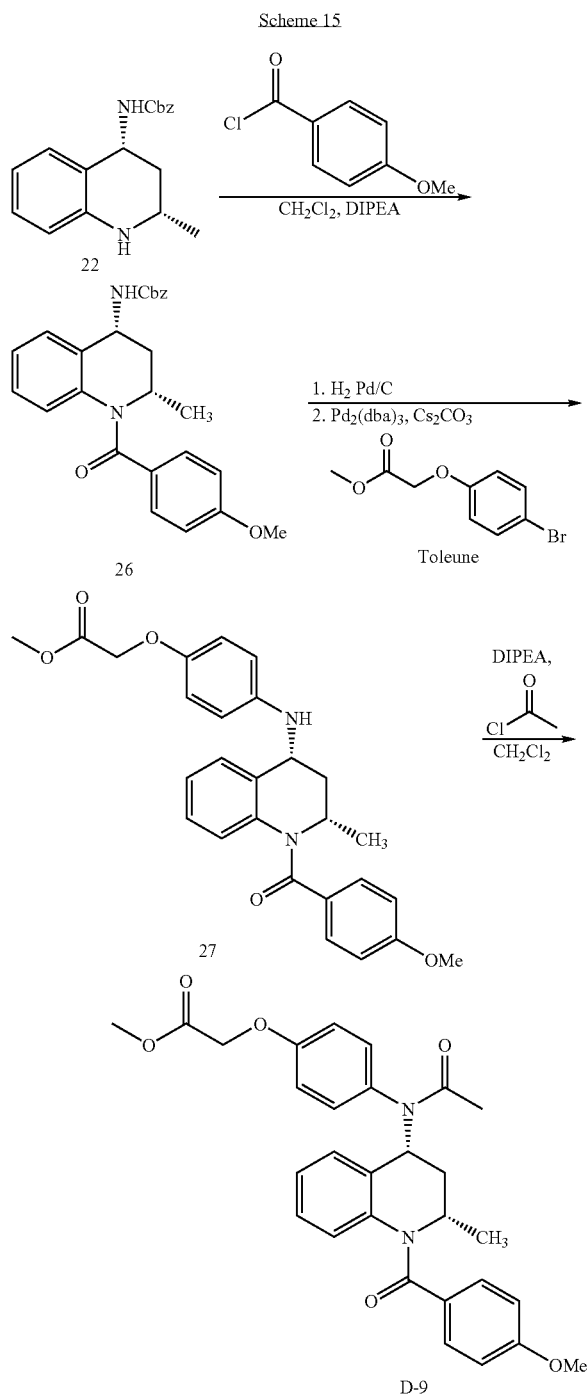

(2S,4R)-((4-{Acetyl-[1-(4-methoxy-benzoyl)-2-methyl-1,2,3,4-tetrahydro-quinolin-4-yl]-amino}-phenoxy)-acetic acid methyl ester (D-9)

(2S,4R)-((4-{Acetyl-[1-(4-methoxy-benzoyl)-2-methyl-1,2,3,4-tetrahydro-quinolin-4-yl]-amino}-phenoxy)-acetic acid methyl ester was prepared from (2S,4R)-(2-methyl-1,2,3,4-tetrahydro-quinolin-4-yl)-carbamic acid benzyl ester as shown below. (2S,4R)-(2-Methyl-1,2,3,4-tetrahydro-quinolin-4-yl)-carbamic acid benzyl ester (7.6 g, 25.65 mmol) was dissolved in dichloromethane (50 mL) and the resulting solution was cooled to 0° C. Triethylamine (14.3 mL) followed by freshly distilled anisoyl chloride (8.75 mL, 51.3 mmol) dissolved in dichloromethane (15 mL) were added dropwise to this solution. The resulting reaction mixture was allowed to warm to room temperature and stir over night. The mixture was partitioned between dichloromethane and 1 M sodium hydroxide. The extracts were washed with brine, dried over magnesium sulfate, filtered and concentrated. The crude amide was purified by silica gel chromatography (2:1 hexane:ethyl acetate) to afford pure product (10 g, 91%).

The (2S,4R)-[1-(4-methoxy-benzoyl)-2-methyl-1,2,3,4-tetrahydro-quinolin-4-yl]-carbamic acid benzyl ester thus formed (10 g) was dissolved in ethanol (400 mL). Palladium (10% on Carbon) was added. The black suspension was stirred under an atmosphere of hydrogen for 3 h. The mixture was filtered and concentrated. The crude amine was purified by filtration through a short silica plug (elution with ethyl acetate to 90/10 ethyl acetate/methanol gradient) to afford pure amine (5.17 g, 72%).

(2S,4R)-(4-Amino-2-methyl-3,4-dihydro-2H-quinolin-1-yl)-(4-methoxyphenyl)-methanone (100 mg, 0.34 mmol), methyl-2-(4-bromophenoxy)-acetate (91 mg, 0.37 mmol), $Pd_2(dba)_3$ (17 mg, 0.02 mmol), 2-dicyclohexylphosphino-2'-(N,N-dimethylamino)biphenyl (8 mg, 0.00002 mol) and cesium carbonate (0.163 g, 0.0005 mol) were taken in a round bottom flask which was then flushed with nitrogen gas through a rubber septum. Toluene (2 mL) was injected into the flask through the rubber septum and the reaction mixture was stirred at 100° C. for 24 h. After cooling to room temperature the reaction mixture was filtered through Celite® and evaporated to give the crude product (0.236 g). This crude product was purified by silica gel chromatography eluting with 100% hexanes to 50/50 hexanes/ethyl acetate gradient give the title compound (37 mg, 24%).

Freshly distilled acetyl chloride (0.5 mL) was added to a solution of the aniline thus prepared (0.037 g, 0.00008 mol) followed by diisopropylethylamine (0.0114 g, 0.015 mL, 0.088 mmol) in dichloromethane (0.5 mL); the mixture was stirred at room temperature for 2-days. The reaction mixture was neutralized with 1 M sodium bicarbonate. The organic layer was separated, washed thrice with water, brine, dried over magnesium sulfate and evaporated. The resulting crude product was purified by silica gel chromatography eluting with (0% to 70% ethyl acetate in hexanes to afford the titled compound (15 mg, 38%).

$^1$H-NMR (CDCl$_3$) δ: 1.12–1.14 (4H, m), 2.02 (3H, s), 2.18–2.43 (1H, m), 3.75 (3H, s) 3.82 (3H, s), 4.65 (2H, s), 4.67–4.82 (1H, m), 5.45–5.73 (1H, broad), 6.52 (1H), 6.68 (2H, d), 6.89–6.95 (3H, m), 7.13–7.21 (5H, m), 7.32 (1H, d).

MS m/z: 504 (M+1).

(2S,4R)-(4-{Acetyl-[1-(4-methoxybenzoyl)-2-methyl-1,2,3,4-tetrahydro-quinolin-4-yl]-amino}-phenoxy)-acetic Acid (D-10)

(2S,4R)-(4-{Acetyl-[1-(4-methoxybenzoyl)-2-methyl-1,2,3,4-tetrahydro-quinolin-4-yl]-amino}-phenoxy)-acetic acid was prepared from (2S,4R)-(4-{acetyl-[1-(4-methoxy-benzoyl)-2-methyl-1,2,3,4-tetrahydro-quinolin-4-yl]-amino}-phenoxy)-acetic acid methyl ester (15 mg, 0.03 mmol). The methyl ester was dissolved in methanol (1 mL), sodium hydroxide (1 mL, 0.1 M in water) was added and the resulting solution was stirred at room temperature for 18 h. The reaction mixture was acidified with hydrochloric acid (1 M) and concentrated under reduced pressure. The residue was extracted with ethyl acetate and the extract was washed thrice with water, brine, dried over sodium sulphate, filtered and concentrated to yield the title compound (13 mg, 89%).

¹H-NMR (CDCl₃) δ: 1.07 (4H, m), 1.99 (3H, s), 2.12–2.38 (1H, broad), 3.7 (4H, s), 4.61 (2H, s), 4.66–4.78 (1H, m), 5.47–5.75 (1H, broad), 6.49 (1H, d), 6.64 (2H, d), 6.86–6.9 (3H, m), 7.09–7.16 (5H, m), 7.27 (1H, d).

MS m/z 489 (M⁺), 490 (M+1)

(2S,4R)-2-(4-{Acetyl-[1-(4-methoxy-benzoyl)-2-methyl-1,2,3,4-tetrahydro-quinolin-4-yl]-amino}-phenyl)-2-methyl-propionic Acid (D-1)

(2S,4R)-2-(4-{Acetyl-[11-(4-methoxy-benzoyl)-2-methyl-1,2,3,4-tetrahydro-quinolin-4-yl]-amino}-phenyl)-2-methyl-propionic acid was prepared via saponification of 2-(4-{acetyl-[1-(4-methoxy-benzoyl)-2-methyl-1,2,3,4-tetrahydro-quinolin-4-yl]-amino}-phenyl)-2-methyl-propionic acid methyl ester, as described in the synthesis of (2S,4R)-(4-{acetyl-[1-(4-methoxybenzoyl)-2-methyl-1,2,3,4-tetrahydro-quinolin-4-yl]-amino}-phenoxy)-acetic acid. The methyl ester was prepared following general procedure D, substituting 2-(4-bromo-phenyl)-2-methyl-propionic acid for methyl-2-(4-bromophenoxy)-acetate.

¹H-NMR (300 MHz, CD₃OD) δ: 1.07–1.18 (m, 4H), 1.58 (s, 6H), 2.02 (s, 3H), 2.42–2.56 (m, 1H), 3.76 (s, 3H), 4.74 (ddd, 1H), 5.55 (br s, 1H), 6.56 (d, 1H), 6.75 (d, 2H), 6.97 (dd, 1H), 7.13–7.27 (m, 3H), 7.36 (d, 2H), 7.42–7.55 (m, 3H).

(2S,4R)-4-(4-{Acetyl-[1-(4-methoxy-benzoyl)-2-methyl-1,2,3,4-tetrahydro-quinolin-4-yl]-amino}-2-chloro-phenyl)-4-oxo-butyric acid (D-2)

(2S,4R)-4-(4-{Acetyl-[11-(4-methoxy-benzoyl)-2-methyl-1,2,3,4-tetrahydro-quinolin-4-yl]-amino}-2-chloro-phenyl)-4-oxo-butyric acid was prepared from the corresponding methyl ester following the procedure above for the synthesis of (2S,4R)-(4-{acetyl-[1-(4-methoxybenzoyl)-2-methyl-1,2,3,4-tetrahydro-quinolin-4-yl]-anmino}-phenoxy)-acetic acid. The corresponding methyl ester was prepared following general procedure D, substituting 4-(4-bromo-2-chloro-phenyl)-4-oxo-butyric acid methyl ester for methyl-2-(4-bromophenoxy)-acetate.

¹H-NMR (300 MHz, CD₃OD) δ: 1.10–1.19 (m, 4H), 2.08 (br s, 3H), 2.41–2.56 (m, 1H), 2.69–2.74 (m, 2H), 3.20–3.26 (m, 2H), 3.75 (s, 3H), 4.74 (ddd, 1H), 5.45–5.62 (brs, 1H), 6.57 (d, 1H), 6.74 (d, 2H), 6.98 (dd, 1H), 7.16 (d, 2H), 7.20–7.27 (m, 1H), 7.42–7.49 (m, 2H), 7.60 (br s, 1), 7.73 (d, 1H).

MS m/z: 549 (M+1).

(2S,4R)-N-(4-Dimethylsulfamoyl-phenyl)-N-[1-(4-methoxy-benzoyl)-2-methyl-1,2,3,4-tetrahydro-quinolin-4-yl]-acetamide (D-3)

(2S,4R)-N-(4-Dimethylsulfamoyl-phenyl)-N-[1-(4-methoxy-benzoyl)-2-methyl-1,2,3,4-tetrahydro-quinolin-4-yl]-acetamide was prepared following general procedure D, substituting 4-bromo-N,N-dimethyl-benzenesulfonamide for methyl-2-(4-bromophenoxy)-acetate.

¹H-NMR (CDCl₃) δ: 1.1 (3H, d), 1.1 (1H, m), 2.0 (3H, s), 2.3 (1H, m), 2.8 (6H, s), 3.8 (3H, s), 4.8 (1H, m), 5.6 (1H, m), 6.6 (1H, d), 6.7 (2H, d), 6.9 (1H, t), 7.2 (3H, m), 7.3 (1H, m), 7.5 (2H, d), 7.8 (2H, d).

MS m/z: 522 (M+1).

(2S,4R)-N-[1-(4-Methoxy-benzoyl)-2-methyl-1,2,3,4-tetrahydro-quinolin-4-yl]-N-[4-(pyrrolidine-1-sulfonyl)-phenyl]-acetamide (D-4)

(2S,4R)-N-[1-(4-Methoxy-benzoyl)-2-methyl-1,2,3,4-tetrahydro-quinolin-4-yl]-N-[4-(pyrrolidine-1-sulfonyl)-phenyl]-acetamide was prepared following general procedure D, substituting 1-(4-bromo-benzenesulfonyl)-pyrrolidine for methyl-2-(4-bromophenoxy)-acetate.

¹H-NMR (CDCl₃) δ: 1.1 (3H, d), 1.1 (1H, m), 1.7 (4H, m), 2.0 (3H, s), 2.3 (1H, m), 3.3 (4H, m), 3.7 (3H, s), 4.7 (1H, m), 5.6 (1H, m), 6.5 (1H, d), 6.6 (2H, d), 6.9 (1H, t), 7.3 (4H, m), 7.4 (2H, d), 7.9 (2H, d).

MS m/z: 548 (M+1).

(2S,4R)-N-(4-Methanesulfonyl-phenyl)-N-[1-(4-methoxy-benzoyl)-2-methyl-1,2,3,4-tetrahydro-quinolin-4-yl]-acetamide (D-5)

(2S,4R)-N-(4-Methanesulfonyl-phenyl)-N-[1-(4-methoxy-benzoyl)-2-methyl-1,2,3,4-tetrahydro-quinolin-4-yl]-acetamide was made following general procedure D, substituting 1-bromo-4-methanesulfonyl-benzene for methyl-2-(4-bromophenoxy)-acetate.

¹H-NMR (CDCl₃) δ: 1.1–1.2 (3H, m), 2.0–2.2 (4H, m), 2.3 (1H, m), 3.1 (3H, s), 3.7 (3H, s), 4.8 (1H), 5.6–5.8 (1H, br), 6.5 (1H, d), 6.6 (2H, d), 6.9 (1H, t), 7.1–7.3 (4H, m), 7.4 (2H, d), 8.0 (2H, d).

MS m/z: 493 (M+1).

(2S,4R)-3-(4-{Acetyl-[1-(4-methoxy-benzoyl)-2-methyl-1,2,3,4-tetrahydro-quinolin-4-yl]-amino}-phenyl)-propionic acid (D-6)

(2S,4R)-3-(4-{Acetyl-[1-(4-methoxy-benzoyl)-2-methyl-1,2,3,4-tetrahydro-quinolin-4-yl]-amino}-phenyl)-propionic acid was prepared from (2S,4R)-N-(4-bromo-phenyl)-N-[1-(4-methoxy-benzoyl)-2-methyl-1,2,3,4-tetrahydro-quinolin-4-yl]-acetamide. (2S,4R)-N-(4-Bromo-phenyl)-N-[1-(4-methoxy-benzoyl)-2-methyl-1,2,3,4-tetrahydro-quinolin-4-yl]-acetamide was converted to the acrylic acid using the same procedure described in the synthesis of (±)-3-[4-[(4-chloro-phenyl)-propionyl-amino]-1-(4-fluoro-benzoyl)-2-methyl-1,2,3,4-tetrahydro-quinolin-6-yl]-acrylic acid. The reduction and saponification were carried out as in the procedure describing the preparation of (2S,4R)-3-(4-{4-[acetyl-(4-chloro-phenyl)-amino]-2-methyl-3,4-dihydro-2H-quinoline-1-carbonyl}-phenyl)-propionic acid.

¹H-NMR (CDCl₃ 300 MHz) δ 1.12 (3H, d), 1.20–1.24 (1H, m), 2.00 (3H, s), 2.22–2.38 (1H, m), 2.52 (2H, t), 3.00 (2H, t), 3.72 (3H, s), 4.64–4.79 (1H, m), 5.44–5.70 (1H, m), 6.50 (1H, d), 6.65 (2H, d), 6.90 (1H, t), 7.10–7.28 (7H, m), 7.32 (1H, d).

(2S,4R)-3-(4-{Acetyl-[1-(4-methoxy-benzoyl)-2-methyl-1,2,3,4-tetrahydro-quinolin-4-yl]-amino}-phenyl)-propionamide (D-7)

(2S,4R)-3-(4-{Acetyl-[1-(4-methoxy-benzoyl)-2-methyl-1,2,3,4-tetrahydro-quinolin-4-yl]-amino}-phenyl)-propionamide was prepared from (2S,4R)-3-(4-{Acetyl-[1-(4-methoxy-benzoyl)-2-methyl-1,2,3,4-tetrahydro-quinolin-4-yl]-amino}-phenyl)-propionic acid. To a solution of 3-(4-{acetyl-[1-(4-methoxy-benzoyl)-2-methyl-1,2,3,4-tetrahydro-quinolin-4-yl]-amino}-phenyl)-propionic acid (21 mg, 0.042 mmol) in dimethylformamide (200 µl) was added HATU (24 mg, 0.063 mmol), HOBt (8.5 mg, 0.063 mmol), NH₄Cl (4.5 mg, 0.084 mmol) and DIPEA (29 µl, 0.168 mmol). Upon consumption of the starting unit (2.5 hours), the mixture was diluted with EtOAc (10 ml) and washed with sat. NaHCO₃ (4×10 ml). The EtOAc layer was collected, dried over Na₂SO₄, filtered, and concentrated to afford the title compound (17.2 mg, 82%).

¹H-NMR (CDCl₃ 300 MHz) δ 1.09 (3H, d), 1.20–1.24 (1H, m), 2.02 (3H, s), 2.22–2.38 (1H, m), 2.52 (2H, t), 3.00 (2H, t), 3.73 (3H, s), 4.64–4.79 (1H, m), 5.30–5.70 (3H, m), 6.50 (1H, d), 6.68 (2H, d), 6.91 (1H, t), 7.10–7.28 (7H, m), 7.32 (1H, d).

343

(2S,4R)-N-[1-(4-Methoxy-benzoyl)-2-methyl-1,2,3,4-tetrahydro-quinolin-4-yl]-N-(4-nitro-phenyl)-acetamide (D-8)

(2S,4R)-N-[1-(4-Methoxy-benzoyl)-2-methyl-1,2,3,4-tetrahydro-quinolin-4-yl]-N-(4-nitro-phenyl)-acetamide was made following general procedure D, substituting 4-bromonitrobenzene for methyl-2-(4-bromophenoxy)-acetate.

$^1$H-NMR (CDCl$_3$ 300 MHz) δ 1.12 (3H, d), 1.20–1.24 (1H, m), 2.07 (3H, s), 2.20–2.35 (1H, m), 3.73 (3H, s), 4.66–4.81 (1H, m), 5.50–5.78 (1H, m), 6.55 (1H, d), 6.68 (2H, d), 6.96 (1H, t), 7.10–7.32 (4H, m), 7.46 (2H, d), 8.28 (2H, d).

MS m/z: 460 (M+1).

TABLE 4

Compounds Derived from General Procedure D

| No. | Structure |
|---|---|
| D-1 | 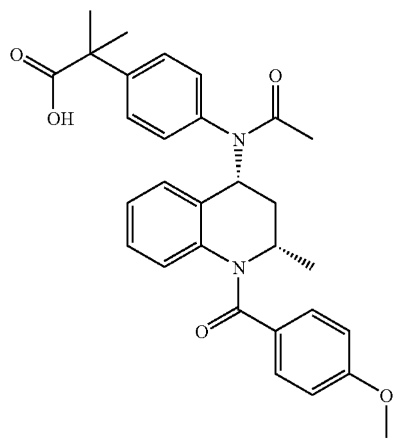 |
| D-2 | 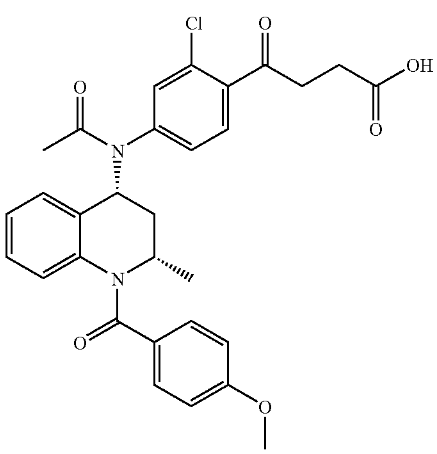 |

344

TABLE 4-continued

Compounds Derived from General Procedure D

| No. | Structure |
|---|---|
| D-3 | 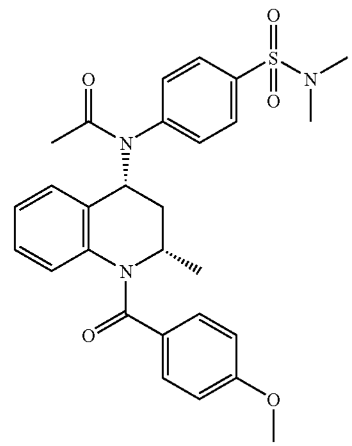 |
| D-4 | 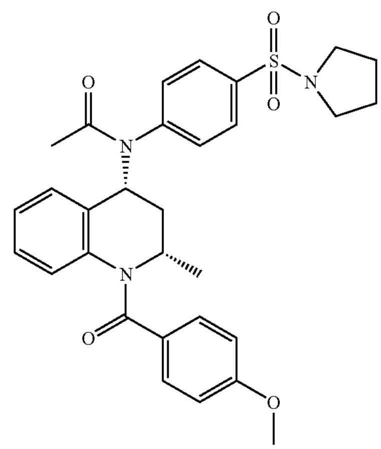 |
| D-5 | 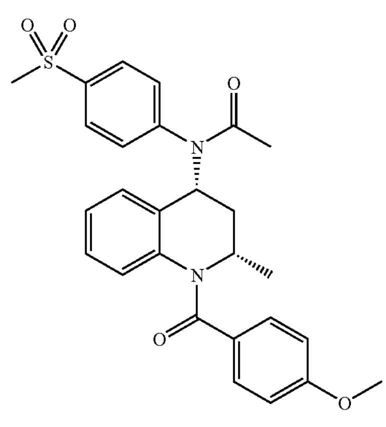 |

TABLE 4-continued
Compounds Derived from General Procedure D
| No. | Structure |
|---|---|
| D-6 | 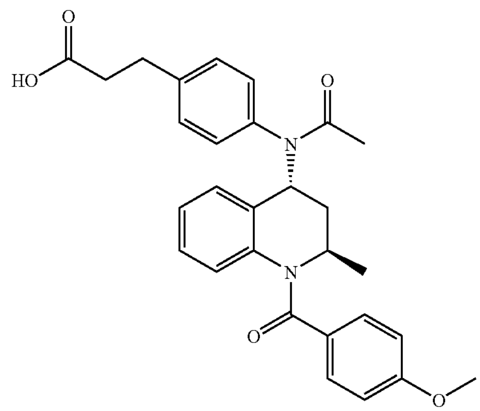 |
| D-7 | 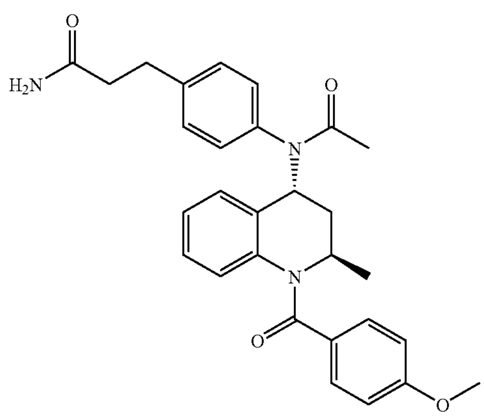 |
| D-8 | 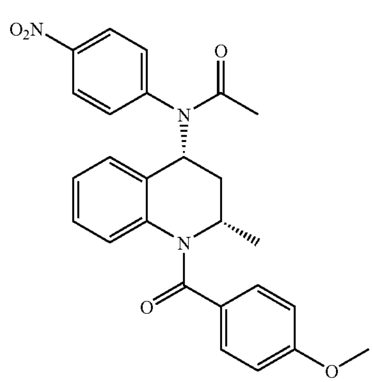 |
| D-9 | |
| D-10 | |
General Procedure E
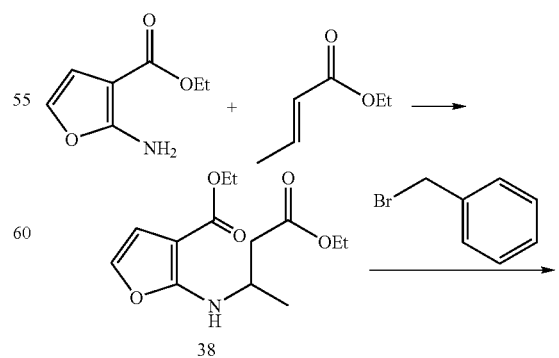

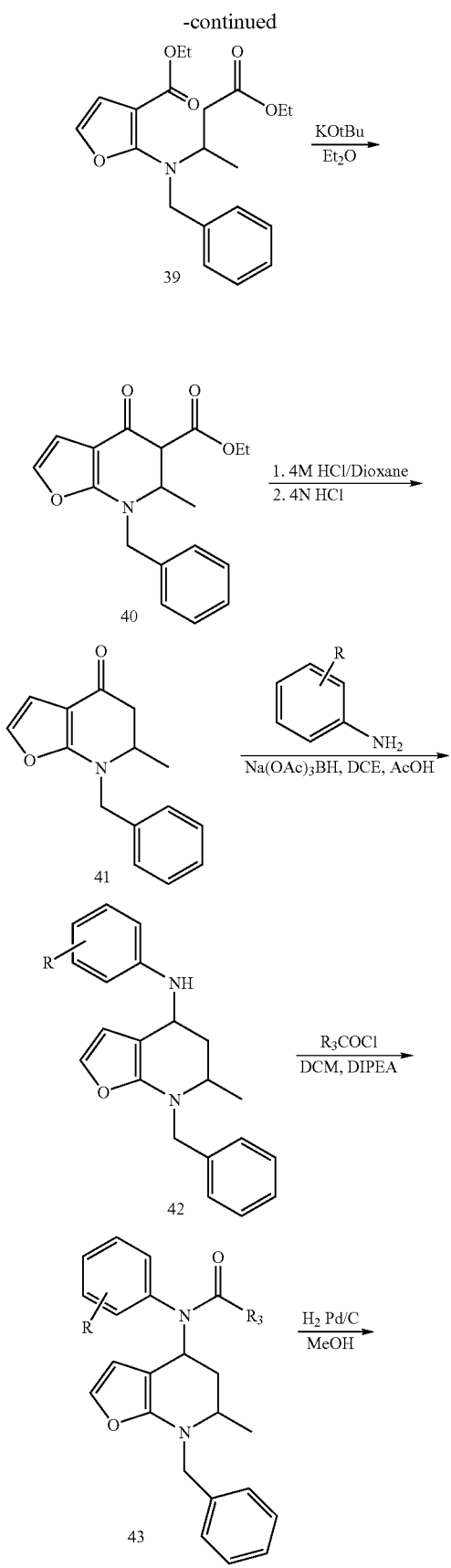

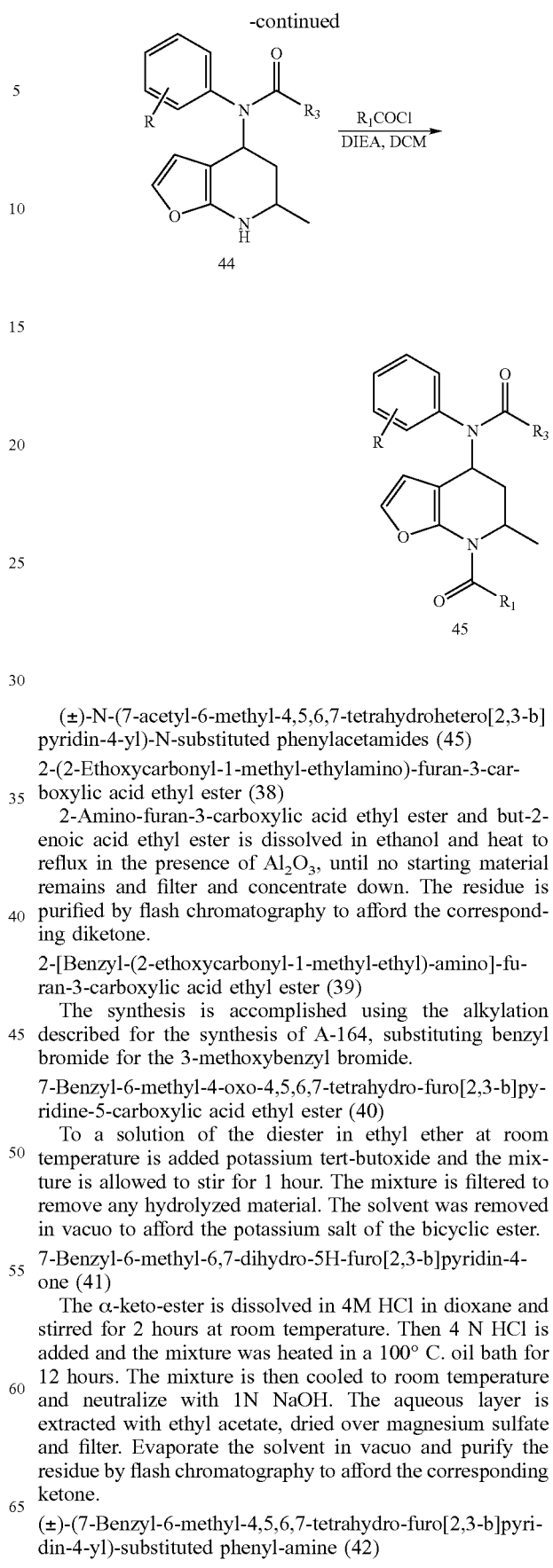

(±)-N-(7-acetyl-6-methyl-4,5,6,7-tetrahydrohetero[2,3-b]pyridin-4-yl)-N-substituted phenylacetamides (45)

2-(2-Ethoxycarbonyl-1-methyl-ethylamino)-furan-3-carboxylic acid ethyl ester (38)

2-Amino-furan-3-carboxylic acid ethyl ester and but-2-enoic acid ethyl ester is dissolved in ethanol and heat to reflux in the presence of $Al_2O_3$, until no starting material remains and filter and concentrate down. The residue is purified by flash chromatography to afford the corresponding diketone.

2-[Benzyl-(2-ethoxycarbonyl-1-methyl-ethyl)-amino]-furan-3-carboxylic acid ethyl ester (39)

The synthesis is accomplished using the alkylation described for the synthesis of A-164, substituting benzyl bromide for the 3-methoxybenzyl bromide.

7-Benzyl-6-methyl-4-oxo-4,5,6,7-tetrahydro-furo[2,3-b]pyridine-5-carboxylic acid ethyl ester (40)

To a solution of the diester in ethyl ether at room temperature is added potassium tert-butoxide and the mixture is allowed to stir for 1 hour. The mixture is filtered to remove any hydrolyzed material. The solvent was removed in vacuo to afford the potassium salt of the bicyclic ester.

7-Benzyl-6-methyl-6,7-dihydro-5H-furo[2,3-b]pyridin-4-one (41)

The α-keto-ester is dissolved in 4M HCl in dioxane and stirred for 2 hours at room temperature. Then 4 N HCl is added and the mixture was heated in a 100° C. oil bath for 12 hours. The mixture is then cooled to room temperature and neutralize with 1N NaOH. The aqueous layer is extracted with ethyl acetate, dried over magnesium sulfate and filter. Evaporate the solvent in vacuo and purify the residue by flash chromatography to afford the corresponding ketone.

(±)-(7-Benzyl-6-methyl-4,5,6,7-tetrahydro-furo[2,3-b]pyridin-4-yl)-substituted phenyl-amine (42)

Synthesis of the substituted phenyl amine is accomplished using the procedure described for F-1, substituting aniline for the corresponding aniline.

(±)-N-(7-Benzyl-6-methyl-4,5,6,7-tetrahydro-furo[2,3-b]pyridin-4-yl)-N-substituted phenyl-substituted amide (45)

Synthesis of the corresponding phenyl amide is accomplished using the hydrogenation and acylation procedures described in general procedure B with the corresponding acid chlorides. Representative examples of compound 45 are shown in the table below.

Compounds E-1–E-30 can be prepared by the schemes set forth in Schemes 18 and by the general procedures E and others described herein. Those skilled in the art will be able to recognize, or be able to ascertain, using no more than routine experimentation, many equivalents to the specific embodiments of the invention described herein.

TABLE 5

Examples using General Procedure E

| No. | Structure |
|---|---|
| E-1 | |
| E-2 | |
| E-3 | |
| E-4 | 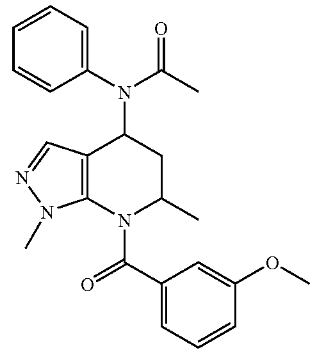 |
| E-5 | 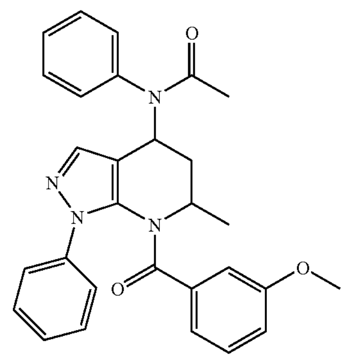 |
| E-6 | 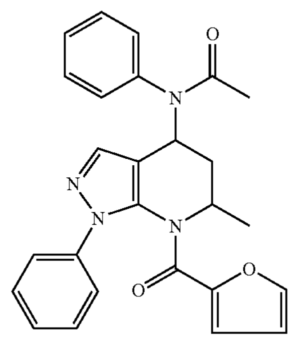 |
| E-7 | 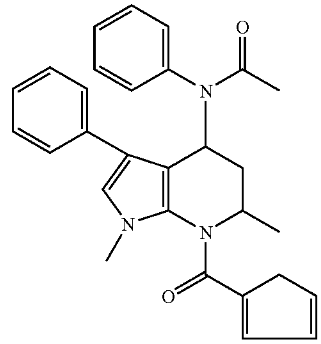 |

TABLE 5-continued

Examples using General Procedure E

| No. | Structure |
|---|---|
| E-8 | 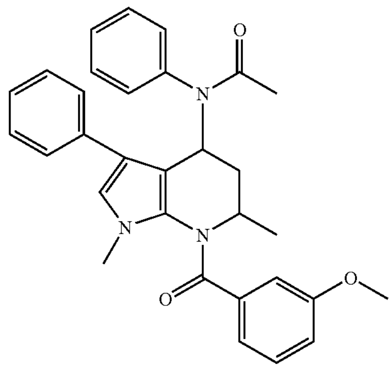 |
| E-9 | 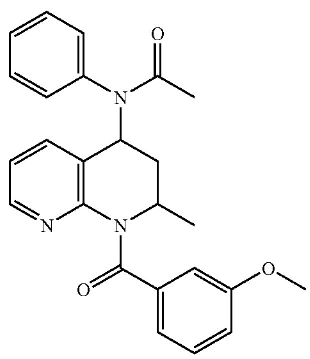 |
| E-10 | 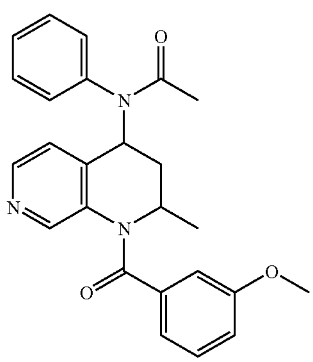 |
| E-11 | 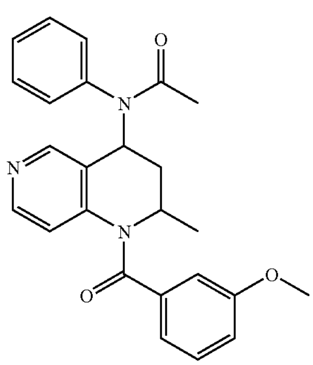 |
| E-12 | |
| E-13 | |
| E-14 | |
| E-15 | |

TABLE 5-continued

Examples using General Procedure E

| No. | Structure |
|---|---|
| E-16 | 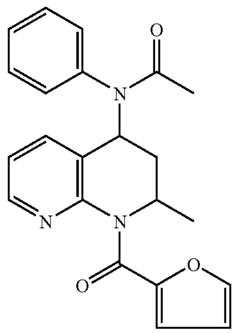 |
| E-17 | 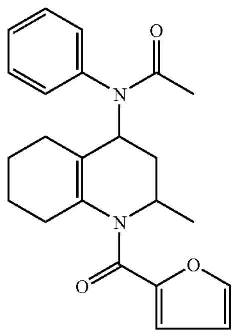 |
| E-18 | 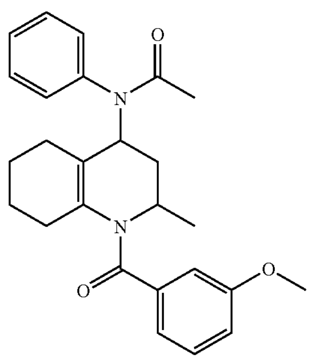 |
| E-19 | 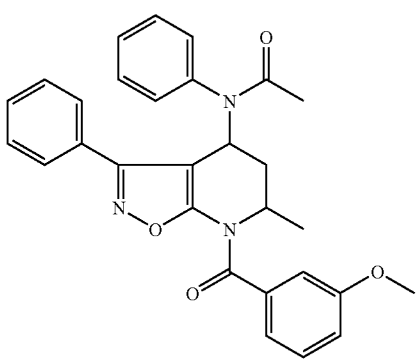 |
| E-20 | |
| E-21 | |
| E-22 | |
| E-23 | |

TABLE 5-continued

Examples using General Procedure E

| No. | Structure |
|---|---|
| E-24 | 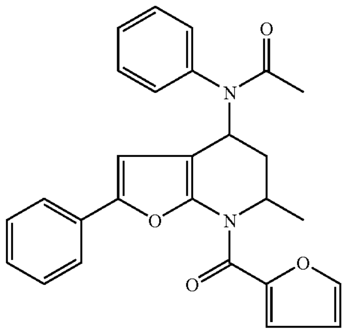 |
| E-25 | 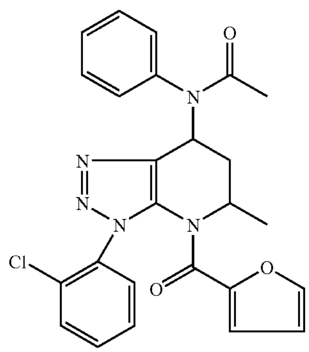 |
| E-26 | 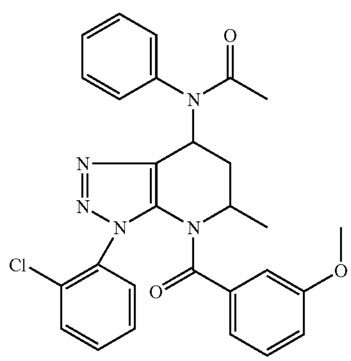 |
| E-27 | 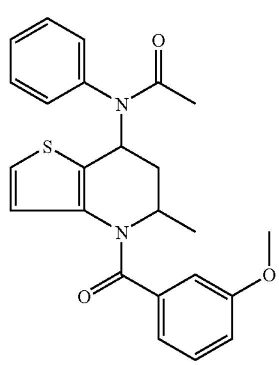 |
| E-28 | 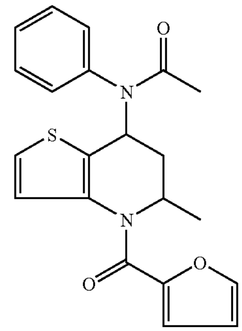 |
| E-29 | 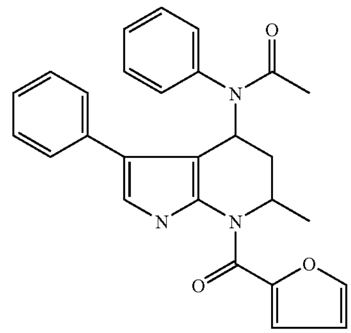 |
| E-30 | 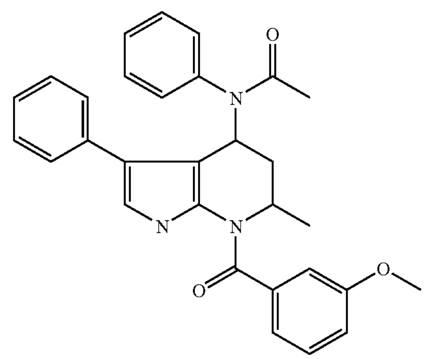 |

Procedures F

N-[1-(3-Methoxy-benzoyl)-2,2-dimethyl-1,2,3,4-tetrahydro-quinolin-4-yl]-N-phenyl-acetamide (F-1)

N-[1-(3-Methoxy-benzoyl)-2,2-dimethyl-1,2,3,4-tetrahydro-quinolin-4-yl]-N-phenyl-acetamide from 4-(hydroxy-2,2-dimethyl-3,4-dihydro-2H-quinolin-1-yl)-(3-methoxyphenyl)-methanone which was synthesized according to reference Hamann, L. G.; Higuchi, R. I.; Zhi, L.; Edwards, J. P.; Wang, X.; Marrschke, K. B.; Kong, J. W.; Farmer, L. J.; Jones, T. D. *J. Med. Chem* 1998, 41, 623. This was further elaborated to N-[1-(3-methoxy-benzoyl)-2,2-dimethyl-1,2,3,4-tetrahydro-quinolin-4-yl]-N-phenyl-acetamide using an in-situ formation of the iodide and displacement with the aniline according to the following procedure To a chilled solution of (4-hydroxy-2,2-dimethyl-3,4-dihydro-2H-quinolin-1-yl)-(3-methoxy-phenyl)-methanone (500 mg, 1.6 mmol) in 10 ml dichloromethane was added slowly 0.8 ml iodotrimethylsilane (5.6 mmol) at 0° C. The resulting reaction mixture was stirred at 0° C. for 6 hours.

Then the mixture was concentrated under vacuum. The residue was dissolved in 12 ml TIF. BaCO$_3$ (630 mg, 3.2 mmol) and aniline (0.17 ml, 1.92 mmol) was added. The mixture was stirred at RT overnight. The mixture was filtered and the filtrate was concentrated under vacuum. The residue was purified by silica gel chromatography, eluting with ethyl acetate-hexane (1:4) to give (2,2-dimethyl-4-phenylamino-3,4-dihydro-2H-quinolin-1-yl)-(3-methoxy-phenyl)-methanone (150 mg, 24%).

To a solution of (2,2-dimethyl-4-phenylamino-3,4-dihydro-2H-quinolin-1-yl)-(3-methoxy-phenyl)-methanone in methylene chloride (5 mL) was added diisopropylethylamine followed by acetyl chloride. The mixture was sturred at room temperature over night. The mixture was poured into water and extracted with dichloromethane. The extracts were washed with 1 M (aq) NaOH and brine, dried over magnesium sulfate, filtered, dried and concentrated. The crude residue was purified by silica gel chromatography (50% hexanes/50% ethyl acetate) to afford N-[1-(3-methoxy-benzoyl)-2,2-dimethyl, 1,2,3,4-tetrahydro-quinolin-4-yl]-N-phenyl-acetamide.

$^1$H-NMR (CDCl$_3$) δ: 1.5 (1H, m), 1.6 (3H, s), 1.7 (3H, s), 1.9 (1H, m), 2.0 (3H, 3), 3.7 (3H, m), 5.8 (1H, m), 6.5 (1H, d), 6.6–7.1 (8H, m), 7.2 (1H, m), 7.3–7.5 (3H, d).

MS m/z: 429 (M+1).

(2S,4R)-4-Chloro-N-ethyl-N-[1-(4-methoxy-benzoyl)-2-methyl-1,2,3,4-tetrahydro-quinolin-4-yl]-benzamide (F-2)

(2S,4R)-4-Chloro-N-ethyl-N-[1-(4-methoxy-benzoyl)-2-methyl-1,2,3,4-tetrahydro-quinolin-4-yl]-benzamide was synthesized as described in general procedure C, except following benzyl carbamate removal the amine was modified in the following manner. To a solution of (2S,4R)-(4-amino-2-methyl-3,4-dihydro-2H-quinolin-1-yl)-(4-methoxy-phenyl)-methanone (200 mg, 0.68 mmol) in 20 ml dichloromethane was added acetaldehyde (0.042 mL, 0.75 mmol). The reaction mixture was stirred 30 min at room temperature. Then sodium triacetoxyborohydride (0.156 g, 0.75 mmol) was added and the resulting reaction mixture was stirred at room temperature for 6 hours. N,N-diisopropylethylamine (0.3 mL, 2.3 mmol) and 4-chlorobenzoyl chloride (0.4 mL, 3.1 mmol) was added and stirred at room temperature overnight. Dichloromethane (40 ml) was added. The mixture was washed with 30 ml sodium hydroxide (1N). The organic layer was dried with magnesium sulfate, filtered and concentrated in vacuo. The residue was purified by silica gel chromatography, eluting with ethyl acetate-dichloromethane (1:4) to give 80 mg (24%) title compound $^1$H-NMR (CDCl$_3$) δ: 1.2–1.4 (7H, m), 1.7 (1H, m), 2.7 (1H, m), 3.1 (1H, m), 3.8 (3H, s), 4.2 (1H, m), 4.8 (1H, m), 6.5 (1H, d), 6.6 (2H, d), 6.8 (2H, m), 6.9 (1H, m), 7.1–7.5 (6H, m)

MS m/z: 463 (M+1).

N-[1-(3-Methoxy-benzoyl)-1,2,3,4-tetrahydro-quinolin-4-yl]-N-phenyl-acetamide (F-3)

N-[1-(3-Methoxy-benzoyl)-1,2,3,4-tetrahydro-quinolin-4-yl]-N-phenyl-acetamide was made from 1-(4-methoxy-benzoyl)-2,3-dihydro-1H-quinolin-4-one which was synthesized according to reference Bellassou-Fargeau, M. C.; Graffe, B.; Sacquet, M. C.; Maitte, P. *J. of Heter. Chem.* 1985,22(3), 713. This was further elaborated to (4-hydroxy-3,4-dihydro-2H-quinolin-1-yl)-(3-methoxy-phenyl)-methanone by reduction of the ketone to the alcohol and in-situ formation of the iodide and displacement with the aniline according to the following procedure the following procedure. To a solution of 1-(3-methoxy-benzoyl)-2,3-dihydro-1H-quinolin-4-one (310 mg, 1.1 mmol) in 5 ml methanol was added 410 mg sodium borohydride (4.4 mmol). The resulting reaction mixture was stirred at room temperature for 3 hours. The mixture was concentrated under vacuum and the residue was purified by silica gel chromatography, eluting with ethyl acetate-hexane (1:2) to give (4-hydroxy-3,4-dihydro-2H-quinolin-1-yl)-(3-methoxy-phenyl)-methanone (215 mg, 69%). This was further elaborated to (3-methoxy-phenyl)-(4-phenylamino-3,4-dihydro-2H-quinolin-1-yl)-methanone using the following procedure. To a chilled solution of (4-hydroxy-3,4-dihydro-2H-quinolin-1-yl)-(4-methoxy-phenyl)-methanone in dichloromethane was added slowly iodotrimethylsilane at 0° C. The resulting reaction mixture was stirred at 0° C. for 6 hours. Then the mixture was concentrated under vacuum. The residue was dissolved in THF. BaCO$_3$ and aniline was added. The mixture was stirred at room temperature overnight. The mixture was filtered and the filtrate was concentrated under vacuum. The residue was purified by silica gel chromatography, eluting with ethyl acetate-hexane (1:4) to give (4-phenylamino-3,4-dihydro-2H-quinolin-1-yl)-(3-methoxy-phenyl)-methanone To a solution of (4-phenylamino-3,4-dihydro-2H-quinolin-1-yl)-(4-methoxy-phenyl)-methanone in methylene chloride was added diisopropylethylamine followed by acetyl chloride. The mixture was stirred at room temperature over night. The mixture was poured into water and extracted with dichloromethane. The extracts were washed with 1 M (aq) NaOH and brine, dried over magnesium sulfate, filtered dried and concentrated. The crude residue was purified by silica gel chromatography (50% hexanes/50% ethyl acetate) to afford (±)-N-[1-(3-methoxy-benzoyl)-1,2,3,4-tetrahydro-quinolin-4-yl]-N-phenyl-acetamide.

$^1$H-NMR (CDCl$_3$) δ: 1.2 (1H, m), 1.9 (3H, s), 2.1 (1H, m), 2.3 (1H, m), 3.5 (1H, m), 3.7 (3H, m), 4.1 (1H, m), 6.4 (2H, m), 6.6 (1H, m), 6.8–7.3 (6H, m), 7.4 (3H, m), 7.5 (1H, d).

MS m/z: 401 (M+1).

TABLE 6

Structurally Diverse Series

| No. | Structure | No. | Structure |
|-----|-----------|-----|-----------|
| F-1 | 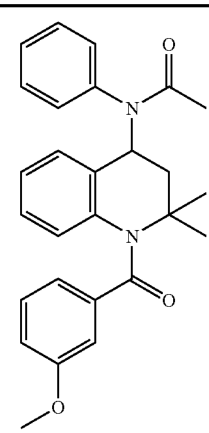 | | |

TABLE 6-continued

Structurally Diverse Series

| No. | Structure | No. | Structure |
|---|---|---|---|
| F-2 | 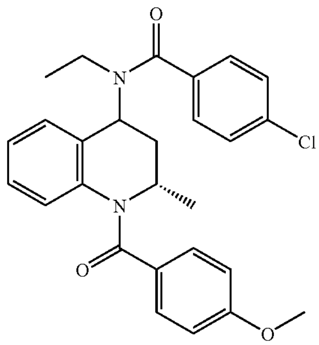 | | |
| F-3 | 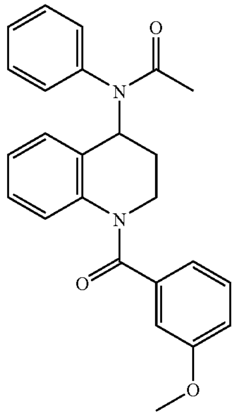 | | |

The Disclosed Compounds Inhibit Binding of PGD$_2$ to CRTH2

This radioligand membrane binding assay evaluates the ability of compounds to inhibit [$^3$H] Prostaglandin D$_2$ (PGD$_2$) binding to the cloned human CRTH2 receptor stably expressed in HEK-293 cells (expressing human CRTh2 receptor and □subunit or the heterotrimeric G protein 16 were prepared by Biosignal Company) using Scintillation Proximity Assay.

A binding buffer containing 50 mM Tris-HCl (pH 7.5), 5 mM MgCl$_2$ and 1 mM EDTA was prepared immediately prior to performing the assay. A bead/membrane solution at twice the final assay concentration comprising membranes (membranes bought from Biosignal) from the HEK-293 cells cloned to express CRTH2 receptor bound to and [$^3$H] PGD$_2$ at two times the final assay concentration were prepared and stored on ice before adding to wells. Cold PGD$_2$ at twenty times the final assay concentration was prepared and stored on ice before adding to wells defining non-specific binding (NSB) coming plates #3653 were used for this assay.

10 mM stock concentrations of compounds in 100% DMSO were prepared and stored at room temperature. A 10 point concentration response curve was then constructed for each compound, starting at 10 μM (final assay concentration). The compounds were prepared at 40 times final assay concentrations with nine consequent-3-fold dilutions.

0.1 μl of each concentration of compound were added to the appropriate well of the 384 plate and 2 μl of cold PGD$_2$ was added into the wells defining NSB. 20 μl of [$^3$H] PGD$_2$ and then 20 μl of 2× of bead/membrane solution were then added to each well.

The plates were allowed to incubate at room temperature for approximately 2 hours and then counted on Packard Topcount using SPA tritium protocol for 1 minute/well.

The percent inhibition of PGD$_2$ binding (PGD$_2$ used at the K$_D$ value or lower) to the HEK-293 cell membranes was determined, the assay was always run as duplicate for n=1 for a total of n=2.

FIG. 1: K$_i$ of PGD2 binding to CRTH2 (uM)

Compounds A-3, A-11, A-16, A-17, A-20, A-24, A-35, A-49, A-51, A-54, A-55, A-67, A-70, A-72, A-73, A-81, A-82, A-120, A-130, A-131, A-132, A-143, A-144, A-147, A-153, A-156, A-157, A-159, B-7, B-9, B-11, B-13, B-18, B-20, B-26, B-28, B-34, B-39, B-40, B-47, B-51, B-58, B-59, B-63 to B-66, B-68, B-70, B-73, B-74, B-84, B-86, B-97, B-101 to B-112, C-33, C-37, C-38, D-1, D-2, D-6, D-10, F-3 have K$_i$<10 uM Compounds A-8, A-53, A-58, A-124, A-126, A-154, B-53, B-100, F-1 have K$_i$<60 uM All remaining compounds have K$_i$<1 uM While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following structural formula:

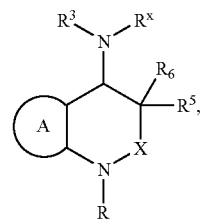

or a pharmaceutically acceptable salt thereof, wherein:
Ring A is an optionally substituted monocyclic aromatic ring;
R is —X$_1$—R$^1$;
R$^x$ is —X$_2$—R$^4$, and R$^3$ is an optionally substituted aromatic group; or —NR$^x$R$^3$, taken together, is an optionally substituted non-aromatic nitrogen containing heterocyclic group;
X is —C(O)— or —C(R$^2$)$_2$—;
X$_1$ and X$_2$ are each independently a bond, S(O), S(O)$_2$, C(O) or C(O)NH;
R$^1$ is H or an optionally substituted, cycloaliphatic group, aromatic group or non-aromatic heterocyclic group;
provided that when X$_1$ is a bond, SO or SO$_2$, then R$^1$ is not H;
each R$^2$ independently H, —X$_4$—R$^8$ or an optionally substituted, aliphatic group, cycloaliphatic group, aromatic group or non-aromatic heterocyclic group;
R$^4$ is H, —X$_6$—R$^{10}$ an optionally substituted, aliphatic group, cycloaliphatic group, aromatic group or non-aromatic heterocyclic group;

provided that when $X_2$ is a bond, SO or $SO_2$, then $R^4$ is not H;

$X_4$ and $X_6$ are each independently a straight or branched hydrocarbyl group optionally substituted with one or more groups selected from the group consisting of halo, —OH, =O, $C_1$–$C_3$ alkoxy, nitro and cyano;

$R^5$ and $R^6$ are each independently H or $C_1$–$C_3$ alkyl; and $R^8$ and $R^{10}$ are each independently H, —C(O)OR' or an optionally substituted, cycloaliphatic group, aromatic group or non-aromatic heterocyclic group;

where, the optional substituents on the aliphatic group, the cycloaliphatic group or the non-aromatic heterocydic group are one to three groups each independently selected from the group consisting of halo, $R^{11}$, =O, =S, =NNHR*, =NN(R*)$_2$, =NNHC(O)R*, =NNHCO$_2$(alkyl), =NNHSO$_2$ (alkyl) and =NR*;

the optional substituents on unsaturated carbon atoms of the aromatic group is $R^{11}$;

the optional substituents on a nitrogen atom of the aromatic group or the nitrogen atom of the non-aromatic nitrogen containing heterocyclic group are one to three groups each independently selected from the group consisting of R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$ and —NR$^+$SO$_2$R$^+$;

$R^{11}$ is one to four substituents each independently selected from the group consisting of halo, R°, —OH, —OR°, —SH, —SR°, 1,2-methylenedioxy, 1,2-ethylenedioxy, protected —OH, phenyl, [R$^{12}$]-phenyl, —O(phenyl), —O([R$^{12}$]-phenyl), —CH$_2$(phenyl), —CH$_2$([R$_{12}$]-phenyl), —CH$_2$CH$_2$(phenyl), —CH$_2$CH$_2$([R$^{12}$]-phenyl), —NO$_2$, —CN, —N(R')$_2$, —NR'CO$_2$R°, —NR'C(O)R°, —NR'NR'C(O)R°, —N(R')C(O)N(R')$_2$, —NR'NR'C(O)N(R')$_2$, —NR'NR'CO$_2$R°, —C(O)C(O)R°, —C(O)CH$_2$C(O)R', —CO$_2$R', —C(O)R°, —C(O)N(R')$_2$, —OC(O)N(R')$_2$, —S(O)$_2$R°, —SO$_2$N(R')$_2$, —S(O)R', —NR'SO$_2$N(R')$_2$, —NR'SO$_2$R°, —C(=S)N(R')$_2$, —(CH$_2$)$_y$N(R')$_2$, —C(=NH)—N(R')$_2$, —(CH$_2$)$_y$C(O)N(R')$_2$, —(CH$_2$)$_y$NHC(O)R' or —(CH$_2$)$_y$NHC(O)CH(V—R')(R');

R' is H, R°, —CO$_2$R°, —SO$_2$R° or —C(O)R°;

y is 0–6;

V is $C_1$–$C_6$ alkylene;

each R* is independently H, an aliphatic group or an aliphatic group substituted with R$^{12}$;

R$^+$ is H, phenyl, [R$^{12}$]-phenyl, —O(phenyl), —O([R$^{12}$]-phenyl), —CH$_2$(phenyl), —CH$_2$([R$^{12}$]-phenyl), a heteroaryl group, a non-aromatic heterocyclic group, an aliphatic group or an aliphatic group substituted with R$^{12}$;

R° is an aliphatic group, a cycloaliphatic group, an aromatic group, an aralkyl group or a non-aromatic hererocyclic group, each group being optionally substituted with R$^{12}$;

$R^{12}$ is one to four substituents each independently selected from the group consisting of halo, $C_1$–$C_6$ ailcyl, (halo)$_{r1}$–$C_6$ alkyl, $C_3$–$C_8$ cycloalkyl, (halo)$_r$$C_3$–$C_8$ cycloalkyl, —CN, —CF$_3$, —CHF$_2$, —CH$_2$F, —OCF$_3$, —OCHF$_2$, —OCH$_2$F, —OR', —OR$^{13}$C(O)R', —C(O)OR', —C(O)N(R$^{16}$)$_2$, —N(R$^{16}$)$_2$, —NO$_2$, —NR$^{16}$C(O)R', —NR$^{16}$C(O)OR', —NR$^{16}$C(O)N(R$^{16}$)$_2$, —NR$^{16}$SO$_2$R$^{17}$, —S(O)$_q$R$^{17}$, —R$^{13}$NR$^{16}$C(O)R', —R$^{13}$C(O)R', —R$^{13}$NR$^{16}$C(O)OR', tetrazolyl, imidazolyl or oxadiazolyl;

$R^{13}$ is $C_1$–$C_6$ alkyl or $C_3$–$C_8$ cycloalkyl;

each $R^{16}$ is independently R' or benzyl;

$R^{17}$ is $R^{13}$ or —CF$_3$;

q is 0–2; and r is 1–3;

provided that the compound is not 2-methyl-N-phenyl-N-[1,2,3,4-tetrahydro-2-methyl-1-(2-methyl-1-oxobutyl)-4-quinolinyl]-butamide; N-(1-Acetyl-1,2,3,4-tetrahydro-2-methyl-4-quinolinyl)-N-phenyl-heptamide; N-phenyl-N-[1,2,3,4-tetrahydro-2-methyl-1-(1-oxo-3-phenylpropyl)-4-quinolinyl]-benzenepropanamide; N-phenyl-N-[1,2,3,4-tetrahydro-2-methyl-1-(3-nitrobenzoyl)-4-quinolinyl]-hexanamide; N-[1,1'-biphenyl]-3-yl-N-[1,2,3,4-tetrahydro-1-(4-methoxybenzoyl)-2-methyl-4-quinolinyl]-acetamide; N-(1-benzoyl-1,2,3,4-tetrahydro-2-methyl-4-quinolinyl)-N-(4-nitrophenyl)-heptanamide; N-(1-benzoyl-1,2,3,4-tetrahydro-2-methyl-4-quinolinyl)-N-(4-methoxyphenyl)-2-methyl-propanamide; N-[1-(4-fluorobenzoyl)-1,2,3,4-tetrahydro-2-methyl-4-quinolinyl]-N-phenyl-butanamide; N-phenyl-N-[1,2,3,4-tetrahydro-1-(3-methoxybenzoyl)-2-methyl-4-quinolinyl]-pentanamide; 2-ethyl-N-[1-(2-ethyl-1-oxobutyl)-1,2,3,4-tetrahydro-2,8-dimethyl-4-quinolinyl]-N-[2-methylphenyl)-butanamide; N-[1-[(4-fluorophenyl)acetyl]-1,2,3,4-tetrahydro-2-methyl-4-quinolinyl]-N-phenyl-propanamide; N-phenyl -N-[1,2,3,4-tetrahydro-2-methyl-1-(4-nitrobenzoy1)-4-quinolinyl]-octanamide; N-cyclohexyl-4-[(cyclohexylamino)carbonyl]phenylamino]-3,4-dihydro-2-methyl-1(2H)-quinolinecarboxamide; N-[1-(4-ethylbenzoyl)-1,2,3,4-tetrahydro-2,8-dimethyl-4-quinolinyl]-N-[2-methylphenyl]-3-(4-nitrophenyl)-2-propenamide; 3-(4-methoxyphenyl)-N-phenyl-N-(1,2,3,4-tetrahydro-1-[3-(4-methoxyphenyl)-1-oxo-2-propenyl]-2-methyl-4-quinolinyl]-2-propenamide; 4-[(ethoxyoxoacetyl)phenylamino]-3,4-dihydro-2-methyl-∀-oxo-ethyl ester-1(2H)-quinolineacetic acid; N-(1-(3-cyclohexyl-1-oxopropyl)-1,2,3,4-trahydro-2-methyl-4-quinolinyl)-N-phenyl -cyclohexanepropanamide; 4-(acetylphenylamino)-3,4-dihydro-2-methyl-gamma-oxo-1(2H) -quinolinepentanoic acid; N-(1-benzoyl-1,2,3,4-tetrahydro-2-methyl-4-quinolinyl)-2,2-dimethyl-N -phenyl-propanamide; N-(1-benzoyl-6-bromo-1,2,3,4-tetrahydro-2-methyl-4-quinolinyl)-N-phenyl -pentanamide; N-[1-(2-furanylcarbonyl)-1,2,3,4-tetrahydro-2-methyl-4-quinolinyl]-N-phenyl -acetamide; 2-methyl-N-phenyl-N-[1,2,3,4-tetrahydro-1-(3-methoxybenzoyl)-2-methyl-4-quinolinyl]-propanamide; N-[1-[(1,3-dihydro-1,3-dioxo-2H-isoindol-2-yl)acetyl]-1,2,3,4-tetrahydro-2-methyl-4-quinolinyl]-N-phenyl-acetamide; 2,2,2-trifluoro-N-phenyl-N-[1,2,3,4-tetrahydro-1-(3-methoxybenzoyl)-2-methyl-4-quinolinyl]-acetamide; 2-ethyl-N-[1-(2-ethyl-1-oxobutyl)-1,2,3,4-tetrahydro-2-methyl-4-quinolinyl]-N-phenyl-butanamide; N-(1-benzoyl-1,2,3,4-tetrahydro-2-methyl-4-quinolinyl)-N-(3-methoxyphenyl)-acetamide; N-phenyl-N-[1,2,3,4-tetrahydro-2-methyl-1-(1-oxohexyl)-4-quinolinyl]-acetamide; N-(1-acetyl-1,2,3,4-tetrahydro-2-methyl-4-quinolinyl)-N-phenyl-2-thiophenecarboxamide; N-[1-(2-fluorobenzoyl)-1,2,3,4-tetrahydro-2-methyl-4-quinolinyl]-N-phenyl-hexanamide; N-phenyl-N-[1,2,3,4-tetrahydro-1-(4-methoxybenzoyl)-2-methyl-4-quinolinyl]-hexanamide; N-phenyl-N-[1,2,3,4-tetrahydro-1-(4-methoxybenzoyl)-2-methyl-4-quinolinyl]-hexanamide; N-[1-(cyclopropylcarbonyl)-

1,2,3,4-tetrahydro-2-methyl-4-quinolinyl]-N-phenyl-cyclopropanecarboxamide; N-(1-benzoyl-1,2,3,4-tetrahydro-2-methyl-4-quinolinyl)-N-(4-methylphenyl)-acetamide; 2-methyl-N-phenyl-N-[1,2,3,4-tetrahydro-2-methyl-1-(2-methyl-1-oxopropyl)-4-quinolinyl]-propananide; N-phenyl-N-[1,2,3,4-tetrahydro-1-(4-methoxybenzoyl)-2-methyl-4-quinolinyl]-2-thiophenecarboxamide; 1-(3,5-dinitrobenzoyl)-N-formyl-1,2,3,4-tetrahydro-2-methyl-N-phenyl-4-quinolinamine; N-[1-(4-chloro-3-nitrobenzoyl)-1,2,3,4-tetrahydro-2-methyl-4-quinolinyl]-N-phenyl-acetamide; N-phenyl-N -[1,2,3,4-tetrahydro-2-methyl-1-(3-nitrobenzoyl)-4-quinolinyl]-acetamide; N-phenyl-N-[1,2,3,4-tetrahydro-1-(3-methoxybenzoyl)-2-methyl-4-quinolinyl]-hexanamide; N-[1-(2-furanylcarbonyl) -1,2,3,4-tetrahydro-2-methyl-quinolinyl]-N-phenyl-2-furancarboxamide; N-phenyl-N-[1,2,3,4-tetrahydro-2-methyl-1-(1-oxopropyl)-4-quinolinyl]-acetamide; N-phenyl-N-[1,2,3,4-tetrahydro-1-[3-(4-methoxyphenyl)-1-oxo-2-propenyl]-2-methyl-4-quinolinyl]-acetamide; 3-(2-furanyl)-N-[1-[3-(2-furanyl)-1-oxo-2-propenyl]-1,2,3,4-tetrahydro-2-methyl-4-quinolinyl]-N-phenyl-2-propenamide; N-[1-[2-(1,3-dihydro-1,3-dioxo-2H-isoindol-2-yl)-1-oxo-3-phenylpropyl]-1,2,3,4-tetrahydro-2-methyl-4-quinolinyl]-N-phenyl-octanamide; N-(1-(3-chlorobenzoyl)-1,2,3,4-tetrahydro-2-methyl-4-quinolinyl]-N-phenyl-acetamide; Relative stereochemistry N-phenyl-N -[(2R,4S)-1,2,3,4-tetrahydro-2-methyl-1-(1-oxopropyl)-4-quinolinyl]-acetamide; Relative stereochemistry N-[(2R,4S)-1-benzoyl-1,2,3,4-tetrahydro-2-methyl-4-quinolinyl]-2-methyl-N -phenyl-propanamide; Relative stereochemistry N-[(2R,4S)-1-acetyl-1,2,3,4-tetrahydro-2-methyl -4-quinolinyl]-N-phenyl-hexanamide; Relative stereochemistry N-[(2R,4S)-1-acetyl-1,2,3,4-tetrahydro-2-methyl-4-quinolinyl]-N-phenyl-propanamide; Relative stereochemistry N-[(2R,4S)-1-acetyl-1,2,3,4-tetrahydro-2-methyl-4-quinolinyl]-N-phenyl-heptanamide; Relative stereochemistry N-[(2R,4S)-1-benzoyl-1,2,3,4-tetrahydro-2-methyl-1-quinolinyl]-2,2-dimethyl-N-phenyl -propanamide; N-[1-(3-fluorobenzoyl)-1,2,3,4-tetrahydro-2-methyl-4-quinolinyl]-N-phenyl -acetamide; N-[1-[4-(1,1-dimethylethyl)benzoyl]-1,2,3,4-tetrahydro-2-methyl-4-quinolinyl]-N -phenyl-acetamide; N-(1-acetyl-1,2,3,4-tetrahydro-2-methyl-4-quinobinyl)-2-methyl-N-phenyl -propanamide; 2,2,2-trifluoro-N-phenyl-N-[1,2,3,4-tetrahydro-2-methyl-1-(trifluoro-acetyl)-4-quinolinyl)-acetamide; Relative stereochemistry N-((2R,4S)-1-acetyl-1,2,3,4-tetrahydro-2-methyl -4-quinolinyl]-2,2-dimethyl-N-phenyl-propanamide; Relative stereochemistry N-[(2R,4S)-1-acetyl -1,2,3,4-tetrahydro-2-methyl-4-quinolinyl]-N-phenyl-butanamide; Relative stereochemistry N -((2R,4S)-1-benzoyl-1,2,3,4-tetrahydro-2-methyl-4-quinolinyl)-N-phenyl-acetamide; Relative stereochemistry N-phenyl-N-[(2R,4S)-1,2,3,4-tetrahydro-2-methyl-1-(1-oxoheptyl)-4-quinolinyl]-acetamide; Relative stereochemistry N-phenyl-N-[(2R,4S)-1,2,3,4-tetrahydro-2-methyl-1-(1-oxohexyl)-4-quinolinyl]-acetamide; Relative stereochemistry N-[(2R,4S)-1-acetyl-1,2,3,4-tetrahydro-2-methyl-4-quinolinyl]-N-phenyl-pentanamide; N-phenyl-N-[1,2,3,4-tetrahydro-2-methyl-1-(1-oxo-3-phenyl-2-propenyl)-4-quinolinyl]-acetamide; Relative stereochemistry N -[(2R,4S)-1-benzoyl-1,2,3,4-tetrahydro-2-methyl-4-quinolinyl]-N-phenyl-heptanamide; Relative stereochemistry N-[(2R,4S)-1-acetyl-1,2,3,4-tetrahydm-2-methyl-4-quinolinyl]-N-phenyl -acetanude; Relative stereochemistry N-[(2R,4S)-1-benzoyl-1,2,3,4-tetrahydro-2-methyl-4-quinolinyl]-N-phenyl-pentanamide; N-phenyl-N-[1,2,3,4-tetrahydro-2-methyl-1-(tricyclo [3.3.1.13,7]dec-1-ylcarbonyl)-4-quinolinyl]-acetamide; N-phenyl-N-[1,2,3,4-tetrahydro-2-methyl-1-(1-oxopropyl)-4-quinolinyl]-propanamide; N-phenyl-N-[1,2,3,4-tetrahydro-2-methyl-1-(2-thienylcarbonyl)-4-quinolinyl]-acetamide; N-phenyl-N-[1,2,3,4-tetrahydro-1-(4-methoxybenzoyl)-2-methyl-4-quinolinyl]-2-furancarboxamide; N-phenyl-N-[1,2,3,4-tetrahydro-1-(4-methoxybenzoyl)-2-methyl-quinolinyl]-acetamide; N-[1-(3,5-dinitrobenzoyl)-1,2,3,4-tetrahydro-2-methyl-quinolinyl]-N-phenyl-acetamide; N-phenyl-N-[1,2,3,4-tetrahydro-2-methyl -1-(4-nitrobenzoyl)-4-quinolinyl]-acetamide; N-phenyl-N-[1,2,3,4-tetrahydro-1-(2-iodobenzoyl)-2-methyl-4-quinolinyl]-acetamide; N-phenyl-N-[1,2,3,4-tetrahydro-2-methyl-1-(2-methyl-1-oxopropyl)-4-quinolinyl]-acetamide; N-phenyl-N-[1,2,3,4-tetrahydro-2-methyl-1-[(4-methylphenyl)sulfonyl]-4-quinolinyl]-acetamide; N-phenyl-N-[1,2,3,4-tetrahydro-2-methyl-1-[(4-nitrophenyl)methyl]-4-quinolinyl]-acetamide; N-phenyl-N-[1,2,3,4-tetrahydro-1-(3-methoxybenzoyl)-2-methyl-4-quinolinyl]-acetamide; N-(1-acetyl-1,2,3,4-tetrahydro-2-methyl-4-quinolinyl)-N-phenyl-butanamide; N-phenyl-N-[1,2,3,4-tetrahydro-2-methyl-1-(1-oxobutyl)-4-quinolinyl]-acetamide; N-(1-benzoyl-1,2,3,4-tetrahydro-2-methyl-4-quinolinyl)-N-phenyl -hexanamide; N-(1-benzoyl-1,2,3,4-tetrahydro-2-methyl-4-quinolinyl)-N-phenyl-pentanamide; N -(1-benzoyl-1,2,3,4-tetmhydro-2-methyl-4-quinolinyl)-N-phenyl-propanamide; 1-benzoyl-1,2,3,4-tetrahydro-4-(N-phenylacetamido)quinaldine; N-(1-acetyl-6-bromo-1,2,3,4-tetrahydro-2-methyl-4-quinolinyl)-N-phenyl-acetamide; N-(1-acetyl-1,2,3,4-tetrahydro-2-methyl-6-nitro-4-quinolyl) -acetanilide; N-(1-acetyl-6-chloro-1,2,3,4-tetrahydro-2-methyl-4-quinolyl)-acetanilide; N-(1-acetyl -1,2,3,4-tetrahydro-2-methyl-4-quinolinyl)-N-phenyl-acetamide; N-(1-benzoyl-6-bromo-1,2,3,4-tetrahydro-2-methyl-4-quinolinyl)-N-phenyl-acetamide; N-(1-benzoyl-6-chloro-1,2,3,4-tetrahydro -2-methyl-quinolinyl)-N-phenyl-acetamide; N-(1-benzoyl-1,2,3,4-tetrahydro-2-methyl-4-quinolinyl)-N-phenyl-butanamide; N-phenyl-N-[1,2,3,4-tetrahydro-1-(3-fluorobenzoyl)-2-methyl -4-quinolinyl]-hexanamide; N-[1-(3-chloro-benzoyl)-2-methyl-1,2,3,4-tetrahydro-quinolin-4-yl]-N -phenyl-acetamide; N-[1-(4-fluoro-benzoyl)-2-methyl-6-nitro-1,2,3,4-tetrahydro-quinolin-4-yl]-N -phenyl-acetamide; pentanoic acid (1-benzoyl-bromo-2-methyl-1,2,3,4-tetrahydro-quinolin-4-yl) -phenyl-amide; N-(1-benzoyl-6-chloro-2-methyl-1,2,3,4-tetrahydro-quinolin-4-yl)-N-phenyl -acetamide; N-[6-chloro-1-(4-fluoro-benzoyl)-2-methyl-1,2,3,4-tetrahydro-quinolin-4-yl]-N-phenyl -acetanlide; N-[6-bromo-1-(4-fluoro-benzoyl)-2-methyl-1,2,3,4-tetrehydro-quinolin-4-yl]-N-phenyl -acetamide; N-(1-benzoyl-6-nitro-2-methyl-1,2,3,4-tetrahydro-quinolin-4-yl)-N-phenyl-acetamide; N-(1-benzoyl-2-methyl-1,2,3,4-tetrahydro-quinolin-4-yl)-N-phenyl-butyramide; or N-[1-(3-methoxy-benzoyl)-2-methyl-1,2,3,4-tetrahydro-quinoiin-4-yl]-2,2-dimethyl-N-phenyl -propionamide.

2. The compound of claim 1 wherein:
X is —CHR$^2$—;
R$^2$ is H, methyl or ethyl;
R$^3$ is an optionally substituted aromatic group; and
R$^5$ and R$^6$ are each H.

3. The compound of claim 2 wherein the compound is represented by the following structural formula:

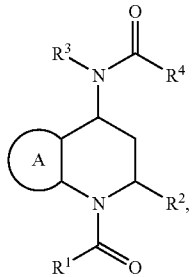

4. The compound of claim 3 wherein R$^1$ is optionally substituted phenyl.

5. The compound of claim 3, wherein R4 is methyl, ethyl, propyl, iso-propyl, n-butyl, sec-butyl, tert-butyl, —CH2OCH3 or —CH2OCH2CH3.

6. The compound of claim 5 wherein:
R$^3$ is [R$^{11}$]-phenyl, where R$^{11}$ is Br, Cl, —CH$_3$, —N(R')$_2$, —NHC(O)OR', —S(O)$_2$CH$_3$, —S(O)$_2$N(R')$_2$ or —(CH$_2$)$_\gamma$C(O)N(R')$_2$; and
R$^4$ is methyl, ethyl or —CH$_2$OCH$_3$.

7. The compound of claim 6 wherein R$^{11}$ is one substituent at the para position.

8. The compound of claim 3 wherein:
R$^1$ is H or an optionally substituted, cycloalkyl group, aromatic group or non-aromatic heterocyclic group;
R$^3$ is phenyl or [R$^{11}$]-phenyl;
R$^4$ is H, —CH$_2$C(O)R$^{14}$, —CH$_2$R$^{15}$, —CH$_2$OR$^{14}$ or an optionally substituted, C$_1$–C$_3$ alkyl group, cycloalkyl group, aromatic group or non-aromatic heterocyclic group;
R$^{14}$ is H or an optionally substituted, alkyl group, aromatic group, cycloalkyl group or non-aromatic heterocyclic group; and
R$^{15}$ is an optionally substituted, aromatic group, cycloalkyl group or non-aromatic heterocyclic group.

9. The compound of claim 3 wherein:
Ring A is phenyl or [R$^{11}$]-phenyl, where R$^{11}$ is at the five, six, seven and/or eight position;
R$^1$ is R$^{18}$;
R$^4$ is R$^{18}$, C$_1$–C$_4$ alkyl, —CH$_2$OH, —CH$_2$OCH$_3$, —CH$_2$OCH$_2$CH$_3$, —CH$_2$CH$_2$OCH$_3$ or —CH$_2$CH$_2$OCH$_2$CH$_3$; and
R$^{18}$ is an optionally substituted, phenyl, pyridyl, furanyl, thiophenyl, isoxazolyl, imidazolyl, pyrazolyl, pyrrolyl, benzofuranyl, tetrazolyl, thiazolyl, benzyl, benzothiazolyl, benzoimidazolyl, benzotriazolyl, benzomorpholinyl, benzopyrazolyl, indolyl, —CH$_2$—(N-pyridyl), —CH$_2$-furanyl, —CH$_2$-thiophienyl, —CH$_2$-isoxazolyl, —CH$_2$-imidazolyl, —CH$_2$-pyrazolyl, —CH$_2$-pyrollyl, —CH$_2$-benzofuranyl, —CH$_2$-tetrazolyl, —CH$_2$-thiazolyl, —CH$_2$-tetrazolyl, —CH$_2$-benzothiazolyl, —CH$_2$-benzimidazolyl, —CH$_2$—O-phenyl, —CH$_2$C(O)-phenyl, naphthalimidyl, tetrahydrofuranyl, cyclohexyl, cyclopentyl or cyclopropyl group.

10. The compound of claim 9 wherein:
Ring A is phenyl or [R$^{11}$]-phenyl, where R$^{11}$ is at the six and/or seven position;
R$^1$ is phenyl, thiophenyl, furanyl, pyridyl, pyrmidinyl, oxazolyl, isoxazolyl, benzotriazolyl or benzomorpholinyl, each group being optionally substituted with R$^{11}$;
R$^3$ is [R$^{11}$]-phenyl; and
R$^4$ is methyl, ethyl, propyl, iso-propyl, n-butyl, sec-butyl, tert-butyl, —CH$_2$OCH$_3$ or —CH$_2$OCH$_3$CH$_3$.

11. The compound of claim 3 wherein:
R$^1$ is thiophenyl, [R$^{11}$]-thiophenyl, isoxazolyl, [R$^{11}$]-isoxazolyl, pyridinyl, [R$^{11}$]-pyridinyl, benzotriazolyl, [R$^{11}$]-benzotriazolyl, benzomorpholinyl or [R$^{11}$]-benzomorpholinyl or R$^1$ is phenyl or [R$^{11}$]-phenyl, where R$^{11}$ is halo, —OR$^o$, —N(R')$_2$, oxazolyl or

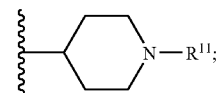

R$^3$ is [R$^{11}$]-phenyl, where R$^{11}$ is Br, Cl, —CH$_3$, —N(R')$_2$, —NHC(O)OR', —S(O)$_2$CH$_3$, —S(O)$_2$N(R')$_2$ or —(CH$_2$)$_\gamma$C(O)N(R')$_2$; and
R$^4$ is methyl, ethyl or —CH$_2$OCH$_3$.

12. The compound of claim 11 wherein R$^3$ is [R$^{11}$]-phenyl, where R$^{11}$ is one substituent at the para position.

13. The compound of claim 1 wherein:
X is —CHR$^2$; and
R$^2$ and NR$^x$R$^3$ are in a cis configuration relative to one another.

14. The compound of claim 13 where the cis configuration is 2S,4R or 2R,4S:

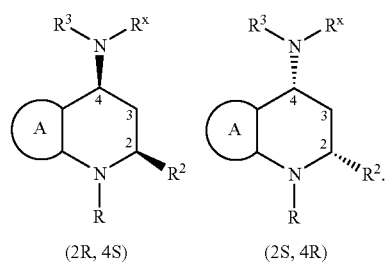

15. The compound of claim 5 wherein:
X is —CHR$^2$; and
R$^2$ and NR$^x$R$^3$ are in a cis configuration relative to one another, wherein the cis configuration is 2S,4R:

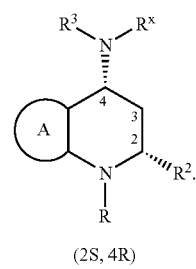

16. The compound of claim 15 wherein:

R is —C(O)R$^1$, wherein R$^1$ is optionally substituted phenyl;

R$^2$ is H, methyl, or ethyl;

R$^3$ is phenyl or [R$^{11}$]-phenyl;

R$^x$ is —C(O)R$^4$; wherein R$^4$ is methyl, ethyl, propyl, iso-propyl, n-butyl, sec-butyl, tert-butyl, —CH$_2$OCH$_3$ or —CH$_2$OCH$_2$CH$_3$; and Ring A is phenyl or [R$^{11}$]-phenyl, where R$^{11}$ is at the six and/or seven position.

17. The compound of claim 15 wherein:

R$^3$ is [R$^{11}$]-phenyl, where R$^{11}$ is Br, Cl, —CH$_3$, —N(R')$_2$, —NHC(O)OR', —S(O)$_2$CH$_3$, —S(O)$_3$N(R')$_2$ or —(CH$_2$)$_\gamma$C(O)N(R')$_2$; and R$^4$ is methyl, ethyl or —CH$_2$OCH$_3$.

18. The compound of claim 17 wherein R$^{11}$ is one substituent at the para position.

19. A pharmaceutical composition comprising the compound of claim 1 and a pharmaceutically acceptable diluent, excipient or carrier.

20. The compound of claim 1 which is represented by a structural formula selected from the group consisting of:

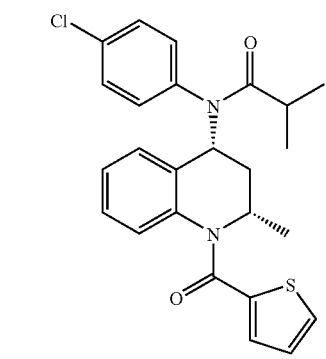

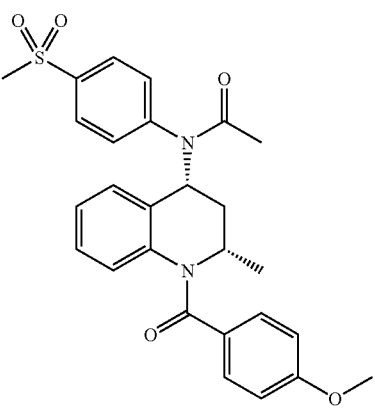

-continued

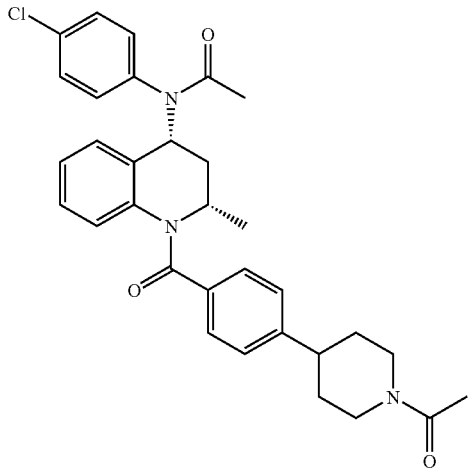

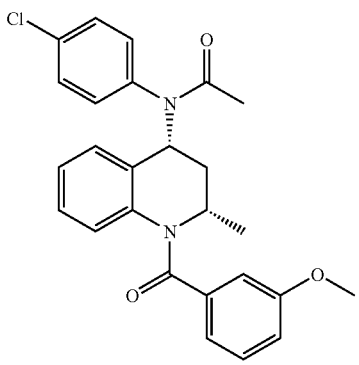

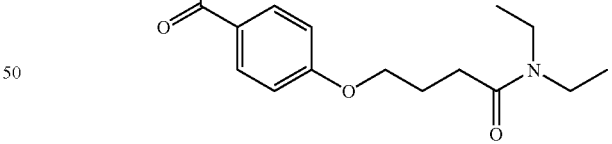

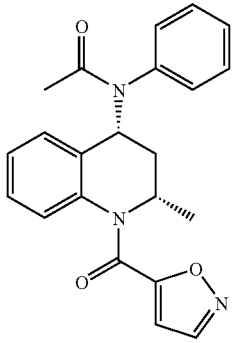

369
-continued
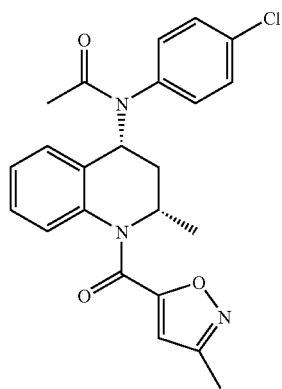
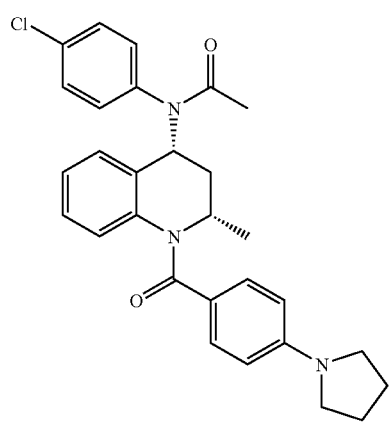
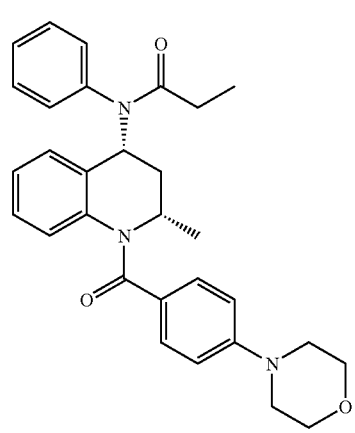
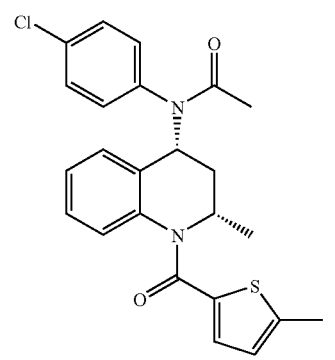
370
-continued
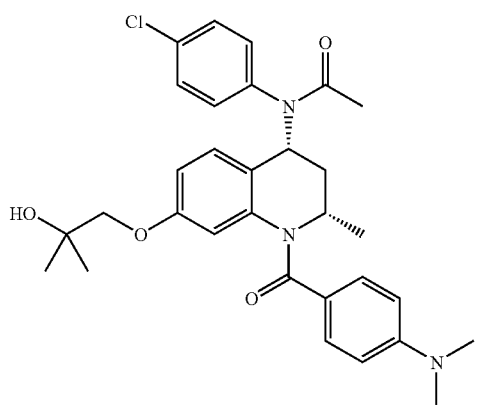
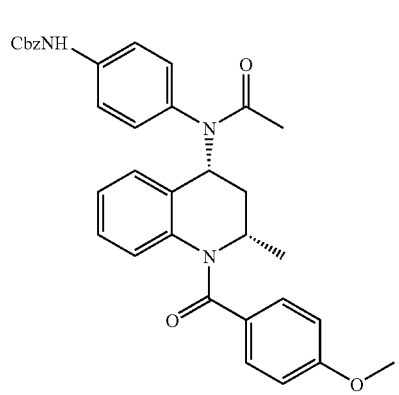
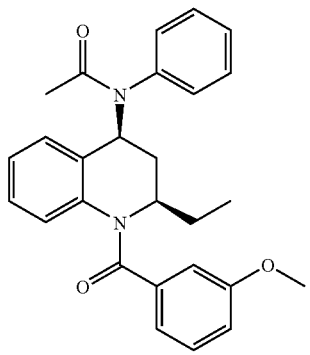
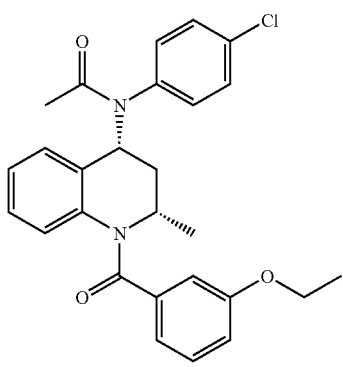

371
-continued
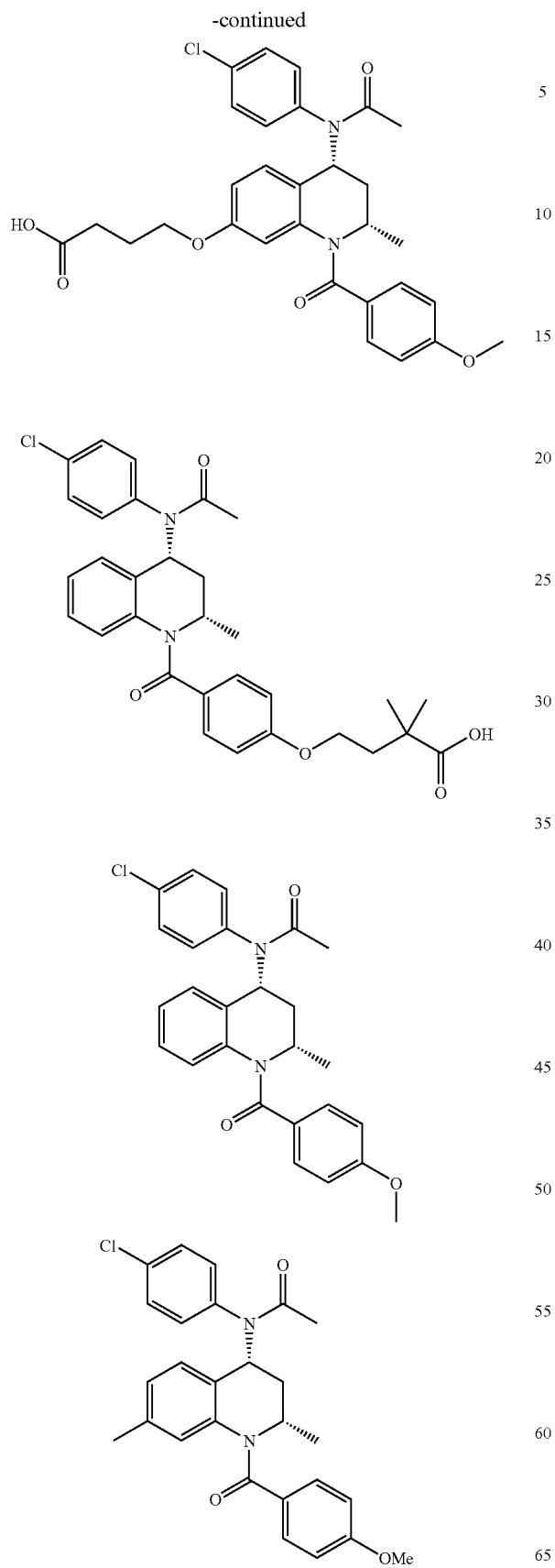
372
-continued
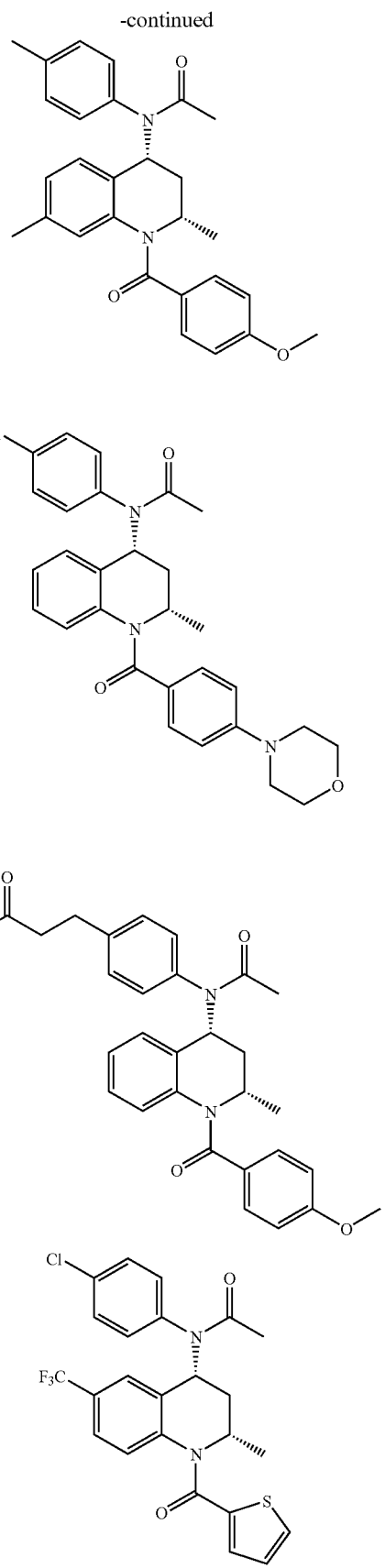

373
-continued
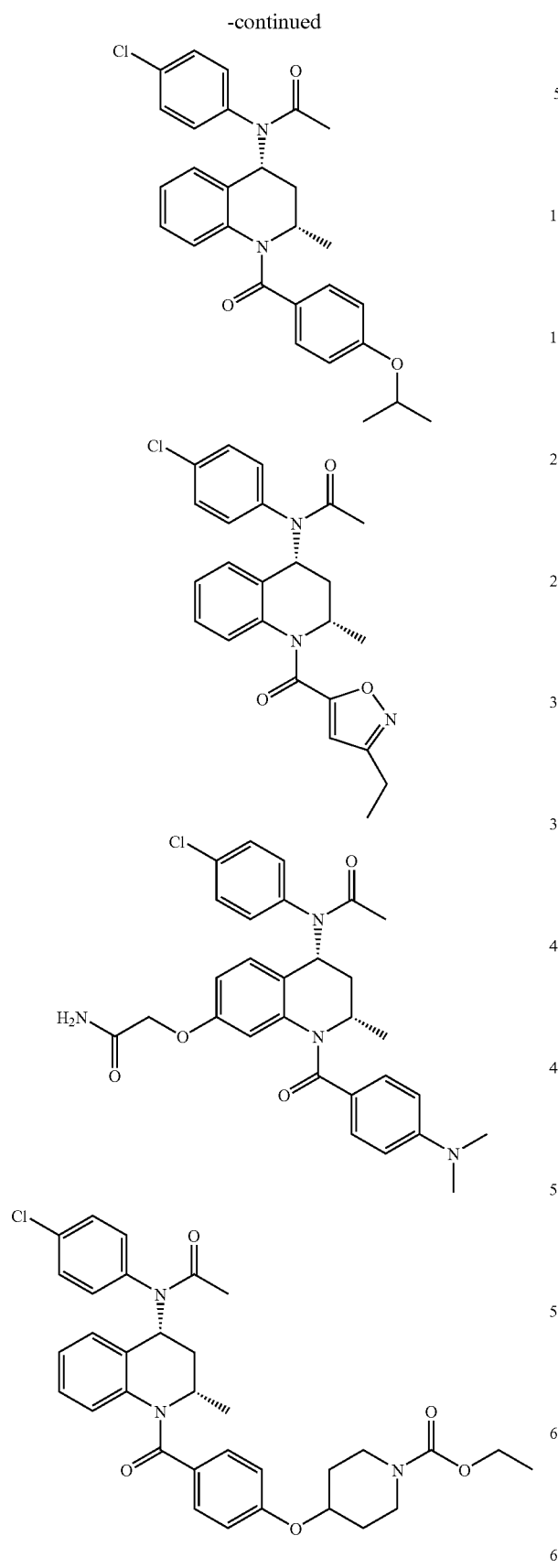
374
-continued
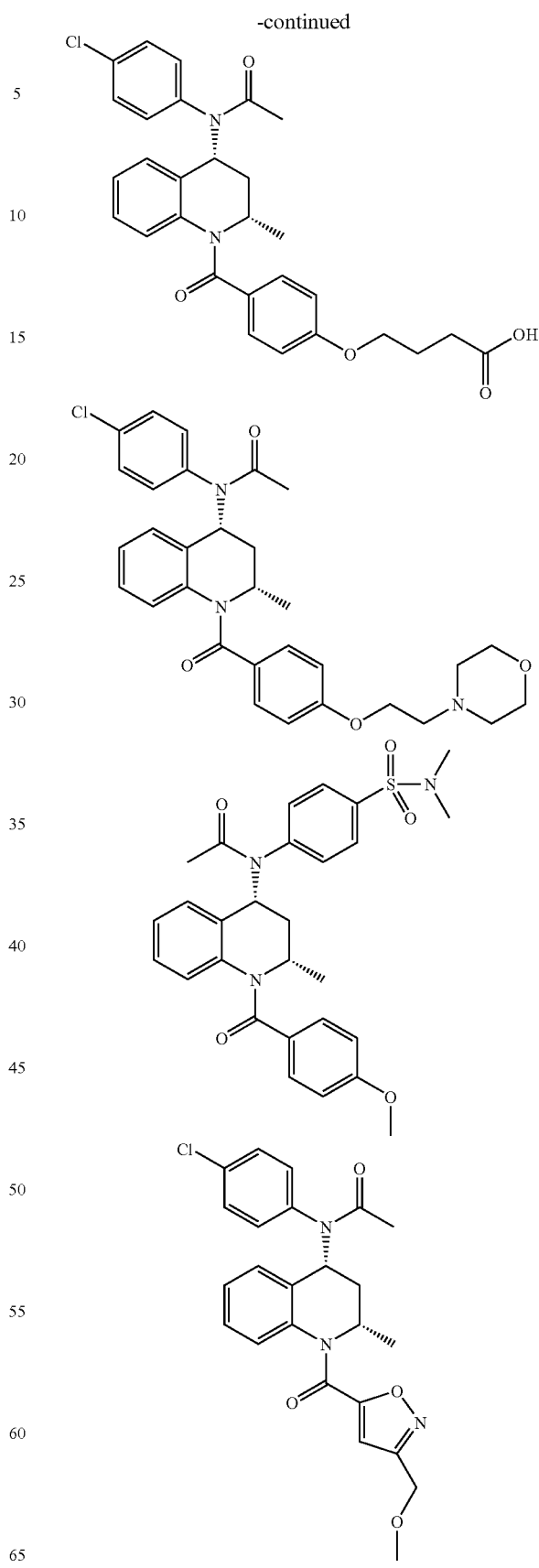

375
-continued
376
-continued
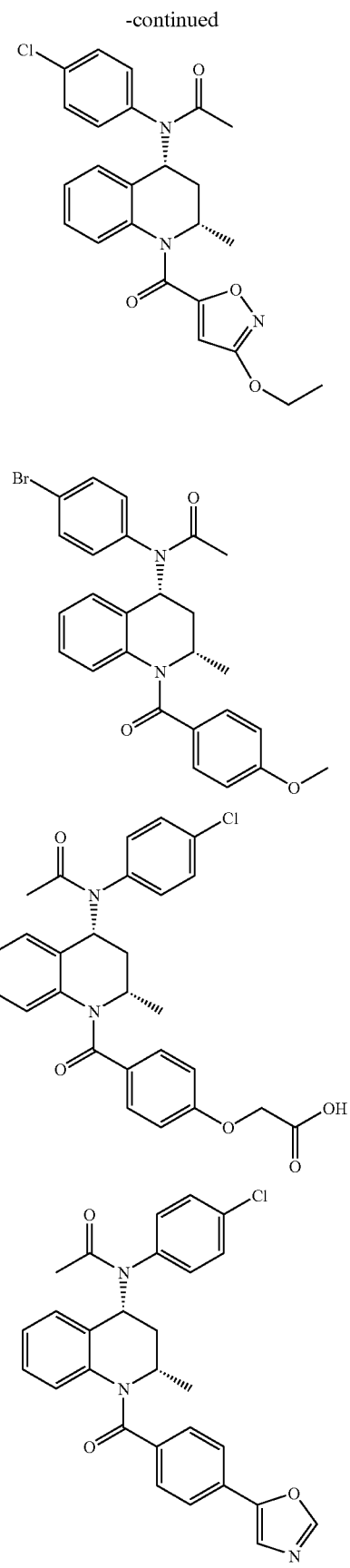
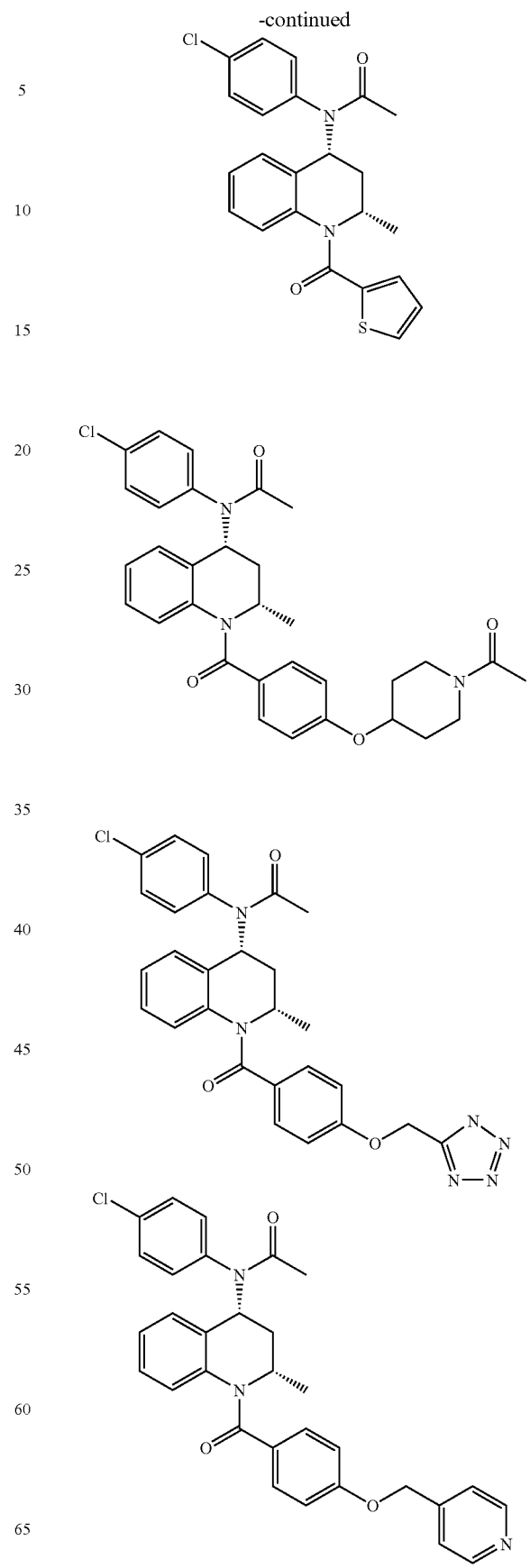

377
-continued
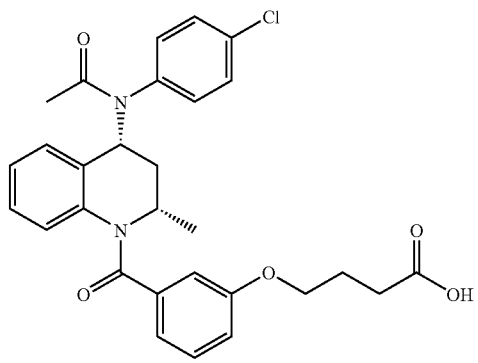
378
-continued
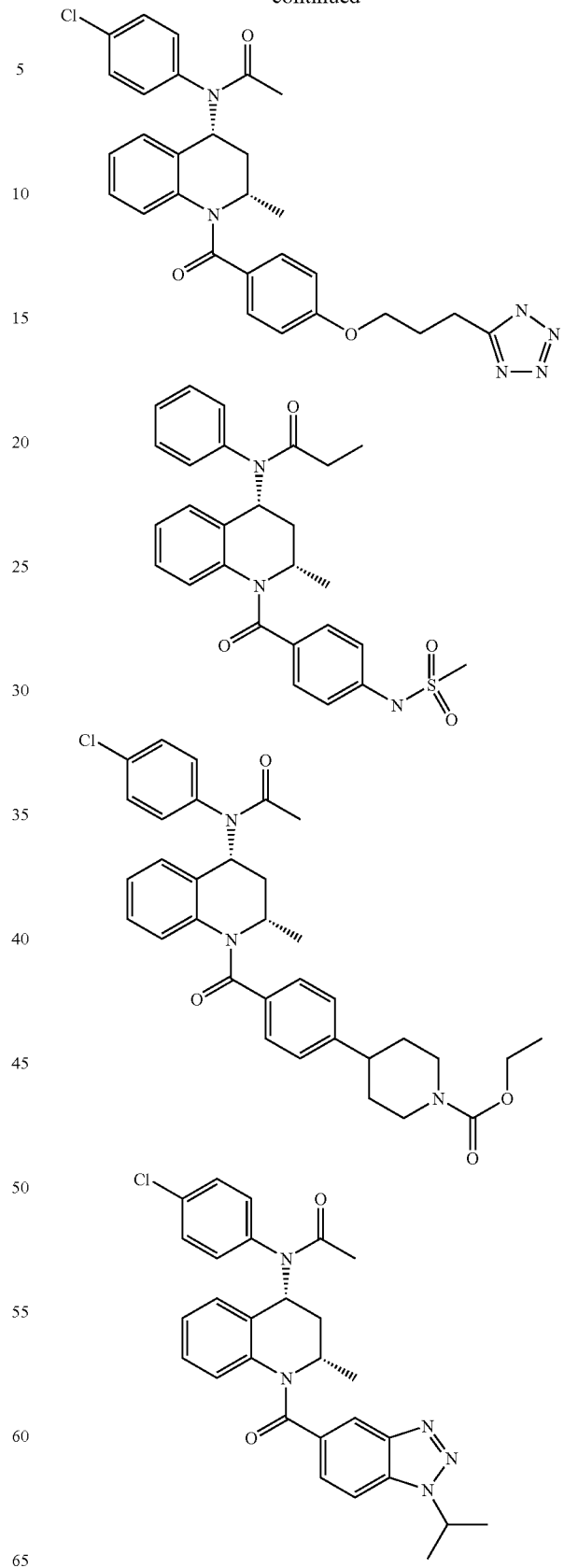

379
-continued
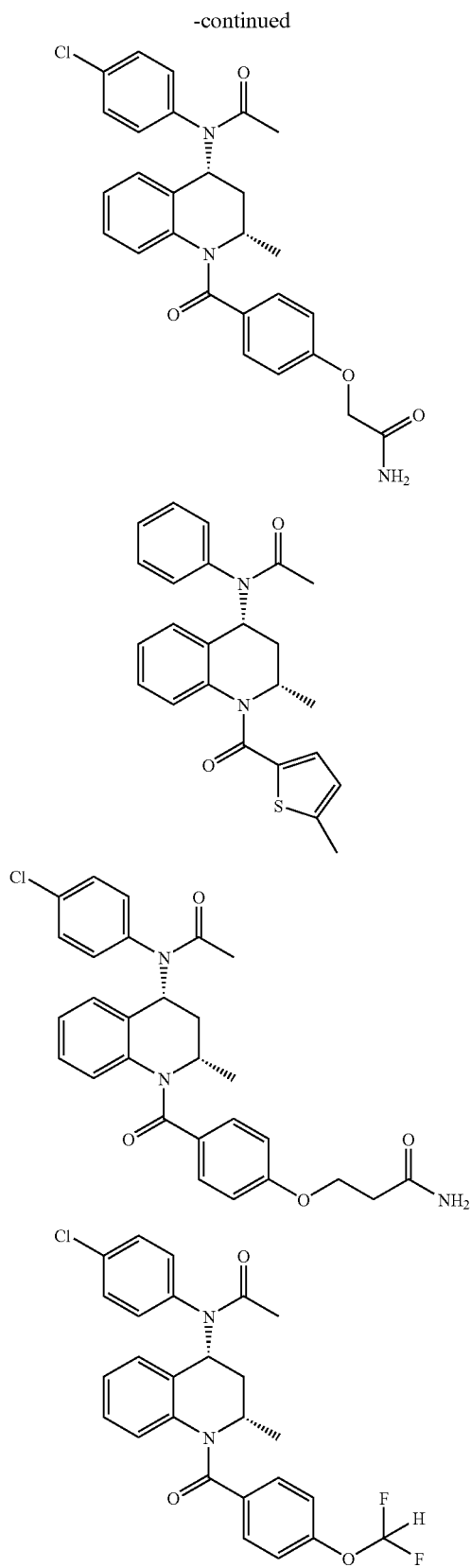
380
-continued
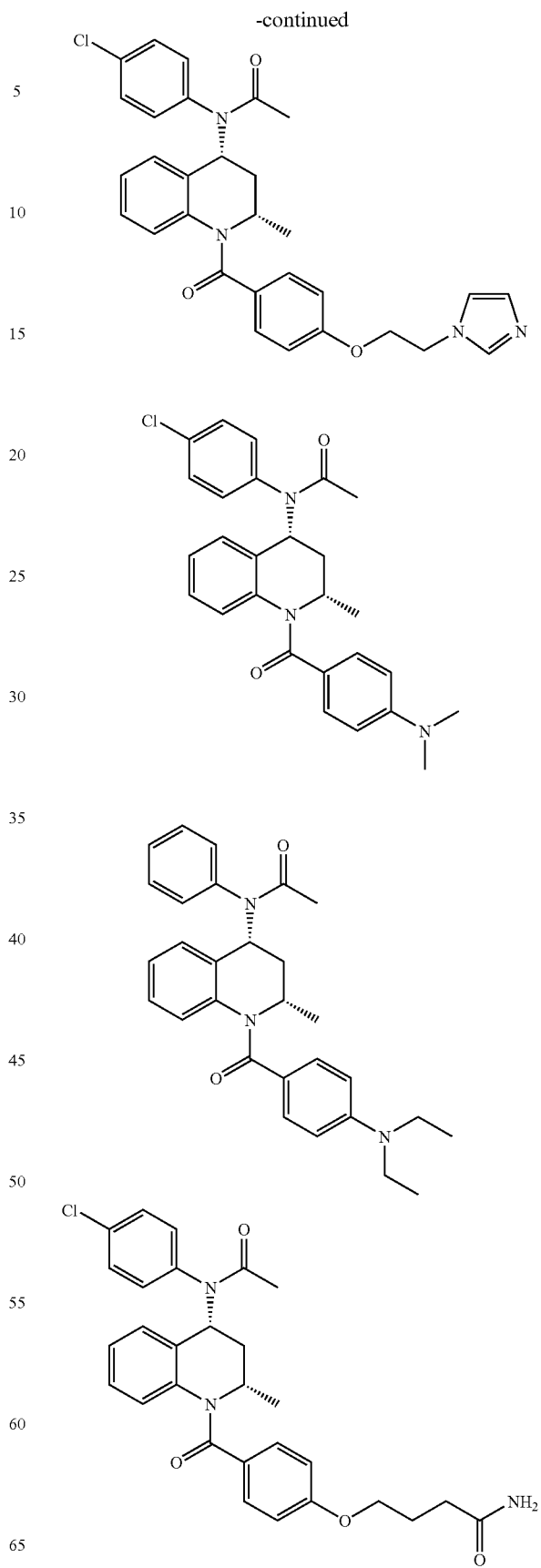

381
-continued
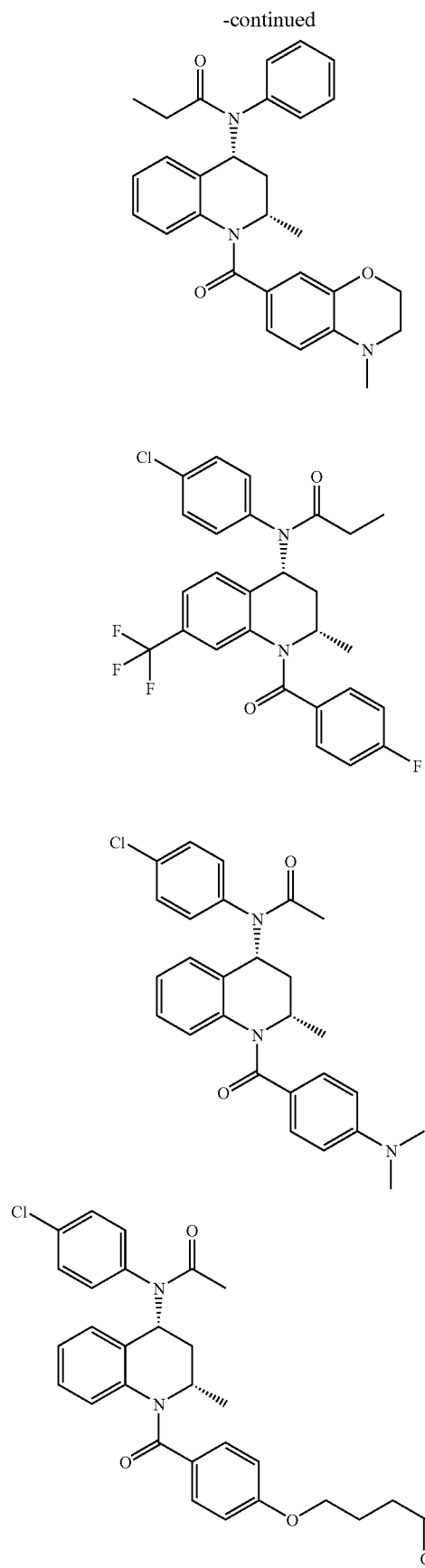
382
-continued
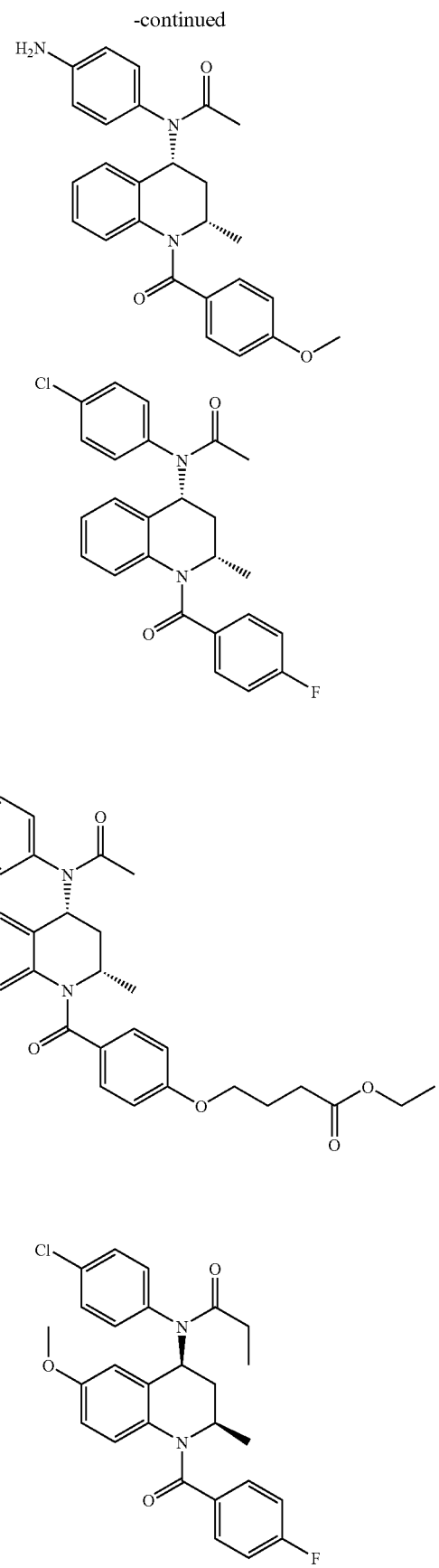

-continued
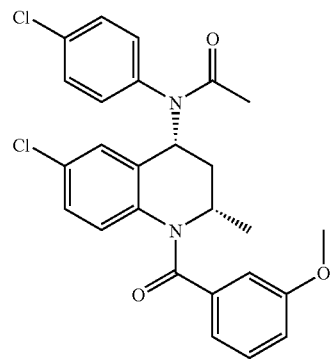
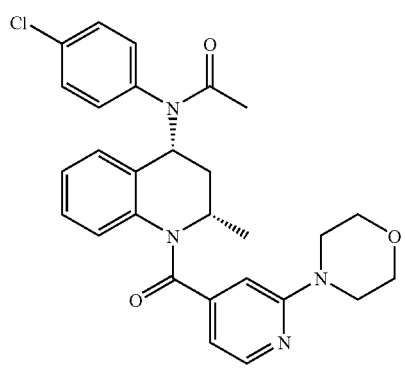
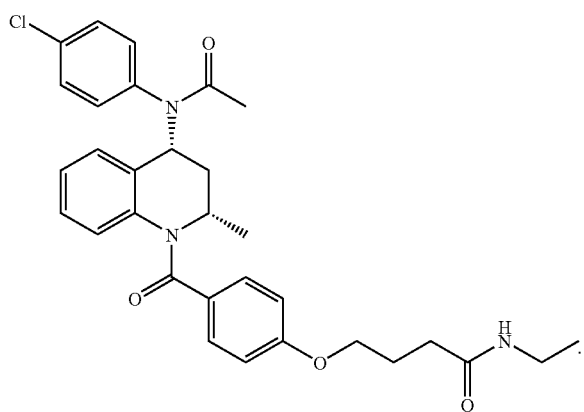
and
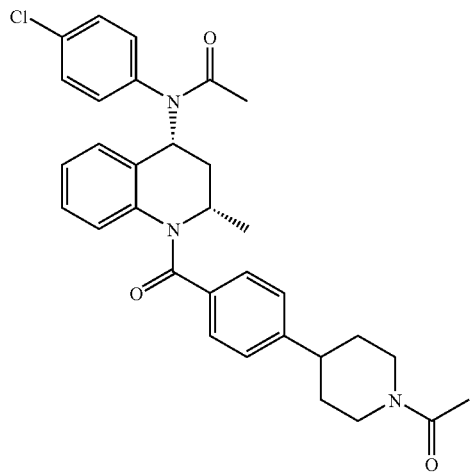
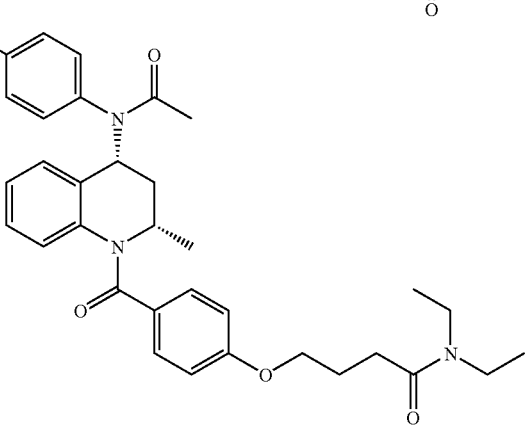
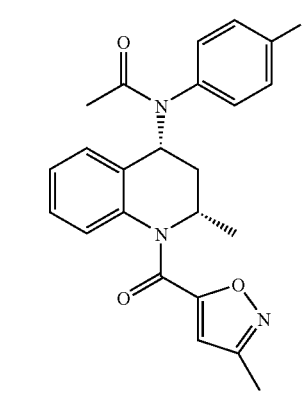
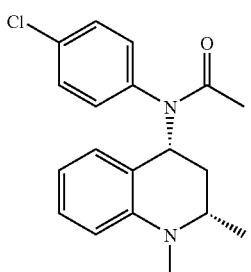
21. A compound which is represented by a structural formula selected form the group consisting of:

385
-continued
386
-continued
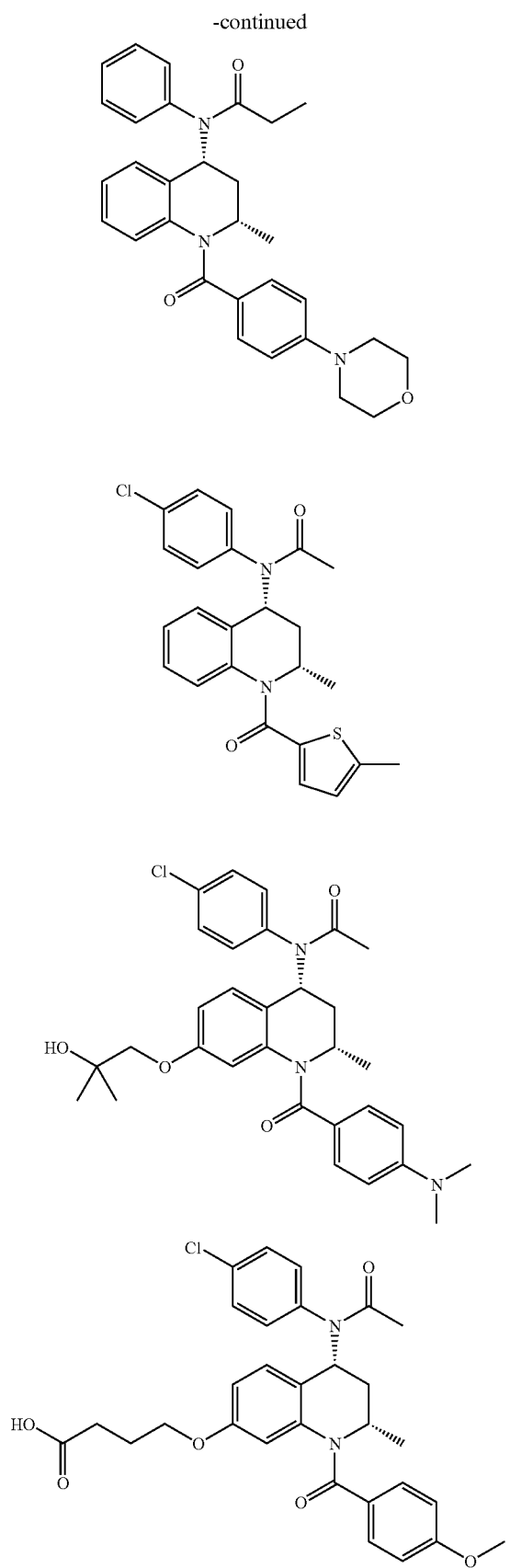
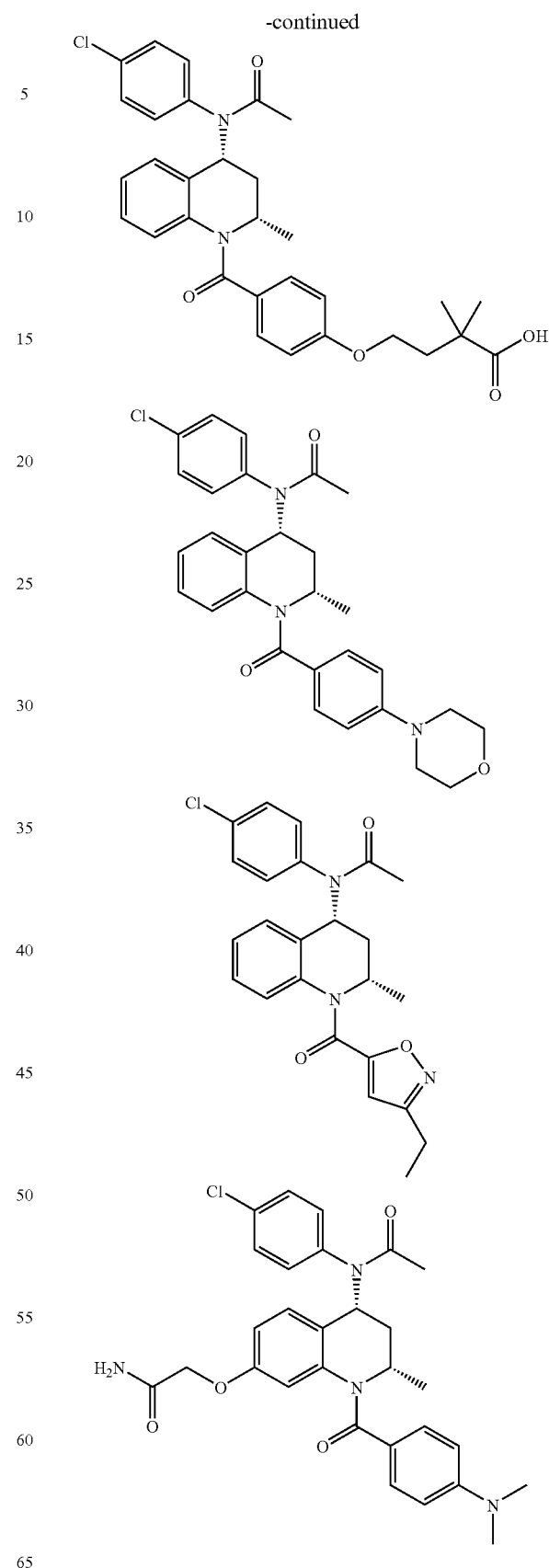

387 388
-continued -continued

389 -continued
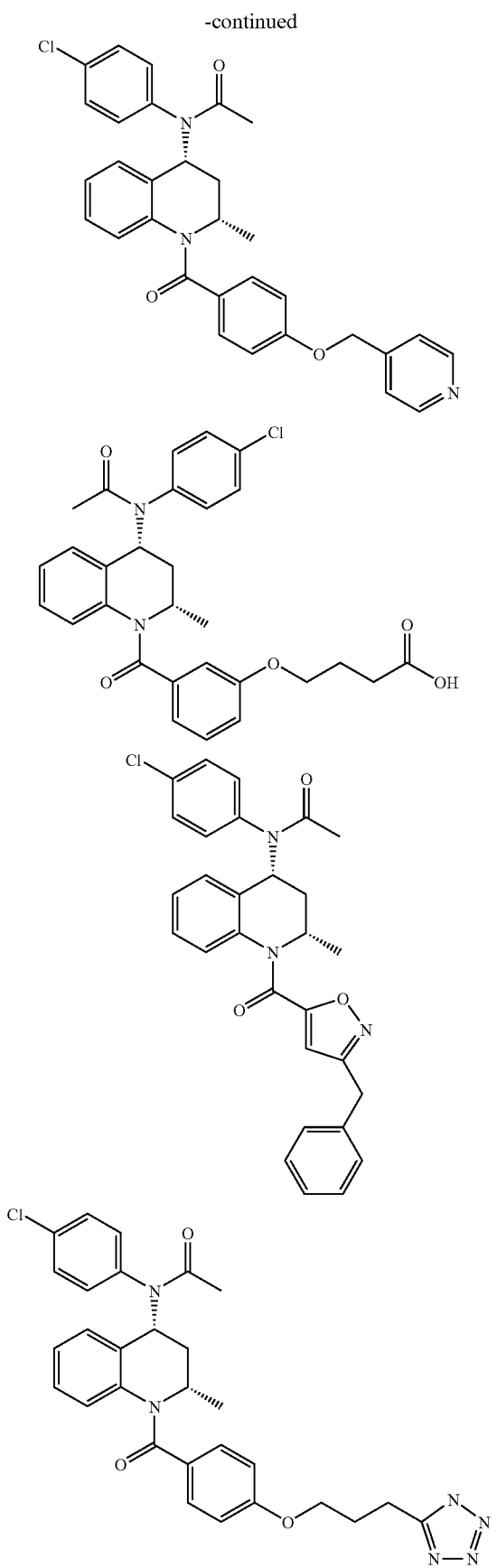
390 -continued
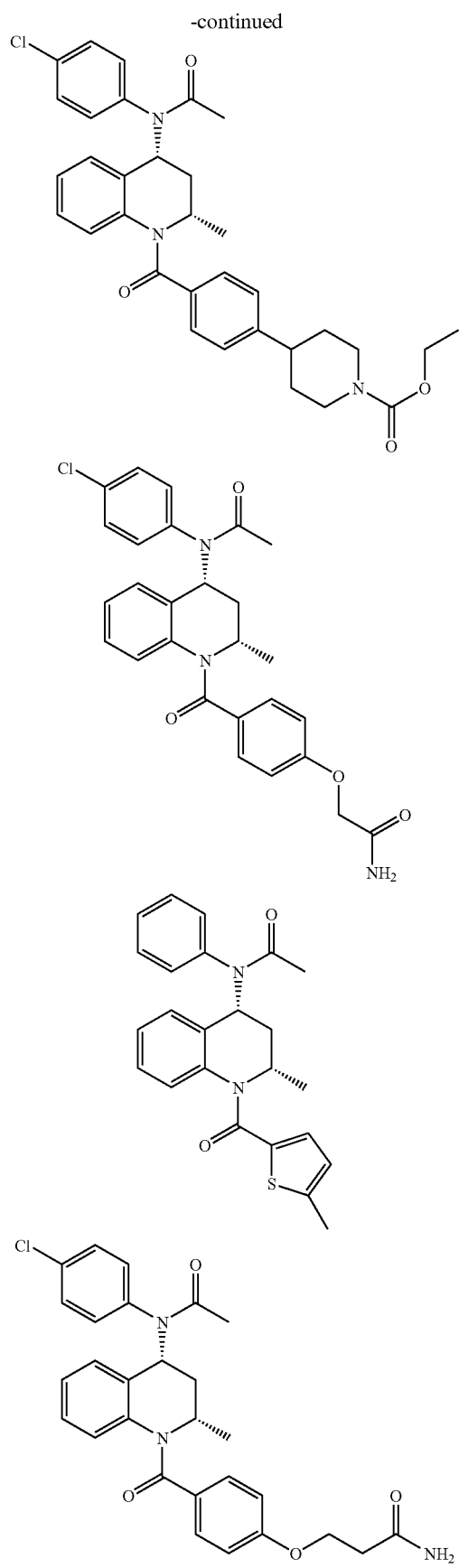

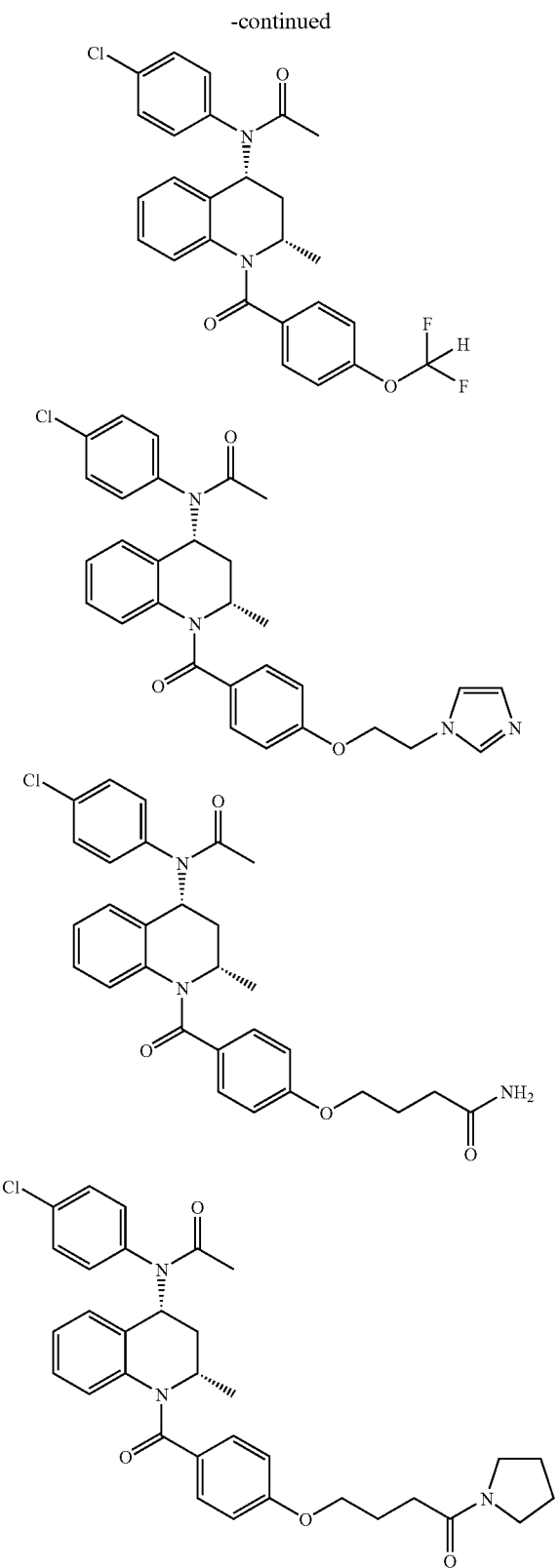
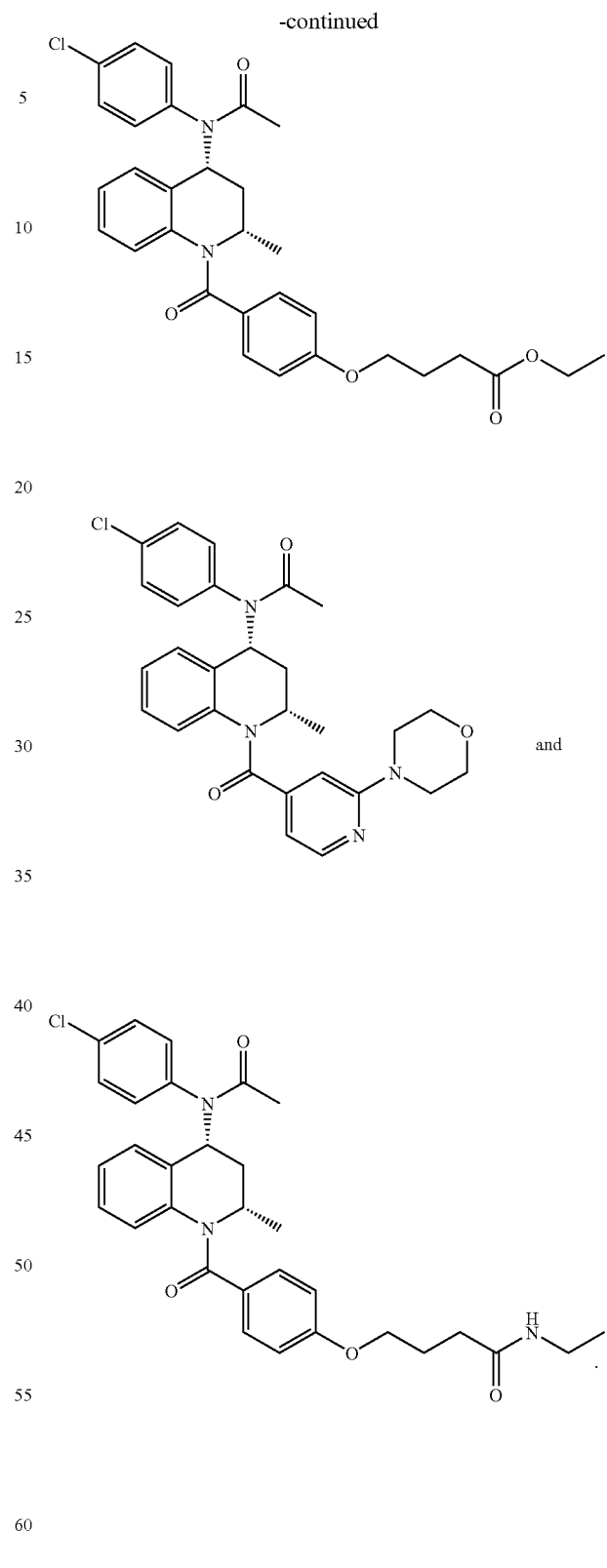
* * * * *